US011401325B2

(12) United States Patent
Maier et al.

(10) Patent No.: US 11,401,325 B2
(45) Date of Patent: Aug. 2, 2022

(54) HUMAN-DERIVED ANTI-HUNTINGTIN (HTT) ANTIBODIES AND USES THEREOF

(71) Applicant: Neurimmune Holding AG, Schlieren (CH)

(72) Inventors: Marcel Maier, Zürich (CH); Jan Grimm, Dübendorf (CH)

(73) Assignee: Neurimmune Holding AG, Schlieren (CH)

( * ) Notice: Subject to any disclaimer, the term of this patent is extended or adjusted under 35 U.S.C. 154(b) by 0 days.

(21) Appl. No.: 16/784,645

(22) Filed: Feb. 7, 2020

(65) Prior Publication Data

US 2020/0392217 A1    Dec. 17, 2020

Related U.S. Application Data

(62) Division of application No. 15/323,784, filed as application No. PCT/EP2015/067327 on Jul. 29, 2015, now Pat. No. 10,556,946.

(30) Foreign Application Priority Data

Jul. 29, 2014 (EP) .................................. 14179004

(51) Int. Cl.
*A61K 39/395* (2006.01)
*A61K 39/00* (2006.01)
*C12P 21/08* (2006.01)
*C07K 16/18* (2006.01)
*G01N 33/68* (2006.01)
*C07K 14/47* (2006.01)

(52) U.S. Cl.
CPC .......... *C07K 16/18* (2013.01); *A61K 39/3955* (2013.01); *C07K 14/47* (2013.01); *G01N 33/6896* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/52* (2013.01); *C07K 2317/56* (2013.01); *C07K 2317/565* (2013.01); *C07K 2317/92* (2013.01); *C07K 2319/00* (2013.01); *C07K 2319/30* (2013.01); *G01N 2333/47* (2013.01); *G01N 2800/2835* (2013.01)

(58) Field of Classification Search
CPC .... C07K 16/18; C07K 14/47; C07K 2317/34; C07K 2317/24; C07K 2317/565; C07K 2317/56; C07K 2317/76; C07K 16/00; C07K 2317/622; C07K 2317/31; C07K 2317/92; C07K 2317/52; C07K 2319/00; A61K 2039/505; A61K 38/17; A61K 39/0007; A61K 39/00; A61P 25/14; A61P 25/28; G01N 33/6896; G01N 33/6854
See application file for complete search history.

(56) References Cited

U.S. PATENT DOCUMENTS

| | | | |
|---|---|---|---|
| 5,686,288 A | 11/1997 | MacDonald et al. | |
| 7,045,290 B2 * | 5/2006 | Lindquist | A61P 25/16 435/6.16 |
| 7,375,194 B2 * | 5/2008 | Khoshnan | C07K 16/18 530/387.3 |
| 7,589,189 B2 * | 9/2009 | Ichiro | A61K 31/7088 536/24.5 |
| 8,022,268 B2 * | 9/2011 | Grimm | A61P 25/28 800/18 |
| 8,039,209 B2 * | 10/2011 | Lindquist | G01N 33/6896 435/6.13 |
| 9,518,284 B2 * | 12/2016 | Lindquist | A61P 25/28 |
| 9,932,394 B2 * | 4/2018 | Henderson | C07K 16/18 |
| 10,053,518 B2 * | 8/2018 | Smrzka | G01N 33/6896 |
| 10,406,197 B2 * | 9/2019 | Smrzka | C07K 14/705 |
| 10,556,946 B2 * | 2/2020 | Maier | C07K 14/47 |
| 2003/0232052 A1 | 12/2003 | Khoshnan et al. | |
| 2005/0282252 A1 | 12/2005 | Siegel | |
| 2009/0304590 A1 | 12/2009 | Gill et al. | |
| 2010/0233180 A1 | 9/2010 | Khoshnan et al. | |
| 2017/0166631 A1 | 6/2017 | Maier et al. | |

FOREIGN PATENT DOCUMENTS

| WO | WO-99/06838 A2 | 2/1999 |
|---|---|---|
| WO | WO-2005/052002 A2 | 6/2005 |
| WO | WO-2008/081008 A1 | 7/2008 |
| WO | WO-2013/013025 A2 | 1/2013 |
| WO | WO-2016/005545 A1 | 1/2016 |
| WO | WO-2016/005547 A1 | 1/2016 |

OTHER PUBLICATIONS

MacCallum et al.,J. Mol. Biol.,1996; 262: 732-745.*
Pascalis et al.,The Journal of Immunology, 2002; 169: 3076-3084.*
Casset et al., BBRC, 2003; 307: 198-205.*
Vajdos et al.,J. Mol. Biol. 2002; 320: 415-428.*
Holm et al.,Mol. Immunol., 2007; 44: 1075-1084.*
Chen et al. ,J. Mol. Bio., 1999;293: 865-881.*
Wu et al. ,J. Mol. Biol., 1999; 294:151-162.*
Burgess et al. J of Cell Bio. 1990, 111:2129-2138.*

(Continued)

*Primary Examiner* — Chang-Yu Wang

(74) *Attorney, Agent, or Firm* — Clark & Elbing LLP; Susan M. Michaud

(57) ABSTRACT

Provided are novel human-derived anti-huntingtin (HTT) antibodies and biotechnological derivatives thereof, preferably capable of binding mutated and/or aggregated HTT species and or fragments thereof, as well as methods related thereto. The human-derived anti-HTT antibodies and biotechnological derivatives can be used in pharmaceutical and diagnostic compositions for HTT targeted immunotherapy of Huntington Disease and diagnosis thereof.

12 Claims, 75 Drawing Sheets

Specification includes a Sequence Listing.

(56) References Cited

OTHER PUBLICATIONS

Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Butler et al., "Bifunctional anti-huntingtin proteasome-directed intrabodies mediate efficient degradation of mutant huntingtin exon 1 protein fragments," PLoS One. 6(12):e29199 (2011) (11 pages).
Butler et al., "Engineered antibody therapies to counteract mutant huntingtin and related toxic intracellular proteins," Prog Neurobiol. 97(2):190-204 (2012).
Colby et al., "Development of a human light chain variable domain (V(L)) intracellular antibody specific for the amino terminus of huntingtin via yeast surface display," J Mol Biol. 342(3):901-12 (2004).
Colby et al., "Potent inhibition of huntingtin aggregation and cytotoxicity by a disulfide Bond-Free Single-Domain Intracellular Antibody," Proc Natl Acad Sci USA. 101 (51):17616-21 (2004).
Dehay et al., "Mapping of the epitope of monoclonal antibody 2B4 to the proline-rich region of human Huntingtin, a region critical for aggregation and toxicity," Biotechnol J. 2(5):559-64 (2007).
Huang et al., "Single-chain fragment variable passive immunotherapies for neurodegenerative diseases," Int J Mol Sci. 14(9):19109-27 (2013).
International Preliminary Report on Patentability for International Patent Application No. PCT/EP2015/067327, dated Jan. 31, 2017 (17 pages).
International Search Report and Written Opinion for International Patent Application No. PCT/EP2015/067327, dated Jan. 26, 2016 (26 pages).
Khoshnan et al., "Antibodies and intrabodies against huntingtin: production and ccreening of monoclonals and single-chain recombinant forms," Methods Mol Biol. 1010:231-51 (2013).
Khoshnan et al., "Effects of intracellular expression of anti-huntingtin antibodies of various specificities on mutant huntingtin aggregation and toxicity," Proc Natl Acad Sci USA. 99(2):1002-7 (2002).
Ko et al., "New anti-huntingtin monoclonal antibodies: implications for huntingtin conformation and its binding proteins," Brain Res Bull. 56(3-4):319-29 (2001).
Landles et al., "Proteolysis of mutant huntingtin produces an exon 1 fragment that accumulates as an aggregated protein in neuronal nuclei in Huntington disease," J Biol Chem. 285(12):8808-23 (2010) (22 pages).
Lecerf et al., "Human single-chain Fv intrabodies counteract in situ huntingtin aggregation in cellular models of Huntington's disease," Proc Natl Acad Sci U S A. 98(8):4764-9 (2001).
Legleiter et al., "Monoclonal antibodies recognize distinct conformational epitopes formed by polyglutamine in a mutant huntingtin fragment," J Biol Chem. 284(32):21647-58 (2009) (14 pages).
Lippow et al., "Computational design of antibody-affinity improvement beyond in vivo maturation," Nat Biotechnol. 25(10):1171-6 (2007).
Padlan et al., "Structure of an antibody-antigen complex: crystal structure of the HyHEL-10 fab-lysozyme complex," Proc Natl Acad Sci USA. 86(15):5938-42 (1989).
Paul, Chapter 9: Structure and function of immunoglobulins, *Fundamental Immunology, Third Edition*. Raven Press, New York. 292-5 (1993).
Rajpal et al., "A general method for greatly improving the affinity of antibodies by using combinatorial libraries," Proc Natl Acad Sci USA. 102(24):8466-71 (2005).
Rudikoff et al., "Single amino acid substitution altering antigen-binding specificity," Proc Natl Acad Sci USA. 79(6):1979-83 (1982).
Sheets et al., "Efficient construction of a large nonimmune phage antibody library: the production of high-affinity human single-chain antibodies to protein antigens," Proc Natl Acad Sci USA. 95(11):6157-62 (1998).
Southwell et al., "Intrabodies binding the proline-rich domains of mutant huntingtin increase its turnover and reduce neurotoxicity," J Neurosci. 28(36):9013-20 (2008).
Southwell et al., "Intrabody gene therapy ameliorates motor, cognitive, and neuropathological symptoms in multiple mouse models of Huntington's disease," J Neurosci. 29(43):13589-602 (2009).
Vajdos et al., "Comprehensive functional maps of the antigen-binding site of an anti-ErbB2 antibody obtained with shotgun scanning mutagenesis," J Mol Biol. 320(2):415-28 (2002).
Wolfgang et al., "Suppression of Huntington's disease pathology in *Drosophila* by human single-chain Fv antibodies," Proc Natl Acad Sci USA. 102(32):11563-8 (2005).
Iizuka et al., "Anti-vascular endothelial growth factor receptor (VEGFR) 2 autoantibody identification in glioblastoma patient using single B cell-based antibody gene cloning," Immunol. Lett. 159(1-2):15-22 (2014).
Klein et al., "Somatic hypermutation in normal and transformed human B cells," Immunol. Rev. 162:261-280 (1998) (21 pages).
Krause et al., "An insertion mutation that distorts antibody binding site architecture enhances function of a human antibody," mBio 2(1):e00345-10 (2011) (8 pages).
Wiens et al.,"Somatic mutation in VH complementarity-determining region 2 and framework Region 2: differential effects on antigen binding and Ig secretion," J. Immunol. 159(3):1293-1302 (1997).
Wilson et al., "Somatic hypermutation introduces insertions and deletions into immunoglobulin V genes," J. Exp. Med. 187(1):59-70 (1998).
Office Action dated Aug. 18, 2021 for Japanese Patent Application No. 2020-096056, Maier et al., "Human-Derived Anti-Huntingtin (HTT) Antibodies and Uses Thereof," filed Jun. 2, 2020 (93 pages).
Southwell et al., "Perturbation with Intrabodies Reveals That Calpain Cleavage Is Required for Degradation of Huntingtin Exon 1," PLoS One. 6(1):e16676 (2011) (10 pages).
European Medicines Agency, Committee for Medicinal Product for Human Use (CHMP), "Guideline on Human Cell-Based Medicinal Products," (2008) (25 pages).
Schindler et al., "Small, Seeding-Competent Huntingtin Fibrils are Prominent Aggregate Species in Brains of zQ175 Huntington's Disease Knock-in Mice," Front. Neurosci. 15:682172 (2021) (14 pages).
Messer et al., "Intrabodies as Neuroprotective Therapeutics," Neurotherapeutics 10(3):447-458 (2013).
Southwell, Amber, Dissertation: "Intrabodies as Therapeutics for Huntington's Disease," PhD, California Institute of Technology, 2009, pp. i-xii, 1-207, Retrieved on Aug. 11, 2021 from thesis. library.caltech.edu/2522>, (219 pages).

* cited by examiner

(A) NI-302.33C11 VH (variable heavy chain sequence VH) (SEQ ID NO: 2)
```
FR1-----------------------------CDR1-FR2-----------CDR2-------------FR3
EVQLVESGGGVVQPGNSLRLSCAASGFRFSDFGMHWVRQAPGKGLEWLALIWYDGGYKYYADSVKGRFT ------------------------------CDR3----------FR4---------
ISRDNSKNTMFLQMNSLRAEDTAVYYCATHLEYCSRTTCYLGHWGQGTLVTVSS
```

NI-302.33C11 VK (variable light chain sequence VK) (SEQ ID NO: 4)
```
FR1-------------------CDR1-------FR2-----------CDR2---FR3----------
DIQLTQSPSFLSASVGDTVTFTCRASQGISDYLAWFQQKPGIAPKLLIYAASTLQTGVPSRFSGSGSGT -------------------CDR3-----FR4-------
EFTLTIRSLQSEDFGTYYCQQLKTYPYTFGQGTKVEIK
```

(B) NI-302.63F3 VH (variable heavy chain sequence VH) (SEQ ID NO: 6)
```
FR1-----------------------------CDR1-FR2-----------CDR2-------------FR3
QVQLVQSGSAFKKPGTSVKVSCKASGYTFETRSMNWVRQAPGQGLEYMGWINTNTGNRTYVQAFRGRFV ------------------------------CDR3------FR4---------
FSLDTSVSTAYLQISNLKTEDTAVYYCARGAGGGYWFDSWGQGTLVTVSS
```

NI-302.63F3 VK (variable light chain sequence VK) (SEQ ID NO: 8)
```
FR1-----------------CDR1----------FR2------------CDR2---FR3-----
DIQMTQSPDSLAVSLGERATINCKSNQSLFYSSNNNNYLAWYQHKSGQPPKLLVYWGSTRESGVPDRFS -------------------CDR3-----FR4-------
GSGSGTDFTLTISSLQAEDVAIYYCHQYYHNPYTFGQGTKLEIK
```

(C) NI-302.35C1 VH (variable heavy chain sequence VH) (SEQ ID NO: 10)
```
FR1-------------------------------CDR1-FR2-----------CDR2-------------FR3
EVQLVESGGNLVQPGGSLRLSCTASGFTFSITALSWVRQAPEKGPQWVSAITGNAYGTYYADSVKGRFT ------------------------------CDR3--------FR4---------
ISRDNAKNTLYLQMNGLRAEDTAIYYCVKGIASDSSGYSAFWGPGTLVTVSS
```

NI-302.35C1 VK (variable light chain sequence VK) (SEQ ID NO: 12)
```
FR1-----------------CDR1--------FR2-----------CDR2----FR3-----------
EIVLTQSPATLSLSPGERATLSCRASQSVDNQFAWYQQKPGQAPRLLIYDASRRAPGIPDRFSGSGSGT -------------------CDR3-----FR4-------
DFTLTISSLEPEDFAIYYCQHRYTWLYTFGQGTRLEIK
```

Fig. 1

(D) NI-302.31F11 VH (variable heavy chain sequence VH) (SEQ ID NO: 14)
```
FR1-------------------------------CDR1-FR2-----------CDR2------------FR3-
EVQLVESGGGLIQPGGSLRLSCAASGFTVSSTYMSWVRQAPGKGLECVSVIFSGADTYYADSVKGRFTV -----------------------------------CDR3------FR4--------
SRDNSKNTLFLQMNSLRVEDTATYYCVRHYYGSDLPSDFWGQGTLVTVSS
```

NI-302.31F11 VK (variable light chain sequence VK) (SEQ ID NO: 16)
```
FR1-------------------CDR1----------FR2------------CDR2---FR3-----
DVVMTQSPLSLPVAPGEPASISCRSSQSLLYSNGYNYLDWYLQKPGKPPQLLVYLGSDRASGVPDRFSG ------------------------CDR3-----FR4--------
SGSGKDFTLNISRVEAEDVGVYYCMQGLQSPWTFGQGTKLEIK
```

(E) NI-302.2A2 VH (variable heavy chain sequence VH) (SEQ ID NO: 18)
```
FR1----------------------------CDR1-FR2-----------CDR2-------------FR3
EVQLVESGGGLVQPGGSLRLSCAASGFTFSTYWMNWVRQAPGKGLEWVANIKPDGSDKYYVDSVKGRFT -----------------------------CDR3-----FR4--------
ISRDNAKNSLYLQMNSLRDEDTAVYYCARGDGSGWNVYWGQGTLVTVSS
```

NI-302.2A2 VK (variable light chain sequence VK) (SEQ ID NO: 20)
```
FR1-----------------CDR1---------------FR2-------------CDR2----FR3-
DIQMTQSPDSLAVSLGERATINCKSSQSLLYTSKNKDSKNYLGWYQQKPGQPPKLLIYWASTRESGVPD ---------------------------CDR3-----FR4--------
RFSGSGSGTDFTLTISSLQAEDVAVYYCQQYYTTPQFGGGTKVEIK
```

(F) NI-302.6N9 VH (variable heavy chain sequence VH) (SEQ ID NO: 22)
```
FR1-----------------------------CDR1-FR2------------CDR2-------------FR3
EVQLVESGGDLVQPGGSLRLSCVVSGFTFSSYAMTWVRQAPGKGLAWVSTISATGGSTFYTDSVRGRFT -----------------------------CDR3----------FR4--------
ISRDNSKNTLYLQMNSLRTDDTAIYYCVKDLFGVDTSYYGMDVWGQGTTVTVSS
```

NI-302.6N9 VK (variable light chain sequence VK) (SEQ ID NO: 24)
```
FR1---------------------CDR1---------FR2-----------CDR2----FR3---------
EIVLTQSPGTLSLSPGERATLSCRPSQSVSGRYVAWYQQKPGQAPRLLFYAASNRAIGIPDRFSGSGSG -------------------------CDR3-----FR4--------
TDFTLTISRLEPEDFAVYYCQHYGASSYTFGPGTKVDIK
```

Fig. 1 (continued)

(G)     NI-302.74C11 VH (variable heavy chain sequence VH) (SEQ ID NO: 26)

```
FR1--------------------------CDR1-FR2-----------CDR2---------FR3----
EVQLVQSGTEVQKPGASVKVSCKASGYSFTGYFLHWVRQAPGQGLEWMGWINPNSGDTNYAEKFRGRII

--------------------------------CDR3--------FR4---------
MTRDTSVSTAHMELSSLRFDDTALYYCTREAPDPGAETDVWGQGTTVTVSS
```

NI-302.74C11 VL (variable light chain sequence VL) (SEQ ID NO: 28)

```
FR1-------------------CDR1-------FR2------------CDR2----FR3-----------
QSVLTQPPSVSVSPGQTARITCSGDAVPKQYIYWYQQKPGQAPILVIYKDTQRPSGIPERFSGSNSGTT

-------------------CDR3------FR4-------
VTLTITGVQADDEGDYYCQSADSSATWVFGGGTKLTVL
```

(H)     NI-302.15F9 VH (variable heavy chain sequence VH) (SEQ ID NO: 30)

```
FR1----------------------------CDR1-FR2-----------CDR2---------------FR
EVQLVESGGGLVTPGGSLRLSCEASGFLFKNSSMNWVRQTPGKGLEWVSSIDTSATNYKYYADSVKGRF

3---------------------------CDR3--------FR4----------
TISRDDATNSLYLQMNSLRADDTATYYCARGYYTPRDFDYWGQGTLVTVSS
```

NI-302.15F9 VK (variable light chain sequence VK) (SEQ ID NO: 32)

```
FR1-----------------CDR1------------FR2--------------CDR2----FR3------
DVVMTQSPQTLSVSLGQAASISCRSSQSLLYRDNNTYLNWFHQRPGQSPRRLIYRASDRDSGVPDRFSG

---------------------------CDR3-----FR4--------
GGSGTDFTLKISGVEAEDVGTYYCMQGTHWPRTFGQGTKVEIK
```

(I)     NI-302.39G12 VH (variable heavy chain sequence VH) (SEQ ID NO: 34)

```
FR1---------------------------CDR1-FR2------------CDR2---------------FR3-
EVQLVQSGGGLVHPWGSLRLSCAASGFSVSNYAITWVRRAPGKGLQYISVIYRDGRTYYGDSVRGRFTI

--------------------------CDR3--------FR4---------
SRDDSKNTLYLQMNSLRFEDTAVYYCARAHGQYYYGVDVWGQGTTVTVSS
```

NI-302.39G12 VK (variable light chain sequence VK) (SEQ ID NO: 36)

```
FR1-----------------CDR1------------FR2--------------CDR2---FR3------
DVVMTQSPLSLSVSPGEPASISCRSSQSLLHSNGYNYLDWYRQKPGQSPQLLIYLSSNRPSGVPDRFSA

------------------------CDR3-----FR4--------
SGSGTEFTLQISRVEAEDVGVYYCMQSLQTFTFGGGTKVDIK
```

Fig. 1 (continued)

(J) NI-302.11A4 VH (variable heavy chain sequence VH) (SEQ ID NO: 38)

```
FR1---------------------------------CDR1-FR2-----------CDR2-------------FR3-
EVQLVESGGGLIQPGGSLRLSCAASGFPVSSSYMSWVRQAPGEGLEWVSVLYRDGDTYYADSVQGRFTI

-----------------------------CDR3---------FR4--------
SRDNSQNTFYLQMNSLKAEDTAVYYCAGDRRSSHYYYGMDVWGQGTTVTVSS
```

NI-302.11A4 VK (variable light chain sequence VK) (SEQ ID NO: 40)

```
FR1---------------CDR1----------FR2-------------CDR2----FR3-----------
EIVMTQSPGTLSLSPGERATLSCRASQSVSSSYFAWYQQKPGQAPRLLIYGTSRRATAIPDRFSGSGSG

---------------------CDR3-----FR4--------
TDFTLTISRLEPEDFAVYYCQQYGSSWTFGPGTKVEIK
```

(K) NI-302.22H9 VH (variable heavy chain sequence VH) (SEQ ID NO: 42)

```
FR1---------------------------CDR1-FR2-------------CDR2--------------FR3-
EVQLVESGGGLVHPWGSLRVSCAASGFSVSNYAITWVRQAPGKGLEYISVIYRDGRTYYGDSVRGRFTI

-----------------------------CDR3--------FR4---------
SRDDSKNTIYLQMNSLRFEDTAVYYCARAHGQYYYGVDVWGQGTTVTVSS
```

NI-302.22H9 VK (variable light chain sequence VK) (SEQ ID NO: 44)

```
FR1------------------------CDR1-------------FR2-------------CDR2----FR3------
DVVMTQSPLSLSVSPGEPASISCRSSQSLLHSNGYNYLDWYRQKPGQSPQLLIYLNSNRASGVPDRFSG

---------------------------CDR3-----FR4--------
SGSGTEFTLTISRVEAEDVGVYYCMQSLQTFTFGGGTKVEIK
```

(L) NI-302.44D7 VH (variable heavy chain sequence VH) (SEQ ID NO: 46)

```
FR1--------------------------CDR1-FR2-------------CDR2---------------FR3
EVQLVQSGGGLVQPGGSLRLSCAASGFTFSSYAMSWVRQAPGKGLEWVSGIGYSDTSTYYADSVKGRFT

---------------------------CDR3------FR4---------
VSRDISKNTLYLQMNSLRAEDTAVYYCAKGTRDYYGMDVWGQGTMVTVSS
```

NI-302.44D7 VL (variable light chain sequence VL) (SEQ ID NO: 48)

```
FR1---------------CDR1----------FR2-------------CDR2----FR3---------
QTVVTQEPSFSVSPGGTVTLTCGLSSGSVSTSYYPSWYQQTPGRAPRTLIYSTNTRSSGVPDRFSGSIL

------------------------CDR3------FR4--------
GNKAALTITGAQADDESDYYCVLFMGSGIGVFGGGTRLTVL
```

Fig. 1 (continued)

(M) NI-302.37C12 VH (variable heavy chain sequence VH) (SEQ ID NO: 50)

```
FR1----------------------------------CDR1-FR2-----------CDR2-----------FR3--
EVQLVESGGGLVQPGGSLRLSCVASALTVTNSQMTWVRRAPGRGLEWVSVIYTSGSAYYADSVKGRFTI

-------------------------------CDR3-------FR4---------
SRDNSKNTVFLQMNSLRVEDTAVYYCAKGPSAYYYGLDLWGQGTTVTVSS
```

NI-302.37C12 VK (variable light chain sequence VK) (SEQ ID NO: 52)

```
FR1-------------------CDR1------------FR2-----------CDR2---FR3-----
DIVMTQSPLSLPVTPGEPASISCRSSQSLLHSNGYNYLDWYLQKPGQSPQLLIYLGSTRASGVPDRFSG

-----------------------------CDR3-----FR4---------
SGSGTDFTLKISRVEAEDVGVYYCMQGLQTYTFGQGTKLEIK
```

(N) NI-302.55D8 VH (variable heavy chain sequence VH) (SEQ ID NO: 54)

```
FR1-----------------------------CDR1-FR2------------CDR2-----------------
QVQLVQSGSEVKKPGASVKVSCKASGYTFTDYYIHWVRQAPGQGLEWMGRINPNNGGTNYAQNFQGWVT

--FR3----------------------CDR3--------------FR4---------
MTRDTSISTAYMELSRLRSDDTAVYYCARVGGELLREGGYHYYMDVWGKGTTVTVSS
```

NI-302.55D8 VL (variable light chain sequence VL) (SEQ ID NO: 56)

```
FR1-----------------CDR1-----------FR2---------------CDR2----FR3---------
QSVLTQPPSVSGAPGQRVTISCTGNSSNIGAGYDVHWYQQLPGTAPKLLIFDNTNRPSGVPDRFSGSKS

---------------------------CDR3---------FR4--------
GTSASLAITGLQAEDEANYHCQSYDNSLSGSWVFGGGTKLTVL
```

(O) NI-302.7A8 VH (variable heavy chain sequence VH) (SEQ ID NO: 58)

```
FR1----------------------------CDR1-FR2-----------CDR2---------------FR3
EVQLVESGGGSVQPGGSLRLSCVASGFIFRNSWMTWVRQDPGKGLEWVANIKEDGSRTYYVDSVKGRFT

------------------------------CDR3----------FR4---------
ISRDNAKNSLYLQMNSLRAEDTAVYYCARGDYNSGIYYFPGDYWGQGTLVTVSS
```

NI-302.7A8 VK (variable light chain sequence VK) (SEQ ID NO: 60)

```
FR1-------------------CDR1-----------FR2------------CDR2---FR3-----
DVVMTQSPLSLPVTLGQPASISCRSSQSLVYSDGNTYLNWFQQRPGQSPRRLIYKVSNRDSGVPDRFSG

-----------------------------CDR3------FR4---------
SGSGTDFTLRISRVEAEDVGIYYCMQGTHWPGTFGQGTKVEIK
```

Fig. 1 (continued)

(P)        NI-302.78H12 VH (variable heavy chain sequence VH) (SEQ ID NO: 62)

```
FR1-----------------------------CDR1--FR2----------CDR2-------------FR3
QVQLQESGPGLVKPSETLSLTCLVSSYSISNGYYWGWIRQPPGKGLEWIGSIYHNGNTYYNPSLKSRVI

-----------------------------------CDR3--------------FR4--------
ISVDTSKNQFSLKLRSVTAADTAVYYCAMPSATYYGSGTQFHAFDVWGQGTTVTVSS
```

NI-302.78H12 VL (variable light chain sequence VL) (SEQ ID NO: 64)

```
FR1-------------------CDR1----------FR2------------CDR2----FR3---------
QSALTQPRSVSGSPGQSVTISCTGTSRDVGNYNYVSWYQQHPGEVPKLIIYDVSERPSGVPDRFSGSKS

------------------------CDR3--------FR4--------
GNTASLTISGLQAEDEADYYCCSYAGSYTFEVFGGGTKLTVL
```

(Q)        NI-302.71F6 VH (variable heavy chain sequence VH) (SEQ ID NO: 66)

```
FR1---------------------------------CDR1-FR2-----------CDR2-------------FR3-
QVQLQQWGAGLLKPSETLSLTCAVYGGSLSGYYWSWIRQPPGKGLEWIGEVNHSGGTNLNSSLKSRVII

--------------------------------CDR3--------FR4---------
SVDKSKKQFSLKLSSVTAADTAMYFCARGYSYDPKYYFDSWSQGTLVTVSS
```

NI-302.71F6 VL (variable light chain sequence VK) (SEQ ID NO: 68)

```
FR1---------------------CDR1----------FR2-------------CDR2---FR3---------
QSALTQPASVSGSPGQAITISCTGTSSDIGSYDFVSWYQQDPGKAPKVIIYGVNKRPSGVSNRFSGSKS

---------------------CDR3------FR4--------
GNTASLTISGLQADDEADYYCCSYAGSTTWVFGGGTKLTVL
```

(R)        NI-302.11H6 VH (variable heavy chain sequence VH) (SEQ ID NO: 70)

```
FR1----------------------------------CDR1-FR2-----------CDR2---------------FR3
EVQLVQSGAVMKKPGDSVRVSCRASTYSFSTYSFTWVRQVPGQGLEWMGWISAYNGHTNYVDSFQGRLT

---------------------------CDR3---------FR4---------
LTTDTSASTAYMELRSLRSDDTAIYYCAAVDTTYYYYGMDVWGQGTLVTVSS
```

NI-302.11H6 VL (variable light chain sequence VL) (SEQ ID NO: 72)

```
FR1--------------------CDR1----------FR2-------------CDR2---FR3---------
QTVVTQEPTFSVSPGGTVTLTCALRFGSVSSSYYPSWFQQTPGQAPRTLIYSTNTRSSGVPARFSGSIL

-----------------------CDR3-------FR4--------
GNKAALTIAGAQANDEADYYCVLYMGSGIGVFGGGTKLTVL
```

Fig. 1 (continued)

(S) NI-302.3D8 VH (variable heavy chain sequence VH) (SEQ ID NO: 74)

```
FR1------------------------------CDR1-FR2-----------CDR2------------FR3
EVQLVQSGGGLVQPGGSLRLSCEASGFIFKTYAMSWVRQLPGRGLEWVSAISATGGSTFYAESVKGRLT

-------------------------------CDR3------FR4--------
ISRDTAKNTVYLQMNNLRAEDTAMYYCAKGSTAVYLFDSWGQGTLVTVSS
```

NI-302.3D8 VK (variable light chain sequence VK) (SEQ ID NO: 76)

```
FR1---------------------CDR1-------FR2--------------CDR2---FR3----------
DIQMTQSPSSLSASVGDRVTLTCRASQDIRNFLAWIQQKPGKPPKSLIYAASTLQSGVPSRFSGSGSGT

----------------------CDR3------FR4--------
DFTLTISSLHPEDFATYYCQQFYNYPPTFGQGTKVEIK
```

(T) NI-302.18A1 VH (variable heavy chain sequence VH) (SEQ ID NO: 78)

```
FR1-----------------------------CDR1-FR2--------------CDR2------------FR
QLQLQESGPGLVKPSEALSLTCTVSGGSITTDYYYWGWIRQSPGKGLEWVGTIYFGGATYYNPSLRNRV

3----------------------------CDR3-------FR4----------
SISVDTSNTRLSLRLISLSAADTAVYYCARVGYLDRSGLLVGQGTLVTVSS
```

NI-302.18A1 VK (variable light chain sequence VK) (SEQ ID NO: 80)

```
FR1--------------------CDR1----------FR2-------------CDR2---FR3------
EIVLTQSPLSVPVTPGEPASISCRSSQSLLHNNGYNYLDWYLKKPGQSPQLLIYLGSTRASGVPDRFSA

------------------------CDR3------FR4--------
SGSGTDFTLEISRVEAEDVGVYYCMQALQTPPTFGRGTKVEIK
```

(U) NI-302.8F1 VH (variable heavy chain sequence VH) (SEQ ID NO: 82)

```
FR1------------------------------CDR1-FR2-----------CDR2---------------F
EVQLVESGGGLVKPGGSLTISCAASGFTFSNAWMNWVRQAPGKGLEWVGHIRTQAEGGTSDYAAPVKGR

R3--------------------------------CDR3---------FR4---------
FTISRDDSKNTLYLQMNSLKTEDTAVYYCIPPPYYYYGLDVWGQGTTVTVSS
```

NI-302.8F1 VL (variable light chain sequence VL) (SEQ ID NO: 84)

```
FR1----------------CDR1----------FR2--------------CDR2---FR3----------
QSALTQPASVSGSPGQSITISCTGASSDVGTYDLVSWYQQHPGKAPKLIIYEVNKRPSGVSYRFSASKS

----------------------CDR3------FR4--------
ANTASLTISGLQAEDEAEYYCCSYAGYSTVFGGGTKLTVL
```

Fig. 1 (continued)

(V)   NI-302.52C9 VH  (variable heavy chain sequence VH) (SEQ ID NO: 86)
```
FR1-------------------------CDR1-FR2----------CDR2------------FR3-
EVQLVQSGGGLVQPGGSLRLSCAGSGFTVSDTYMSWVRQAPGKGLEWVSGIHAGGETYYADSVKGRFTI -----------------------------CDR3------FR4---------
SRDNSKNTLYLQMNRLTPEDTAVFYCARHYYGNDDDTDYWGQGTLVTVSS
```

NI-302.52C9 VK  (variable light chain sequence VK) (SEQ ID NO: 88)
```
FR1-------------------CDR1----------FR2-----------CDR2---FR3-----
DVVMTQSPLSLPVTPGEPASISCRSSQSLLHSNGYNYLDWYVQKPGQSPQLLIYLGSTRASGVPDRFSG -----------------------CDR3-----FR4-------
SGSGTDFTLKISRVEAEDVGVYYCLQAQQIPWTFGQGTKVEIK
```

(W)   NI-302.46C9 VH (variable heavy chain sequence VH) (SEQ ID NO: 90)
```
FR1-----------------------CDR1-FR2------------CDR2-----------FR
QVQLQESGPGLVKPSQTLSLTCTVSGASVSSGAYYWSWIRQPAGKRLEWIGRVYPTWSTNYNPSLESRV 3----------------------------CDR3---------FR4--------
TISLDTSNNQFSLKLTSLTAADTAVYYCAREAPGDYDAAPLAYWGQGTLVTVSS
```

NI-302.46C9 VK (variable light chain sequence VK) (SEQ ID NO: 92)
```
FR1--------------------CDR1----------FR2-----------CDR2---FR3-----
DIQMTQSPSSLSASVGDRVTITCRASQYISHYLNWYRQKPGKAPQLVIYAASSLQSEVPSRFSGSGSGP ----------------------------CDR3-----FR4--------
EFTLTISSLQPEDFATYYCQQSYTTPRTFGQGTKLEIK
```

(X)   NI-302.64E5 VH (variable heavy chain sequence VH) (SEQ ID NO: 165)
```
FR1----------------------------CDR1-FR2----------CDR2--------------F
EVQLVETGGGLVKPGGSLRLSCAASGFTFDQAWMSWVRQVPGKGLEWVGRIKTKTEGEATDYAAPVRGR R3--------------------------CDR3---------FR4--------
FTISRDDSEDTVFLQMNSLKTEDTALYYCTSTGVLAAAVDVYWGQGTLVTVSS
```

NI-302.64E5 VK (variable light chain sequence VK) (SEQ ID NO: 169)
```
FR1-------------------CDR1-----------FR2--------------CDR2----FR3-----
DIQLTQSPDSLAVSLGERATMTCKSSQSLFYSYNNENYLAWYQQRPGQPPKLLIYWASTRESGVPDRFS -----------------------------CDR3------FR4--------
GSGSGTDFTLTISSLQAEDVAVYYCQQYYSTPQTFGQGTKVDIK
```

Fig. 1 (continued)

(Y)      NI-302.7D8 VH  (variable heavy chain sequence VH) (SEQ ID NO: 173)
```
FR1-----------------------------CDR1-FR2-----------CDR2-------------FR3
QVQLVQSGSELKKPGASVKVSCKASGYNFNNYAINWLRQAPGQGLEWMGWINTITGHPTYAQGFKGRFV --------------------------------CDR3------FR4---------
FSLDTSVSTAYLQISSLKPEDTAVYYCARTYSNYGEFDYWGQGTLVTVSS
```

NI-302.7D8 VL (variable light chain sequence VL) (SEQ ID NO: 175)
```
FR1--------------------CDR1----------FR2------------CDR2---FR3---------
QSALTQPASVSGSRGQSITISCTGTSSDVGSYNLVSWYQQYPGKAPKLIIHEGSERPSGVSNRFSGSKS -------------------------CDR3-------FR4--------
GNTASLTISGLQAEDEADYYCCSYAGTTTFVLFGGGTKLTVL
```

(Z)      NI-302.72F10 VH (variable heavy chain sequence VH) (SEQ ID NO: 177)
```
FR1-----------------------------CDR1-FR2-----------CDR2-------------FR3
EVQLVETGGGFVQPGGSLRLSCAASGFNFGSYAMSWVRQAPGKGLEWVSDISGIGSNTYYADSVKGRFT -----------------------------CDR3------FR4---------
ISRDNSDNTLYLDMSSLRAEDTARYYCAKDRKRSGWYEQWGQGTLVTVSS
```

NI-302. 72F10 (variable light chain sequence VK) (SEQ ID NO: 181)
```
FR1-------------------------CDR1-------FR2------------CDR2---FR3----------
EIVMTQSPATLTLSPGERATLSCRASQSISAYLGWYQQKPGQAPRLLIYDASIRATGIPDRFSGSGSGT ----------------------CDR3-----FR4--------
DFTLTISSLEPEDSAVYYCHQRSKWPLTFGGGTKVEIK
```

(AA)     NI-302.4A6 VH (variable heavy chain sequence VH) (SEQ ID NO: 185)
```
FR1-------------------------------CDR1-FR2-----------CDR2-------------FR3
EVQLVESGGGLVQPGGSLRLSCAASGFTFSAYAMSWVRQAPGKGLEWVSTISGSGGSTYYADSVKGRFS -------------------------CDR3--------------FR4---------
ISRDNSKNTLYLQMNSLRAEDTAVYFCAKVTTELYGANSYYYYMDVWGKGTTVTVSS
```

NI-302.4A6 VK (variable light chain sequence VK) (SEQ ID NO: 187)
```
FR1--------------------------CDR1----------FR2-------------CDR2---FR3---------
EIVLTQSPGTLSLSPGERATLSCRASQSVVSRYLAWYQQKPGQAPRLLIYGASSRATGIPDRFSGSGSG ---------------------------CDR3-----FR4--------
TDFTLTISRLEPEDFAMYYCQLYGNSQTFGQGTKVEIK
```

Fig. 1 (continued)

(AB)        NI-302.12H2 VH (variable heavy chain sequence VH) (SEQ ID NO: 189)

```
FR1-----------------------------CDR1-FR2-----------CDR2-------------FR3
EVQLVQSGGGLVQPGGSLRLSCEASGFTFSNYAMGWVRQAPGKGLEWVSVISGTGGSTYYADSVKGRFT

----------------------------------CDR3-------------FR4---------
ISRDNSMNTLYLQMNSPRADDTAVYYCAKDLRKISGPLYYYGMDVWGQGTTVTVSS
```

NI-302.12H2 VK (variable light chain sequence VK) (SEQ ID NO: 193)

```
FR1----------------------CDR1-------FR2------------CDR2---FR3---------
EIVLTQSPGTLSLSPGERATLSCRASQSVSSGYLAWYQQKPGQAPRLLIYGASTRATGIPDRFSGSGSG

-----------------------CDR3------FR4--------
TDFTLTISRLEPEDFAVYYCQHYGASSYTFGQGTKLEIK
```

(AC)        NI-302.8M1 VH (variable heavy chain sequence VH) (SEQ ID NO: 195)

```
FR1--------------------------------CDR1-FR2-----------CDR2--------------FR3
EVQLVQSGAEVKKPGASVKVSCKASGYTFTIYYMHWVRQAPGQGLEWMGGISPSGAHTMYAQNFQGRVT

-------------------------------CDR3---------FR4----------
VTRDTSTSTVYMELSSLRSEDTAVYYCARGSTVTNYRPFDYWGQGTLVTVSS
```

NI-302.8M1 VK (variable light chain sequence VK) (SEQ ID NO: 199)

```
FR1--------------------CDR1--------FR2-------------CDR2---FR3----------
DIQMTQSPSSLSASVGDRVTITCRASQDISNYLAWYQQKPGKVPKLLIFAASTLQSGVPSRFGGSGSGT

------------------------CDR3------FR4-------
DFTLTISSLQPEDVATYYCQNYNSGPPPFGPGTKVDIK
```

(AD)        NI-302.33C11-PIMC VH (variable heavy chain sequence VH) (SEQ ID NO: 98)

```
FR1--------------------------------CDR1-FR2-----------CDR2--------------FR3
QVQLVESGGGVVQPGNSLRLSCAASGFRFSDFGMHWVRQAPGKGLEWLALIWYDGGYKYYADSVKGRFT

----------------------------------CDR3----------FR4---------
ISRDNSKNTMFLQMNSLRAEDTAVYYCATHLEYCSRTTCYLGHWGQGTLVTVSS
```

NI-302.33C11-PIMC VK (variable light chain sequence VK) (SEQ ID NO: 100)

```
FR1--------------------CDR1--------FR2---------------CDR2----FR3-----------
DIQLTQSPSFLSASVGDTVTFTCRASQGISDYLAWFQQKPGIAPKLLIYAASTLQTGVPSRFSGSGSGT

-----------------------CDR3------FR4--------
EFTLTIRSLQSEDFGTYYCQQLKTYPYTFGQGTKLEIK
```

Fig. 1 (continued)

(AE) NI-307.63F3-PIMC VK (variable light chain sequence VK) (SEQ ID NO: 102)
```
FR1---------------------CDR1-------------FR2-----------CDR2---FR3----
DIVMTQSPDSLAVSLGERATINCKSNQSLFYSSNNNNYLAWYQHKSGQPPKLLVYWGSTRESGVPDRFS --------------------------------CDR3-----FR4--------
GSGSGTDFTLTISSLQAEDVAIYYCHQYYHNPYTFGQGTKLEIK
```

NI-307.63F3-PIMC-NS VK (variable light chain sequence VK) (SEQ ID NO: 104)
```
FR1---------------------CDR1-------------FR2-----------CDR2---FR3----
DIVMTQSPDSLAVSLGERATINCKSSQSLFYSSNNNNYLAWYQHKSGQPPKLLVYWGSTRESGVPDRFS --------------------------------CDR3-----FR4--------
GSGSGTDFTLTISSLQAEDVAIYYCHQYYHNPYTFGQGTKLEIK
```

NI-307.63F3-PIMC-SG VK (variable light chain sequence VK) (SEQ ID NO: 106)
```
FR1---------------------CDR1-------------FR2-----------CDR2---FR3----
DIVMTQSPDSLAVSLGERATINCKSNQGLFYSSNNNNYLAWYQHKSGQPPKLLVYWGSTRESGVPDRFS --------------------------------CDR3-----FR4--------
GSGSGTDFTLTISSLQAEDVAIYYCHQYYHNPYTFGQGTKLEIK
```

NI-307.63F3-PIMC-NQ VK (variable light chain sequence VK) (SEQ ID NO: 108)
```
FR1---------------------CDR1-------------FR2-----------CDR2---FR3----
DIVMTQSPDSLAVSLGERATINCKSQQSLFYSSNNNNYLAWYQHKSGQPPKLLVYWGSTRESGVPDRFS --------------------------------CDR3-----FR4--------
GSGSGTDFTLTISSLQAEDVAIYYCHQYYHNPYTFGQGTKLEIK
```

(AF) NI-302.35C1-PIMC VK (variable light chain sequence VK) (SEQ ID NO: 110)
```
FR1---------------------CDR1------FR2-----------CDR2---FR3----------
EIVLTQSPATLSLPGERATLSCRASQSVDNQFAWYQQKPGQAPRLLIYDASRRAPGIPDRFSGSGSGT

----------------CDR3------FR4--------
DFTLTISSLEPEDFAIYYCQHRYTWLYTFGQGTKLEIK
```

Fig. 1 (continued)

(AG)     NI-302.31F11-PIMC VK (variable light chain sequence VK) (SEQ ID NO: 112)

```
FR1-------------------CDR1-----------FR2-----------CDR2---FR3-----
DIVMTQSPLSLPVAPGEPASISCRSSQSLLYSNGYNYLDWYLQKPGKPPQLLVYLGSDRASGVPDRFSG

-------------------------CDR3------FR4--------
SGSGKDFTLNISRVEAEDVGVYYCMQGLQSPWTFGQGTKVEIK
```

(AH)     NI-302.2A2-PIMC VK (variable light chain sequence VK) (SEQ ID NO: 114)

```
FR1-------------------CDR1----------------FR2-------------CDR2---FR3-
DIVMTQSPDSLAVSLGERATINCKSSQSLLYTSKNKDSKNYLGWYQQKPGQPPKLLIYWASTRESGVPD

-----------------------------CDR3----FR4--------
RFSGSGSGTDFTLTISSLQAEDVAVYYCQQYYTTPQFGGGTKVEIK
```

(AJ)     NI-302.74C11-PIMC VH  (variable heavy chain sequence VH) (SEQ ID NO: 116)

```
FR1-----------------------------CDR1-FR2-----------CDR2----------FR3----
QVQLVQSGTEVQKPGASVKVSCKASGYSFTGYFLHWVRQAPGQGLEWMGWINPNSGDTNYAEKFRGRII

-------------------------------CDR3--------FR4---------
MTRDTSVSTAHMELSSLRFDDTALYYCTREAPDPGAETDVWGQGTTVTVSS
```

NI-302.74C11-PIMC VL (variable light chain sequence VL) (SEQ ID NO: 118)

```
FR1---------------------CDR1-------FR2-------------CDR2---FR3-------------
SYELTQPPSVSVSPGQTARITCSGDAVPKQYIYWYQQKPGQAPILVIYKDTQRPSGIPERFSGSNSGTT

---------------CDR3------FR4--------
VTLTITGVQADDEGDYYCQSADSSATWVFGGGTKLTVL
```

(AK)     NI-302.39G12-PIMC VH (variable heavy chain sequence VH) (SEQ ID NO: 120)

```
FR1-------------------------CDR1-FR2-----------CDR2------------FR3-
EVQLVESGGGLVHPWGSLRLSCAASGFSVSNYAITWVRRAPGKGLQYISVIYRDGRTYYGDSVRGRFTI

--------------------------CDR3--------FR4---------
SRDDSKNTLYLQMNSLRFEDTAVYYCARAHGQYYYGVDVWGQGTTVTVSS
```

Fig. 1 (continued)

NI-302.39G12-PIMC VK (variable light chain sequence VK) (SEQ ID NO: 122)

```
FR1----------------------CDR1----------FR2------------CDR2---FR3-----
DIVMTQSPLSLSVSPGEPASISCRSSQSLLHSNGYNYLDWYRQKPGQSPQLLIYLSSNRPSGVPDRFSA

---------------------------CDR3-----FR4--------
SGSGTEFTLQISRVEAEDVGVYYCMQSLQTFTFGGGTKVEIK
```

(AL) NI-302.11A4-PIMC VK (variable light chain sequence VK) (SEQ ID NO: 124)

```
FR1----------------------CDR1--------FR2------------CDR2---FR3---------
EIVLTQSPGTLSLSPGERATLSCRASQSVSSSYFAWYQQKPGQAPRLLIYGTSRRATAIPDRFSGSGSG

-----------------------CDR3-----FR4--------
TDFTLTISRLEPEDFAVYYCQQYGSSWTFGPGTKVEIK
```

(AM) NI-302.22H9-PIMC VK (variable light chain sequence VK) (SEQ ID NO: 126)

```
FR1----------------------CDR1------------FR2-------------CDR2---FR3-----
DIVMTQSPLSLSVSPGEPASISCRSSQSLLHSNGYNYLDWYRQKPGQSPQLLIYLNSNRASGVPDRFSG

---------------------------CDR3----FR4--------
SGSGTEFTLTISRVEAEDVGVYYCMQSLQTFTFGGGTKVEIK
```

(AN) NI-302.44D7-PIMC VH (variable heavy chain sequence VH) (SEQ ID NO: 128)

```
FR1-------------------------------CDR1-FR2-----------CDR2--------------FR3
EVQLVESGGGLVQPGGSLRLSCAASGFTFSSYAMSWVRQAPGKGLEWVSGIGYSDTSTYYADSVKGRFT

--------------------------------CDR3-------FR4--------
VSRDISKNTLYLQMNSLRAEDTAVYYCAKGTRDYYGMDVWGQGTTVTVSS
```

(AO) NI-302.78H12-PIMC VH (variable heavy chain sequence VH) (SEQ ID NO: 130)

```
FR1-------------------------CDR1--FR2-----------CDR2------------FR3
QLQLQESGPGLVKPSETLSLTCLVSSYSISNGYYWGWIRQPPGKGLEWIGSIYHNGNTYYNPSLKSRVI

----------------------------CDR3---------------FR4--------
ISVDTSKNQFSLKLRSVTAADTAVYYCAMPSATYYYGSGTQFHAFDVWGQGTMVTVSS
```

Fig. 1 (continued)

(AP)  NI-302.15E8 VH  (variable heavy chain sequence VH) (SEQ ID NO: 132)
```
FR1-------------------------------CDR1-FR2----------CDR2--------------FR
EVQLVESGGGLIQPGGSLRLSCAVSGFTVSSYSMNWVRQAPGKGLEWVSYTSSSRSNTKKYADSVKGRF 3-----------------------------CDR3-------------FR4---------
TISRDNARNSLYLQMNSLRDEDTAVYYCARAGDFGELLTGEGYYGMDVWGQGTTVTVSS
```

NI-302.15E8 VL (variable light chain sequence VL) (SEQ ID NO: 134)
```
FR1--------------------CDR1------FR2------------CDR2---FR3------------
SYELTQPPSVSVSPGQTATITCSGDELGDKYVGWYQQKPGQSPLLVIYQDAKRPSGIPERFSGSNSGNT -----------------------CDR3------FR4--------
ATLTISGTQAMDEADYYCQAWDSGTMVFGGGTRLTVL
```

(AQ)  NI-302.15D3 VH  (variable heavy chain sequence VH) (SEQ ID NO: 136)
```
FR1-------------------------------CDR1-FR2----------CDR2-------------FR3
EVQLVESGGDLVQPGGSLRLSCAASGFTFSSYWMHWVRQAPGKGLVWVSRISNDGSSKTYADSVKGRFT -----------------------------CDR3-----------FR4---------
ISRDNAKNTLYLQMNSLRAEDTAVYYCAILGGYCSSTSCRPFDNWGQGTLVTVSS
```

(AR)  NI-302.15D3 VL (variable light chain sequence VL) (SEQ ID NO: 138)
```
FR1----------------------CDR1-----------FR2-----------------CDR2---FR3----------
QSALTQPASVSGSPGQSITISCTGTSSDVGVYNYVSWYQQHPGKAPKLMIFDVSNRPSGISNRFSGSKS -----------------------CDR3-----FR4--------
GNTASLTISGLQAEDEADYYCSSYTSSDTWVFGGGTKLTIL
```

(AS)  NI-302.64E5-PIMC VH (variable heavy chain sequence VH) (SEQ ID NO: 167)
```
FR1-------------------------------CDR1-FR2-----------CDR2----------------F
EVQLVESGGGLVKPGGSLRLSCAASGFTFDQAWMSWVRQVPGKGLEWVGRIKTKTEGEATDYAAPVRGR R3-------------------------------CDR3--------FR4---------
FTISRDDSEDTVFLQMNSLKTEDTALYYCTSTGVLAAAVDVYWGQGTLVTVSS
```

Fig. 1 (continued)

NI-302.64E5-PIMC VK (variable light chain sequence VK) (SEQ ID NO: 171)
```
FR1-----------------------CDR1--------------FR2-----------CDR2----FR3----
DIVMTQSPDSLAVSLGERATMTCKSSQSLFYSYNNENYLAWYQQRPGQPPKLLIYWASTRESGVPDRFS -------------------------CDR3-----FR4--------
GSGSGTDFTLTISSLQAEDVAVYYCQQYYSTPQTFGQGTKVEIK
```

(AT)  NI-302.72F10-PIMC VH (variable heavy chain sequence VH) (SEQ ID NO: 179)
```
FR1---------------------------CDR1-FR2----------CDR2-------------FR3
EVQLVESGGGFVQPGGSLRLSCAASGFNFGSYAMSWVRQAPGKGLEWVSDISGIGSNTYYADSVKGRFT ----------------------------CDR3-------FR4---------
ISRDNSDNTLYLDMSSLRAEDTARYYCAKDRKRSGWYEQWGQGTLVTVSS
```

NI-302.72F10-PIMC VK (variable light chain sequence VK) (SEQ ID NO: 183)
```
FR1--------------------CDR1-------FR2------------CDR2----FR3-----------
EIVLTQSPATLTLSPGERATLSCRASQSISAYLGWYQQKPGQAPRLLIYDASIRATGIPDRFSGSGSGT -------------------CDR3------FR4--------
DFTLTISSLEPEDSAVYYCHQRSKWPLTFGGGTKVEIK
```

(AU)  NI-302.12H2-PIMC VH (variable heavy chain sequence VH) (SEQ ID NO: 191)
```
FR1---------------------------CDR1-FR2-----------CDR2-------------FR3
EVQLVESGGGLVQPGGSLRLSCEASGFTFSNYAMGWVRQAPGKGLEWVSVISGTGGSTYYADSVKGRFT ---------------------------CDR3------------FR4---------
ISRDNSMNTLYLQMNSPRADDTAVYYCAKDLRKISGPLYYYGMDVWGQGTTVTVSS
```

NI-302.8M1-PIMC VH (variable heavy chain sequence VH) (SEQ ID NO: 197)
```
FR1---------------------------CDR1-FR2-----------CDR2-------------FR3
QVQLVQSGAEVKKPGASVKVSCKASGYTFTIYYMHWVRQAPGQGLEWMGGISPSGAHTMYAQNFQGRVT ---------------------------CDR3---------FR4--------
VTRDTSTSTVYMELSSLRSEDTAVYYCARGSTVTNYRPFDYWGQGTLVTVSS
```

Fig. 1 (continued)

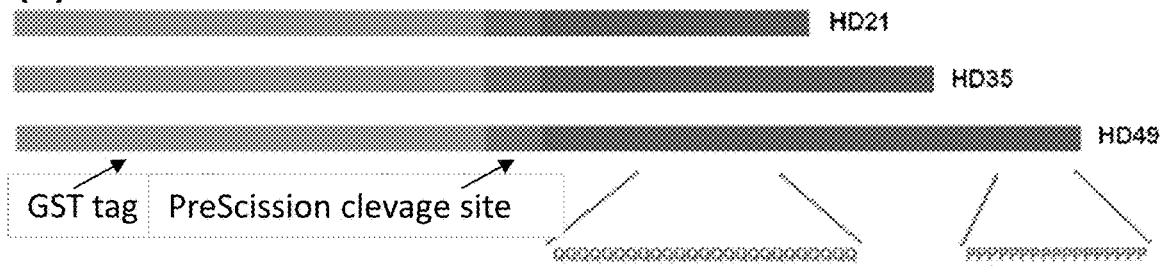
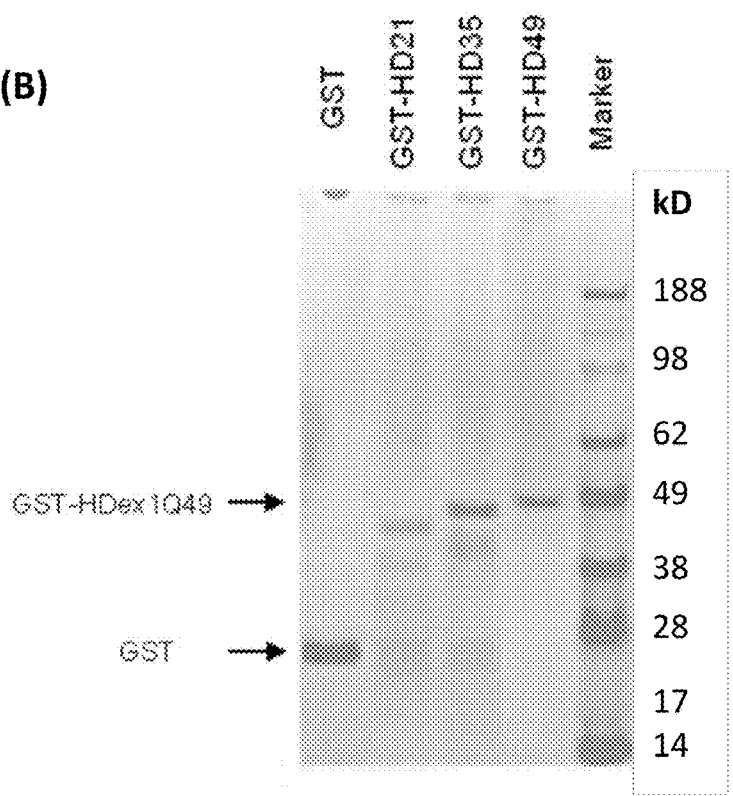
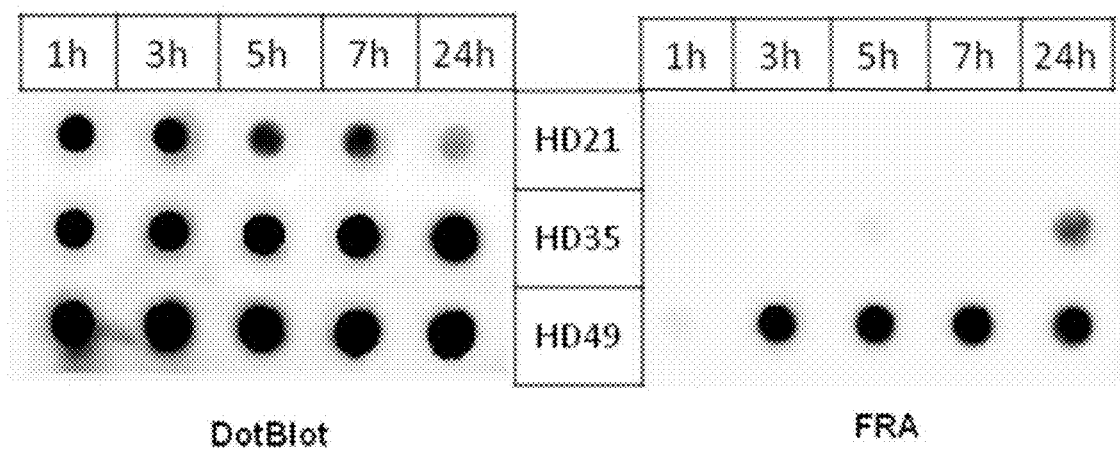
Fig. 2

33C11 1µg/ml
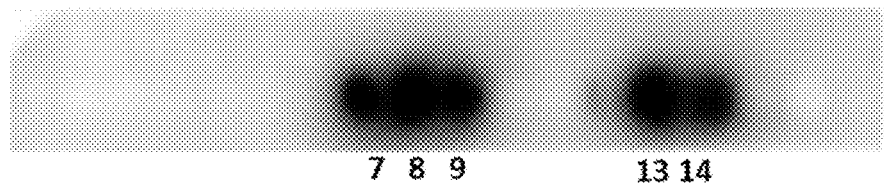
7 8 9    13 14
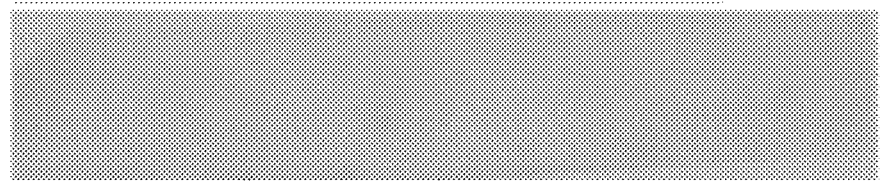
```
       28      30                35                40   42              47        50    52
7    Q  Q  Q  Q  Q  Q  Q  P  P  P  P  P  P  P  P                            (SEQ ID NO: 203)
8                   Q  Q  P  P  P  P  P  P  P  P  P  P  Q  L               (SEQ ID NO: 204)
9              (SEQ ID NO: 205)  P  P  P  P  P  P  P  P  Q  L  P  Q  P  P  P
consesus:                        P  P  P  P  P  P  P  P                    (SEQ ID NO: 139)
       58      60      63        67       70   72        75    77
13   L  P  Q  P  Q  P  P  P  P  P  P  P  P  P                              (SEQ ID NO: 206)
14               P  P  P  P  P  P  P  P  P  P  G  P  A  V  A               (SEQ ID NO: 207)
consensus:       P  P  P  P  P  P  P  P  P                                 (SEQ ID NO: 208)
```
Fig. 4

63F3 1ug/ml (21 Spot membrane)
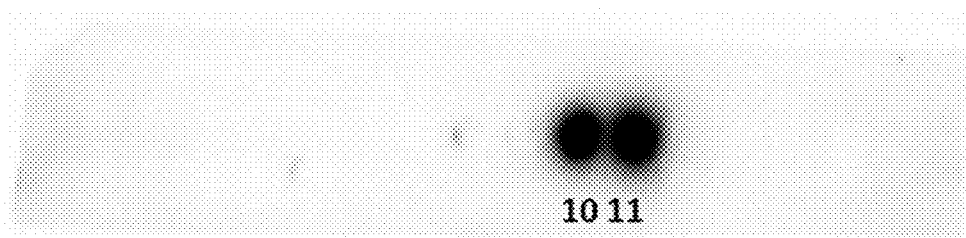
2nd AB only goat anti human (H+L)
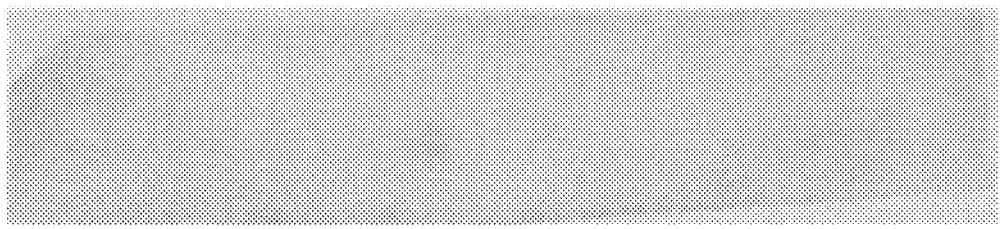
```
              43        47     50  52      55   57       60    62
10            P  P  P   Q  L   P   Q  P  P  P   Q  A  Q  P  L  (SEQ ID NO: 209)
11  (SEQ ID NO: 210)    P  Q   P   P  P  Q  A   Q  P  L  L  P  Q  P  Q
consensus:                     P   Q  P  P  P   Q  A  Q  P  L  (SEQ ID NOs: 140)
```
Fig. 8

(A)

● NI-302.31F11 (P-rich Ab)
■ NI-302.35C1 (C-term Ab)

(B)
Plasma levels

| antibody | Mice | | | Mean | SD | CV |
|---|---|---|---|---|---|---|
| | µg/ml | | | µg/ml | µg/ml | % |
| 31F11 | 265 | 476 | 440 | 394 | 113 | 29 |
| 35C1 | 442 | 431 | 371 | 414 | 38 | 9 |

Brain levels

| antibody | Mice | | | Mean | SD | CV |
|---|---|---|---|---|---|---|
| | ng/g | | | µg/ml | µg/ml | % |
| 31F11 | 391 | 504 | 608 | 501 | 109 | 22 |
| 35C1 | 1222 | 676 | 687 | 861 | 312 | 36 |

Brain-plasma penetration ratio [%]

| antibody | Mice | | | Mean | SD | CV |
|---|---|---|---|---|---|---|
| | µg/ml | | | µg/ml | µg/ml | % |
| 31F11 | 0.15 | 0.11 | 0.14 | 0.13 | 0.02 | 17 |
| 35C1 | 0.28 | 0.16 | 0.19 | 0.21 | 0.06 | 30 |

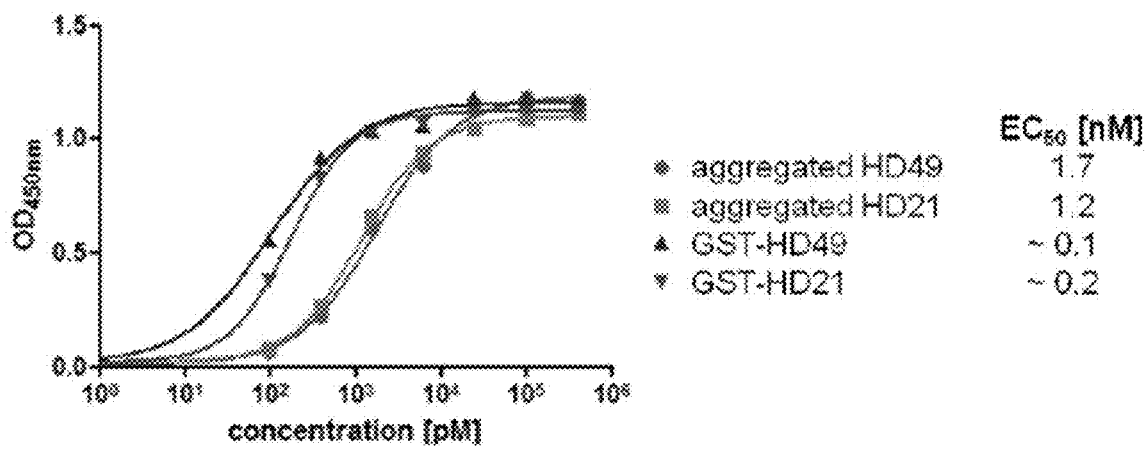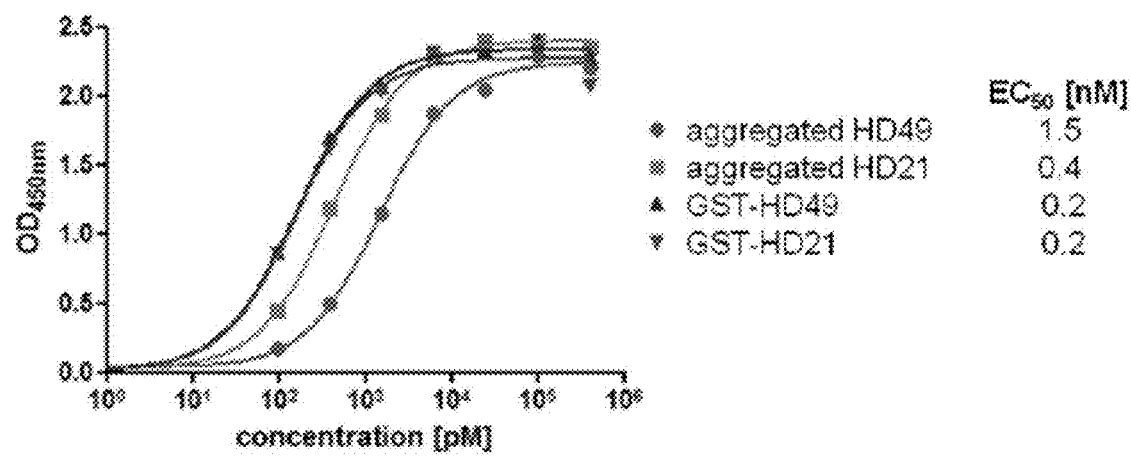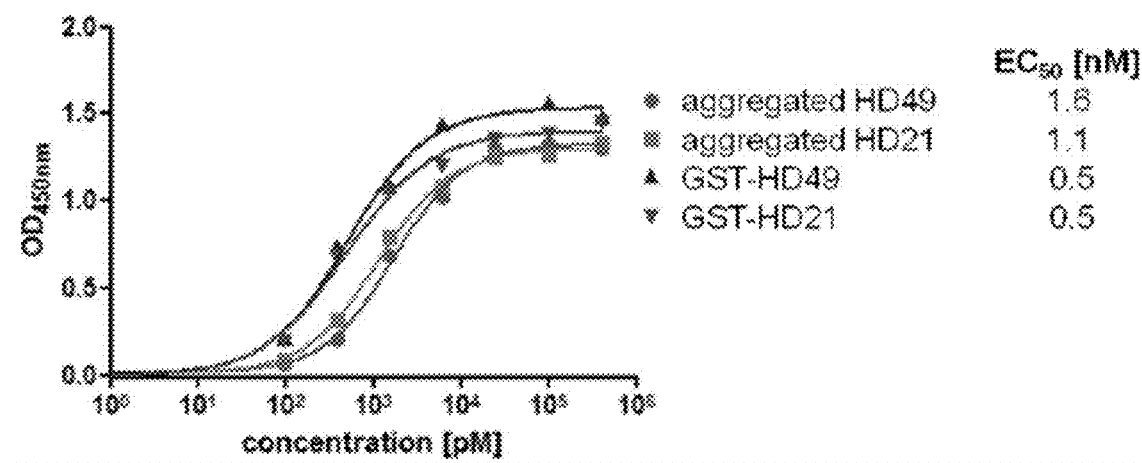
Fig. 19 (continued)

| Antibody | aggr HD49 EC50 [nM] | aggr HD21 EC50 [nM] | GST-HD49 EC50 [nM] | GST-HD21 EC50 [nM] | peptide EC50 [nM] | epitope | SEQ ID NO: |
|---|---|---|---|---|---|---|---|
| NI-302.33C11 | 0.15 | 0.13 | 0.13 | 0.11 | 0.1 (polyP) | PPPPPPPP | 139 |
| NI-302.63F3 | 0.4 | 0.3 | 0.2 | 0.2 | 0.3 (P-rich) | PQPPPQAQPL (P-rich) | 140 |
| NI-302.31F11 | 0.6 | 4.3 | 0.5 | 0.9 | 0.5 (P-rich) | PPPQLPQPPP (P-rich) | 141 |
| NI-302.2A2 | >100 | 12.3 | >100 | 10.1 | 1.4 (P-rich) | QAQPLLPQPQPPPPP (P-rich) | 142 |
| NI-302.15D3 | 15 | 6.4 | 4.0 | 4.2 | 1.2 (P-rich) | PPPQLPQPPPQAQPL (P-rich) | 143 |
| NI-302.35C1 | 2.7 | 7.9 | 5.1 | 4.6 | 0.7 (endEx1) | PPGPAVAEEPLHRP (endEx1) | 145 |
| NI302.15E8 | >100 | >100 | 15 | 9.3 | 0.1 (N-term) | KAFESLKSFQQ (N-term) | 144 |
| NI-302.64E5 | 1.6 | 0.7 | 0.05 | 1.4 | 0.1 (P-rich) | PQPPPQAQPL (P-rich) | 200 |
| NI-302.7D8 | 17 | >100 | 6 | 51 | n.d. (Q/P) | QQQQQQQPPP (polyQ/P) | 201 |
| NI-302.72F10 | 26 | 4 | >100 | 10 | 0.1 (endEx1) | PPPGPAVAEEPLH (endEx1) | 202 |
| NI-302.4A6 | 3 | 3 | 6 | 3 | neg. | no signal on linear peptide | |
| NI-302.12H2 | 0.04 | 0.05 | 0.04 | 0.04 | neg. | no signal on linear peptide | |
| NI-302.8M1 | 0.003 | 0.002 | 0.003 | 0.002 | neg. | no signal on linear peptide | |
| NI-302.6N9 | 0.19 | 0.21 | 0.15 | 0.24 | neg. | no signal on linear peptide | |
| NI-302.74C11 | 0.5 | 0.5 | 0.5 | 0.5 | n.d. | PPPPPPPPPP | 146 |
| NI-302.15F9 | 6 | 35 | 5 | 11 | n.d. | PPPPPPPPPPP | 147 |

Fig. 20

| Antibody | aggr HD49 EC50 [nM] | aggr HD21 EC50 [nM] | GST-HD49 EC50 [nM] | GST-HD21 EC50 [nM] | peptide EC50 [nM] | epitope | SEQ ID NO: |
|---|---|---|---|---|---|---|---|
| NI-302.39G12 | 28 | 15 | 3.8 | 3.4 | n.d. | pppppppppp | 148 |
| NI-302.11A4 | 19 | 18 | 0.8 | 1.4 | n.d. | pppppppppp | 149 |
| NI-302.22H9 | 22 | 11 | 1.4 | 1.6 | n.d. | pppppppppp | 150 |
| NI-302.44D7 | 10 | 11 | 1.2 | 5.4 | n.d. | pppppppp | 151 |
| NI-302.37C12 | 4.9 | 2.5 | 0.23 | 0.33 | n.d. | pppppppppp | 152 |
| NI-302.55D8 | 1.7 | 1.2 | 0.1 | 0.2 | n.d. | pppppppppp | 153 |
| NI-302.7A8 | 1.5 | 0.4 | 0.2 | 0.2 | n.d. | pppppppp | 154 |
| NI-302.78H12 | 1.6 | 1.1 | 0.5 | 0.5 | n.d. | pppppppppp | 155 |
| NI-302.71F6 | 4.4 | 7.6 | 3.2 | 3.0 | n.d. | pppppppppp | 156 |
| NI-302.11H6 | 0.2 | 1.2 | 0.1 | 0.2 | n.d. | pppppp | 157 |
| NI-302.3D8 | 0.03 | 0.02 | 0.3 | 0.05 | n.d. | pppppppp | 158 |
| NI-302.18A1 | 0.03 | 0.02 | 0.07 | 0.04 | n.d. | pppppp | 159 |
| NI-302.8F1 | 1.9 | 1.6 | 0.4 | 0.8 | n.d. | polyP | 160 |
| NI-302.52C9 | 30 | 28 | 4.9 | 10.2 | n.d. | pppppp | 161 |
| NI-302.46C9 | 0.05 | 0.3 | 0.05 | 0.07 | n.d. | pppppppp | |

Fig. 20 (continued)

(A)
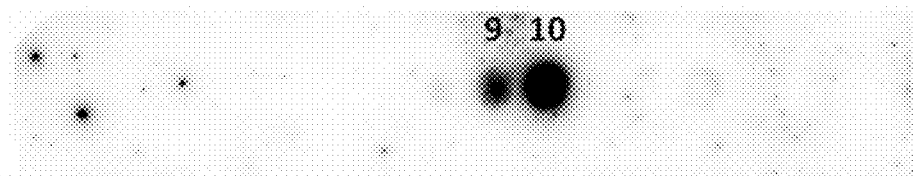
|   |   | 38 | 40 |   |   |   |   |   |   | 50 | 52 |   | 55 | 57 |   |   |
|---|---|----|----|---|---|---|---|---|---|----|----|---|----|----|---|---|
| 9 |   | P  | P  | P | P | P | P | P | Q | L  | P  | Q | P  | P  | P | SEQ ID NO: 205 ++ |
| 10 | SEQ ID NO: 209 | P | P | P | Q | L | P | Q | P | P | P | Q | A | Q | P | L  SEQ ID NO: ++ |
| consesus: |   |   |   |   | P | P | P | Q | L | P | Q | P | P | P |   | SEQ ID NO: 141 |
(B)
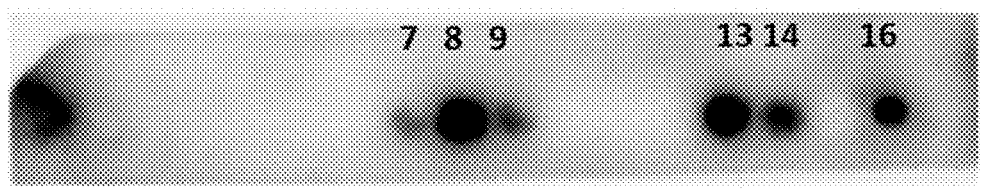
|   |   | 28 | 30 |   |   | 35 |   |   |   | 40 | 42 |   |   |   | 47 |   | 50 | 52 |   |
|---|---|----|----|---|---|----|---|---|---|----|----|---|---|---|----|---|----|----|---|
| 7 | Q | Q  | Q  | Q | Q | Q  | P | P | P | P  | P  | P | P | SEQ ID NO: 207 |
| 8 |   |    | Q  | Q | P | P  | P | P | P | P  | P  | P | P | Q | L  | SEQ ID NO: 204 |
| 9 |   |    |    | SEQ ID NO: 205 | P | P | P | P | P | P | P | P | Q | L | P | Q | P | P |
| consesus: |   |   |   |   |   |    | P | P | P | P  | P  | P | P | P | SEQ ID NO: 214 |
|   |   | 58 | 60 |   |   | 63 |   |   | 67 |   |   | 70 |   | 72 |   | 75 | 77 |   |
|---|---|----|----|---|---|----|---|---|----|---|---|----|---|----|---|----|----|---|
| 13 | L | P | Q | P | Q | P | P | P | P | P | P | P | P | P | SEQ ID NO: 206 |
| 14 |   |   |   |   |   | P | P | P | P | P | P | P | P | P | G | A | V | A | SEQ ID NO: 207 |
| consensus: |   |   |   |   |   | P | P | P | P | P | P | P | P | P | SEQ ID NO: 208 |
|   |   | 70 |   | 75 |   |   | 80 |   |   | 84 |   |   |
|---|---|----|---|----|---|---|----|---|---|----|---|---|
| 16 | P | P | P | G | P | A | V | A | E | E | P | L | H | R | P | SEQ ID NO: 215 |
Fig. 23

(C) NI-302.15F9 1μg/ml (16 Spot membrane)

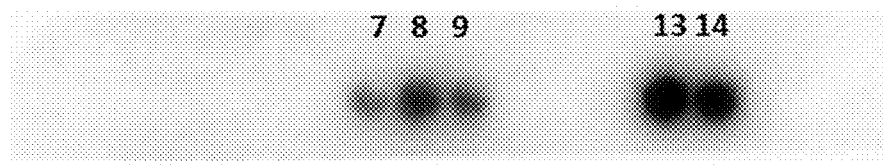

```
     28    30           35            40   42           47      50    52
7   Q Q Q Q Q Q  P  P  P  P  P  P  P  P  SEQ ID NO: 203
8            Q Q  P  P  P  P  P  P  P  P  P  P  Q  L SEQ ID NO: 204
9        SEQ ID NO: 205  P  P  P  P  P  P  P  P  Q  L  P  Q  P  P  P
consesus:         P  P  P  P  P  P  P  P  P  P  P  SEQ ID NO: 147

58    60     63        67     70   72       75   77
13  L  P  Q  P  Q  P  P  P  P  P  P  P  P  P  SEQ ID NO: 206
14              P  P  P  P  P  P  P  P  P  G  P  A  V  A SEQ ID NO: 207
consensus:      P  P  P  P  P  P  P  P  P  P  SEQ ID NO: 208
```

(D) NI-302.39G12 1μgml (16 Spot membrane)

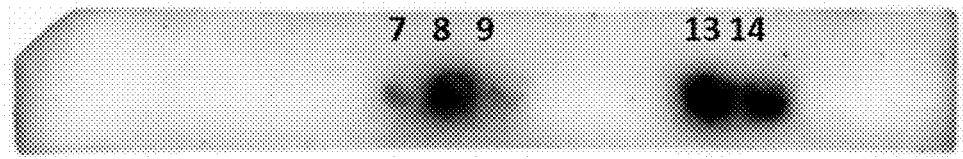

```
     28    30           35            40   42           47      50    52
7   Q Q Q Q Q Q  P  P  P  P  P  P  P  P  SEQ ID NO: 203
8            Q Q  P  P  P  P  P  P  P  P  P  P  Q  L SEQ ID NO: 204
9        SEQ ID NO: 205  P  P  P  P  P  P  P  P  Q  L  P  Q  P  P  P
consesus:         P  P  P  P  P  P  P  P  P  P  P  SEQ ID NO: 148

58    60     63        67     70   72       75   77
13  L  P  Q  P  Q  P  P  P  P  P  P  P  P  P  SEQ ID NO: 206
14              P  P  P  P  P  P  P  P  P  G  P  A  V  A SEQ ID NO: 207
consensus:      P  P  P  P  P  P  P  P  P  P  SEQ ID NO: 208
```

Fig. 23 (continued)

(E) NI-302.11A4 1µg/ml (16 Spot membrane)

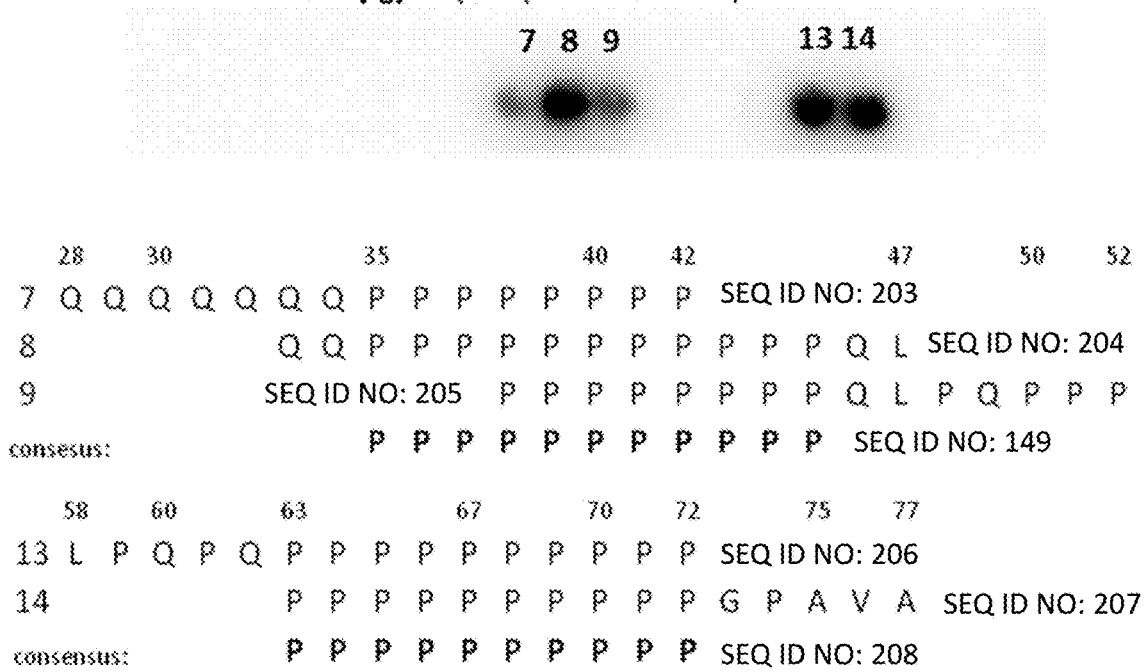

```
        28      30          35              40      42              47          50      52
7    Q  Q  Q   Q  Q  Q  Q   P   P   P   P   P   P   P   P   SEQ ID NO: 203
8                   Q   Q   P   P   P   P   P   P   P   P   P   P   Q   L   SEQ ID NO: 204
9                       SEQ ID NO: 205   P   P   P   P   P   P   P   P   Q   L   P   Q   P   P   P
consesus:                        P   P   P   P   P   P   P   P   P   P   P   SEQ ID NO: 149

58      60      63          67          70      72          75      77
13   L  P  Q   P  Q  P  P  P  P  P  P  P  P  P  SEQ ID NO: 206
14                   P  P  P  P  P  P  P  P  P  G  P  A  V  A  SEQ ID NO: 207
consensus:           P  P  P  P  P  P  P  P  P  SEQ ID NO: 208
```

(F) NI-302.22H9 1µg/ml (16 Spot membrane)

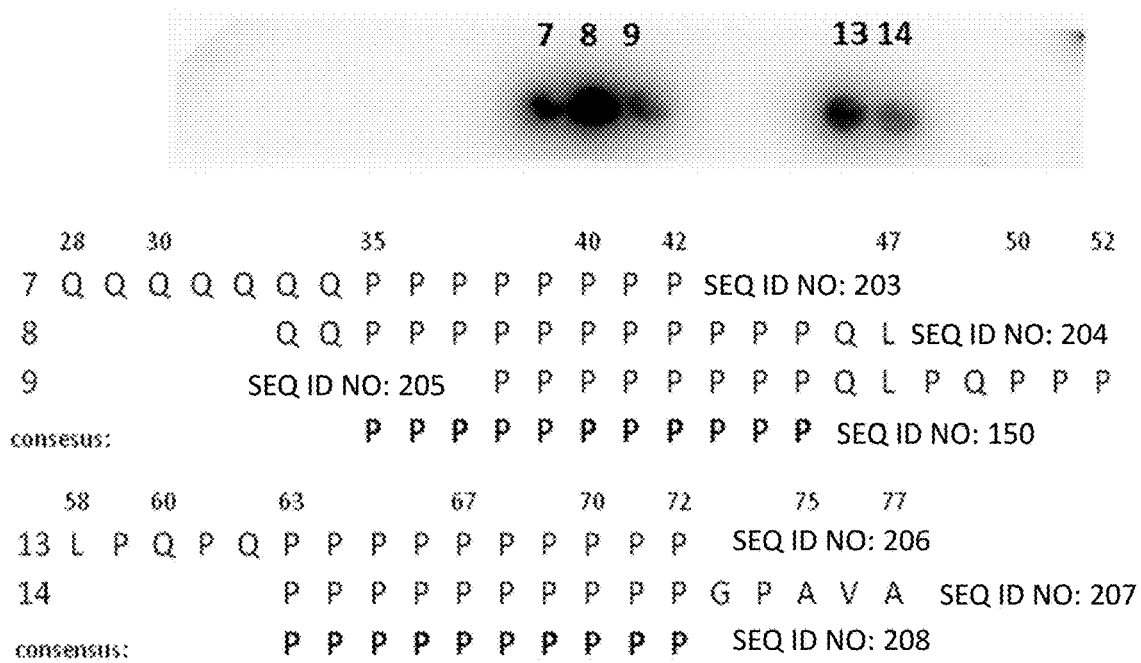

```
        28      30          35              40      42              47          50      52
7    Q  Q  Q   Q  Q  Q  Q   P   P   P   P   P   P   P   P   SEQ ID NO: 203
8                   Q   Q   P   P   P   P   P   P   P   P   P   P   Q   L   SEQ ID NO: 204
9                       SEQ ID NO: 205   P   P   P   P   P   P   P   P   Q   L   P   Q   P   P   P
consesus:                        P   P   P   P   P   P   P   P   P   P   P   SEQ ID NO: 150

58      60      63          67          70      72          75      77
13   L  P  Q   P  Q  P  P  P  P  P  P  P  P  P  SEQ ID NO: 206
14                   P  P  P  P  P  P  P  P  P  G  P  A  V  A  SEQ ID NO: 207
consensus:           P  P  P  P  P  P  P  P  P  SEQ ID NO: 208
```

Fig. 23 (continued)

(G) NI-302.44D7 1μg/ml (16 Spot membrane)

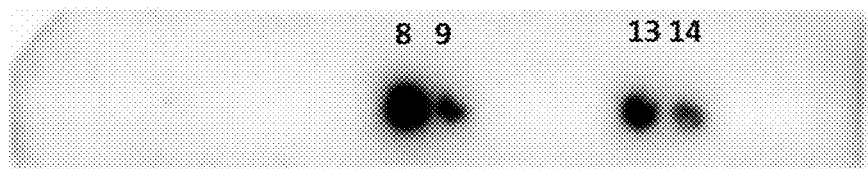

|  | 33 | 35 |  |  | 40 | 42 |  |  |  | 47 |  | 50 | 52 |  |
|---|---|---|---|---|---|---|---|---|---|---|---|---|---|---|
| 8 | Q | Q | P | P | P | P | P | P | P | P | P | P | Q | L | SEQ ID NO: 204 |
| 9 |  | SEQ ID NO: 205 | P | P | P | P | P | P | P | P | Q | L | P | Q | P P P |
| consensus: |  |  | P | P | P | P | P | P | P | P | Q | L |  |  | SEQ ID NO: 216 |

|  | 58 |  | 60 |  | 63 |  |  | 67 |  | 70 |  | 72 |  | 75 |  | 77 |  |
|---|---|---|---|---|---|---|---|---|---|---|---|---|---|---|---|---|---|
| 13 | L | P | Q | P | Q | P | P | P | P | P | P | P | P | P |  |  | SEQ ID NO: 206 |
| 14 |  |  |  |  |  | P | P | P | P | P | P | P | P | P | G | P | A V A SEQ ID NO: 207 |
| consensus: |  |  |  |  |  | P | P | P | P | P | P | P | P | P |  |  | SEQ ID NO: 208 |

(H) NI-302.37C12 1μg/ml (16 Spot membrane)

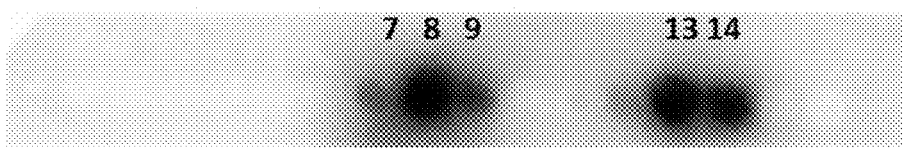

|  | 28 |  | 30 |  |  | 35 |  |  |  | 40 |  | 42 |  |  | 47 |  | 50 | 52 |
|---|---|---|---|---|---|---|---|---|---|---|---|---|---|---|---|---|---|---|
| 7 | Q | Q | Q | Q | Q | Q | P | P | P | P | P | P | P | P | SEQ ID NO: 203 |
| 8 |  |  |  |  | Q | Q | P | P | P | P | P | P | P | P | P | P | Q | L | SEQ ID NO: 204 |
| 9 |  |  |  |  |  | SEQ ID NO: 205 | P | P | P | P | P | P | P | P | Q | L | P | Q | P P P |
| consensus: |  |  |  |  |  |  | P | P | P | P | P | P | P | P | P | P |  |  | SEQ ID NO: 152 |

|  | 58 |  | 60 |  | 63 |  |  | 67 |  | 70 |  | 72 |  | 75 |  | 77 |  |
|---|---|---|---|---|---|---|---|---|---|---|---|---|---|---|---|---|---|
| 13 | L | P | Q | P | Q | P | P | P | P | P | P | P | P | P |  |  | SEQ ID NO: 206 |
| 14 |  |  |  |  |  | P | P | P | P | P | P | P | P | P | G | P | A V A SEQ ID NO: 207 |
| consensus: |  |  |  |  |  | P | P | P | P | P | P | P | P | P |  |  | SEQ ID NO: 208 |

Fig. 23 (continued)

(I) 55D8 1µg/ml (16 Spot membrane)

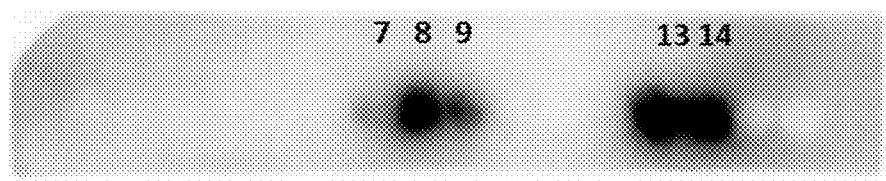

|   | 28 | 30 |   |   |   | 35 |   |   |   |   | 40 |   | 42 |   |   |   | 47 |   | 50 |   | 52 |   |
|---|----|----|---|---|---|----|---|---|---|---|----|---|----|---|---|---|----|---|----|---|----|---|
| 7 | Q  | Q  | Q | Q | Q | Q  | Q | P | P | P | P  | P | P  | P | P | P | SEQ ID NO: 203 |
| 8 |    |    |   |   |   | Q  | Q | P | P | P | P  | P | P  | P | P | P | P | P | Q | L | SEQ ID NO: 204 |
| 9 |    |    |   |   |   |    | SEQ ID NO: 205 | P | P | P | P | P | P | P | P | Q | L | P | Q | P | P | P |
| consesus: |  |  |  |  |  |  | P | P | P | P | P | P | P | P | P | P | SEQ ID NO: 153 |

|    | 58 |   | 60 |   | 63 |   |   |   | 67 |   |   | 70 |   | 72 |   |   | 75 |   | 77 |
|----|----|---|----|---|----|---|---|---|----|---|---|----|---|----|---|---|----|---|----|
| 13 | L  | P | Q  | P | Q  | P | P | P | P  | P | P | P  | P | P  | P | P | SEQ ID NO: 206 |
| 14 |    |   |    |   | P  | P | P | P | P  | P | P | P  | P | P  | G | P | A  | V | A | SEQ ID NO: 207 |
| consensus: |  |  |  | P | P | P | P | P | P | P | P | P | P | P | SEQ ID NO: 208 |

(J) 7A8 1µg/ml (21 Spot membrane)

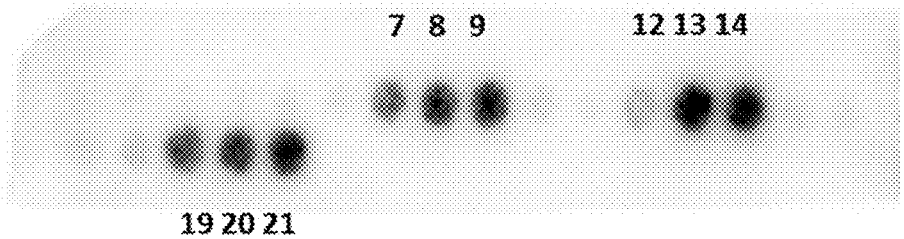

|   | 28 | 30 |   |   |   | 35 |   |   |   |   | 40 |   | 42 |   |   |   | 47 |   | 50 |   | 52 |
|---|----|----|---|---|---|----|---|---|---|---|----|---|----|---|---|---|----|---|----|---|----|
| 7 | Q  | Q  | Q | Q | Q | Q  | Q | P | P | P | P  | P | P  | P | P | P | SEQ ID NO: 203 |
| 8 |    |    |   |   |   | Q  | Q | P | P | P | P  | P | P  | P | P | P | P | P | Q | L | SEQ ID NO: 204 |
| 9 |    |    |   |   |   |    | SEQ ID NO: 205 | P | P | P | P | P | P | P | P | Q | L | P | Q | P | P | P |
| consesus: |  |  |  |  |  |  | P | P | P | P | P | P | P | P | P | P | SEQ ID NO: 217 |

|    | 58 |   | 60 |   | 63 |   |   |   | 67 |   |   | 70 |   | 72 |   |   | 75 |   | 77 |
|----|----|---|----|---|----|---|---|---|----|---|---|----|---|----|---|---|----|---|----|
| 13 | L  | P | Q  | P | Q  | P | P | P | P  | P | P | P  | P | P  | P | P | SEQ ID NO: 206 |
| 14 |    |   |    |   | P  | P | P | P | P  | P | P | P  | P | P  | G | P | A  | V | A | SEQ ID NO: 207 |
| consensus: |  |  |  | P | P | P | P | P | P | P | P | P | P | P | SEQ ID NO: 208 |
| 19 |    |   |    |   | A  | A | P | P | P  | P | P | P  | P | P  | A | A | A  | A | A | SEQ ID NO: 218 |
| 20 |    |   |    |   |    | A | A | P | P  | P | P | P  | P | P  | P | A | A  | A |   | SEQ ID NO: 219 |
| 21 |    |   |    |   |    |   | P | P | P  | P | P | P  | P | P  | P | P | A  | A | A | SEQ ID NO: 220 |
| consensus: |  |  |  |  |  | P | P | P | P | P | P | P | P |  |  |  | SEQ ID NO: 154 |

Fig. 23 (continued)

(K) NI-302.78H12 1µg/ml (16 Spot membrane)

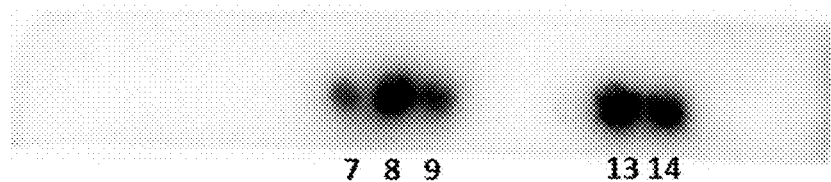

```
      28    30           35              40    42              47        50     52
7  Q  Q  Q  Q  Q  Q  Q  P  P  P  P  P  P  P  P  P                    SEQ ID NO: 203
8                    Q  Q  P  P  P  P  P  P  P  P  P  P  Q  L        SEQ ID NO: 204
9              SEQ ID NO: 205  P  P  P  P  P  P  P  P  Q  L  P  Q  P  P  P
consesus:                      P  P  P  P  P  P  P  P  P  P  P        SEQ ID NO: 155

58    60     63        67        70    72        75    77
13 L  P  Q  P  Q  P  P  P  P  P  P  P  P  P  P                      SEQ ID NO: 206
14             P  P  P  P  P  P  P  P  P  P  G  P  A  V  A          SEQ ID NO: 207
consensus:     P  P  P  P  P  P  P  P  P  P                          SEQ ID NO: 208
```

(L) NI-302.71F6 1µg/ml (16 Spot membrane)

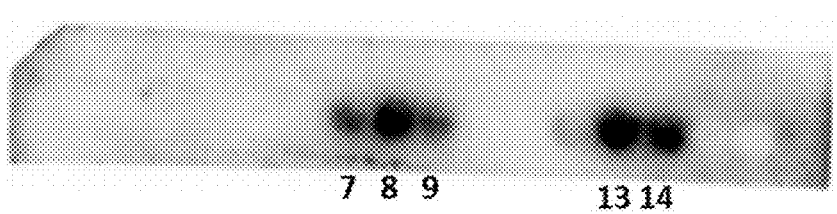

```
      28    30           35              40    42              47        50     52
7  Q  Q  Q  Q  Q  Q  Q  P  P  P  P  P  P  P  P  P                    SEQ ID NO: 203
8                    Q  Q  P  P  P  P  P  P  P  P  P  P  Q  L        SEQ ID NO: 204
9              SEQ ID NO: 205  P  P  P  P  P  P  P  P  Q  L  P  Q  P  P  P
consesus:                      P  P  P  P  P  P  P  P  P  P  P        SEQ ID NO: 156

58    60     63        67        70    72        75    77
13 L  P  Q  P  Q  P  P  P  P  P  P  P  P  P  P                      SEQ ID NO: 206
14             P  P  P  P  P  P  P  P  P  P  G  P  A  V  A          SEQ ID NO: 207
consensus:     P  P  P  P  P  P  P  P  P  P                          SEQ ID NO: 208
```

Fig. 23 (continued)

(M) NI-302.11H6 1μg/ml (21 Spot membrane)

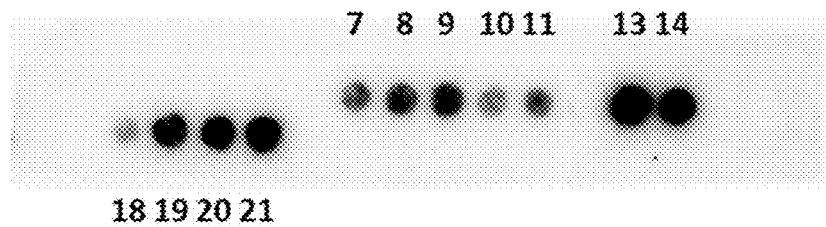

```
        28    30         35              40    42              47    50    52         55    57         60    62
 7      Q  Q  Q  Q  Q  Q  Q  P  P  P  P  P  P  P  P  SEQ ID NO: 203
 8                     Q  Q  P  P  P  P  P  P  P  P  P  P  P  Q  L  SEQ ID NO: 204
 9                              P  P  P  P  P  P  P  P  Q  L  P  Q  P  P  P  SEQ ID NO: 205
10                    SEQ ID NO: 209   P  P  P  Q  L  P  Q  P  P  P  Q  A  Q  P  L
11                              SEQ ID NO: 210   P  Q  P  P  P  Q  A  Q  P  L  L  P  Q  P  Q
consensus:                 P  P  P  P  P  P  P  P  Q  L  P  Q  P  P  P  SEQ ID NO: 223
```

```
        58    60         63              67         70    72         75    77
13      L  P  Q  P  Q  P  P  P  P  P  P  P  P  P  P  SEQ ID NO: 206
14                  P  P  P  P  P  P  P  P  P  G  P  A  V  A      SEQ ID NO: 207
consensus:         P  P  P  P  P  P  P  P  P  P  SEQ ID NO: 208
```

```
18                  A  A  P  P  P  P  P  P  A  A  A  A  A  A  SEQ ID NO: 221
19                  A  A  P  P  P  P  P  P  P  A  A  A  A     SEQ ID NO: 222
20                  A  A  P  P  P  P  P  P  P  P  A  A  A     SEQ ID NO: 219
21                  P  P  P  P  P  P  P  P  P  P  P  A  A  A  SEQ ID NO: 220
consesus:              P  P  P  P  P  P  SEQ ID NO: 147
```

|    | 28 | 30 |    |    |    | 35 |    |    |    |    | 40 |    | 42 |    |    |    |    | 47 |    | 50 |    | 52 |             |
|----|----|----|----|----|----|----|----|----|----|----|----|----|----|----|----|----|----|----|----|----|----|----|-------------|
| 7  | Q  | Q  | Q  | Q  | Q  | Q  | Q  | P  | P  | P  | P  | P  | P  | P  | P  |    |    |    |    |    |    |    | SEQ ID NO: 203 |
| 8  |    |    |    |    |    | Q  | Q  | P  | P  | P  | P  | P  | P  | P  | P  | P  | P  | P  | P  | Q  | L  |    | SEQ ID NO: 204 |
| 9  |    |    |    |    | SEQ ID NO: 205 |  |  | P | P | P | P | P | P | P | P | P | Q | L | P | Q | P | P | P |
| consesus: |  |  |  |  |  |  |  | P | P | P | P | P | P | P | P |  |  |  |  |  |  |  | SEQ ID NO: 139 |

|    | 53 |    |    |    | 58 |    | 60 |    |    | 63 |    |    |    | 67 |    |    | 70 |    | 72 |    |    | 75 |    | 77 |             |
|----|----|----|----|----|----|----|----|----|----|----|----|----|----|----|----|----|----|----|----|----|----|----|----|----|-------------|
| 12 | Q  | A  | Q  | P  | L  | L  | P  | Q  | P  | Q  | P  | P  | P  | P  |    |    |    |    |    |    |    |    |    |    | SEQ ID NO: 224 |
| 13 |    |    |    |    |    | L  | P  | Q  | P  | Q  | P  | P  | P  | P  | P  | P  | P  | P  | P  |    |    |    |    |    | SEQ ID NO: 206 |
| 14 |    |    |    |    | SEQ ID NO: 207 |  |  | P | P | P | P | P | P | P | P | P | P | P | G | P | A | V | A |
| consensus: |  |  |  |  |  |  |  | P | P | P | P | P | P | P | P | P | P |  |  |  |  |  |  |  | SEQ ID NO: 208 |

| 18 | A A P P P P P A A A A A A SEQ ID NO: 221 |
| 19 | A A P P P P P P A A A A A SEQ ID NO: 222 |
| 20 | A A P P P P P P P A A A SEQ ID NO: 219 |
| 21 | P P P P P P P P P P A A A SEQ ID NO: 220 |
| consesus: | P P P P P P SEQ ID NO: 159 |

(O) NI-302.3D8 1µg/ml (21 Spot membrane)

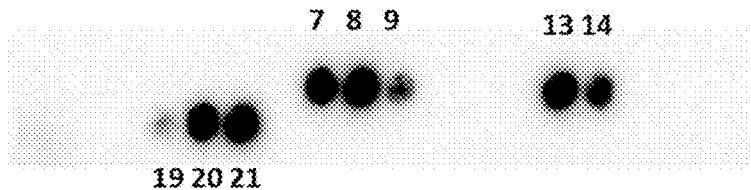

|    | 28 | 30 |   | 35 |   |   | 40 | 42 |   |   | 47 |   | 50 | 52 |               |
|----|----|----|---|----|---|---|----|----|---|---|----|---|----|----|---------------|
| 7  | Q  | Q  | Q | Q  | Q | Q | P  | P  | P | P | P  | P | P  | P  | SEQ ID NO: 203 |
| 8  |    |    | Q | Q  | P | P | P  | P  | P | P | P  | P | Q  | L  | SEQ ID NO: 204 |
| 9  |    |    | SEQ ID NO: 205 | | | P | P | P | P | P | P | P | Q | L | P | Q | P | P |
| consesus: |    |    |   | P  | P | P | P  | P  | P | P | P  | P | P  |    | SEQ ID NO: 217 |

|    | 58 | 60 |   | 63 |   |   | 67 |   |   | 70 |   | 72 |   | 75 |   | 77 |               |
|----|----|----|---|----|---|---|----|---|---|----|---|----|---|----|---|----|---------------|
| 13 | L  | P  | Q | P  | Q | P | P  | P | P | P  | P | P  | P | P  | P |    | SEQ ID NO: 206 |
| 14 |    |    |   |    |   | P | P  | P | P | P  | P | P  | P | P  | G | P A V A | SEQ ID NO: 207 |
| consensus: |    |    |   |    |   | P | P  | P | P | P  | P | P  | P | P  | P |    | SEQ ID NO: 208 |

| 19 |  |  |  |  | A | A | P | P | P | P | P | P | P | A | A | A | A | A | SEQ ID NO: 222 |
| 20 |  |  |  |  | A | A | P | P | P | P | P | P | P | P | A | A | A |   | SEQ ID NO: 219 |
| 21 |  |  |  |  | P | P | P | P | P | P | P | P | P | P | A | A | A |   | SEQ ID NO: 220 |
| consensus: |  |  |  |  |  |  | P | P | P | P | P | P | P | P |  |  |   |   | SEQ ID NO: 158 |

(P) NI-302.46C9 1µg/ml (21 Spot membrane)

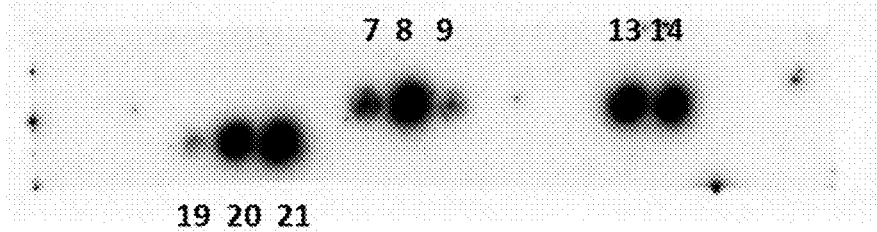

|    | 28 | 30 |   | 35 |   |   | 40 | 42 |   |   | 47 |   | 50 | 52 |               |
|----|----|----|---|----|---|---|----|----|---|---|----|---|----|----|---------------|
| 7  | Q  | Q  | Q | Q  | Q | Q | P  | P  | P | P | P  | P | P  | P  | SEQ ID NO: 203 |
| 8  |    |    | Q | Q  | P | P | P  | P  | P | P | P  | P | Q  | L  | SEQ ID NO: 204 |
| 9  |    |    | SEQ ID NO: 205 | | | P | P | P | P | P | P | P | Q | L | P | Q | P | P |
| consesus: |    |    |   | P  | P | P | P  | P  | P | P | P  | P | P  |    | SEQ ID NO: 217 |

|    | 58 | 60 |   | 63 |   |   | 67 |   |   | 70 |   | 72 |   | 75 |   | 77 |               |
|----|----|----|---|----|---|---|----|---|---|----|---|----|---|----|---|----|---------------|
| 13 | L  | P  | Q | P  | Q | P | P  | P | P | P  | P | P  | P | P  | P |    | SEQ ID NO: 206 |
| 14 |    |    |   |    |   | P | P  | P | P | P  | P | P  | P | P  | G | P A V A | SEQ ID NO: 207 |
| consensus: |    |    |   |    |   | P | P  | P | P | P  | P | P  | P | P  | P |    | SEQ ID NO: 208 |

| 19 |  |  |  |  | A | A | P | P | P | P | P | P | P | A | A | A | A | A | SEQ ID NO: 222 |
| 20 |  |  |  |  | A | A | P | P | P | P | P | P | P | P | A | A | A |   | SEQ ID NO: 219 |
| 21 |  |  |  |  | P | P | P | P | P | P | P | P | P | P | A | A | A |   | SEQ ID NO: 220 |
| consensus: |  |  |  |  |  |  | P | P | P | P | P | P | P | P |  |  |   |   | SEQ ID NO: 161 |

Fig. 23 (continued)

(Q) NI-302.52C9 1ug/ml (21 Spot membrane)

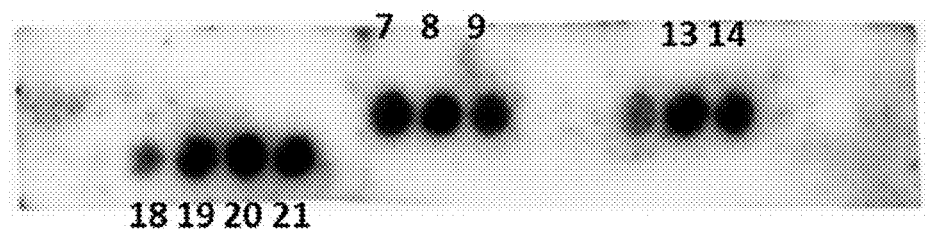

| | 28 | 30 | | | 35 | | | | 40 | 42 | | | 47 | | 50 | 52 | |
|---|---|---|---|---|---|---|---|---|---|---|---|---|---|---|---|---|---|
| 7 | Q | Q | Q | Q | Q | Q | Q | P | P | P | P | P | P | P | P | | | SEQ ID NO: 203 |
| 8 | | | | | Q | Q | P | P | P | P | P | P | P | P | P | P | Q L | SEQ ID NO: 204 |
| 9 | | | | | SEQ ID NO: 205 | | P | P | P | P | P | P | P | P | Q | L | P Q P P P | |
| consesus: | | | | | | | P | P | P | P | P | P | P | P | P | P | | SEQ ID NO: 217 |

| | 58 | 60 | | 63 | | | 67 | | 70 | | 72 | | 75 | 77 | |
|---|---|---|---|---|---|---|---|---|---|---|---|---|---|---|---|
| 13 | L | P | Q | P | Q | P | P | P | P | P | P | P | P | P | SEQ ID NO: 206 |
| 14 | | | | P | P | P | P | P | P | P | P | P | G | P A V A | SEQ ID NO: 207 |
| consensus: | | | | P | P | P | P | P | P | P | P | P | P | | SEQ ID NO: 208 |

| | | | | | | | | | | | | | | | |
|---|---|---|---|---|---|---|---|---|---|---|---|---|---|---|---|
| 18 | | A | A | P | P | P | P | P | P | A | A | A | A | A | A | SEQ ID NO: 221 |
| 19 | | A | A | P | P | P | P | P | P | P | A | A | A | A | A | SEQ ID NO: 222 |
| 20 | | A | A | P | P | P | P | P | P | P | P | A | A | A | | SEQ ID NO: 219 |
| 21 | | P | P | P | P | P | P | P | P | P | P | P | A | A | A | SEQ ID NO: 220 |
| consesus: | | | | P | P | P | P | P | P | | | | | | | SEQ ID NO: 160 |

(R) NI-302.2A2 1ug/ml (21 Spot membrane)

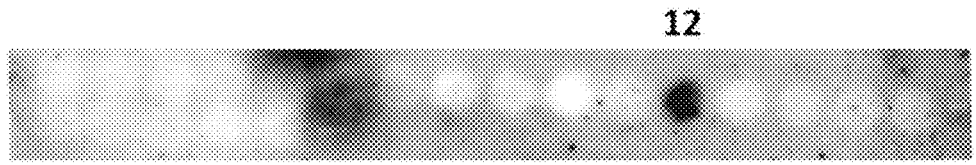

| | 53 | | | | 58 | 60 | | 63 | | | 67 | | | |
|---|---|---|---|---|---|---|---|---|---|---|---|---|---|---|
| 12 | Q | A | Q | P | L | L | P | Q | P | Q | P | P | P | P | SEQ ID NO: 142 |

Fig. 23 (continued)

(S) NI-302.15E8 1ug/ml (21 Spot membrane)
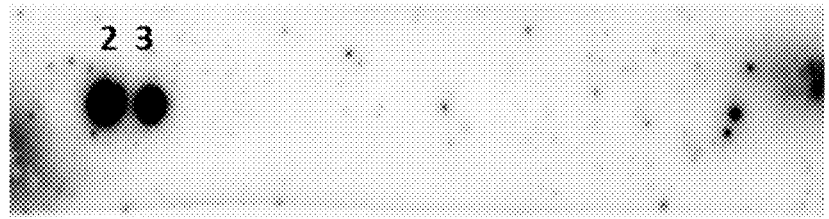
|   | 5 |   |   |   |   | 10 |   |   |   |   |   |   |   |   | 20 |   |   |
|---|---|---|---|---|---|---|---|---|---|---|---|---|---|---|---|---|---|
| 2 | E | K | L | M | K | A | F | E | S | L | K | S | F | Q | Q |   | SEQ ID NO: 225 |
| 3 |   |   |   |   |   | K | A | F | E | S | L | K | S | F | Q | Q Q Q Q | SEQ ID NO: 226 |
| consesus: |   |   |   |   |   | K | A | F | E | S | L | K | S | F | Q | Q | SEQ ID NO: 144 |
(T) NI-302.15D3 1ug/ml (21 Spot membrane)
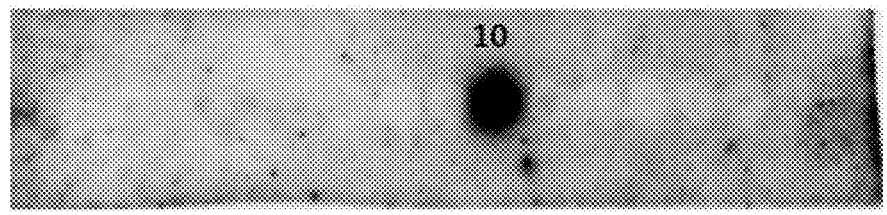
|    | 43 |   |   |   |   |   | 50 |   |   |   |   |   | 57 |   |
|----|----|---|---|---|---|---|----|---|---|---|---|---|----|---|
| 10 | P  | P | P | Q | L | P | Q  | P | P | P | Q | A | Q P L | SEQ ID NO: 143 |
Fig. 23 (continued)

(D)
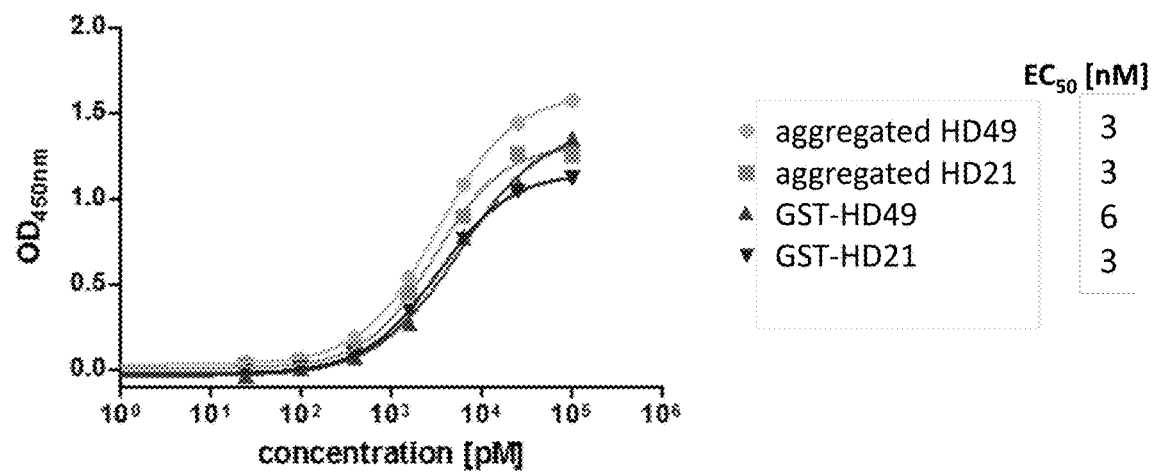
(E)
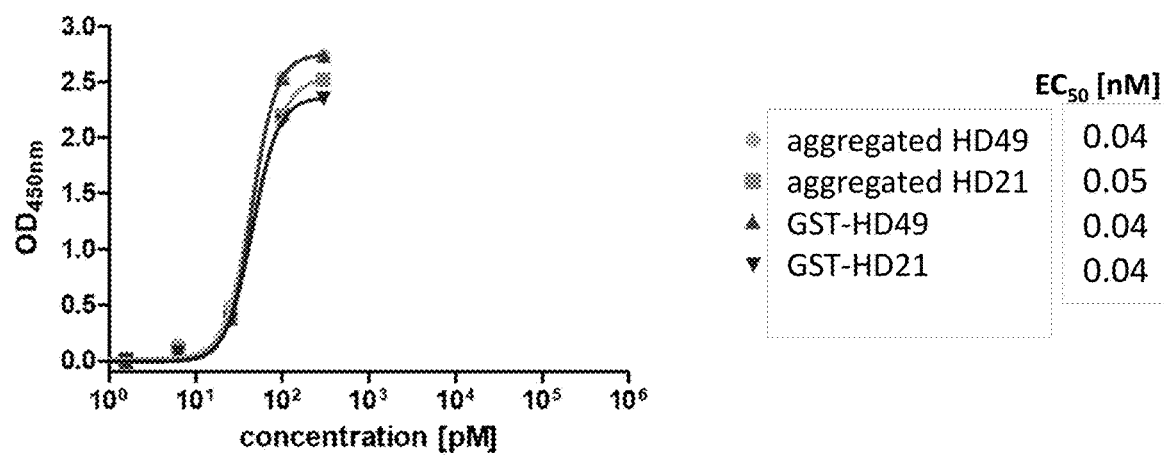
(F)
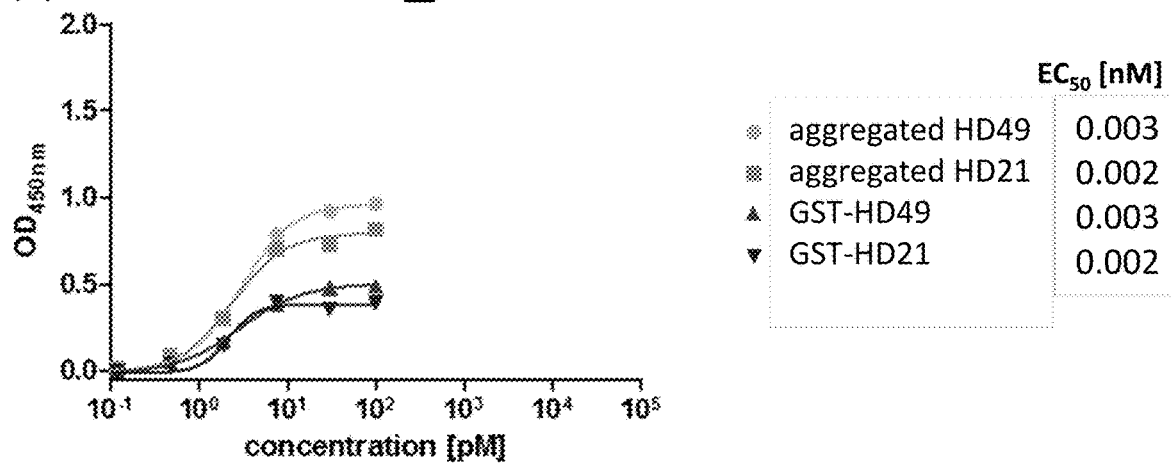
Fig. 31 (continued)

(A)
NI-302.64E5
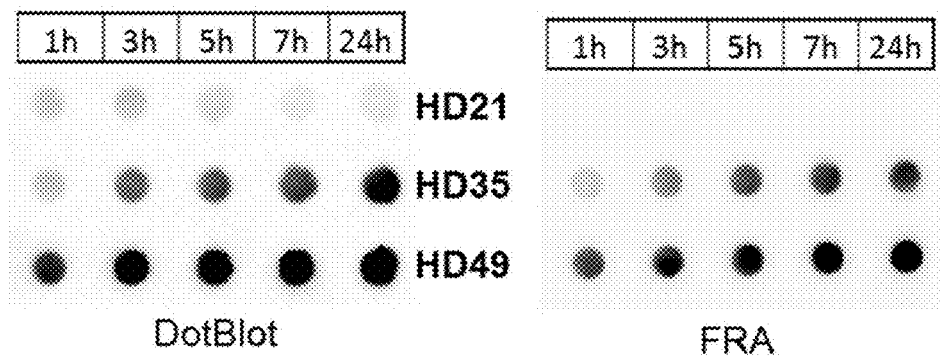
(B)
NI-302.7D8
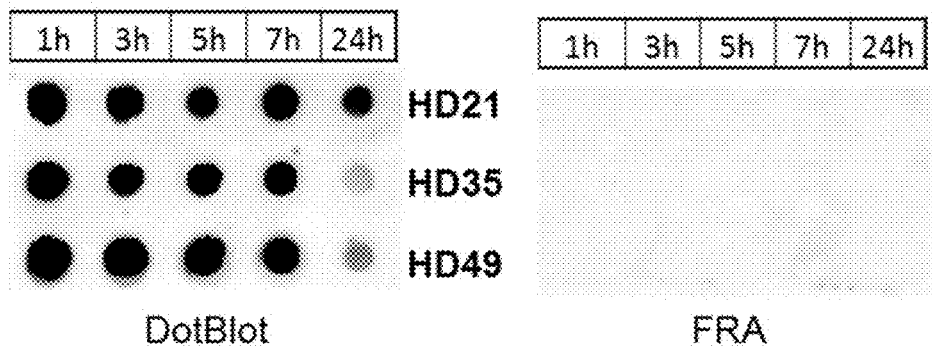
(C)
NI-302.72F10
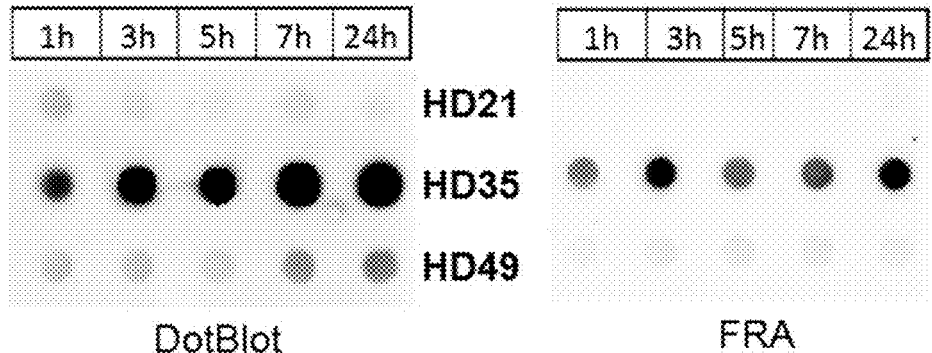
Fig. 32

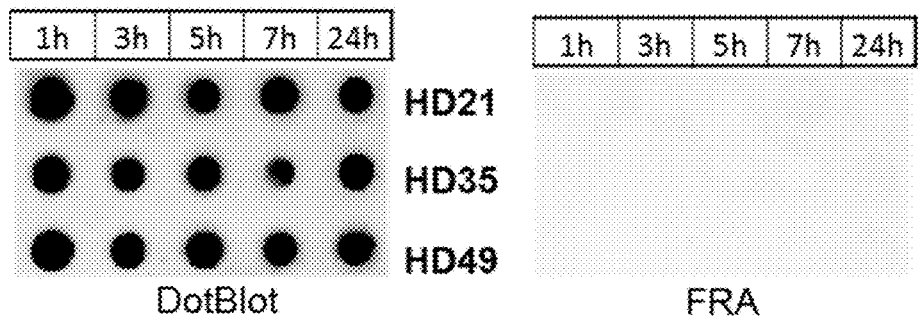
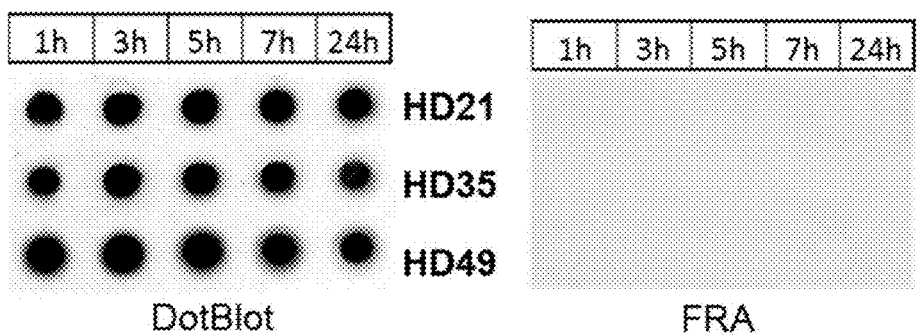
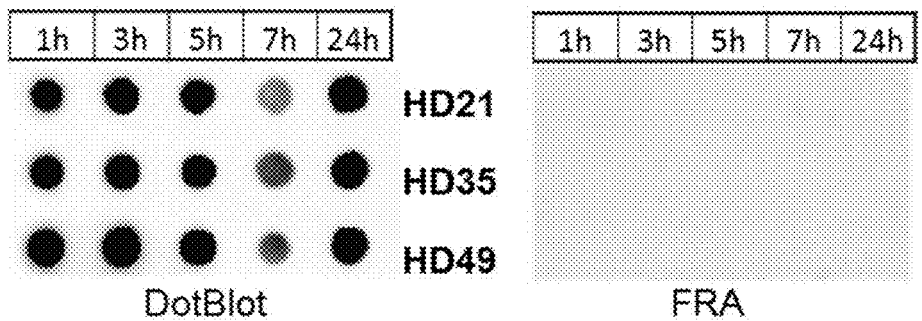
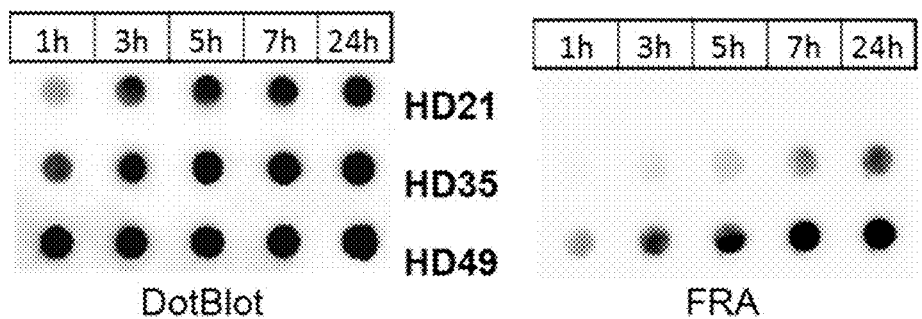
Fig. 32 (continued)

(A)
64E5 1ug/ml
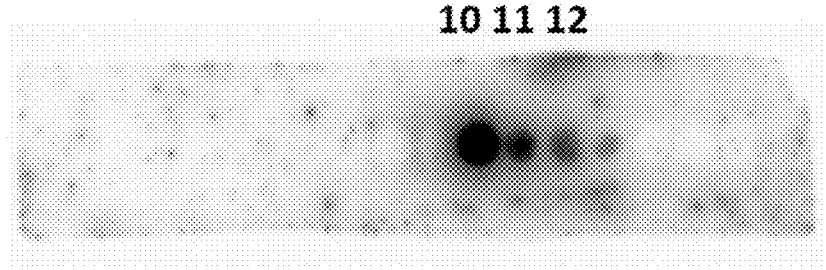
|  | 43 | | | | | 50 | | | | | | | 57 | | 60 | | | | 67 |
|---|---|---|---|---|---|---|---|---|---|---|---|---|---|---|---|---|---|---|---|
| 10 | P | P | P | Q | L | P | Q | P | P | P | Q | A | Q | P | L | SEQ ID NO: 209 | | | |
| 11 | SEQ ID NO: 210 | | | P | Q | P | P | P | Q | A | Q | P | L | L | P | Q | P | Q | |
| 12 | | | | | | SEQ ID NO: 224 | | | Q | A | Q | P | L | L | P | Q | P | Q | P P P P |
| consensus: | | | | | | P | Q | P | P | P | Q | A | Q | P | L | SEQ ID NO: 200 | | | |
(B)
7D8 1ug/ml
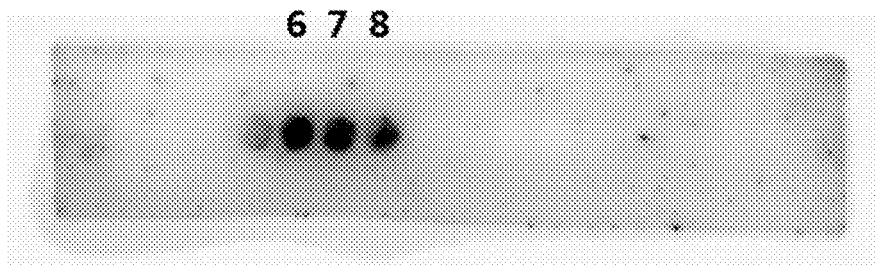
|  | 28 | 30 | | | 35 | | | | 40 | 42 | | | | 47 | | 50 | 52 | |
|---|---|---|---|---|---|---|---|---|---|---|---|---|---|---|---|---|---|---|
| 6 | Q | Q | Q | Q | Q | Q | Q | Q | Q | Q | Q | P | P | P | SEQ ID NO: 227 | | | |
| 7 | | | | | Q | Q | Q | Q | Q | Q | Q | P | P | P | P | P | P | SEQ ID NO: 203 |
| 8 | | | | | | | | Q | Q | P | P | P | P | P | P | P | P P Q L | SEQ ID NO: 204 |
| consensus: | | | | | Q | Q | Q | Q | Q | Q | Q | P | P | P | SEQ ID NO: 201 | | | |
Fig. 35

(C) 72F10 1ug/ml
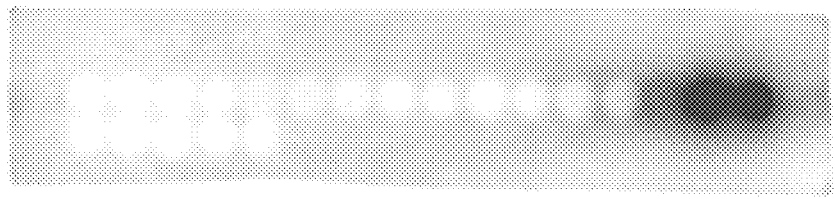
```
         68  70            75            80         84
15        P  P  P  P  P  G  P  A  V  A  E  E  P  L  H       SEQ ID NO: 228
16           P  P  P  G  P  A  V  A  E  E  P  L  H  R  P   SEQ ID NO: 229
consensus    P  P  P  G  P  A  V  A  E  E  P  L  H          SEQ ID NO: 202
```
(D) 4A6 1ug/ml    No binding
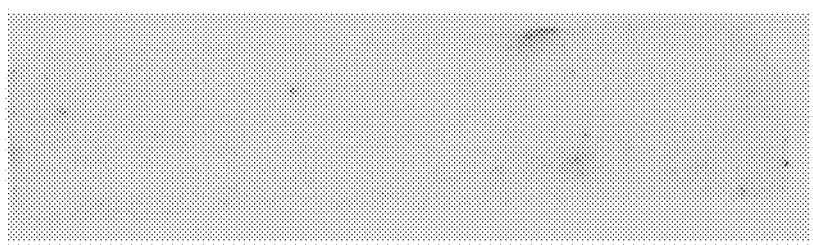
(E) 12H2 1ug/ml
No binding
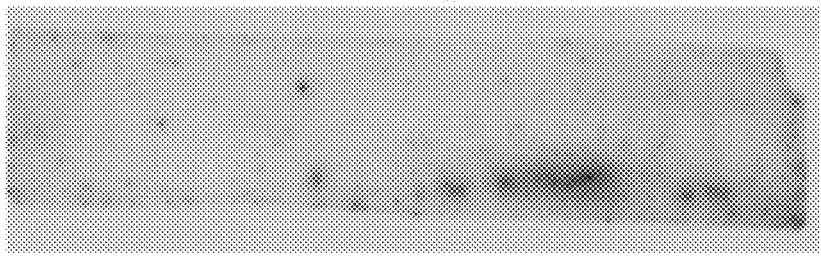
(F) 8M1 1ug/ml
No binding
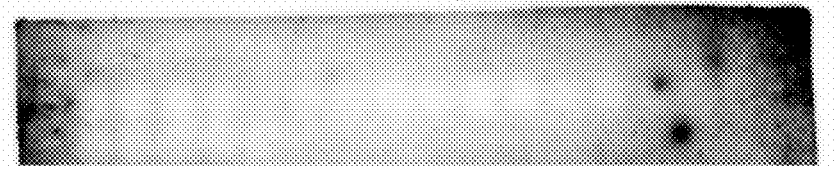
Fig. 35 (continued)

SEQUENCE LISTING

```
<160> NUMBER OF SEQ ID NOS: 287

<210> SEQ ID NO 1
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-302.33C11-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 1 gag gtg cag ctg gtg gag tct ggg gga ggc gtt gtc cag cct ggg aac       48
Glu Val Gln Leu Val Glu Ser Gly Gly Gly Val Val Gln Pro Gly Asn
1               5                   10                  15 tcc ctg aga ctc tcc tgt gca gcg tct gga ttc agg ttc agt gac ttt       96
Ser Leu Arg Leu Ser Cys Ala Ala Ser Gly Phe Arg Phe Ser Asp Phe
            20                  25                  30 ggc atg cac tgg gtc cgc cag gct cca ggc aag gga ctg gag tgg ctg      144
Gly Met His Trp Val Arg Gln Ala Pro Gly Lys Gly Leu Glu Trp Leu
        35                  40                  45 gca ctt ata tgg tat gat gga ggg tat aag tac tat gca gac tcc gtg      192
Ala Leu Ile Trp Tyr Asp Gly Gly Tyr Lys Tyr Tyr Ala Asp Ser Val
    50                  55                  60 aag ggc cga ttc acc atc tcc aga gac aat tcc aag aat acg atg ttt      240
Lys Gly Arg Phe Thr Ile Ser Arg Asp Asn Ser Lys Asn Thr Met Phe
65                  70                  75                  80 cta caa atg aac agc ctg aga gcc gag gac acg gct gtt tat tac tgt      288
Leu Gln Met Asn Ser Leu Arg Ala Glu Asp Thr Ala Val Tyr Tyr Cys
                85                  90                  95 gcg acc cac cta gaa tat tgc agt aga acc acc tgc tat ctc ggc cac      336
Ala Thr His Leu Glu Tyr Cys Ser Arg Thr Thr Cys Tyr Leu Gly His
            100                 105                 110 tgg ggc cag gga acc ctg gtc acc gtc tcc tcg                          369
Trp Gly Gln Gly Thr Leu Val Thr Val Ser Ser
        115                 120

<210> SEQ ID NO 2
```

```
<211> LENGTH: 123
<212> TYPE: PRT
<213> ORGANISM: Homo sapiens

<400> SEQUENCE: 2

Glu Val Gln Leu Val Glu Ser Gly Gly Val Val Gln Pro Gly Asn
1               5                   10                  15

Ser Leu Arg Leu Ser Cys Ala Ala Ser Gly Phe Arg Phe Ser Asp Phe
            20                  25                  30

Gly Met His Trp Val Arg Gln Ala Pro Gly Lys Gly Leu Glu Trp Leu
        35                  40                  45

Ala Leu Ile Trp Tyr Asp Gly Gly Tyr Lys Tyr Ala Asp Ser Val
    50                  55                  60

Lys Gly Arg Phe Thr Ile Ser Arg Asp Asn Ser Lys Asn Thr Met Phe
65                  70                  75                  80

Leu Gln Met Asn Ser Leu Arg Ala Glu Asp Thr Ala Val Tyr Tyr Cys
                85                  90                  95

Ala Thr His Leu Glu Tyr Cys Ser Arg Thr Thr Cys Tyr Leu Gly His
            100                 105                 110

Trp Gly Gln Gly Thr Leu Val Thr Val Ser Ser
        115                 120

<210> SEQ ID NO 3
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.33C11-VK variable light-kappa chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 3 gac atc cag ttg acc cag tct ccg tcc ttc cta tct gcg tct gtg gga    48
Asp Ile Gln Leu Thr Gln Ser Pro Ser Phe Leu Ser Ala Ser Val Gly
1               5                   10                  15 gac aca gtc acc ttc act tgc cgg gcc agt cag ggc att agc gat tat    96
Asp Thr Val Thr Phe Thr Cys Arg Ala Ser Gln Gly Ile Ser Asp Tyr
            20                  25                  30 tta gcc tgg ttt cag cag aaa cca ggg att gcc cct aag ctc ctg atc   144
Leu Ala Trp Phe Gln Gln Lys Pro Gly Ile Ala Pro Lys Leu Leu Ile
        35                  40                  45 tat gct gcg tcc act ttg caa acc ggg gtc cca tca agg ttc agc ggc   192
Tyr Ala Ala Ser Thr Leu Gln Thr Gly Val Pro Ser Arg Phe Ser Gly
    50                  55                  60 agt gga tct ggg aca gaa ttc act ctc aca atc cgc agc ctg cag tct   240
Ser Gly Ser Gly Thr Glu Phe Thr Leu Thr Ile Arg Ser Leu Gln Ser
65                  70                  75                  80 gaa gat ttt gga act tat tac tgt cag cag ctt aaa act tac ccg tac   288
```

```
Glu Asp Phe Gly Thr Tyr Tyr Cys Gln Gln Leu Lys Thr Tyr Pro Tyr
                85                  90                  95 act ttt ggc cag ggg acc aag gtg gaa atc aaa                            321
Thr Phe Gly Gln Gly Thr Lys Val Glu Ile Lys
            100                 105

<210> SEQ ID NO 4
<211> LENGTH: 107
<212> TYPE: PRT
<213> ORGANISM: Homo sapiens

<400> SEQUENCE: 4

Asp Ile Gln Leu Thr Gln Ser Pro Ser Phe Leu Ser Ala Ser Val Gly
1               5                   10                  15

Asp Thr Val Thr Phe Thr Cys Arg Ala Ser Gln Gly Ile Ser Asp Tyr
            20                  25                  30

Leu Ala Trp Phe Gln Gln Lys Pro Gly Ile Ala Pro Lys Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Glu Phe Thr Leu Thr Ile Arg Ser Leu Gln Ser
65                  70                  75                  80

Glu Asp Phe Gly Thr Tyr Tyr Cys Gln Gln Leu Lys Thr Tyr Pro Tyr
                85                  90                  95

Thr Phe Gly Gln Gly Thr Lys Val Glu Ile Lys
            100                 105

<210> SEQ ID NO 5
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.63F3 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 5 cag gtg cag ctg gtg caa tct ggg tct gcg ttc aag aag cct ggg acc        48
Gln Val Gln Leu Val Gln Ser Gly Ser Ala Phe Lys Lys Pro Gly Thr
1               5                   10                  15 tca gtg aaa gtt tcc tgc aag gcc tct gga tac acc ttc gag acc cgt        96
Ser Val Lys Val Ser Cys Lys Ala Ser Gly Tyr Thr Phe Glu Thr Arg
            20                  25                  30 tct atg aac tgg gtg cga cag gcc cct gga caa ggg ctt gaa tac atg       144
Ser Met Asn Trp Val Arg Gln Ala Pro Gly Gln Gly Leu Glu Tyr Met
        35                  40                  45 gga tgg atc aac acc aac act ggc aac cgc acg tat gtc cag gcc ttc       192
Gly Trp Ile Asn Thr Asn Thr Gly Asn Arg Thr Tyr Val Gln Ala Phe
    50                  55                  60
```

```
aga gga cga ttt gtc ttc tcc ttg gac acc tct gtc agc acg gca tat       240
Arg Gly Arg Phe Val Phe Ser Leu Asp Thr Ser Val Ser Thr Ala Tyr
65                  70                  75                  80 ctg cag atc agc aac tta aag act gag gac act gcc gtg tat tac tgt       288
Leu Gln Ile Ser Asn Leu Lys Thr Glu Asp Thr Ala Val Tyr Tyr Cys
                85                  90                  95 gcg aga ggg gca ggt ggg gga tat tgg ttc gac tcc tgg ggc cag gga       336
Ala Arg Gly Ala Gly Gly Gly Tyr Trp Phe Asp Ser Trp Gly Gln Gly
            100                 105                 110 acc ctg gtc acc gtc tcc tcg                                           357
Thr Leu Val Thr Val Ser Ser
        115

<210> SEQ ID NO 6
<211> LENGTH: 119
<212> TYPE: PRT
<213> ORGANISM: Homo sapiens

<400> SEQUENCE: 6

Gln Val Gln Leu Val Gln Ser Gly Ser Ala Phe Lys Lys Pro Gly Thr
1               5                   10                  15

Ser Val Lys Val Ser Cys Lys Ala Ser Gly Tyr Thr Phe Glu Thr Arg
            20                  25                  30

Ser Met Asn Trp Val Arg Gln Ala Pro Gly Gln Gly Leu Glu Tyr Met
        35                  40                  45

Gly Trp Ile Asn Thr Asn Thr Gly Asn Arg Thr Tyr Val Gln Ala Phe
    50                  55                  60

Arg Gly Arg Phe Val Phe Ser Leu Asp Thr Ser Val Ser Thr Ala Tyr
65                  70                  75                  80

Leu Gln Ile Ser Asn Leu Lys Thr Glu Asp Thr Ala Val Tyr Tyr Cys
                85                  90                  95

Ala Arg Gly Ala Gly Gly Gly Tyr Trp Phe Asp Ser Trp Gly Gln Gly
            100                 105                 110

Thr Leu Val Thr Val Ser Ser
        115

<210> SEQ ID NO 7
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-302.63F3 VK  variable light-kappa chain (VK)
      sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 7 gac atc cag atg acc cag tct cca gac tcc ctg gct gtg tct ctg ggc       48
Asp Ile Gln Met Thr Gln Ser Pro Asp Ser Leu Ala Val Ser Leu Gly
```

```
            1               5                   10                  15
gag agg gcc acc atc aac tgc aag tcc aat cag agt ctt ttc tac agt      96
Glu Arg Ala Thr Ile Asn Cys Lys Ser Asn Gln Ser Leu Phe Tyr Ser
                20                  25                  30 tcc aac aat aac aac tac tta gct tgg tac cag cac aaa tcc gga cag     144
Ser Asn Asn Asn Asn Tyr Leu Ala Trp Tyr Gln His Lys Ser Gly Gln
            35                  40                  45 cct cct aag ctg ctc gtt tac tgg gga tct acc cgg gaa tcc ggg gtc     192
Pro Pro Lys Leu Leu Val Tyr Trp Gly Ser Thr Arg Glu Ser Gly Val
    50                  55                  60 cct gac cgc ttc agt ggc agc ggg tct ggg act gac ttc act ctc acc     240
Pro Asp Arg Phe Ser Gly Ser Gly Ser Gly Thr Asp Phe Thr Leu Thr
65                  70                  75                  80 atc agc agc ctg cag gct gag gat gtt gca att tat tac tgt cac caa     288
Ile Ser Ser Leu Gln Ala Glu Asp Val Ala Ile Tyr Tyr Cys His Gln
                85                  90                  95 tat tat cat aat ccg tac act ttt ggc cag ggg acc aag ctg gag atc     336
Tyr Tyr His Asn Pro Tyr Thr Phe Gly Gln Gly Thr Lys Leu Glu Ile
            100                 105                 110 aaa                                                                  339
Lys

<210> SEQ ID NO 8
<211> LENGTH: 113
<212> TYPE: PRT
<213> ORGANISM: Homo sapiens

<400> SEQUENCE: 8

Asp Ile Gln Met Thr Gln Ser Pro Asp Ser Leu Ala Val Ser Leu Gly
1               5                   10                  15

Glu Arg Ala Thr Ile Asn Cys Lys Ser Asn Gln Ser Leu Phe Tyr Ser
                20                  25                  30

Ser Asn Asn Asn Asn Tyr Leu Ala Trp Tyr Gln His Lys Ser Gly Gln
            35                  40                  45

Pro Pro Lys Leu Leu Val Tyr Trp Gly Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Tyr His Asn Pro Tyr Thr Phe Gly Gln Gly Thr Lys Leu Glu Ile
            100                 105                 110

Lys

<210> SEQ ID NO 9
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-302.35C1 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
```

```
        VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 9 gag gtg cag ctg gtg gag tct ggg gga aac ttg gta cag ccg ggg ggg      48
Glu Val Gln Leu Val Glu Ser Gly Gly Asn Leu Val Gln Pro Gly Gly
1               5                   10                  15 tcc ctg aga ctc tcc tgt act gcc tct gga ttc acc ttt agt ata acg      96
Ser Leu Arg Leu Ser Cys Thr Ala Ser Gly Phe Thr Phe Ser Ile Thr
            20                  25                  30 gcc ctg agt tgg gtc cgc cag gct cca gaa aag ggg ccg cag tgg gtc     144
Ala Leu Ser Trp Val Arg Gln Ala Pro Glu Lys Gly Pro Gln Trp Val
        35                  40                  45 tca gca atc act gga aat gct tat ggg aca tac tac gca gac tcc gtg     192
Ser Ala Ile Thr Gly Asn Ala Tyr Gly Thr Tyr Tyr Ala Asp Ser Val
    50                  55                  60 aag ggc cgg ttc acc att tcc aga gac aac gcc aag aac aca ctg tac     240
Lys Gly Arg Phe Thr Ile Ser Arg Asp Asn Ala Lys Asn Thr Leu Tyr
65                  70                  75                  80 ttg caa atg aac ggc ctg aga gcc gag gac acg gcc atc tat tac tgt     288
Leu Gln Met Asn Gly Leu Arg Ala Glu Asp Thr Ala Ile Tyr Tyr Cys
                85                  90                  95 gtg aaa gga att gcc tcc gat agt agt ggt tat tct gcc ttc tgg ggc     336
Val Lys Gly Ile Ala Ser Asp Ser Ser Gly Tyr Ser Ala Phe Trp Gly
            100                 105                 110 ccg ggc acc ctg gtc acc gtc tcc tcg                                 363
Pro Gly Thr Leu Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Glu Val Gln Leu Val Glu Ser Gly Gly Asn Leu Val Gln Pro Gly Gly
1               5                   10                  15

Ser Leu Arg Leu Ser Cys Thr Ala Ser Gly Phe Thr Phe Ser Ile Thr
            20                  25                  30

Ala Leu Ser Trp Val Arg Gln Ala Pro Glu Lys Gly Pro Gln Trp Val
        35                  40                  45

Ser Ala Ile Thr Gly Asn Ala Tyr Gly Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Ile Tyr Tyr Cys
                85                  90                  95

Val Lys Gly Ile Ala Ser Asp Ser Ser Gly Tyr Ser Ala Phe Trp Gly
            100                 105                 110

Pro Gly Thr Leu Val Thr Val Ser Ser
        115                 120

<210> SEQ ID NO 11
<211> LENGTH: 321
<212> TYPE: DNA
<213> ORGANISM: Homo sapiens
<220> FEATURE:
```

```
<221> NAME/KEY: CDS
<222> LOCATION: (1)..(321)
<223> OTHER INFORMATION: NI-302.35C1 VK variable light -kappa chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 11 gaa att gtg ctg act cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt caa agt gtt gac aac cag      96
Glu Arg Ala Thr Leu Ser Cys Arg Ala Ser Gln Ser Val Asp Asn Gln
            20                  25                  30 ttt gcc tgg tac caa cag aaa cct ggc cag gct ccc agg ctc ctc att     144
Phe Ala Trp Tyr Gln Gln Lys Pro Gly Gln Ala Pro Arg Leu Leu Ile
        35                  40                  45 tat gat gca tcc agg agg gcc cct ggc atc cca gac agg ttc agt ggc     192
Tyr Asp Ala Ser Arg Arg Ala Pro Gly Ile Pro Asp Arg Phe Ser Gly
    50                  55                  60 agt ggg tct ggg aca gac ttc act ctc acc att agc agc cta gag cct     240
Ser Gly Ser Gly Thr Asp Phe Thr Leu Thr Ile Ser Ser Leu Glu Pro
65                  70                  75                  80 gaa gat ttc gca att tat tac tgt cag cat cgt tac acc tgg ctc tac     288
Glu Asp Phe Ala Ile Tyr Tyr Cys Gln His Arg Tyr Thr Trp Leu Tyr
                85                  90                  95 act ttt ggc cag ggg aca cga ctg gag att aaa                         321
Thr Phe Gly Gln Gly Thr Arg Leu Glu Ile Lys
            100                 105

<210> SEQ ID NO 12
<211> LENGTH: 107
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asn Gln
            20                  25                  30

Phe Ala Trp Tyr Gln Gln Lys Pro Gly Gln Ala Pro Arg Leu Leu Ile
        35                  40                  45

Tyr Asp Ala Ser Arg Arg Ala Pro Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln His Arg Tyr Thr Trp Leu Tyr
                85                  90                  95

Thr Phe Gly Gln Gly Thr Arg Leu Glu Ile Lys
            100                 105
```

```
<210> SEQ ID NO 13
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.31F11 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 13 gag gtg cag ctg gtg gag tcc gga gga ggc ttg atc cag ccg ggg ggg      48
Glu Val Gln Leu Val Glu Ser Gly Gly Gly Leu Ile Gln Pro Gly Gly
1               5                   10                  15 tcc ctg aga ctc tcc tgt gca gcc tct ggg ttc acc gtc agc agc acc      96
Ser Leu Arg Leu Ser Cys Ala Ala Ser Gly Phe Thr Val Ser Ser Thr
            20                  25                  30 tac atg agt tgg gtc cgc cag gct cca ggg aag ggg ctt gag tgc gtc     144
Tyr Met Ser Trp Val Arg Gln Ala Pro Gly Lys Gly Leu Glu Cys Val
        35                  40                  45 tca gtt att ttt agt ggc gct gac aca tat tac gca gac tcc gtg aag     192
Ser Val Ile Phe Ser Gly Ala Asp Thr Tyr Tyr Ala Asp Ser Val Lys
    50                  55                  60 ggc cga ttc acc gtc tcc aga gac aat tcc aag aac aca ctg ttt ctt     240
Gly Arg Phe Thr Val Ser Arg Asp Asn Ser Lys Asn Thr Leu Phe Leu
65                  70                  75                  80 cag atg aac agc ctg aga gtc gag gac acg gcc aca tat tac tgt gtg     288
Gln Met Asn Ser Leu Arg Val Glu Asp Thr Ala Thr Tyr Tyr Cys Val
                85                  90                  95 aga cat tat tat ggt tca gac ctt cca tct gac ttc tgg ggc cag ggc     336
Arg His Tyr Tyr Gly Ser Asp Leu Pro Ser Asp Phe Trp Gly Gln Gly
            100                 105                 110 acc ctg gtc acc gtc tcc tcg                                         357
Thr Leu Val Thr Val Ser Ser
        115

<210> SEQ ID NO 14
<211> LENGTH: 119
<212> TYPE: PRT
<213> ORGANISM: Homo sapiens

<400> SEQUENCE: 14

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Thr
            20                  25                  30

Tyr Met Ser Trp Val Arg Gln Ala Pro Gly Lys Gly Leu Glu Cys Val
        35                  40                  45

Ser Val Ile Phe Ser Gly Ala Asp Thr Tyr Tyr Ala Asp Ser Val Lys
    50                  55                  60
```

```
Gly Arg Phe Thr Val Ser Arg Asp Asn Ser Lys Asn Thr Leu Phe Leu
 65                  70                  75                  80

Gln Met Asn Ser Leu Arg Val Glu Asp Thr Ala Thr Tyr Tyr Cys Val
                85                  90                  95

Arg His Tyr Tyr Gly Ser Asp Leu Pro Ser Asp Phe Trp Gly Gln Gly
            100                 105                 110

Thr Leu Val Thr Val Ser Ser
        115
```

```
<210> SEQ ID NO 15
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.31F11 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 15
```

```
gat gtt gtg atg act cag tct cca ctc tcc ctg ccc gtc gcc cct gga     48
Asp Val Val Met Thr Gln Ser Pro Leu Ser Leu Pro Val Ala Pro Gly
  1               5                  10                  15 gag ccg gcc tcc atc tcc tgc agg tct agt cag agc ctc cta tac agt    96
Glu Pro Ala Ser Ile Ser Cys Arg Ser Ser Gln Ser Leu Leu Tyr Ser
                 20                  25                  30 aat gga tac aac tat ttg gat tgg tac ctg cag aag cca ggg aag cct   144
Asn Gly Tyr Asn Tyr Leu Asp Trp Tyr Leu Gln Lys Pro Gly Lys Pro
             35                  40                  45 cca cag ctc ctg gtc tat ttg ggt tct gat cgg gcc tcc ggg gtc cct   192
Pro Gln Leu Leu Val Tyr Leu Gly Ser Asp Arg Ala Ser Gly Val Pro
         50                  55                  60 gac agg ttc agt ggc agt gga tca ggc aaa gat ttt aca ctg aac atc   240
Asp Arg Phe Ser Gly Ser Gly Ser Gly Lys Asp Phe Thr Leu Asn Ile
 65                  70                  75                  80 agc aga gtg gag gct gag gat gtt ggg gtt tat tac tgc atg caa ggt   288
Ser Arg Val Glu Ala Glu Asp Val Gly Val Tyr Tyr Cys Met Gln Gly
                 85                  90                  95 cta caa agt ccg tgg acg ttc ggc caa ggg acc aag ctg gag atc aaa   336
Leu Gln Ser Pro Trp Thr Phe Gly Gln Gly Thr Lys Leu Glu Ile Lys
            100                 105                 110
```

```
<210> SEQ ID NO 16
<211> LENGTH: 112
<212> TYPE: PRT
<213> ORGANISM: Homo sapiens

<400> SEQUENCE: 16
```

```
Asp Val Val Met Thr Gln Ser Pro Leu Ser Leu Pro Val Ala Pro Gly
  1               5                  10                  15
```

```
Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Lys Pro
        35                  40                  45

Pro Gln Leu Leu Val Tyr Leu Gly Ser Asp Arg Ala Ser Gly Val Pro
    50                  55                  60

Asp Arg Phe Ser Gly Ser Gly Ser Gly Lys Asp Phe Thr Leu Asn Ile
65                  70                  75                  80

Ser Arg Val Glu Ala Glu Asp Val Gly Val Tyr Tyr Cys Met Gln Gly
                85                  90                  95

Leu Gln Ser Pro Trp Thr Phe Gly Gln Gly Thr Lys Leu Glu Ile Lys
            100                 105                 110

<210> SEQ ID NO 17
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: NI-302.2A2 VH  variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(321)
<223> OTHER INFORMATION: complementarity determining region (CDR)
      VH-CDR3

<400> SEQUENCE: 17 gag gtg cag ctg gtg gag tct ggg gga ggc ttg gtc cag cct ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt acc tat     96
Ser Leu Arg Leu Ser Cys Ala Ala Ser Gly Phe Thr Phe Ser Thr Tyr
            20                  25                  30 tgg atg aac tgg gtc cgc cag gct cca ggg aag ggg ctg gag tgg gtg    144
Trp Met Asn Trp Val Arg Gln Ala Pro Gly Lys Gly Leu Glu Trp Val
        35                  40                  45 gcc aac ata aaa cca gat gga agt gac aaa tac tat gtg gac tct gtg    192
Ala Asn Ile Lys Pro Asp Gly Ser Asp Lys Tyr Tyr Val Asp Ser Val
    50                  55                  60 aag ggc cga ttc acc atc tcc aga gac aac gcc aag aac tca ctg tat    240
Lys Gly Arg Phe Thr Ile Ser Arg Asp Asn Ala Lys Asn Ser Leu Tyr
65                  70                  75                  80 ctg caa atg aac agc ctg aga gac gag gac acg gct gtg tat tac tgt    288
Leu Gln Met Asn Ser Leu Arg Asp Glu Asp Thr Ala Val Tyr Tyr Cys
                85                  90                  95 gcg aga ggg gac ggc agt ggc tgg aac gtc tac tgg ggc cag gga acc    336
Ala Arg Gly Asp Gly Ser Gly Trp Asn Val Tyr Trp Gly Gln Gly Thr
            100                 105                 110 ctg gtc acc gtc tcc tcg                                            354
Leu Val Thr Val Ser Ser
            115
```

<210> SEQ ID NO 18
<211> LENGTH: 118
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Asn Trp Val Arg Gln Ala Pro Gly Lys Gly Leu Glu Trp Val
        35                  40                  45

Ala Asn Ile Lys Pro Asp Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Asp Gly Ser Gly Trp Asn Val Tyr Trp Gly Gln Gly Thr
            100                 105                 110

Leu Val Thr Val Ser Ser
        115

<210> SEQ ID NO 19
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION: NI-302.2A2 VK variable light-kappa chain (VK)
      sequence
<220> FEATURE:
<221> NAME/KEY: V_region
<222> LOCATION: (70)..(129)
<223> OTHER INFORMATION: complementarity determining region (CDR)
      VK-CDR1
<220> FEATURE:
<221> NAME/KEY: V_region
<222> LOCATION: (175)..(195)
<223> OTHER INFORMATION: complementarity determining region (CDR)
      VK-CDR2
<220> FEATURE:
<221> NAME/KEY: V_region
<222> LOCATION: (292)..(315)
<223> OTHER INFORMATION: complementarity determining region (CDR)
      VK-CDR3

<400> SEQUENCE: 19 gac atc cag atg acc cag tct cca gac tcc ctg gct gtg tct ctg ggc    48
Asp Ile Gln Met Thr Gln Ser Pro Asp Ser Leu Ala Val Ser Leu Gly
1               5                   10                  15 gag agg gcc acc atc aac tgc aag tcc agc cag agt ctt tta tac acc    96
Glu Arg Ala Thr Ile Asn Cys Lys Ser Ser Gln Ser Leu Leu Tyr Thr
            20                  25                  30 tcc aaa aat aag gac agt aag aac tac tta ggt tgg tac cag cag aaa   144
Ser Lys Asn Lys Asp Ser Lys Asn Tyr Leu Gly Trp Tyr Gln Gln Lys
        35                  40                  45 cca gga cag cct cct aag ctg ctc att tac tgg gca tct acc cgg gaa   192
Pro Gly Gln Pro Pro Lys Leu Leu Ile Tyr Trp Ala Ser Thr Arg Glu
    50                  55                  60 tcc ggg gtc cct gac cga ttc agt ggc agc ggg tct ggg aca gat ttc   240
Ser Gly Val Pro Asp Arg Phe Ser Gly Ser Gly Ser Gly Thr Asp Phe
65                  70                  75                  80

```
act ctc acc atc agc agc ctg cag gct gag gat gtg gca gtt tat tac      288
Thr Leu Thr Ile Ser Ser Leu Gln Ala Glu Asp Val Ala Val Tyr Tyr
            85                  90                  95 tgt cag cag tat tat act act cct cag ttc ggc gga ggg acc aag gtg      336
Cys Gln Gln Tyr Tyr Thr Thr Pro Gln Phe Gly Gly Gly Thr Lys Val
               100                 105                 110 gag atc aaa                                                          345
Glu Ile Lys
       115

<210> SEQ ID NO 20
<211> LENGTH: 115
<212> TYPE: PRT
<213> ORGANISM: Homo sapiens

<400> SEQUENCE: 20

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Thr
            20                  25                  30

Ser Lys Asn Lys Asp Ser Lys Asn Tyr Leu Gly Trp Tyr Gln Gln Lys
        35                  40                  45

Pro Gly Gln Pro Pro Lys Leu Leu Ile Tyr Trp Ala Ser Thr Arg Glu
    50                  55                  60

Ser Gly Val Pro Asp Arg Phe Ser Gly Ser Gly Ser Gly Thr Asp Phe
65                  70                  75                  80

Thr Leu Thr Ile Ser Ser Leu Gln Ala Glu Asp Val Ala Val Tyr Tyr
                85                  90                  95

Cys Gln Gln Tyr Tyr Thr Thr Pro Gln Phe Gly Gly Gly Thr Lys Val
            100                 105                 110

Glu Ile Lys
        115

<210> SEQ ID NO 21
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-302.6N9 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 21 gag gtg cag ctg gtg gag tct ggg gga gac ttg gtg cag cct ggg ggg      48
Glu Val Gln Leu Val Glu Ser Gly Gly Asp Leu Val Gln Pro Gly Gly
1               5                   10                  15 tcc ctg aga ctc tcc tgt gta gtc tct gga ttc acc ttt agt agt tat      96
Ser Leu Arg Leu Ser Cys Val Val Ser Gly Phe Thr Phe Ser Ser Tyr
```

```
                  20                  25                  30
gcc atg acc tgg gtc cgc cag gct cca ggg aag ggg ctg gcc tgg gtc      144
Ala Met Thr Trp Val Arg Gln Ala Pro Gly Lys Gly Leu Ala Trp Val
         35                  40                  45 tca aca att agt gct act ggt ggt agt aca ttc tac aca gac tcc gtg      192
Ser Thr Ile Ser Ala Thr Gly Gly Ser Thr Phe Tyr Thr Asp Ser Val
 50                  55                  60 agg ggc cgg ttc acc atc tcc cga gac aat tcc aag aac aca ctg tat      240
Arg Gly Arg Phe Thr Ile Ser Arg Asp Asn Ser Lys Asn Thr Leu Tyr
 65                  70                  75                  80 ctg caa atg aat agc ctg aga acc gac gac acg gcc ata tat tat tgt      288
Leu Gln Met Asn Ser Leu Arg Thr Asp Asp Thr Ala Ile Tyr Tyr Cys
                 85                  90                  95 gtg aaa gat cta ttt gga gtg gac acc tcc tac tac ggt atg gac gtc      336
Val Lys Asp Leu Phe Gly Val Asp Thr Ser Tyr Tyr Gly Met Asp Val
            100                 105                 110 tgg ggc caa ggg acc acg gtc acc gtc tcc tcg                          369
Trp Gly Gln Gly Thr Thr Val Thr Val Ser Ser
        115                 120

<210> SEQ ID NO 22
<211> LENGTH: 123
<212> TYPE: PRT
<213> ORGANISM: Homo sapiens

<400> SEQUENCE: 22

Glu Val Gln Leu Val Glu Ser Gly Gly Asp Leu Val Gln Pro Gly Gly
 1               5                  10                  15

Ser Leu Arg Leu Ser Cys Val Val Ser Gly Phe Thr Phe Ser Ser Tyr
             20                  25                  30

Ala Met Thr Trp Val Arg Gln Ala Pro Gly Lys Gly Leu Ala Trp Val
         35                  40                  45

Ser Thr Ile Ser Ala Thr Gly Gly Ser Thr Phe Tyr Thr Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Asp Asp Thr Ala Ile Tyr Tyr Cys
                 85                  90                  95

Val Lys Asp Leu Phe Gly Val Asp Thr Ser Tyr Tyr Gly Met Asp Val
            100                 105                 110

Trp Gly Gln Gly Thr Thr Val Thr Val Ser Ser
        115                 120

<210> SEQ ID NO 23
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-302.6N9 VK variable light-kappa chain (VK)
      sequence
<220> FEATURE:
<221> NAME/KEY: V_region
<222> LOCATION: (70)..(105)
<223> OTHER INFORMATION: complementarity determining region (CDR)
      VK-CDR1
<220> FEATURE:
<221> NAME/KEY: V_region
<222> LOCATION: (151)..(171)
<223> OTHER INFORMATION: complementarity determining region (CDR)
      VK-CDR2
<220> FEATURE:
```

```
<221> NAME/KEY: V_region
<222> LOCATION: (268)..(294)
<223> OTHER INFORMATION: complementarity determining region (CDR)
      VK-CDR3

<400> SEQUENCE: 23 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg ccc agt cag agt gtc agc ggc agg      96
Glu Arg Ala Thr Leu Ser Cys Arg Pro Ser Gln Ser Val Ser Gly Arg
            20                  25                  30 tat gtg gcc tgg tat cag cag aaa cct ggc cag gct ccc agg ctc ctc     144
Tyr Val Ala Trp Tyr Gln Gln Lys Pro Gly Gln Ala Pro Arg Leu Leu
        35                  40                  45 ttc tat gct gca tcc aac agg gcc att ggc atc cca gac agg ttc agt     192
Phe Tyr Ala Ala Ser Asn Arg Ala Ile Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cac tat ggt gcc tca tcg     288
Pro Glu Asp Phe Ala Val Tyr Tyr Cys Gln His Tyr Gly Ala Ser Ser
                85                  90                  95 tac act ttt ggc ccg ggg acc aaa gtg gat atc aaa                     324
Tyr Thr Phe Gly Pro Gly Thr Lys Val Asp Ile Lys
            100                 105

<210> SEQ ID NO 24
<211> LENGTH: 108
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Pro Ser Gln Ser Val Ser Gly Arg
            20                  25                  30

Tyr Val Ala Trp Tyr Gln Gln Lys Pro Gly Gln Ala Pro Arg Leu Leu
        35                  40                  45

Phe Tyr Ala Ala Ser Asn Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ala Ser Ser
                85                  90                  95

Tyr Thr Phe Gly Pro Gly Thr Lys Val Asp Ile Lys
            100                 105

<210> SEQ ID NO 25
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-302.74C11 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
```

```
<220> FEATURE:
<221> NAME/KEY: V_region
<222> LOCATION: (148)..(186)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 25 gag gtg cag ctg gtg cag tct ggg act gag gtg cag aag cct ggg gcc      48
Glu Val Gln Leu Val Gln Ser Gly Thr Glu Val Gln Lys Pro Gly Ala
1               5                   10                  15 tca gta aaa gtc tcc tgc aag gct tct gga tac agt ttc acc ggc tac      96
Ser Val Lys Val Ser Cys Lys Ala Ser Gly Tyr Ser Phe Thr Gly Tyr
            20                  25                  30 ttt ttg cac tgg gta cga cag gcc cct gga caa ggg ctt gag tgg atg     144
Phe Leu His Trp Val Arg Gln Ala Pro Gly Gln Gly Leu Glu Trp Met
        35                  40                  45 ggg tgg atc aac cct aac agt ggt gac aca aac tat gca gag aag ttt     192
Gly Trp Ile Asn Pro Asn Ser Gly Asp Thr Asn Tyr Ala Glu Lys Phe
50                  55                  60 cgg ggc aga atc atc atg acc agg gac acg tct gtc agc aca gcc cac     240
Arg Gly Arg Ile Ile Met Thr Arg Asp Thr Ser Val Ser Thr Ala His
65                  70                  75                  80 atg gag ttg agc agc ctg aga ttt gac gac acg gcc cta tat tac tgt     288
Met Glu Leu Ser Ser Leu Arg Phe Asp Asp Thr Ala Leu Tyr Tyr Cys
                85                  90                  95 acg aga gag gcc cct gac ccg ggc gct gag acg gac gtc tgg ggc caa     336
Thr Arg Glu Ala Pro Asp Pro Gly Ala Glu Thr Asp Val Trp Gly Gln
            100                 105                 110 ggg acc acg gtc acc gtc tcc tcg                                     360
Gly Thr Thr Val Thr Val Ser Ser
        115                 120

<210> SEQ ID NO 26
<211> LENGTH: 120
<212> TYPE: PRT
<213> ORGANISM: Homo sapiens

<400> SEQUENCE: 26

Glu Val Gln Leu Val Gln Ser Gly Thr Glu Val Gln Lys Pro Gly Ala
1               5                   10                  15

Ser Val Lys Val Ser Cys Lys Ala Ser Gly Tyr Ser Phe Thr Gly Tyr
            20                  25                  30

Phe Leu His Trp Val Arg Gln Ala Pro Gly Gln Gly Leu Glu Trp Met
        35                  40                  45

Gly Trp Ile Asn Pro Asn Ser Gly Asp Thr Asn Tyr Ala Glu Lys Phe
50                  55                  60

Arg Gly Arg Ile Ile Met Thr Arg Asp Thr Ser Val Ser Thr Ala His
65                  70                  75                  80

Met Glu Leu Ser Ser Leu Arg Phe Asp Asp Thr Ala Leu Tyr Tyr Cys
                85                  90                  95

Thr Arg Glu Ala Pro Asp Pro Gly Ala Glu Thr Asp Val Trp Gly Gln
            100                 105                 110

Gly Thr Thr Val Thr Val Ser Ser
        115                 120

<210> SEQ ID NO 27
```

```
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.74C11 VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 27 cag tct gtg ctg act cag cca ccc tcg gtg tca gtg tcc cca gga cag      48
Gln Ser Val Leu Thr Gln Pro Pro Ser Val Ser Val Ser Pro Gly Gln
1               5                   10                  15 acg gcc agg atc acc tgc tct gga gat gca gtg cca aag cag tat att      96
Thr Ala Arg Ile Thr Cys Ser Gly Asp Ala Val Pro Lys Gln Tyr Ile
            20                  25                  30 tat tgg tac cag cag aag cca ggc cag gcc cct att ctg gtg ata tat     144
Tyr Trp Tyr Gln Gln Lys Pro Gly Gln Ala Pro Ile Leu Val Ile Tyr
        35                  40                  45 aaa gac act cag agg cct tca ggg atc cct gag cga ttc tct ggc tcc     192
Lys Asp Thr Gln Arg Pro Ser Gly Ile Pro Glu Arg Phe Ser Gly Ser
    50                  55                  60 aac tca ggg aca aca gtc acg ttg acc ata act ggc gtc cag gca gac     240
Asn Ser Gly Thr Thr Val Thr Leu Thr Ile Thr Gly Val Gln Ala Asp
65                  70                  75                  80 gac gag ggt gac tat tac tgt caa tca gca gac agt agt gct act tgg     288
Asp Glu Gly Asp Tyr Tyr Cys Gln Ser Ala Asp Ser Ser Ala Thr Trp
                85                  90                  95 gtg ttc ggc gga ggg acc aaa ttg acc gtc cta                         321
Val Phe Gly Gly Gly Thr Lys Leu Thr Val Leu
            100                 105

<210> SEQ ID NO 28
<211> LENGTH: 107
<212> TYPE: PRT
<213> ORGANISM: Homo sapiens

<400> SEQUENCE: 28

Gln Ser Val Leu Thr Gln Pro Pro Ser Val Ser Val Ser Pro Gly Gln
1               5                   10                  15

Thr Ala Arg Ile Thr Cys Ser Gly Asp Ala Val Pro Lys Gln Tyr Ile
            20                  25                  30

Tyr Trp Tyr Gln Gln Lys Pro Gly Gln Ala Pro Ile Leu Val Ile Tyr
        35                  40                  45

Lys Asp Thr Gln Arg Pro Ser Gly Ile Pro Glu Arg Phe Ser Gly Ser
    50                  55                  60

Asn Ser Gly Thr Thr Val Thr Leu Thr Ile Thr Gly Val Gln Ala Asp
65                  70                  75                  80

Asp Glu Gly Asp Tyr Tyr Cys Gln Ser Ala Asp Ser Ser Ala Thr Trp
                85                  90                  95
```

Val Phe Gly Gly Gly Thr Lys Leu Thr Val Leu
            100                 105

<210> SEQ ID NO 29
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-302.15F9 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(201)
<223> OTHER INFORMATION: complementarity determining region (CDR)
      VH-CDR2
<220> FEATURE:
<221> NAME/KEY: V_region
<222> LOCATION: (298)..(327)
<223> OTHER INFORMATION: complementarity determining region (CDR)
      VH-CDR3

<400> SEQUENCE: 29 gag gtg cag ctg gtg gag tct ggg gga ggc ctg gtc acg ccg ggg ggg        48
Glu Val Gln Leu Val Glu Ser Gly Gly Gly Leu Val Thr Pro Gly Gly
1               5                   10                  15 tcc ctg aga ctc tcg tgt gag gcc tct gga ttt ctc ttc aag aat tct        96
Ser Leu Arg Leu Ser Cys Glu Ala Ser Gly Phe Leu Phe Lys Asn Ser
            20                  25                  30 agc atg aac tgg gtc cgt cag act ccg ggg aag ggg ctg gag tgg gtc       144
Ser Met Asn Trp Val Arg Gln Thr Pro Gly Lys Gly Leu Glu Trp Val
        35                  40                  45 tcg tcc att gac act tct gct aca aat tat aag tat tat gca gac tct       192
Ser Ser Ile Asp Thr Ser Ala Thr Asn Tyr Lys Tyr Tyr Ala Asp Ser
    50                  55                  60 gtg aag ggc cga ttt acc atc tcc agg gat gac gcc acc aac tct ctc       240
Val Lys Gly Arg Phe Thr Ile Ser Arg Asp Asp Ala Thr Asn Ser Leu
65                  70                  75                  80 tat ctg caa atg aat agc ctg cga gcc gac gac acg gct act tat tac       288
Tyr Leu Gln Met Asn Ser Leu Arg Ala Asp Asp Thr Ala Thr Tyr Tyr
                85                  90                  95 tgt gcg cga ggt tat tat acc ccc cgg gac ttt gac tac tgg ggc cag       336
Cys Ala Arg Gly Tyr Tyr Thr Pro Arg Asp Phe Asp Tyr Trp Gly Gln
            100                 105                 110 ggc acc ctg gtc acc gtc tcc tcg                                       360
Gly Thr Leu Val Thr Val Ser Ser
        115                 120

<210> SEQ ID NO 30
<211> LENGTH: 120
<212> TYPE: PRT
<213> ORGANISM: Homo sapiens

<400> SEQUENCE: 30

Glu Val Gln Leu Val Glu Ser Gly Gly Gly Leu Val Thr Pro Gly Gly
1               5                   10                  15

Ser Leu Arg Leu Ser Cys Glu Ala Ser Gly Phe Leu Phe Lys Asn Ser
            20                  25                  30

Ser Met Asn Trp Val Arg Gln Thr Pro Gly Lys Gly Leu Glu Trp Val

```
              35                  40                  45
Ser Ser Ile Asp Thr Ser Ala Thr Asn Tyr Lys Tyr Tyr Ala Asp Ser
        50                  55                  60

Val Lys Gly Arg Phe Thr Ile Ser Arg Asp Asp Ala Thr Asn Ser Leu
65                  70                  75                  80

Tyr Leu Gln Met Asn Ser Leu Arg Ala Asp Thr Ala Thr Tyr Tyr
                85                  90                  95

Cys Ala Arg Gly Tyr Tyr Thr Pro Arg Asp Phe Asp Tyr Trp Gly Gln
            100                 105                 110

Gly Thr Leu Val Thr Val Ser Ser
            115                 120

<210> SEQ ID NO 31
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.15F9 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 31 gat gtt gtg atg act cag tct cca cag acc ctg tcc gtc agc ctt gga      48
Asp Val Val Met Thr Gln Ser Pro Gln Thr Leu Ser Val Ser Leu Gly
1               5                   10                  15 cag gcg gcc tcc atc tcc tgc agg tcg agt caa agc ctc ttg tat cgt      96
Gln Ala Ala Ser Ile Ser Cys Arg Ser Ser Gln Ser Leu Leu Tyr Arg
            20                  25                  30 gat aac aac aca tac ttg aat tgg ttt cac cag agg cca ggc caa tct     144
Asp Asn Asn Thr Tyr Leu Asn Trp Phe His Gln Arg Pro Gly Gln Ser
        35                  40                  45 cca agg cgc ctc att tat agg gct tct gac cgg gac tct ggg gtc cca     192
Pro Arg Arg Leu Ile Tyr Arg Ala Ser Asp Arg Asp Ser Gly Val Pro
    50                  55                  60 gac aga ttc agc ggc ggt ggg tca ggc act gat ttc aca ttg aaa atc     240
Asp Arg Phe Ser Gly Gly Gly Ser Gly Thr Asp Phe Thr Leu Lys Ile
65                  70                  75                  80 agt gga gtg gag gct gaa gat gtt ggc act tat tac tgc atg caa gga     288
Ser Gly Val Glu Ala Glu Asp Val Gly Thr Tyr Tyr Cys Met Gln Gly
            85                  90                  95 aca cac tgg cct cgg acg ttc ggc caa ggg acc aag gtg gag atc aaa     336
Thr His Trp Pro Arg Thr Phe Gly Gln Gly Thr Lys Val Glu Ile Lys
            100                 105                 110

<210> SEQ ID NO 32
<211> LENGTH: 112
<212> TYPE: PRT
<213> ORGANISM: Homo sapiens
```

<400> SEQUENCE: 32

Asp Val Val Met Thr Gln Ser Pro Gln Thr Leu Ser Val Ser Leu Gly
1               5                   10                  15

Gln Ala Ala Ser Ile Ser Cys Arg Ser Ser Gln Ser Leu Leu Tyr Arg
            20                  25                  30

Asp Asn Asn Thr Tyr Leu Asn Trp Phe His Gln Arg Pro Gly Gln Ser
        35                  40                  45

Pro Arg Arg Leu Ile Tyr Arg Ala Ser Asp Arg Asp Ser Gly Val Pro
    50                  55                  60

Asp Arg Phe Ser Gly Gly Gly Ser Gly Thr Asp Phe Thr Leu Lys Ile
65                  70                  75                  80

Ser Gly Val Glu Ala Glu Asp Val Gly Thr Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 33
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.39G12 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 33 gag gtg cag ctg gtg cag tct ggg gga ggc ttg gtc cac cct tgg ggg    48
Glu Val Gln Leu Val Gln Ser Gly Gly Gly Leu Val His Pro Trp Gly
1               5                   10                  15 tcc ctg aga ctc tcc tgt gca gcc tct gga ttc agc gtc tct aat tac    96
Ser Leu Arg Leu Ser Cys Ala Ala Ser Gly Phe Ser Val Ser Asn Tyr
            20                  25                  30 gcc ata act tgg gtc cgc cgg gct cca ggg aag ggg ctg caa tat att   144
Ala Ile Thr Trp Val Arg Arg Ala Pro Gly Lys Gly Leu Gln Tyr Ile
        35                  40                  45 tca gta att tat cgt gat ggc agg aca tac tac gga gac tcc gtg agg   192
Ser Val Ile Tyr Arg Asp Gly Arg Thr Tyr Tyr Gly Asp Ser Val Arg
    50                  55                  60 ggc cgc ttc acc atc tct agg gac gat tcc aag aac act ctc tat ctt   240
Gly Arg Phe Thr Ile Ser Arg Asp Asp Ser Lys Asn Thr Leu Tyr Leu
65                  70                  75                  80 caa atg aac agc ctg aga ttt gag gac acg gct gtg tat tac tgt gcg   288
Gln Met Asn Ser Leu Arg Phe Glu Asp Thr Ala Val Tyr Tyr Cys Ala
                85                  90                  95 aga gcg cac ggc caa tat tac tat ggt gtg gac gtc tgg ggc caa ggg   336
Arg Ala His Gly Gln Tyr Tyr Tyr Gly Val Asp Val Trp Gly Gln Gly
            100                 105                 110

```
acc acg gtc acc gtc tcc tcg                                              357
Thr Thr Val Thr Val Ser Ser
        115
```

```
<210> SEQ ID NO 34
<211> LENGTH: 119
<212> TYPE: PRT
<213> ORGANISM: Homo sapiens

<400> SEQUENCE: 34
```

```
Glu Val Gln Leu Val Gln Ser Gly Gly Gly Leu Val His Pro Trp Gly
1               5                   10                  15

Ser Leu Arg Leu Ser Cys Ala Ala Ser Gly Phe Ser Val Ser Asn Tyr
            20                  25                  30

Ala Ile Thr Trp Val Arg Arg Ala Pro Gly Lys Gly Leu Gln Tyr Ile
        35                  40                  45

Ser Val Ile Tyr Arg Asp Gly Arg Thr Tyr Tyr Gly Asp Ser Val Arg
    50                  55                  60

Gly Arg Phe Thr Ile Ser Arg Asp Asp Ser Lys Asn Thr Leu Tyr Leu
65                  70                  75                  80

Gln Met Asn Ser Leu Arg Phe Glu Asp Thr Ala Val Tyr Tyr Cys Ala
                85                  90                  95

Arg Ala His Gly Gln Tyr Tyr Tyr Gly Val Asp Val Trp Gly Gln Gly
            100                 105                 110

Thr Thr Val Thr Val Ser Ser
        115
```

```
<210> SEQ ID NO 35
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.39G12 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 35
```

```
gat gtt gtg atg act cag tct cca ctc tcc ctg tcc gtc agc cct gga   48
Asp Val Val Met Thr Gln Ser Pro Leu Ser Leu Ser Val Ser Pro Gly
1               5                   10                  15 gag ccg gcc tcc atc tcc tgc agg tct agt cag agc ctc cta cat agt   96
Glu Pro Ala Ser Ile Ser Cys Arg Ser Ser Gln Ser Leu Leu His Ser
            20                  25                  30 aat gga tac aac tat ttg gat tgg tac cgg cag aaa cca ggg cag tct   144
Asn Gly Tyr Asn Tyr Leu Asp Trp Tyr Arg Gln Lys Pro Gly Gln Ser
        35                  40                  45 cca cag ctc ctg atc tat ttg agt tct aat cgg ccc tcc ggg gtc cct   192
Pro Gln Leu Leu Ile Tyr Leu Ser Ser Asn Arg Pro Ser Gly Val Pro
    50                  55                  60
```

```
gat agg ttc agt gcc agt gga tca ggc aca gag ttc aca ctg caa atc      240
Asp Arg Phe Ser Ala Ser Gly Ser Gly Thr Glu Phe Thr Leu Gln Ile
 65                  70                  75                  80 agc aga gtg gag gct gag gat gtt ggg gtt tat tac tgc atg caa tct      288
Ser Arg Val Glu Ala Glu Asp Val Gly Val Tyr Tyr Cys Met Gln Ser
             85                  90                  95 ctg caa acg ttc act ttc ggc gga ggg acc aaa gtg gat atc aaa          333
Leu Gln Thr Phe Thr Phe Gly Gly Gly Thr Lys Val Asp Ile Lys
        100                 105                 110
```

<210> SEQ ID NO 36
<211> LENGTH: 111
<212> TYPE: PRT
<213> ORGANISM: Homo sapiens

<400> SEQUENCE: 36

```
Asp Val Val Met Thr Gln Ser Pro Leu Ser Leu Ser Val Ser Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Arg Gln Lys Pro Gly Gln Ser
         35                  40                  45

Pro Gln Leu Leu Ile Tyr Leu Ser Ser Asn Arg Pro Ser Gly Val Pro
     50                  55                  60

Asp Arg Phe Ser Ala Ser Gly Ser Gly Thr Glu Phe Thr Leu Gln Ile
 65                  70                  75                  80

Ser Arg Val Glu Ala Glu Asp Val Gly Val Tyr Tyr Cys Met Gln Ser
             85                  90                  95

Leu Gln Thr Phe Thr Phe Gly Gly Gly Thr Lys Val Asp Ile Lys
        100                 105                 110
```

<210> SEQ ID NO 37
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-302.11A4 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(330)
<223> OTHER INFORMATION: complementarity determining region (CDR)
      VH-CDR3

<400> SEQUENCE: 37

```
gag gtg cag ctg gtg gag tct gga gga ggc ttg atc cag ccg ggg ggg      48
Glu Val Gln Leu Val Glu Ser Gly Gly Gly Leu Ile Gln Pro Gly Gly
 1               5                  10                  15 tcc ctg aga ctc tcc tgt gca gcc tct ggg ttc ccc gtc agt agc agt      96
Ser Leu Arg Leu Ser Cys Ala Ala Ser Gly Phe Pro Val Ser Ser Ser
             20                  25                  30 tac atg agc tgg gtc cgc cag gct cca gga gag ggg ctg gag tgg gtc      144
```

```
Tyr Met Ser Trp Val Arg Gln Ala Pro Gly Glu Gly Leu Glu Trp Val
         35                  40                  45 tca gtt ctt tat aga gac ggt gac aca tac tac gca gac tcc gtg cag    192
Ser Val Leu Tyr Arg Asp Gly Asp Thr Tyr Tyr Ala Asp Ser Val Gln
 50                  55                  60 ggc cga ttc acc atc tcc aga gac aat tcc cag aac acg ttc tat ctt    240
Gly Arg Phe Thr Ile Ser Arg Asp Asn Ser Gln Asn Thr Phe Tyr Leu
 65                  70                  75                  80 caa atg aac agc ctg aaa gcc gag gac acg gcc gtg tat tac tgt gcg    288
Gln Met Asn Ser Leu Lys Ala Glu Asp Thr Ala Val Tyr Tyr Cys Ala
                 85                  90                  95 ggt gat aga agg tcg tca cac tac tat tac ggt atg gac gtc tgg ggc    336
Gly Asp Arg Arg Ser Ser His Tyr Tyr Tyr Gly Met Asp Val Trp Gly
            100                 105                 110 cag ggg acc acg gtc acc gtc tcc tcg                                363
Gln Gly Thr Thr Val Thr Val Ser Ser
        115                 120

<210> SEQ ID NO 38
<211> LENGTH: 121
<212> TYPE: PRT
<213> ORGANISM: Homo sapiens

<400> SEQUENCE: 38

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Pro Val Ser Ser Ser
             20                  25                  30

Tyr Met Ser Trp Val Arg Gln Ala Pro Gly Glu Gly Leu Glu Trp Val
         35                  40                  45

Ser Val Leu Tyr Arg Asp Gly Asp Thr Tyr Tyr Ala Asp Ser Val Gln
 50                  55                  60

Gly Arg Phe Thr Ile Ser Arg Asp Asn Ser Gln Asn Thr Phe Tyr Leu
 65                  70                  75                  80

Gln Met Asn Ser Leu Lys Ala Glu Asp Thr Ala Val Tyr Tyr Cys Ala
                 85                  90                  95

Gly Asp Arg Arg Ser Ser His Tyr Tyr Tyr Gly Met Asp Val Trp Gly
            100                 105                 110

Gln Gly Thr Thr Val Thr Val Ser Ser
        115                 120

<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.11A4 VK variable light-kappa chain (VK)
      sequence
<220> FEATURE:
<221> NAME/KEY: V_region
<222> LOCATION: (70)..(105)
<223> OTHER INFORMATION: complementarity determining region (CDR)
      VK-CDR1
<220> FEATURE:
<221> NAME/KEY: V_region
<222> LOCATION: (151)..(171)
<223> OTHER INFORMATION: complementarity determining region (CDR)
      VK-CDR2
<220> FEATURE:
<221> NAME/KEY: V_region
<222> LOCATION: (268)..(291)
<223> OTHER INFORMATION: complementarity determining region (CDR)
```

VK-CDR2

<400> SEQUENCE: 39

```
gaa att gtg atg aca cag tct cca ggc acc ctg tct ttg tct cca gga      48
Glu Ile Val Met Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 tac ttc gcc tgg tac caa caa aaa cct ggc cag gct ccc agg ctc ctc     144
Tyr Phe Ala Trp Tyr Gln Gln Lys Pro Gly Gln Ala Pro Arg Leu Leu
            35                  40                  45 atc tat ggt acg tcc cgc agg gcc act gcc atc cca gac agg ttc agt     192
Ile Tyr Gly Thr Ser Arg Arg Ala Thr Ala Ile Pro Asp Arg Phe Ser
        50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                 70                  75                  80 cct gaa gat ttt gca gtg tat tac tgt caa cag tat ggt agc tcg tgg     288
Pro Glu Asp Phe Ala Val Tyr Tyr Cys Gln Gln Tyr Gly Ser Ser Trp
                85                  90                  95 acg ttc ggc cca ggg acc aag gtg gag atc aaa                         321
Thr Phe Gly Pro Gly Thr Lys Val Glu Ile Lys
            100                 105
```

<210> SEQ ID NO 40
<211> LENGTH: 107
<212> TYPE: PRT
<213> ORGANISM: Homo sapiens

<400> SEQUENCE: 40

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Phe Ala Trp Tyr Gln Gln Lys Pro Gly Gln Ala Pro Arg Leu Leu
            35                  40                  45

Ile Tyr Gly Thr Ser Arg Arg Ala Thr Ala Ile Pro Asp Arg Phe Ser
        50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Tyr Gly Ser Ser Trp
                85                  90                  95

Thr Phe Gly Pro Gly Thr Lys Val Glu Ile Lys
            100                 105
```

<210> SEQ ID NO 41
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.22H9 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)

<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 41

```
gag gtg cag ctg gtg gag tct ggg gga ggc ttg gtc cac cct tgg ggg      48
Glu Val Gln Leu Val Glu Ser Gly Gly Gly Leu Val His Pro Trp Gly
1               5                   10                  15 tcc ctg aga gtc tcc tgt gca gcc tct gga ttc agc gtc tct aat tac      96
Ser Leu Arg Val Ser Cys Ala Ala Ser Gly Phe Ser Val Ser Asn Tyr
            20                  25                  30 gcc ata act tgg gtc cgc cag gct cca ggg aag ggg ctg gaa tat att     144
Ala Ile Thr Trp Val Arg Gln Ala Pro Gly Lys Gly Leu Glu Tyr Ile
        35                  40                  45 tca gtg att tat cgt gat ggc agg aca tac tac gga gac tcc gtg agg     192
Ser Val Ile Tyr Arg Asp Gly Arg Thr Tyr Tyr Gly Asp Ser Val Arg
    50                  55                  60 ggc cgc ttc acc atc tct agg gac gat tcc aag aac act atc tat ctt     240
Gly Arg Phe Thr Ile Ser Arg Asp Asp Ser Lys Asn Thr Ile Tyr Leu
65                  70                  75                  80 caa atg aac agc ctg aga ttt gag gac acg gct gtg tat tac tgt gcg     288
Gln Met Asn Ser Leu Arg Phe Glu Asp Thr Ala Val Tyr Tyr Cys Ala
                85                  90                  95 aga gcg cac ggc caa tat tat tat ggt gtg gac gtc tgg ggc caa ggg     336
Arg Ala His Gly Gln Tyr Tyr Tyr Gly Val Asp Val Trp Gly Gln Gly
            100                 105                 110 acc acg gtc acc gtc tcc tcg                                         357
Thr Thr Val Thr Val Ser Ser
            115
```

<210> SEQ ID NO 42
<211> LENGTH: 119
<212> TYPE: PRT
<213> ORGANISM: Homo sapiens

<400> SEQUENCE: 42

```
Glu Val Gln Leu Val Glu Ser Gly Gly Gly Leu Val His Pro Trp Gly
1               5                   10                  15

Ser Leu Arg Val Ser Cys Ala Ala Ser Gly Phe Ser Val Ser Asn Tyr
            20                  25                  30

Ala Ile Thr Trp Val Arg Gln Ala Pro Gly Lys Gly Leu Glu Tyr Ile
        35                  40                  45

Ser Val Ile Tyr Arg Asp Gly Arg Thr Tyr Tyr Gly Asp Ser Val Arg
    50                  55                  60

Gly Arg Phe Thr Ile Ser Arg Asp Asp Ser Lys Asn Thr Ile Tyr Leu
65                  70                  75                  80

Gln Met Asn Ser Leu Arg Phe Glu Asp Thr Ala Val Tyr Tyr Cys Ala
                85                  90                  95

Arg Ala His Gly Gln Tyr Tyr Tyr Gly Val Asp Val Trp Gly Gln Gly
            100                 105                 110

Thr Thr Val Thr Val Ser Ser
            115
```

<210> SEQ ID NO 43
<211> LENGTH: 333
<212> TYPE: DNA
<213> ORGANISM: Homo sapiens

```
<220> FEATURE:
<221> NAME/KEY: CDS
<222> LOCATION: (1)..(333)
<223> OTHER INFORMATION: NI-302.22H9 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(303)
<223> OTHER INFORMATION: complementarity determining region (CDR)
      VK-CDR3

<400> SEQUENCE: 43 gat gtt gtg atg act cag tct cca ctc tcc ctg tcc gtc agc cct gga      48
Asp Val Val Met Thr Gln Ser Pro Leu Ser Leu Ser Val Ser Pro Gly
1               5                   10                  15 gag ccg gcc tcc atc tcc tgc agg tct agt cag agc ctc cta cat agt      96
Glu Pro Ala Ser Ile Ser Cys Arg Ser Ser Gln Ser Leu Leu His Ser
            20                  25                  30 aat gga tac aac tat ttg gat tgg tac cgg cag aaa cca ggg cag tct     144
Asn Gly Tyr Asn Tyr Leu Asp Trp Tyr Arg Gln Lys Pro Gly Gln Ser
        35                  40                  45 cca caa ctc ctg atc tat ttg aat tct aat cgg gcc tcc ggg gtc cct     192
Pro Gln Leu Leu Ile Tyr Leu Asn Ser Asn Arg Ala Ser Gly Val Pro
50                  55                  60 gat agg ttc agt ggc agt gga tca ggc aca gag ttc aca ctg aca atc     240
Asp Arg Phe Ser Gly Ser Gly Ser Gly Thr Glu Phe Thr Leu Thr Ile
65                  70                  75                  80 agc aga gtg gag gct gag gat gtt ggg gtt tat tac tgc atg caa tct     288
Ser Arg Val Glu Ala Glu Asp Val Gly Val Tyr Tyr Cys Met Gln Ser
            85                  90                  95 ctg caa acg ttc act ttc ggc gga ggg acc aag gtg gag atc aaa         333
Leu Gln Thr Phe Thr Phe Gly Gly Gly Thr Lys Val Glu Ile Lys
            100                 105                 110

<210> SEQ ID NO 44
<211> LENGTH: 111
<212> TYPE: PRT
<213> ORGANISM: Homo sapiens

<400> SEQUENCE: 44

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Arg Gln Lys Pro Gly Gln Ser
        35                  40                  45

Pro Gln Leu Leu Ile Tyr Leu Asn Ser Asn Arg Ala Ser Gly Val Pro
    50                  55                  60

Asp Arg Phe Ser Gly Ser Gly Ser Gly Thr Glu Phe Thr Leu Thr Ile
65                  70                  75                  80

Ser Arg Val Glu Ala Glu Asp Val Gly Val Tyr Tyr Cys Met Gln Ser
            85                  90                  95

Leu Gln Thr Phe Thr Phe Gly Gly Gly Thr Lys Val Glu Ile Lys
            100                 105                 110
```

<210> SEQ ID NO 45
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.44D7 VH variable heavy chain (VH) sequence
<220> FEATURE:
<221> NAME/KEY: V_region
<222> LOCATION: (91)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(324)
<223> OTHER INFORMATION: complementarity determining region (CDR) VH-CDR3

<400> SEQUENCE: 45

```
gag gtg cag ctg gtg cag tct ggg gga ggc ttg gta cag cct ggg ggg        48
Glu Val Gln Leu Val Gln Ser Gly Gly Gly Leu Val Gln Pro Gly Gly
1               5                   10                  15 tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
            20                  25                  30 gcc atg agt tgg gtc cgc cag gct cca ggg aag ggg ctg gag tgg gtc       144
Ala Met Ser Trp Val Arg Gln Ala Pro Gly Lys Gly Leu Glu Trp Val
        35                  40                  45 tca ggt att ggt tat agt gat act agc aca tat tac gca gac tcc gtg       192
Ser Gly Ile Gly Tyr Ser Asp Thr Ser Thr Tyr Tyr Ala Asp Ser Val
    50                  55                  60 aag ggc cgc ttc acc gtc tcc aga gac att tcc aag aac acg ctg tat       240
Lys Gly Arg Phe Thr Val Ser Arg Asp Ile Ser Lys Asn Thr Leu Tyr
65                  70                  75                  80 ctg caa atg aat agc ctg agg gcc gag gac acg gcc gta tat tac tgc       288
Leu Gln Met Asn Ser Leu Arg Ala Glu Asp Thr Ala Val Tyr Tyr Cys
                85                  90                  95 gcg aaa ggt acc agg gac tat tac ggt atg gac gtc tgg ggc caa ggg       336
Ala Lys Gly Thr Arg Asp Tyr Tyr Gly Met Asp Val Trp Gly Gln Gly
            100                 105                 110 aca atg gtc acc gtc tct tcg                                           357
Thr Met Val Thr Val Ser Ser
        115
```

<210> SEQ ID NO 46
<211> LENGTH: 119
<212> TYPE: PRT
<213> ORGANISM: Homo sapiens

<400> SEQUENCE: 46

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Tyr Ser Asp Thr Ser Thr Tyr Tyr Ala Asp Ser Val
```

```
                    50                  55                  60
Lys Gly Arg Phe Thr Val Ser Arg Asp Ile Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Thr Arg Asp Tyr Tyr Gly Met Asp Val Trp Gly Gln Gly
            100                 105                 110

Thr Met Val Thr Val Ser Ser
        115
```

<210> SEQ ID NO 47
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-302.44D7 VL variable light chain (VL) sequence
<220> FEATURE:
<221> NAME/KEY: V_region
<222> LOCATION: (67)..(108)
<223> OTHER INFORMATION: complementarity determining region (CDR) VL-CDR1
<220> FEATURE:
<221> NAME/KEY: V_region
<222> LOCATION: (192)..(198)
<223> OTHER INFORMATION: complementarity determining region (CDR) VL-CDR2
<220> FEATURE:
<221> NAME/KEY: V_region
<222> LOCATION: (271)..(300)
<223> OTHER INFORMATION: complementarity determining region (CDR) VL-CDR3

<400> SEQUENCE: 47

```
cag act gtg gtg act cag gag cca tcg ttc tca gtg tcc cct gga ggg    48
Gln Thr Val Val Thr Gln Glu Pro Ser Phe Ser Val Ser Pro Gly Gly
 1               5                  10                  15 aca gtc aca ctc act tgt ggc ttg agt tct ggc tca gtt tct act agt    96
Thr Val Thr Leu Thr Cys Gly Leu Ser Ser Gly Ser Val Ser Thr Ser
             20                  25                  30 tac tac ccc agc tgg tac cag cag acc cca ggc cgg gct cca cgc acg   144
Tyr Tyr Pro Ser Trp Tyr Gln Gln Thr Pro Gly Arg Ala Pro Arg Thr
         35                  40                  45 ctc atc tac agc aca aac act cgc tct tct ggg gtc cct gat cgc ttc   192
Leu Ile Tyr Ser Thr Asn Thr Arg Ser Ser Gly Val Pro Asp Arg Phe
     50                  55                  60 tct ggc tcc atc ctt ggg aac aag gct gcc ctc acc atc acg ggg gcc   240
Ser Gly Ser Ile Leu Gly Asn Lys Ala Ala Leu Thr Ile Thr Gly Ala
 65                  70                  75                  80 cag gca gat gat gaa tct gat tat tac tgt gtg ctg ttt atg ggt agt   288
Gln Ala Asp Asp Glu Ser Asp Tyr Tyr Cys Val Leu Phe Met Gly Ser
                 85                  90                  95 ggc att ggg gtg ttc ggc gga ggg acc agg ctg acc gtc cta            330
Gly Ile Gly Val Phe Gly Gly Gly Thr Arg Leu Thr Val Leu
            100                 105                 110
```

<210> SEQ ID NO 48
<211> LENGTH: 110
<212> TYPE: PRT
<213> ORGANISM: Homo sapiens

<400> SEQUENCE: 48

Gln Thr Val Val Thr Gln Glu Pro Ser Phe Ser Val Ser Pro Gly Gly

```
                1               5                   10                  15
            Thr Val Thr Leu Thr Cys Gly Leu Ser Ser Gly Ser Val Ser Thr Ser
                            20                  25                  30

Tyr Tyr Pro Ser Trp Tyr Gln Gln Thr Pro Gly Arg Ala Pro Arg Thr
                            35                  40                  45

Leu Ile Tyr Ser Thr Asn Thr Arg Ser Ser Gly Val Pro Asp Arg Phe
                        50                  55                  60

Ser Gly Ser Ile Leu Gly Asn Lys Ala Ala Leu Thr Ile Thr Gly Ala
            65                  70                  75                  80

Gln Ala Asp Asp Glu Ser Asp Tyr Tyr Cys Val Leu Phe Met Gly Ser
                            85                  90                  95

Gly Ile Gly Val Phe Gly Gly Gly Thr Arg Leu Thr Val Leu
                            100                 105                 110
```

<210> SEQ ID NO 49
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.37C12 VH variable heavy chain (VH) sequence
<220> FEATURE:
<221> NAME/KEY: V_region
<222> LOCATION: (91)..(105)
<223> OTHER INFORMATION: complementarity determining region (CDR) VH-CDR1
<220> FEATURE:
<221> NAME/KEY: V_region
<222> LOCATION: (148)..(192)
<223> OTHER INFORMATION: complementarity determining region (CDR) VH-CDR2
<220> FEATURE:
<221> NAME/KEY: V_region
<222> LOCATION: (292)..(324)
<223> OTHER INFORMATION: complementarity determining region (CDR) VH-CDR3

<400> SEQUENCE: 49

```
gag gtg cag ctg gtg gag tct ggt gga ggc ttg gtc cag cct ggg ggg        48
Glu Val Gln Leu Val Glu Ser Gly Gly Gly Leu Val Gln Pro Gly Gly
 1               5                  10                  15 tcc ctg aga ctc tct tgt gtt gcc tct gca ctc acc gtc act aac agc        96
Ser Leu Arg Leu Ser Cys Val Ala Ser Ala Leu Thr Val Thr Asn Ser
             20                  25                  30 caa atg acc tgg gtc cgc cgg gct cca ggg agg ggg ttg gag tgg gtc       144
Gln Met Thr Trp Val Arg Arg Ala Pro Gly Arg Gly Leu Glu Trp Val
         35                  40                  45 tca gtt att tac acc agt ggt agt gca tac tac gca gac tcc gtg aag       192
Ser Val Ile Tyr Thr Ser Gly Ser Ala Tyr Tyr Ala Asp Ser Val Lys
     50                  55                  60 ggc aga ttc acc atc tcc aga gac aat tcc aag aac aca gtg ttt ctt       240
Gly Arg Phe Thr Ile Ser Arg Asp Asn Ser Lys Asn Thr Val Phe Leu
65                  70                  75                  80 caa atg aac agc ctg aga gtc gaa gac acg gct gtg tat tac tgt gcg       288
Gln Met Asn Ser Leu Arg Val Glu Asp Thr Ala Val Tyr Tyr Cys Ala
                 85                  90                  95 aaa ggc cca tca gcc tat tat tac ggt ttg gac ctt tgg ggc caa ggg       336
Lys Gly Pro Ser Ala Tyr Tyr Tyr Gly Leu Asp Leu Trp Gly Gln Gly
            100                 105                 110 acc acg gtc acc gtc tcc tcg                                           357
Thr Thr Val Thr Val Ser Ser
        115
```

<210> SEQ ID NO 50
<211> LENGTH: 119
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Val Ala Ser Ala Leu Thr Val Thr Asn Ser
            20                  25                  30

Gln Met Thr Trp Val Arg Arg Ala Pro Gly Arg Gly Leu Glu Trp Val
        35                  40                  45

Ser Val Ile Tyr Thr Ser Gly Ser Ala Tyr Tyr Ala Asp Ser Val Lys
    50                  55                  60

Gly Arg Phe Thr Ile Ser Arg Asp Asn Ser Lys Asn Thr Val Phe Leu
65                  70                  75                  80

Gln Met Asn Ser Leu Arg Val Glu Asp Thr Ala Val Tyr Tyr Cys Ala
                85                  90                  95

Lys Gly Pro Ser Ala Tyr Tyr Tyr Gly Leu Asp Leu Trp Gly Gln Gly
            100                 105                 110

Thr Thr Val Thr Val Ser Ser
        115

<210> SEQ ID NO 51
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.37C12 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(303)
<223> OTHER INFORMATION: complementarity determining region (CDR)
      VK-CDR3

<400> SEQUENCE: 51 gat att gtg atg act caa tca cca ctc tcc ctg ccc gtc acc cct gga    48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30 aat gga tac aac tat ttg gat tgg tac ctg cag aag ccg ggg cag tct   144
Asn Gly Tyr Asn Tyr Leu Asp Trp Tyr Leu Gln Lys Pro Gly Gln Ser
        35                  40                  45 cca cag ctc ctg atc tat ttg ggt tct act cgg gcc tcc ggg gtc cct   192
Pro Gln Leu Leu Ile Tyr Leu Gly Ser Thr Arg Ala Ser Gly Val Pro
    50                  55                  60 gac agg ttc agt ggc agt gga tca ggc aca gat ttt aca ctg aag atc   240
Asp Arg Phe Ser Gly Ser Gly Ser Gly Thr Asp Phe Thr Leu Lys Ile

```
                65                  70                  75                  80
agc aga gtg gag gct gag gat gtt ggg gtt tat tac tgc atg caa ggt        288
Ser Arg Val Glu Ala Glu Asp Val Gly Val Tyr Tyr Cys Met Gln Gly
                    85                  90                  95 cta cag acg tac act ttt ggc cag ggg acc aag ctg gag atc aaa            333
Leu Gln Thr Tyr Thr Phe Gly Gln Gly Thr Lys Leu Glu Ile Lys
            100                 105                 110

<210> SEQ ID NO 52
<211> LENGTH: 111
<212> TYPE: PRT
<213> ORGANISM: Homo sapiens

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Tyr Thr Phe Gly Gln Gly Thr Lys Leu Glu Ile Lys
            100                 105                 110

<210> SEQ ID NO 53
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-302.55D8 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(213)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3

<400> SEQUENCE: 53 cag gtg cag ctg gtg cag tct ggg tct gag gtg aag aag cct ggg gcc        48
Gln Val Gln Leu Val Gln Ser Gly Ser Glu Val Lys Lys Pro Gly Ala
1               5                   10                  15 tca gtg aag gtc tcc tgc aag gct tct gga tac acc ttc acc gac tac        96
Ser Val Lys Val Ser Cys Lys Ala Ser Gly Tyr Thr Phe Thr Asp Tyr
            20                  25                  30 tat ata cac tgg gtg cga cag gcc cct gga caa ggg ctt gag tgg atg       144
Tyr Ile His Trp Val Arg Gln Ala Pro Gly Gln Gly Leu Glu Trp Met
        35                  40                  45
```

```
gga cgg atc aac cct aac aat ggt ggc aca aac tat gca cag aac ttt      192
Gly Arg Ile Asn Pro Asn Asn Gly Gly Thr Asn Tyr Ala Gln Asn Phe
 50                  55                  60 cag ggc tgg gtc acc atg acc agg gac acg tcc atc agc aca gcc tac      240
Gln Gly Trp Val Thr Met Thr Arg Asp Thr Ser Ile Ser Thr Ala Tyr
 65                  70                  75                  80 atg gag ctc agc aga ctg aga tct gac gac acg gcc gtc tat tac tgt      288
Met Glu Leu Ser Arg Leu Arg Ser Asp Asp Thr Ala Val Tyr Tyr Cys
                 85                  90                  95 gcg aga gtg ggg ggc gag ctg cta cga gaa ggc ggt tat cac tac tac      336
Ala Arg Val Gly Gly Glu Leu Leu Arg Glu Gly Gly Tyr His Tyr Tyr
            100                 105                 110 atg gac gtc tgg ggc aag ggg acc acg gtc acc gtc tcc tcg              378
Met Asp Val Trp Gly Lys Gly Thr Thr Val Thr Val Ser Ser
            115                 120                 125

<210> SEQ ID NO 54
<211> LENGTH: 126
<212> TYPE: PRT
<213> ORGANISM: Homo sapiens

<400> SEQUENCE: 54

Gln Val Gln Leu Val Gln Ser Gly Ser Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Arg Ile Asn Pro Asn Asn Gly Gly Thr Asn Tyr Ala Gln Asn Phe
 50                  55                  60

Gln Gly Trp Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Val Gly Gly Glu Leu Leu Arg Glu Gly Gly Tyr His Tyr Tyr
            100                 105                 110

Met Asp Val Trp Gly Lys Gly Thr Thr Val Thr Val Ser Ser
            115                 120                 125

<210> SEQ ID NO 55
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.55D8 VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(306)
<223> OTHER INFORMATION: complementarity determining region (CDR)
      VL-CDR3

<400> SEQUENCE: 55
```

```
cag tct gtg ttg acg cag ccg ccc tca gtg tct ggg gcc cca ggg cag        48
Gln Ser Val Leu Thr Gln Pro Pro Ser Val Ser Gly Ala Pro Gly Gln
1               5                   10                  15 agg gtc acc atc tcc tgc act ggg aac agc tcc aac atc ggg gca ggt        96
Arg Val Thr Ile Ser Cys Thr Gly Asn Ser Ser Asn Ile Gly Ala Gly
                20                  25                  30 tat gat gta cac tgg tac cag cag ctt cca gga aca gcc ccc aaa ctc       144
Tyr Asp Val His Trp Tyr Gln Gln Leu Pro Gly Thr Ala Pro Lys Leu
            35                  40                  45 ctc atc ttt gat aat acc aat cgg ccc tca ggg gtc cct gac cga ttc       192
Leu Ile Phe Asp Asn Thr Asn Arg Pro Ser Gly Val Pro Asp Arg Phe
        50                  55                  60 tct ggc tcc aag tct ggc acc tca gcc tcc ctg gcc atc act ggg ctc       240
Ser Gly Ser Lys Ser Gly Thr Ser Ala Ser Leu Ala Ile Thr Gly Leu
65                  70                  75                  80 cag gct gag gat gag gct aat tat cac tgc cag tcc tat gac aac agc       288
Gln Ala Glu Asp Glu Ala Asn Tyr His Cys Gln Ser Tyr Asp Asn Ser
                85                  90                  95 ctg agt ggt tct tgg gtg ttc ggc gga ggg acc aag ctg acc gtc cta       336
Leu Ser Gly Ser Trp Val Phe Gly Gly Gly Thr Lys Leu Thr Val Leu
                100                 105                 110
```

<210> SEQ ID NO 56
<211> LENGTH: 112
<212> TYPE: PRT
<213> ORGANISM: Homo sapiens

<400> SEQUENCE: 56

```
Gln Ser Val Leu Thr Gln Pro Pro Ser Val Ser Gly Ala Pro Gly Gln
1               5                   10                  15

Arg Val Thr Ile Ser Cys Thr Gly Asn Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Phe Asp Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asn Tyr His Cys Gln Ser Tyr Asp Asn Ser
                85                  90                  95

Leu Ser Gly Ser Trp Val Phe Gly Gly Gly Thr Lys Leu Thr Val Leu
                100                 105                 110
```

<210> SEQ ID NO 57
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-302.7A8 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:

```
<221> NAME/KEY: V_region
<222> LOCATION: (295)..(336)
<223> OTHER INFORMATION: complementarity determining region (CDR)
      VH-CDR3

<400> SEQUENCE: 57 gag gtg cag ctg gtg gag tct ggg gga ggc tcg gtc cag cct ggg ggg       48
Glu Val Gln Leu Val Glu Ser Gly Gly Gly Ser Val Gln Pro Gly Gly
1               5                   10                  15 tcc ctg aga ctc tcc tgt gta gcc tct gga ttc ata ttt aga aac agt       96
Ser Leu Arg Leu Ser Cys Val Ala Ser Gly Phe Ile Phe Arg Asn Ser
            20                  25                  30 tgg atg acc tgg gtc cgc cag gat cca ggg aag ggg ctg gag tgg gtg      144
Trp Met Thr Trp Val Arg Gln Asp Pro Gly Lys Gly Leu Glu Trp Val
        35                  40                  45 gcc aac ata aag gaa gat gga agt cgg aca tac tat gtg gac tct gtg      192
Ala Asn Ile Lys Glu Asp Gly Ser Arg Thr Tyr Tyr Val Asp Ser Val
50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
65                  70                  75                  80 ctg cag atg aac agc ctg aga gcc gag gac acg gct gta tat tac tgt      288
Leu Gln Met Asn Ser Leu Arg Ala Glu Asp Thr Ala Val Tyr Tyr Cys
                85                  90                  95 gcg aga gga gat tat aat tcg ggc atc tat tac ttt ccc ggg gac tac      336
Ala Arg Gly Asp Tyr Asn Ser Gly Ile Tyr Tyr Phe Pro Gly Asp Tyr
            100                 105                 110 tgg ggc cag ggc acc ctg gtc acc gtc tcc tcg                          369
Trp Gly Gln Gly Thr Leu Val Thr Val Ser Ser
        115                 120

<210> SEQ ID NO 58
<211> LENGTH: 123
<212> TYPE: PRT
<213> ORGANISM: Homo sapiens

<400> SEQUENCE: 58

Glu Val Gln Leu Val Glu Ser Gly Gly Gly Ser Val Gln Pro Gly Gly
1               5                   10                  15

Ser Leu Arg Leu Ser Cys Val Ala Ser Gly Phe Ile Phe Arg Asn Ser
            20                  25                  30

Trp Met Thr Trp Val Arg Gln Asp Pro Gly Lys Gly Leu Glu Trp Val
        35                  40                  45

Ala Asn Ile Lys Glu Asp Gly Ser Arg Thr Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Asn Ser Gly Ile Tyr Tyr Phe Pro Gly Asp Tyr
            100                 105                 110

Trp Gly Gln Gly Thr Leu Val Thr Val Ser Ser
        115                 120

<210> SEQ ID NO 59
<211> LENGTH: 336
<212> TYPE: DNA
<213> ORGANISM: Homo sapiens
<220> FEATURE:
<221> NAME/KEY: CDS
<222> LOCATION: (1)..(336)
```

```
<223> OTHER INFORMATION: NI-302.7A8 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 59 gat gtt gtg atg act cag tct cca ctc tcc ctg ccc gtc acc ctt gga        48
Asp Val Val Met Thr Gln Ser Pro Leu Ser Leu Pro Val Thr Leu Gly
1               5                   10                  15 cag ccg gcc tcc atc tcc tgt agg tct agt caa agc ctc gta tac agt        96
Gln Pro Ala Ser Ile Ser Cys Arg Ser Ser Gln Ser Leu Val Tyr Ser
            20                  25                  30 gat gga aac acc tac ttg aat tgg ttt cag cag agg cca ggc cag tct       144
Asp Gly Asn Thr Tyr Leu Asn Trp Phe Gln Gln Arg Pro Gly Gln Ser
        35                  40                  45 cca agg cgc ctc att tat aag gtt tct aac cgg gac tct ggg gtc cca       192
Pro Arg Arg Leu Ile Tyr Lys Val Ser Asn Arg Asp Ser Gly Val Pro
    50                  55                  60 gac aga ttc agc ggc agt ggg tca ggc act gat ttc aca ctg aga atc       240
Asp Arg Phe Ser Gly Ser Gly Ser Gly Thr Asp Phe Thr Leu Arg Ile
65                  70                  75                  80 agc agg gtg gag gct gag gat gtt ggc att tat tac tgc atg caa ggt       288
Ser Arg Val Glu Ala Glu Asp Val Gly Ile Tyr Tyr Cys Met Gln Gly
                85                  90                  95 aca cac tgg cct ggg acg ttc ggc caa ggg acc aag gtg gag atc aaa       336
Thr His Trp Pro Gly Thr Phe Gly Gln Gly Thr Lys Val Glu Ile Lys
            100                 105                 110

<210> SEQ ID NO 60
<211> LENGTH: 112
<212> TYPE: PRT
<213> ORGANISM: Homo sapiens

<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Thr His Trp Pro Gly Thr Phe Gly Gln Gly Thr Lys Val Glu Ile Lys
            100                 105                 110

<210> SEQ ID NO 61
```

```
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-302.78H12 VH variable heavy chain (VH)
      sequence
<220> FEATURE:
<221> NAME/KEY: V_region
<222> LOCATION: (91)..(108)
<223> OTHER INFORMATION: complementarity determining region (CDR)
      VH-CDR1
<220> FEATURE:
<221> NAME/KEY: V_region
<222> LOCATION: (151)..(198)
<223> OTHER INFORMATION: complementarity determining region (CDR)
      VH-CDR2
<220> FEATURE:
<221> NAME/KEY: V_region
<222> LOCATION: (295)..(348)
<223> OTHER INFORMATION: complementarity determining region (CDR)
      VH-CDR3

<400> SEQUENCE: 61 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgt ctt gtc tct agt tac tcc atc agc aat ggt      96
Thr Leu Ser Leu Thr Cys Leu Val Ser Ser Tyr Ser Ile Ser Asn Gly
            20                  25                  30 tac tac tgg ggc tgg att cgg cag ccc cca ggg aag ggg ctg gag tgg     144
Tyr Tyr Trp Gly Trp Ile Arg Gln Pro Pro Gly Lys Gly Leu Glu Trp
        35                  40                  45 att ggg agt atc tat cat aat ggg aac acc tat tac aac ccg tcc ctc     192
Ile Gly Ser Ile Tyr His Asn Gly Asn Thr Tyr Tyr Asn Pro Ser Leu
    50                  55                  60 aag agt cga gtc atc att tca gta gac acg tcc aag aac cag ttc tcc     240
Lys Ser Arg Val Ile Ile Ser Val Asp Thr Ser Lys Asn Gln Phe Ser
65                  70                  75                  80 ctg aag ttg agg tct gtg acc gcc gca gac acg gcc gtg tac tac tgt     288
Leu Lys Leu Arg Ser Val Thr Ala Ala Asp Thr Ala Val Tyr Tyr Cys
                85                  90                  95 gcg atg cca agt gcc acc tat tat tat ggt tcg ggg act caa ttc cat     336
Ala Met Pro Ser Ala Thr Tyr Tyr Tyr Gly Ser Gly Thr Gln Phe His
            100                 105                 110 gcg ttt gat gtc tgg ggc caa ggg acc acg gtc acc gtc tcc tcg         381
Ala Phe Asp Val Trp Gly Gln Gly Thr Thr Val Thr Val Ser Ser
        115                 120                 125

<210> SEQ ID NO 62
<211> LENGTH: 127
<212> TYPE: PRT
<213> ORGANISM: Homo sapiens

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Leu Val Ser Ser Tyr Ser Ile Ser Asn Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Asn Gly Asn Thr Tyr Tyr Asn Pro Ser Leu
    50                  55                  60

Lys Ser Arg Val Ile Ile Ser Val Asp Thr Ser Lys Asn Gln Phe Ser
```

```
                   65                  70                  75                  80
Leu Lys Leu Arg Ser Val Thr Ala Ala Asp Thr Ala Val Tyr Tyr Cys
                            85                  90                  95

Ala Met Pro Ser Ala Thr Tyr Tyr Gly Ser Gly Thr Gln Phe His
                100                 105                 110

Ala Phe Asp Val Trp Gly Gln Gly Thr Thr Val Thr Val Ser Ser
            115                 120                 125

<210> SEQ ID NO 63
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.78H12 VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(303)
<223> OTHER INFORMATION: complementarity determining region (CDR)
      VL-CDR3

<400> SEQUENCE: 63 cag tct gcc ctg act cag cct cgc tca gtg tcc ggg tct cct gga cag      48
Gln Ser Ala Leu Thr Gln Pro Arg Ser Val Ser Gly Ser Pro Gly Gln
1               5                   10                  15 tca gtc acc atc tcc tgc act gga acc agc aga gat gtt ggt aat tat     96
Ser Val Thr Ile Ser Cys Thr Gly Thr Ser Arg Asp Val Gly Asn Tyr
            20                  25                  30 aac tat gtc tcc tgg tac caa caa cac cca ggc gaa gtc ccc aaa ctc    144
Asn Tyr Val Ser Trp Tyr Gln Gln His Pro Gly Glu Val Pro Lys Leu
        35                  40                  45 ata att tat gat gtc agt gag cgg ccc tca ggg gtc cct gat cgc ttc    192
Ile Ile Tyr Asp Val Ser Glu Arg Pro Ser Gly Val Pro Asp Arg Phe
    50                  55                  60 tct ggc tcc aag tct ggc aac acg gcc tcg ctg acc atc tct ggg ctc    240
Ser Gly Ser Lys Ser Gly Asn Thr Ala Ser Leu Thr Ile Ser Gly Leu
65                  70                  75                  80 cag gct gag gat gag gct gac tat tac tgc tgc tca tat gct ggc agt    288
Gln Ala Glu Asp Glu Ala Asp Tyr Tyr Cys Cys Ser Tyr Ala Gly Ser
                85                  90                  95 tac acc ttc gag gta ttt ggc gga ggg acc aag ctg acc gtc cta        333
Tyr Thr Phe Glu Val Phe Gly Gly Gly Thr Lys Leu Thr Val Leu
            100                 105                 110

<210> SEQ ID NO 64
<211> LENGTH: 111
<212> TYPE: PRT
<213> ORGANISM: Homo sapiens

<400> SEQUENCE: 64

Gln Ser Ala Leu Thr Gln Pro Arg Ser Val Ser Gly Ser Pro Gly Gln
1               5                   10                  15

Ser Val Thr Ile Ser Cys Thr Gly Thr Ser Arg Asp Val Gly Asn Tyr
```

```
                    20                  25                  30
Asn Tyr Val Ser Trp Tyr Gln Gln His Pro Gly Glu Val Pro Lys Leu
                35                  40                  45

Ile Ile Tyr Asp Val Ser Glu Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Glu Val Phe Gly Gly Gly Thr Lys Leu Thr Val Leu
                100                 105                 110

<210> SEQ ID NO 65
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-302.71F6 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(327)
<223> OTHER INFORMATION: complementarity determining region (CDR)
      VH-CDR3

<400> SEQUENCE: 65 cag gtg cag cta cag cag tgg ggc gca gga cta ttg aag cct tcg gag      48
Gln Val Gln Leu Gln Gln Trp Gly Ala Gly Leu Leu Lys Pro Ser Glu
1               5                   10                  15 acc ctg tcc ctc acg tgc gct gtc tat ggt ggg tcc ctc agt ggt tac      96
Thr Leu Ser Leu Thr Cys Ala Val Tyr Gly Gly Ser Leu Ser Gly Tyr
                20                  25                  30 tac tgg agc tgg atc cgc cag ccc cca ggg aag ggg ctg gag tgg ata     144
Tyr Trp Ser Trp Ile Arg Gln Pro Pro Gly Lys Gly Leu Glu Trp Ile
            35                  40                  45 ggg gaa gtc aat cat agt gga ggc acc aac ctc aat tcg tcc ctc aag     192
Gly Glu Val Asn His Ser Gly Gly Thr Asn Leu Asn Ser Ser Leu Lys
        50                  55                  60 agt cga gtc atc att tca gta gac aag tcc aag aag cag ttc tcc ctg     240
Ser Arg Val Ile Ile Ser Val Asp Lys Ser Lys Lys Gln Phe Ser Leu
65                  70                  75                  80 aaa ctg agc tct gtg acc gcc gcg gac acg gct atg tac ttc tgt gcg     288
Lys Leu Ser Ser Val Thr Ala Ala Asp Thr Ala Met Tyr Phe Cys Ala
                85                  90                  95 aga gga tac agc tat gac cca aaa tac tac ttt gac tcc tgg agc cag     336
Arg Gly Tyr Ser Tyr Asp Pro Lys Tyr Tyr Phe Asp Ser Trp Ser Gln
            100                 105                 110 ggc acc ctg gtc acc gtc tcc tcg                                     360
Gly Thr Leu Val Thr Val Ser Ser
        115                 120

<210> SEQ ID NO 66
```

-continued

```
<211> LENGTH: 120
<212> TYPE: PRT
<213> ORGANISM: Homo sapiens

<400> SEQUENCE: 66

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Glu Val Asn His Ser Gly Gly Thr Asn Leu Asn Ser Ser Leu Lys
    50                  55                  60

Ser Arg Val Ile Ile Ser Val Asp Lys Ser Lys Lys Gln Phe Ser Leu
65                  70                  75                  80

Lys Leu Ser Ser Val Thr Ala Ala Asp Thr Ala Met Tyr Phe Cys Ala
                85                  90                  95

Arg Gly Tyr Ser Tyr Asp Pro Lys Tyr Tyr Phe Asp Ser Trp Ser Gln
            100                 105                 110

Gly Thr Leu Val Thr Val Ser Ser
        115                 120

<210> SEQ ID NO 67
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-302.71F6 VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 67 cag tct gcc ctg act cag cct gcc tcc gtg tct ggg tct cct gga cag      48
Gln Ser Ala Leu Thr Gln Pro Ala Ser Val Ser Gly Ser Pro Gly Gln
1               5                   10                  15 gcg atc acc atc tcc tgc act gga acc agt agt gat att ggg agt tat      96
Ala Ile Thr Ile Ser Cys Thr Gly Thr Ser Ser Asp Ile Gly Ser Tyr
            20                  25                  30 gat ttt gtc tcc tgg tac cag cag gac cca ggc aaa gcc ccc aaa gtc     144
Asp Phe Val Ser Trp Tyr Gln Gln Asp Pro Gly Lys Ala Pro Lys Val
        35                  40                  45 att att tat ggg gtc aat aag cgg ccc tca ggg gtt tct aat cgc ttc     192
Ile Ile Tyr Gly Val Asn Lys Arg Pro Ser Gly Val Ser Asn Arg Phe
    50                  55                  60 tct ggc tcc aag tct ggc aac acg gcc tcc ctg aca atc tct gga ctc     240
Ser Gly Ser Lys Ser Gly Asn Thr Ala Ser Leu Thr Ile Ser Gly Leu
65                  70                  75                  80 cag gct gac gac gag gct gat tat tac tgc tgc tca tat gct ggt agt     288
Gln Ala Asp Asp Glu Ala Asp Tyr Tyr Cys Cys Ser Tyr Ala Gly Ser
```

```
Gln Ala Asp Asp Glu Ala Asp Tyr Tyr Cys Cys Ser Tyr Ala Gly Ser
                85                  90                  95 acc act tgg gtg ttc ggc gga ggg acc aaa ctg acc gtc cta           330
Thr Thr Trp Val Phe Gly Gly Gly Thr Lys Leu Thr Val Leu
            100                 105                 110
```

<210> SEQ ID NO 68
<211> LENGTH: 110
<212> TYPE: PRT
<213> ORGANISM: Homo sapiens

<400> SEQUENCE: 68

```
Gln Ser Ala Leu Thr Gln Pro Ala Ser Val Ser Gly Ser Pro Gly Gln
1               5                   10                  15

Ala Ile Thr Ile Ser Cys Thr Gly Thr Ser Ser Asp Ile Gly Ser Tyr
            20                  25                  30

Asp Phe Val Ser Trp Tyr Gln Gln Asp Pro Gly Lys Ala Pro Lys Val
        35                  40                  45

Ile Ile Tyr Gly Val Asn Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Ala Gly Ser
                85                  90                  95

Thr Thr Trp Val Phe Gly Gly Gly Thr Lys Leu Thr Val Leu
            100                 105                 110
```

<210> SEQ ID NO 69
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-302.11H6 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 69

```
gag gtg cag ctg gtg cag tct gga gct gtg atg aag aag cct gga gac    48
Glu Val Gln Leu Val Gln Ser Gly Ala Val Met Lys Lys Pro Gly Asp
1               5                   10                  15 tca gtg agg gtc tcc tgc agg gct tct act tac agc ttt tcc acc tat   96
Ser Val Arg Val Ser Cys Arg Ala Ser Thr Tyr Ser Phe Ser Thr Tyr
            20                  25                  30 agt ttc acc tgg gtg cga cag gtc cct gga caa ggc ctt gag tgg atg  144
Ser Phe Thr Trp Val Arg Gln Val Pro Gly Gln Gly Leu Glu Trp Met
        35                  40                  45 gga tgg atc agc gct tat aat ggt cac aca aac tat gta gac agc ttc  192
Gly Trp Ile Ser Ala Tyr Asn Gly His Thr Asn Tyr Val Asp Ser Phe
50                  55                  60
```

```
cag ggc aga ctc acg ttg acc aca gac aca tcc gcg agt aca gcg tac      240
Gln Gly Arg Leu Thr Leu Thr Thr Asp Thr Ser Ala Ser Thr Ala Tyr
 65                  70                  75                  80 atg gaa ctg agg agc ctc aga tct gac gac acg gcc atc tat tat tgt      288
Met Glu Leu Arg Ser Leu Arg Ser Asp Asp Thr Ala Ile Tyr Tyr Cys
                 85                  90                  95 gcg gct gta gac acc act tac tac tat tac ggc atg gac gtc tgg ggc      336
Ala Ala Val Asp Thr Thr Tyr Tyr Tyr Tyr Gly Met Asp Val Trp Gly
                100                 105                 110 caa ggc acc ctg gtc acc gtc tcc tcg                                  363
Gln Gly Thr Leu Val Thr Val Ser Ser
        115                 120

<210> SEQ ID NO 70
<211> LENGTH: 121
<212> TYPE: PRT
<213> ORGANISM: Homo sapiens

<400> SEQUENCE: 70

Glu Val Gln Leu Val Gln Ser Gly Ala Val Met Lys Lys Pro Gly Asp
 1               5                  10                  15

Ser Val Arg Val Ser Cys Arg Ala Ser Thr Tyr Ser Phe Ser Thr Tyr
             20                  25                  30

Ser Phe Thr Trp Val Arg Gln Val Pro Gly Gln Gly Leu Glu Trp Met
         35                  40                  45

Gly Trp Ile Ser Ala Tyr Asn Gly His Thr Asn Tyr Val Asp Ser Phe
     50                  55                  60

Gln Gly Arg Leu Thr Leu Thr Thr Asp Thr Ser Ala Ser Thr Ala Tyr
 65                  70                  75                  80

Met Glu Leu Arg Ser Leu Arg Ser Asp Asp Thr Ala Ile Tyr Tyr Cys
                 85                  90                  95

Ala Ala Val Asp Thr Thr Tyr Tyr Tyr Tyr Gly Met Asp Val Trp Gly
                100                 105                 110

Gln Gly Thr Leu Val Thr Val Ser Ser
        115                 120

<210> SEQ ID NO 71
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-302.11H6 VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 71 cag act gtg gtg act cag gag cca acg ttc tca gtg tcc cct gga ggg       48
Gln Thr Val Val Thr Gln Glu Pro Thr Phe Ser Val Ser Pro Gly Gly
```

```
      1               5                  10                 15
aca gtc aca ctc act tgt gcc ttg agg ttt ggc tca gtc tct agt agc          96
Thr Val Thr Leu Thr Cys Ala Leu Arg Phe Gly Ser Val Ser Ser Ser
             20                  25                  30 tac tat ccc agc tgg ttc cag cag acc cca ggc cag gct cca cgc acg        144
Tyr Tyr Pro Ser Trp Phe Gln Gln Thr Pro Gly Gln Ala Pro Arg Thr
             35                  40                  45 ctc atc tac agc aca aac acc cgc tct tcg ggg gtc cct gct cga ttc        192
Leu Ile Tyr Ser Thr Asn Thr Arg Ser Ser Gly Val Pro Ala Arg Phe
             50                  55                  60 tct ggc tcc att ctt ggg aac aaa gct gcc ctc acc atc gcg ggg gcc        240
Ser Gly Ser Ile Leu Gly Asn Lys Ala Ala Leu Thr Ile Ala Gly Ala
 65              70                  75                  80 cag gca aat gat gag gct gac tat tac tgt gtg ctg tat atg ggt agt        288
Gln Ala Asn Asp Glu Ala Asp Tyr Tyr Cys Val Leu Tyr Met Gly Ser
                 85                  90                  95 gga atc ggg gtg ttc ggc gga ggg acc aag ttg acc gtc cta              330
Gly Ile Gly Val Phe Gly Gly Gly Thr Lys Leu Thr Val Leu
                100                 105                 110
```

<210> SEQ ID NO 72
<211> LENGTH: 110
<212> TYPE: PRT
<213> ORGANISM: Homo sapiens

<400> SEQUENCE: 72

```
Gln Thr Val Val Thr Gln Glu Pro Thr Phe Ser Val Ser Pro Gly Gly
 1               5                  10                  15

Thr Val Thr Leu Thr Cys Ala Leu Arg Phe Gly Ser Val Ser Ser Ser
             20                  25                  30

Tyr Tyr Pro Ser Trp Phe Gln Gln Thr Pro Gly Gln Ala Pro Arg Thr
             35                  40                  45

Leu Ile Tyr Ser Thr Asn Thr Arg Ser Ser Gly Val Pro Ala Arg Phe
             50                  55                  60

Ser Gly Ser Ile Leu Gly Asn Lys Ala Ala Leu Thr Ile Ala Gly Ala
 65              70                  75                  80

Gln Ala Asn Asp Glu Ala Asp Tyr Tyr Cys Val Leu Tyr Met Gly Ser
                 85                  90                  95

Gly Ile Gly Val Phe Gly Gly Gly Thr Lys Leu Thr Val Leu
                100                 105                 110
```

<210> SEQ ID NO 73
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.3D8 VH variable heavy chain (VH) sequence
<220> FEATURE:
<221> NAME/KEY: V_region
<222> LOCATION: (88)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(324)
<223> OTHER INFORMATION: complementarity determining region (CDR)

```
        VH-CDR3

<400> SEQUENCE: 73 gag gtg cag ctg gtg cag tct ggg gga ggc ttg gta cag cct ggg ggg      48
Glu Val Gln Leu Val Gln Ser Gly Gly Gly Leu Val Gln Pro Gly Gly
1               5                   10                  15 tcc ctg aga ctc tct tgt gaa gcc tcc gga ttc atc ttt aaa acc tat      96
Ser Leu Arg Leu Ser Cys Glu Ala Ser Gly Phe Ile Phe Lys Thr Tyr
            20                  25                  30 gcc atg agc tgg gtc cgc cag ctt ccc ggg agg ggg ctg gaa tgg gtc     144
Ala Met Ser Trp Val Arg Gln Leu Pro Gly Arg Gly Leu Glu Trp Val
        35                  40                  45 tca gct ata agt gcc act ggt gga agc acc ttc tac gca gag tcc gtg     192
Ser Ala Ile Ser Ala Thr Gly Gly Ser Thr Phe Tyr Ala Glu Ser Val
    50                  55                  60 aag ggc cgg ctc acc att tcc aga gac act gcc aag aat aca gtg tat     240
Lys Gly Arg Leu Thr Ile Ser Arg Asp Thr Ala Lys Asn Thr Val Tyr
65                  70                  75                  80 ctg caa atg aac aac ctg aga gcc gaa gac acg gcc atg tat tac tgt     288
Leu Gln Met Asn Asn Leu Arg Ala Glu Asp Thr Ala Met Tyr Tyr Cys
                85                  90                  95 gcg aaa ggg tcg act gcg gta tat ctc ttt gac tcc tgg ggc cag gga     336
Ala Lys Gly Ser Thr Ala Val Tyr Leu Phe Asp Ser Trp Gly Gln Gly
            100                 105                 110 acc ctg gtc acc gtc tcc tcg                                         357
Thr Leu Val Thr Val Ser Ser
            115

<210> SEQ ID NO 74
<211> LENGTH: 119
<212> TYPE: PRT
<213> ORGANISM: Homo sapiens

<400> SEQUENCE: 74

Glu Val Gln Leu Val Gln Ser Gly Gly Gly Leu Val Gln Pro Gly Gly
1               5                   10                  15

Ser Leu Arg Leu Ser Cys Glu Ala Ser Gly Phe Ile Phe Lys Thr Tyr
            20                  25                  30

Ala Met Ser Trp Val Arg Gln Leu Pro Gly Arg Gly Leu Glu Trp Val
        35                  40                  45

Ser Ala Ile Ser Ala Thr Gly Gly Ser Thr Phe Tyr Ala Glu Ser Val
    50                  55                  60

Lys Gly Arg Leu Thr Ile Ser Arg Asp Thr Ala Lys Asn Thr Val Tyr
65                  70                  75                  80

Leu Gln Met Asn Asn Leu Arg Ala Glu Asp Thr Ala Met Tyr Tyr Cys
                85                  90                  95

Ala Lys Gly Ser Thr Ala Val Tyr Leu Phe Asp Ser Trp Gly Gln Gly
            100                 105                 110

Thr Leu Val Thr Val Ser Ser
            115

<210> SEQ ID NO 75
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.3D8 VK variable light-kappa chain (VK)
      sequence
<220> FEATURE:
```

```
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 75 gac atc cag atg acc cag tct ccg tcc tca ctg tct gca tct gta ggg    48
Asp Ile Gln Met Thr Gln Ser Pro Ser Ser Leu Ser Ala Ser Val Gly
1               5                   10                  15 gac aga gtc acc ctc act tgt cgg gcg agt cag gac atc aga aat ttc    96
Asp Arg Val Thr Leu Thr Cys Arg Ala Ser Gln Asp Ile Arg Asn Phe
            20                  25                  30 ttg gcc tgg att cag cag aag cca ggg aaa ccc cct aag tcc ctg atc   144
Leu Ala Trp Ile Gln Gln Lys Pro Gly Lys Pro Pro Lys Ser Leu Ile
        35                  40                  45 tat gct gcg tcc act ttg caa agt ggg gtc cca tca cga ttc agc ggc   192
Tyr Ala Ala Ser Thr Leu Gln Ser Gly Val Pro Ser Arg Phe Ser Gly
    50                  55                  60 agt gga tcc ggg aca gat ttc act ctc acc atc agc agc ctg cac cct   240
Ser Gly Ser Gly Thr Asp Phe Thr Leu Thr Ile Ser Ser Leu His Pro
65                  70                  75                  80 gaa gat ttt gct act tat tac tgc cag cag ttt tat aat tac cct ccg   288
Glu Asp Phe Ala Thr Tyr Tyr Cys Gln Gln Phe Tyr Asn Tyr Pro Pro
                85                  90                  95 acg ttc ggc caa ggg acc aag gtg gag atc aaa                       321
Thr Phe Gly Gln Gly Thr Lys Val Glu Ile Lys
            100                 105

<210> SEQ ID NO 76
<211> LENGTH: 107
<212> TYPE: PRT
<213> ORGANISM: Homo sapiens

<400> SEQUENCE: 76

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Arg Asn Phe
            20                  25                  30

Leu Ala Trp Ile Gln Gln Lys Pro Gly Lys Pro Pro Lys Ser Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Phe Tyr Asn Tyr Pro Pro
                85                  90                  95

Thr Phe Gly Gln Gly Thr Lys Val Glu Ile Lys
            100                 105

<210> SEQ ID NO 77
<211> LENGTH: 360
<212> TYPE: DNA
<213> ORGANISM: Homo sapiens
```

```
<220> FEATURE:
<221> NAME/KEY: CDS
<222> LOCATION: (1)..(360)
<223> OTHER INFORMATION: NI-302.18A1 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(327)
<223> OTHER INFORMATION: complementarity determining region (CDR)
      VH-CDR3

<400> SEQUENCE: 77 cag ctg cag ctg cag gag tcg ggc cca gga cta gtg aag cct tcg gag    48
Gln Leu Gln Leu Gln Glu Ser Gly Pro Gly Leu Val Lys Pro Ser Glu
1               5                   10                  15 gcc ctg tcc ctc acc tgc act gtc tct ggt ggc tcc atc act act gat    96
Ala Leu Ser Leu Thr Cys Thr Val Ser Gly Gly Ser Ile Thr Thr Asp
            20                  25                  30 tat tac tat tgg ggc tgg atc cgc cag tcc cca ggc aag gga cta gag   144
Tyr Tyr Tyr Trp Gly Trp Ile Arg Gln Ser Pro Gly Lys Gly Leu Glu
        35                  40                  45 tgg gtt ggg aca ata tac ttt ggt ggg gcc acc tac tac aat ccg tcc   192
Trp Val Gly Thr Ile Tyr Phe Gly Gly Ala Thr Tyr Tyr Asn Pro Ser
    50                  55                  60 ctc agg aac cgg gtc tcg ata tct gtg gac acg tcc aac act cgc ctc   240
Leu Arg Asn Arg Val Ser Ile Ser Val Asp Thr Ser Asn Thr Arg Leu
65                  70                  75                  80 tcc ctg aga ctt atc tct ctg agc gcc gct gac acg gcc gtc tat tat   288
Ser Leu Arg Leu Ile Ser Leu Ser Ala Ala Asp Thr Ala Val Tyr Tyr
                85                  90                  95 tgt gcg aga gtg ggc tac ttg gat agg agt ggt ctt ctt gtg ggc cag   336
Cys Ala Arg Val Gly Tyr Leu Asp Arg Ser Gly Leu Leu Val Gly Gln
            100                 105                 110 ggc acc ctg gtc acc gtc tcc tcg                                   360
Gly Thr Leu Val Thr Val Ser Ser
        115                 120

<210> SEQ ID NO 78
<211> LENGTH: 120
<212> TYPE: PRT
<213> ORGANISM: Homo sapiens

<400> SEQUENCE: 78

Gln Leu Gln Leu Gln Glu Ser Gly Pro Gly Leu Val Lys Pro Ser Glu
1               5                   10                  15

Ala Leu Ser Leu Thr Cys Thr Val Ser Gly Gly Ser Ile Thr Thr Asp
            20                  25                  30

Tyr Tyr Tyr Trp Gly Trp Ile Arg Gln Ser Pro Gly Lys Gly Leu Glu
        35                  40                  45

Trp Val Gly Thr Ile Tyr Phe Gly Gly Ala Thr Tyr Tyr Asn Pro Ser
    50                  55                  60

Leu Arg Asn Arg Val Ser Ile Ser Val Asp Thr Ser Asn Thr Arg Leu
65                  70                  75                  80

Ser Leu Arg Leu Ile Ser Leu Ser Ala Ala Asp Thr Ala Val Tyr Tyr
```

```
                    85                  90                  95
Cys Ala Arg Val Gly Tyr Leu Asp Arg Ser Gly Leu Leu Val Gly Gln
                100                 105                 110

Gly Thr Leu Val Thr Val Ser Ser
        115                 120

<210> SEQ ID NO 79
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.18A1 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 79 gaa att gtg ctg acg cag tct cca ctc tcc gtg ccc gtc acc ccc gga      48
Glu Ile Val Leu Thr Gln Ser Pro Leu Ser Val Pro Val Thr Pro Gly
1               5                   10                  15 gag ccg gcc tcc atc tcc tgc agg tct agt cag agc ctc ctg cat aat      96
Glu Pro Ala Ser Ile Ser Cys Arg Ser Ser Gln Ser Leu Leu His Asn
                20                  25                  30 aat gga tac aac tat ttg gat tgg tac ctg aag aag cct ggg cag tct     144
Asn Gly Tyr Asn Tyr Leu Asp Trp Tyr Leu Lys Lys Pro Gly Gln Ser
            35                  40                  45 cca caa ctc ctg atc tat ttg ggc tct act cgg gcc tcc ggg gtc cct     192
Pro Gln Leu Leu Ile Tyr Leu Gly Ser Thr Arg Ala Ser Gly Val Pro
        50                  55                  60 gac agg ttc agt gcc agt gga tca ggc aca gac ttt aca ctg gaa atc     240
Asp Arg Phe Ser Ala Ser Gly Ser Gly Thr Asp Phe Thr Leu Glu Ile
65                  70                  75                  80 agc aga gtg gag gct gaa gat gtt ggc gtt tac tac tgc atg caa gct     288
Ser Arg Val Glu Ala Glu Asp Val Gly Val Tyr Tyr Cys Met Gln Ala
                85                  90                  95 ctg cag act cct ccg act ttc ggc aga ggg acc aag gtg gag atc aaa     336
Leu Gln Thr Pro Pro Thr Phe Gly Arg Gly Thr Lys Val Glu Ile Lys
                100                 105                 110

<210> SEQ ID NO 80
<211> LENGTH: 112
<212> TYPE: PRT
<213> ORGANISM: Homo sapiens

<400> SEQUENCE: 80

Glu Ile Val Leu Thr Gln Ser Pro Leu Ser Val Pro Val Thr Pro Gly
1               5                   10                  15

Glu Pro Ala Ser Ile Ser Cys Arg Ser Ser Gln Ser Leu Leu His Asn
                20                  25                  30

Asn Gly Tyr Asn Tyr Leu Asp Trp Tyr Leu Lys Lys Pro Gly Gln Ser
```

```
                35                  40                  45
Pro Gln Leu Leu Ile Tyr Leu Gly Ser Thr Arg Ala Ser Gly Val Pro
         50                  55                  60

Asp Arg Phe Ser Ala Ser Gly Ser Gly Thr Asp Phe Thr Leu Glu Ile
 65                  70                  75                  80

Ser Arg Val Glu Ala Glu Asp Val Gly Val Tyr Tyr Cys Met Gln Ala
                 85                  90                  95

Leu Gln Thr Pro Pro Thr Phe Gly Arg Gly Thr Lys Val Glu Ile Lys
            100                 105                 110

<210> SEQ ID NO 81
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-302.8F1 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(333)
<223> OTHER INFORMATION: complementarity determining region (CDR)
      VH-CDR3

<400> SEQUENCE: 81 gag gtg cag ctg gtg gag tct ggg gga ggc ttg gtg aag ccg ggg ggg        48
Glu Val Gln Leu Val Glu Ser Gly Gly Gly Leu Val Lys Pro Gly Gly
 1               5                  10                  15 tcc ctt aca atc tcc tgt gca gcc tct ggt ttc acc ttc agt aat gcc        96
Ser Leu Thr Ile Ser Cys Ala Ala Ser Gly Phe Thr Phe Ser Asn Ala
                20                  25                  30 tgg atg aac tgg gtc cgc cag gct cca ggt aag ggg ctg gag tgg gtc       144
Trp Met Asn Trp Val Arg Gln Ala Pro Gly Lys Gly Leu Glu Trp Val
            35                  40                  45 ggc cat att aga acg caa gct gaa gga ggg aca tca gac tat gct gca       192
Gly His Ile Arg Thr Gln Ala Glu Gly Gly Thr Ser Asp Tyr Ala Ala
         50                  55                  60 ccc gtg aaa ggc aga ttc acc atc tca aga gat gac tca aaa aac acg       240
Pro Val Lys Gly Arg Phe Thr Ile Ser Arg Asp Asp Ser Lys Asn Thr
 65                  70                  75                  80 ctg tat ctg caa atg aac agc ctg aaa acc gag gac aca gcc gta tat       288
Leu Tyr Leu Gln Met Asn Ser Leu Lys Thr Glu Asp Thr Ala Val Tyr
                 85                  90                  95 tat tgt atc ccc ccc ccc tac tac tac tat tac ggt ctg gac gtc tgg       336
Tyr Cys Ile Pro Pro Pro Tyr Tyr Tyr Tyr Tyr Gly Leu Asp Val Trp
            100                 105                 110 ggc caa ggg acc acg gtc acc gtc tcc tcg                               366
Gly Gln Gly Thr Thr Val Thr Val Ser Ser
            115                 120

<210> SEQ ID NO 82
<211> LENGTH: 122
<212> TYPE: PRT
<213> ORGANISM: Homo sapiens
```

<400> SEQUENCE: 82

```
Glu Val Gln Leu Val Glu Ser Gly Gly Gly Leu Val Lys Pro Gly Gly
1               5                   10                  15

Ser Leu Thr Ile Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly His Ile Arg Thr Gln Ala Glu Gly Gly Thr Ser Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ile Pro Pro Tyr Tyr Tyr Tyr Gly Leu Asp Val Trp
            100                 105                 110

Gly Gln Gly Thr Thr Val Thr Val Ser Ser
        115                 120
```

<210> SEQ ID NO 83
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-302.8F1 VL variable light chain (VL) sequence
<220> FEATURE:
<221> NAME/KEY: V_region
<222> LOCATION: (67)..(108)
<223> OTHER INFORMATION: complementarity determining region (CDR) VL-CDR1
<220> FEATURE:
<221> NAME/KEY: V_region
<222> LOCATION: (154)..(174)
<223> OTHER INFORMATION: complementarity determining region (CDR) VL-CDR2
<220> FEATURE:
<221> NAME/KEY: V_region
<222> LOCATION: (271)..(297)
<223> OTHER INFORMATION: complementarity determining region (CDR) VL-CDR3

<400> SEQUENCE: 83

```
cag tct gcc ctg act cag cct gcc tcc gtg tct ggg tct cct gga cag      48
Gln Ser Ala Leu Thr Gln Pro Ala Ser Val Ser Gly Ser Pro Gly Gln
1               5                   10                  15 tcg atc acc atc tcc tgc act gga gcc agc agt gat gtt ggg act tat      96
Ser Ile Thr Ile Ser Cys Thr Gly Ala Ser Ser Asp Val Gly Thr Tyr
            20                  25                  30 gac ctt gtc tcc tgg tac caa caa cat cca ggc aaa gcc ccc aaa ctc     144
Asp Leu Val Ser Trp Tyr Gln Gln His Pro Gly Lys Ala Pro Lys Leu
        35                  40                  45 att att tat gag gtc aat aag cgg ccc tca ggg gtt tct tat cgc ttc     192
Ile Ile Tyr Glu Val Asn Lys Arg Pro Ser Gly Val Ser Tyr Arg Phe
    50                  55                  60 tct gcc tcc aag tct gcc aac acg gcc tcc ctg aca ata tct ggg ctc     240
Ser Ala Ser Lys Ser Ala Asn Thr Ala Ser Leu Thr Ile Ser Gly Leu
65                  70                  75                  80 cag gct gag gac gag gct gaa tat tac tgc tgc tca tat gca ggt tat     288
Gln Ala Glu Asp Glu Ala Glu Tyr Tyr Cys Cys Ser Tyr Ala Gly Tyr
                85                  90                  95
```

-continued

```
agc acg gta ttc ggc gga ggg acc aag ctg acc gtc cta          327
Ser Thr Val Phe Gly Gly Gly Thr Lys Leu Thr Val Leu
            100                 105
```

<210> SEQ ID NO 84
<211> LENGTH: 109
<212> TYPE: PRT
<213> ORGANISM: Homo sapiens

<400> SEQUENCE: 84

```
Gln Ser Ala Leu Thr Gln Pro Ala Ser Val Ser Gly Ser Pro Gly Gln
1               5                   10                  15

Ser Ile Thr Ile Ser Cys Thr Gly Ala Ser Ser Asp Val Gly Thr Tyr
            20                  25                  30

Asp Leu Val Ser Trp Tyr Gln Gln His Pro Gly Lys Ala Pro Lys Leu
        35                  40                  45

Ile Ile Tyr Glu Val Asn Lys Arg Pro Ser Gly Val Ser Tyr Arg Phe
    50                  55                  60

Ser Ala Ser Lys Ser Ala Asn Thr Ala Ser Leu Thr Ile Ser Gly Leu
65                  70                  75                  80

Gln Ala Glu Asp Glu Ala Glu Tyr Tyr Cys Cys Ser Tyr Ala Gly Tyr
                85                  90                  95

Ser Thr Val Phe Gly Gly Gly Thr Lys Leu Thr Val Leu
            100                 105
```

<210> SEQ ID NO 85
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.52C9 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 85

```
gag gtg cag ctg gtg cag tct ggg gga ggc ttg gtc caa cct ggg ggg    48
Glu Val Gln Leu Val Gln Ser Gly Gly Gly Leu Val Gln Pro Gly Gly
1               5                   10                  15 tcc ctg aga ctc tcc tgt gca ggc tct gga ttc acc gtc agt gac acc    96
Ser Leu Arg Leu Ser Cys Ala Gly Ser Gly Phe Thr Val Ser Asp Thr
            20                  25                  30 tac atg agt tgg gtc cgc cag gct cca ggg aag ggg ctg gag tgg gtc   144
Tyr Met Ser Trp Val Arg Gln Ala Pro Gly Lys Gly Leu Glu Trp Val
        35                  40                  45 tca ggt att cat gcc ggt ggt gaa aca tat tac gca gac tcc gtg aag   192
Ser Gly Ile His Ala Gly Gly Glu Thr Tyr Tyr Ala Asp Ser Val Lys
    50                  55                  60 ggc cga ttc acc atc tcc aga gac aac tcc aag aac acg ctg tat ctt   240
Gly Arg Phe Thr Ile Ser Arg Asp Asn Ser Lys Asn Thr Leu Tyr Leu
```

```
                65                  70                  75                  80
caa atg aat agg ctg aca cct gag gac acg gct gtc ttt tat tgt gcg        288
Gln Met Asn Arg Leu Thr Pro Glu Asp Thr Ala Val Phe Tyr Cys Ala
                85                  90                  95 aga cac tac tac ggt aat gac gac gac act gat tat tgg ggc cag gga        336
Arg His Tyr Tyr Gly Asn Asp Asp Asp Thr Asp Tyr Trp Gly Gln Gly
            100                 105                 110 acc ctg gtc acc gtc tcc tcg                                            357
Thr Leu Val Thr Val Ser Ser
        115

<210> SEQ ID NO 86
<211> LENGTH: 119
<212> TYPE: PRT
<213> ORGANISM: Homo sapiens

<400> SEQUENCE: 86

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Val Ser Asp Thr
            20                  25                  30

Tyr Met Ser Trp Val Arg Gln Ala Pro Gly Lys Gly Leu Glu Trp Val
        35                  40                  45

Ser Gly Ile His Ala Gly Gly Glu Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Arg Leu Thr Pro Glu Asp Thr Ala Val Phe Tyr Cys Ala
                85                  90                  95

Arg His Tyr Tyr Gly Asn Asp Asp Asp Thr Asp Tyr Trp Gly Gln Gly
            100                 105                 110

Thr Leu Val Thr Val Ser Ser
        115

<210> SEQ ID NO 87
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.52C9 VK variable light-kappa chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 87 gat gtt gtg atg act cag tct cca ctc tcc ctg ccc gtc acc cct gga       48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt       96
```

```
                Glu Pro Ala Ser Ile Ser Cys Arg Ser Ser Gln Ser Leu Leu His Ser
                                 20                  25                  30 aat gga tac aac tat ttg gat tgg tac gtg cag aag cca ggg cag tct      144
Asn Gly Tyr Asn Tyr Leu Asp Trp Tyr Val Gln Lys Pro Gly Gln Ser
             35                  40                  45 cca cag ctc ctc atc tat ttg ggt tct act cgg gcc tcc ggg gtc cct      192
Pro Gln Leu Leu Ile Tyr Leu Gly Ser Thr Arg Ala Ser Gly Val Pro
 50                  55                  60 gac aga ttc agt ggc agt gga tca ggc aca gat ttt aca ctg aaa atc      240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc tta caa gct      288
Ser Arg Val Glu Ala Glu Asp Val Gly Val Tyr Tyr Cys Leu Gln Ala
                 85                  90                  95 caa caa att ccg tgg acg ttc ggc caa ggg acc aag gtg gag atc aaa      336
Gln Gln Ile Pro Trp Thr Phe Gly Gln Gly Thr Lys Val Glu Ile Lys
            100                 105                 110

<210> SEQ ID NO 88
<211> LENGTH: 112
<212> TYPE: PRT
<213> ORGANISM: Homo sapiens

<400> SEQUENCE: 88

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Val Gln Lys Pro Gly Gln Ser
             35                  40                  45

Pro Gln Leu Leu Ile Tyr Leu Gly Ser Thr Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ala
                 85                  90                  95

Gln Gln Ile Pro Trp Thr Phe Gly Gln Gly Thr Lys Val Glu Ile Lys
            100                 105                 110

<210> SEQ ID NO 89
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-302.46C9 VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(336)
<223> OTHER INFORMATION: complementarity determining region (CDR)
      VH-CDR3

<400> SEQUENCE: 89
```

```
cag gtg cag ctg cag gag tcg ggc cca gga ctg gta aag cct tca cag        48
Gln Val Gln Leu Gln Glu Ser Gly Pro Gly Leu Val Lys Pro Ser Gln
1               5                   10                  15 acc ctg tcc ctc acc tgc act gtt tct ggt gcc tcc gtc agc agt ggt        96
Thr Leu Ser Leu Thr Cys Thr Val Ser Gly Ala Ser Val Ser Ser Gly
                20                  25                  30 gcc tac tac tgg agt tgg atc cgg cag ccc gcc ggg aag cga ctg gag       144
Ala Tyr Tyr Trp Ser Trp Ile Arg Gln Pro Ala Gly Lys Arg Leu Glu
            35                  40                  45 tgg att ggg cgt gtc tat ccc act tgg agc acc aac tac aac ccc tcc       192
Trp Ile Gly Arg Val Tyr Pro Thr Trp Ser Thr Asn Tyr Asn Pro Ser
        50                  55                  60 ctc gag agt cga gtc acc ata tcg tta gac acg tcc aac aac cag ttc       240
Leu Glu Ser Arg Val Thr Ile Ser Leu Asp Thr Ser Asn Asn Gln Phe
65                  70                  75                  80 tcc ctg aag ctg acc tct ttg act gcc gca gac acg gcc gtt tat tac       288
Ser Leu Lys Leu Thr Ser Leu Thr Ala Ala Asp Thr Ala Val Tyr Tyr
                85                  90                  95 tgt gcg aga gag gct cct ggt gac tac gat gct gcg ccc cta gcc tac       336
Cys Ala Arg Glu Ala Pro Gly Asp Tyr Asp Ala Ala Pro Leu Ala Tyr
            100                 105                 110 tgg ggc cag ggc acc ctg gtc acc gtc tcc tcg                           369
Trp Gly Gln Gly Thr Leu Val Thr Val Ser Ser
        115                 120

<210> SEQ ID NO 90
<211> LENGTH: 123
<212> TYPE: PRT
<213> ORGANISM: Homo sapiens

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Val Ser Ser Gly
                20                  25                  30

Ala Tyr Tyr Trp Ser Trp Ile Arg Gln Pro Ala Gly Lys Arg Leu Glu
            35                  40                  45

Trp Ile Gly Arg Val Tyr Pro Thr Trp Ser Thr Asn Tyr Asn Pro Ser
        50                  55                  60

Leu Glu Ser Arg Val Thr Ile Ser Leu Asp Thr Ser Asn Asn Gln Phe
65                  70                  75                  80

Ser Leu Lys Leu Thr Ser Leu Thr Ala Ala Asp Thr Ala Val Tyr Tyr
                85                  90                  95

Cys Ala Arg Glu Ala Pro Gly Asp Tyr Asp Ala Ala Pro Leu Ala Tyr
            100                 105                 110

Trp Gly Gln Gly Thr Leu Val Thr Val Ser Ser
        115                 120

<210> SEQ ID NO 91
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.46C9 VK variable light-kappa chain (VK)
      sequence
<220> FEATURE:
<221> NAME/KEY: V_region
<222> LOCATION: (70)..(102)
<223> OTHER INFORMATION: complementarity determining region (CDR)
```

```
         VK-CDR1
<220> FEATURE:
<221> NAME/KEY: V_region
<222> LOCATION: (148)..(168)
<223> OTHER INFORMATION: complementarity determining region (CDR)
         VK-CDR2
<220> FEATURE:
<221> NAME/KEY: V_region
<222> LOCATION: (265)..(291)
<223> OTHER INFORMATION: complementarity determining region (CDR)
         VK-CDR3

<400> SEQUENCE: 91 gac atc cag atg acc cag tct cca tcc tcc ctg tct gca tct gtt gga        48
Asp Ile Gln Met Thr Gln Ser Pro Ser Ser Leu Ser Ala Ser Val Gly
1               5                   10                  15 gac aga gtc acc atc act tgc cgg gca agt cag tac att agc cac tat        96
Asp Arg Val Thr Ile Thr Cys Arg Ala Ser Gln Tyr Ile Ser His Tyr
            20                  25                  30 tta aat tgg tat cgg cag aaa cca ggg aaa gcc cct cag ctc gta atc       144
Leu Asn Trp Tyr Arg Gln Lys Pro Gly Lys Ala Pro Gln Leu Val Ile
        35                  40                  45 tat gct gca tcc agt ttg caa agt gag gtc cca tca agg ttc agt ggg       192
Tyr Ala Ala Ser Ser Leu Gln Ser Glu Val Pro Ser Arg Phe Ser Gly
    50                  55                  60 agt gga tct ggg cca gag ttc act ctc acc atc agc agt ctg caa cct       240
Ser Gly Ser Gly Pro Glu Phe Thr Leu Thr Ile Ser Ser Leu Gln Pro
65                  70                  75                  80 gaa gat ttt gca act tat tac tgt caa cag agt tac act acc cct cga       288
Glu Asp Phe Ala Thr Tyr Tyr Cys Gln Gln Ser Tyr Thr Thr Pro Arg
                85                  90                  95 act ttt ggc cag ggg acc aag ctg gag atc aaa                           321
Thr Phe Gly Gln Gly Thr Lys Leu Glu Ile Lys
                100                 105

<210> SEQ ID NO 92
<211> LENGTH: 107
<212> TYPE: PRT
<213> ORGANISM: Homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser His Tyr
            20                  25                  30

Leu Asn Trp Tyr Arg Gln Lys Pro Gly Lys Ala Pro Gln Leu Val Ile
        35                  40                  45

Tyr Ala Ala Ser Ser Leu Gln Ser Glu Val Pro Ser Arg Phe Ser Gly
    50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
                85                  90                  95

Thr Phe Gly Gln Gly Thr Lys Leu Glu Ile Lys
                100                 105

<210> SEQ ID NO 93
<211> LENGTH: 19
<212> TYPE: PRT
<213> ORGANISM: Artificial Sequence
<220> FEATURE:
<223> OTHER INFORMATION: BSA-coupled synthetic peptides (Schafer-N,
         Denmark) of the HTT exon 1 N-terminal amino acids 1-19
```

<400> SEQUENCE: 93

Met Ala Thr Leu Glu Lys Leu Met Lys Ala Phe Glu Ser Leu Lys Ser
1               5                   10                  15

Phe Gln Gln

<210> SEQ ID NO 94
<211> LENGTH: 21
<212> TYPE: PRT
<213> ORGANISM: Artificial Sequence
<220> FEATURE:
<223> OTHER INFORMATION: BSA-coupled synthetic peptides (Schafer-N,
      Denmark) of the HTT exon 1 P-rich domain

<400> SEQUENCE: 94

Pro Pro Gln Leu Pro Gln Pro Pro Pro Gln Ala Gln Pro Leu Leu Pro
1               5                   10                  15

Gln Pro Gln Pro Pro
            20

<210> SEQ ID NO 95
<211> LENGTH: 11
<212> TYPE: PRT
<213> ORGANISM: Artificial Sequence
<220> FEATURE:
<223> OTHER INFORMATION: BSA-coupled synthetic peptides (Schafer-N,
      Denmark) of the HTT exon 1polyP repeat

<400> SEQUENCE: 95

Pro Pro Pro Pro Pro Pro Pro Pro Pro Pro Pro
1               5                   10

<210> SEQ ID NO 96
<211> LENGTH: 14
<212> TYPE: PRT
<213> ORGANISM: Artificial Sequence
<220> FEATURE:
<223> OTHER INFORMATION: BSA-coupled synthetic peptides (Schafer-N,
      Denmark) of the HTT exon 1 C-terminal amino acids

<400> SEQUENCE: 96

Pro Pro Gly Pro Ala Val Ala Glu Glu Pro Leu His Arg Pro
1               5                   10

<210> SEQ ID NO 97
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-302.33C11-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 97

```
cag gtg cag ctg gtg gag tct ggg gga ggc gtt gtc cag cct ggg aac      48
Gln Val Gln Leu Val Glu Ser Gly Gly Gly Val Val Gln Pro Gly Asn
1               5                   10                  15 tcc ctg aga ctc tcc tgt gca gcg tct gga ttc agg ttc agt gac ttt      96
Ser Leu Arg Leu Ser Cys Ala Ala Ser Gly Phe Arg Phe Ser Asp Phe
            20                  25                  30 ggc atg cac tgg gtc cgc cag gct cca ggc aag gga ctg gag tgg ctg     144
Gly Met His Trp Val Arg Gln Ala Pro Gly Lys Gly Leu Glu Trp Leu
        35                  40                  45 gca ctt ata tgg tat gat gga ggg tat aag tac tat gca gac tcc gtg     192
Ala Leu Ile Trp Tyr Asp Gly Gly Tyr Lys Tyr Tyr Ala Asp Ser Val
    50                  55                  60 aag ggc cga ttc acc atc tcc aga gac aat tcc aag aat acg atg ttt     240
Lys Gly Arg Phe Thr Ile Ser Arg Asp Asn Ser Lys Asn Thr Met Phe
65                  70                  75                  80 cta caa atg aac agc ctg aga gcc gag gac acg gct gtt tat tac tgt     288
Leu Gln Met Asn Ser Leu Arg Ala Glu Asp Thr Ala Val Tyr Tyr Cys
                85                  90                  95 gcg acc cac cta gaa tat tgc agt aga acc acc tgc tat ctc ggc cac     336
Ala Thr His Leu Glu Tyr Cys Ser Arg Thr Thr Cys Tyr Leu Gly His
            100                 105                 110 tgg ggc cag gga acc ctg gtc acc gtc tcc tcg                         369
Trp Gly Gln Gly Thr Leu Val Thr Val Ser Ser
        115                 120
```

<210> SEQ ID NO 98
<211> LENGTH: 123
<212> TYPE: PRT
<213> ORGANISM: Homo sapiens

<400> SEQUENCE: 98

```
Gln Val Gln Leu Val Glu Ser Gly Gly Gly Val Val Gln Pro Gly Asn
1               5                   10                  15

Ser Leu Arg Leu Ser Cys Ala Ala Ser Gly Phe Arg Phe Ser Asp Phe
            20                  25                  30

Gly Met His Trp Val Arg Gln Ala Pro Gly Lys Gly Leu Glu Trp Leu
        35                  40                  45

Ala Leu Ile Trp Tyr Asp Gly Gly Tyr Lys Tyr Tyr Ala Asp Ser Val
    50                  55                  60

Lys Gly Arg Phe Thr Ile Ser Arg Asp Asn Ser Lys Asn Thr Met Phe
65                  70                  75                  80

Leu Gln Met Asn Ser Leu Arg Ala Glu Asp Thr Ala Val Tyr Tyr Cys
                85                  90                  95

Ala Thr His Leu Glu Tyr Cys Ser Arg Thr Thr Cys Tyr Leu Gly His
            100                 105                 110

Trp Gly Gln Gly Thr Leu Val Thr Val Ser Ser
        115                 120
```

<210> SEQ ID NO 99
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.33C11-PIMC VK variable kappa-light chain (VK) sequence
<220> FEATURE:
<221> NAME/KEY: V_region
<222> LOCATION: (70)..(102)

```
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 99 gac atc cag ttg acc cag tct ccg tcc ttc cta tct gcg tct gtg gga      48
Asp Ile Gln Leu Thr Gln Ser Pro Ser Phe Leu Ser Ala Ser Val Gly
1               5                  10                  15 gac aca gtc acc ttc act tgc cgg gcc agt cag ggc att agc gat tat      96
Asp Thr Val Thr Phe Thr Cys Arg Ala Ser Gln Gly Ile Ser Asp Tyr
                20                  25                  30 tta gcc tgg ttt cag cag aaa cca ggg att gcc cct aag ctc ctg atc     144
Leu Ala Trp Phe Gln Gln Lys Pro Gly Ile Ala Pro Lys Leu Leu Ile
            35                  40                  45 tat gct gcg tcc act ttg caa acc ggg gtc cca tca agg ttc agc ggc     192
Tyr Ala Ala Ser Thr Leu Gln Thr Gly Val Pro Ser Arg Phe Ser Gly
    50                  55                  60 agt gga tct ggg aca gaa ttc act ctc aca atc cgc agc ctg cag tct     240
Ser Gly Ser Gly Thr Glu Phe Thr Leu Thr Ile Arg Ser Leu Gln Ser
65                  70                  75                  80 gaa gat ttt gga act tat tac tgt cag cag ctt aaa act tac ccg tac     288
Glu Asp Phe Gly Thr Tyr Tyr Cys Gln Gln Leu Lys Thr Tyr Pro Tyr
                85                  90                  95 act ttt ggc cag ggg acc aag ctg gag atc aaa                         321
Thr Phe Gly Gln Gly Thr Lys Leu Glu Ile Lys
                100                 105

<210> SEQ ID NO 100
<211> LENGTH: 107
<212> TYPE: PRT
<213> ORGANISM: Homo sapiens

<400> SEQUENCE: 100

Asp Ile Gln Leu Thr Gln Ser Pro Ser Phe Leu Ser Ala Ser Val Gly
1               5                  10                  15

Asp Thr Val Thr Phe Thr Cys Arg Ala Ser Gln Gly Ile Ser Asp Tyr
                20                  25                  30

Leu Ala Trp Phe Gln Gln Lys Pro Gly Ile Ala Pro Lys Leu Leu Ile
            35                  40                  45

Tyr Ala Ala Ser Thr Leu Gln Thr Gly Val Pro Ser Arg Phe Ser Gly
    50                  55                  60

Ser Gly Ser Gly Thr Glu Phe Thr Leu Thr Ile Arg Ser Leu Gln Ser
65                  70                  75                  80

Glu Asp Phe Gly Thr Tyr Tyr Cys Gln Gln Leu Lys Thr Tyr Pro Tyr
                85                  90                  95

Thr Phe Gly Gln Gly Thr Lys Leu Glu Ile Lys
                100                 105

<210> SEQ ID NO 101
<211> LENGTH: 339
<212> TYPE: DNA
<213> ORGANISM: Homo sapiens
<220> FEATURE:
<221> NAME/KEY: CDS
```

```
<222> LOCATION: (1)..(339)
<223> OTHER INFORMATION: NI-307.63F3-PIMC VK variable kappa-light chain
      (VK) sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 101 gat att gtg atg act caa tca cca gac tcc ctg gct gtg tct ctg ggc         48
Asp Ile Val Met Thr Gln Ser Pro Asp Ser Leu Ala Val Ser Leu Gly
 1               5                  10                  15 gag agg gcc acc atc aac tgc aag tcc aat cag agt ctt ttc tac agt         96
Glu Arg Ala Thr Ile Asn Cys Lys Ser Asn Gln Ser Leu Phe Tyr Ser
             20                  25                  30 tcc aac aat aac aac tac tta gct tgg tac cag cac aaa tcc gga cag        144
Ser Asn Asn Asn Asn Tyr Leu Ala Trp Tyr Gln His Lys Ser Gly Gln
         35                  40                  45 cct cct aag ctg ctc gtt tac tgg gga tct acc cgg gaa tcc ggg gtc        192
Pro Pro Lys Leu Leu Val Tyr Trp Gly Ser Thr Arg Glu Ser Gly Val
     50                  55                  60 cct gac cgc ttc agt ggc agc ggg tct ggg act gac ttc act ctc acc        240
Pro Asp Arg Phe Ser Gly Ser Gly Ser Gly Thr Asp Phe Thr Leu Thr
 65                  70                  75                  80 atc agt agc ctg cag gct gag gat gtt gca att tat tac tgt cac caa        288
Ile Ser Ser Leu Gln Ala Glu Asp Val Ala Ile Tyr Tyr Cys His Gln
                 85                  90                  95 tat tat cat aat ccg tac act ttt ggc cag ggg acc aag ctg gag atc        336
Tyr Tyr His Asn Pro Tyr Thr Phe Gly Gln Gly Thr Lys Leu Glu Ile
            100                 105                 110 aaa                                                                    339
Lys

<210> SEQ ID NO 102
<211> LENGTH: 113
<212> TYPE: PRT
<213> ORGANISM: Homo sapiens

<400> SEQUENCE: 102

Asp Ile Val Met Thr Gln Ser Pro Asp Ser Leu Ala Val Ser Leu Gly
 1               5                  10                  15

Glu Arg Ala Thr Ile Asn Cys Lys Ser Asn Gln Ser Leu Phe Tyr Ser
             20                  25                  30

Ser Asn Asn Asn Asn Tyr Leu Ala Trp Tyr Gln His Lys Ser Gly Gln
         35                  40                  45

Pro Pro Lys Leu Leu Val Tyr Trp Gly Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Ile Tyr Tyr Cys His Gln
                 85                  90                  95

Tyr Tyr His Asn Pro Tyr Thr Phe Gly Gln Gly Thr Lys Leu Glu Ile
```

```
                    100             105             110
Lys

<210> SEQ ID NO 103
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-307.63F3-PIMC-NS VK variable kappa-light
      chain (VK) sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 103 gat att gtg atg act caa tca cca gac tcc ctg gct gtg tct ctg ggc       48
Asp Ile Val Met Thr Gln Ser Pro Asp Ser Leu Ala Val Ser Leu Gly
1               5                   10                  15 gag agg gcc acc atc aac tgc aag tcc tca cag agt ctt ttc tac agt       96
Glu Arg Ala Thr Ile Asn Cys Lys Ser Ser Gln Ser Leu Phe Tyr Ser
            20                  25                  30 tcc aac aat aac aac tac tta gct tgg tac cag cac aaa tcc gga cag      144
Ser Asn Asn Asn Asn Tyr Leu Ala Trp Tyr Gln His Lys Ser Gly Gln
        35                  40                  45 cct cct aag ctg ctc gtt tac tgg gga tct acc cgg gaa tcc ggg gtc      192
Pro Pro Lys Leu Leu Val Tyr Trp Gly Ser Thr Arg Glu Ser Gly Val
    50                  55                  60 cct gac cgc ttc agt ggc agc ggg tct ggg act gac ttc act ctc acc      240
Pro Asp Arg Phe Ser Gly Ser Gly Ser Gly Thr Asp Phe Thr Leu Thr
65                  70                  75                  80 atc agt agc ctg cag gct gag gat gtt gca att tat tac tgt cac caa      288
Ile Ser Ser Leu Gln Ala Glu Asp Val Ala Ile Tyr Tyr Cys His Gln
                85                  90                  95 tat tat cat aat ccg tac act ttt ggc cag ggg acc aag ctg gag atc      336
Tyr Tyr His Asn Pro Tyr Thr Phe Gly Gln Gly Thr Lys Leu Glu Ile
            100                 105                 110 aaa                                                                  339
Lys

<210> SEQ ID NO 104
<211> LENGTH: 113
<212> TYPE: PRT
<213> ORGANISM: Homo sapiens

<400> SEQUENCE: 104

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Ser Asn Asn Asn Asn Tyr Leu Ala Trp Tyr Gln His Lys Ser Gly Gln
        35                  40                  45
```

```
Pro Pro Lys Leu Leu Val Tyr Trp Gly Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Tyr His Asn Pro Tyr Thr Phe Gly Gln Gly Thr Lys Leu Glu Ile
            100                 105                 110

Lys

<210> SEQ ID NO 105
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-307.63F3-PIMC-SG VK variable kappa-light
      chain (VK) sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 105 gat att gtg atg act caa tca cca gac tcc ctg gct gtg tct ctg ggc    48
Asp Ile Val Met Thr Gln Ser Pro Asp Ser Leu Ala Val Ser Leu Gly
1               5                   10                  15 gag agg gcc acc atc aac tgc aag tcc aat cag ggc ctt ttc tac agt    96
Glu Arg Ala Thr Ile Asn Cys Lys Ser Asn Gln Gly Leu Phe Tyr Ser
            20                  25                  30 tcc aac aat aac aac tac tta gct tgg tac cag cac aaa tcc gga cag   144
Ser Asn Asn Asn Asn Tyr Leu Ala Trp Tyr Gln His Lys Ser Gly Gln
        35                  40                  45 cct cct aag ctg ctc gtt tac tgg gga tct acc cgg gaa tcc ggg gtc   192
Pro Pro Lys Leu Leu Val Tyr Trp Gly Ser Thr Arg Glu Ser Gly Val
    50                  55                  60 cct gac cgc ttc agt ggc agc ggg tct ggg act gac ttc act ctc acc   240
Pro Asp Arg Phe Ser Gly Ser Gly Ser Gly Thr Asp Phe Thr Leu Thr
65                  70                  75                  80 atc agt agc ctg cag gct gag gat gtt gca att tat tac tgt cac caa   288
Ile Ser Ser Leu Gln Ala Glu Asp Val Ala Ile Tyr Tyr Cys His Gln
                85                  90                  95 tat tat cat aat ccg tac act ttt ggc cag ggg acc aag ctg gag atc   336
Tyr Tyr His Asn Pro Tyr Thr Phe Gly Gln Gly Thr Lys Leu Glu Ile
            100                 105                 110 aaa                                                                339
Lys

<210> SEQ ID NO 106
<211> LENGTH: 113
<212> TYPE: PRT
<213> ORGANISM: Homo sapiens
```

<400> SEQUENCE: 106

Asp Ile Val Met Thr Gln Ser Pro Asp Ser Leu Ala Val Ser Leu Gly
1               5                   10                  15

Glu Arg Ala Thr Ile Asn Cys Lys Ser Asn Gln Gly Leu Phe Tyr Ser
            20                  25                  30

Ser Asn Asn Asn Asn Tyr Leu Ala Trp Tyr Gln His Lys Ser Gly Gln
        35                  40                  45

Pro Pro Lys Leu Leu Val Tyr Trp Gly Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Tyr His Asn Pro Tyr Thr Phe Gly Gln Gly Thr Lys Leu Glu Ile
            100                 105                 110

Lys

<210> SEQ ID NO 107
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-307.63F3-PIMC-NQ VK variable kappa-light
      chain (VK) sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 107 gat att gtg atg act caa tca cca gac tcc ctg gct gtg tct ctg ggc        48
Asp Ile Val Met Thr Gln Ser Pro Asp Ser Leu Ala Val Ser Leu Gly
1               5                   10                  15 gag agg gcc acc atc aac tgc aag tcc caa cag agt ctt ttc tac agt        96
Glu Arg Ala Thr Ile Asn Cys Lys Ser Gln Gln Ser Leu Phe Tyr Ser
            20                  25                  30 tcc aac aat aac aac tac tta gct tgg tac cag cac aaa tcc gga cag       144
Ser Asn Asn Asn Asn Tyr Leu Ala Trp Tyr Gln His Lys Ser Gly Gln
        35                  40                  45 cct cct aag ctg ctc gtt tac tgg gga tct acc cgg gaa tcc ggg gtc       192
Pro Pro Lys Leu Leu Val Tyr Trp Gly Ser Thr Arg Glu Ser Gly Val
    50                  55                  60 cct gac cgc ttc agt ggc agc ggg tct ggg act gac ttc act ctc acc       240
Pro Asp Arg Phe Ser Gly Ser Gly Ser Gly Thr Asp Phe Thr Leu Thr
65                  70                  75                  80 atc agt agc ctg cag gct gag gat gtt gca att tat tac tgt cac caa       288
Ile Ser Ser Leu Gln Ala Glu Asp Val Ala Ile Tyr Tyr Cys His Gln
                85                  90                  95 tat tat cat aat ccg tac act ttt ggc cag ggg acc aag ctg gag atc       336

```
        Tyr Tyr His Asn Pro Tyr Thr Phe Gly Gln Gly Thr Lys Leu Glu Ile
                    100                 105                 110 aaa                                                                         339
Lys <210> SEQ ID NO 108
<211> LENGTH: 113
<212> TYPE: PRT
<213> ORGANISM: Homo sapiens

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Gln Gln Ser Leu Phe Tyr Ser
            20                  25                  30

Ser Asn Asn Asn Tyr Leu Ala Trp Tyr Gln His Lys Ser Gly Gln
        35                  40                  45

Pro Pro Lys Leu Leu Val Tyr Trp Gly Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Tyr His Asn Pro Tyr Thr Phe Gly Gln Gly Thr Lys Leu Glu Ile
            100                 105                 110

Lys

<210> SEQ ID NO 109
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.35C1-PIMC VK variable kappa-light chain
      (VK) sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 109 gaa att gtg ctg act cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt caa agt gtt gac aac cag      96
Glu Arg Ala Thr Leu Ser Cys Arg Ala Ser Gln Ser Val Asp Asn Gln
            20                  25                  30 ttt gcc tgg tac caa cag aaa cct ggc cag gct ccc agg ctc ctc att     144
Phe Ala Trp Tyr Gln Gln Lys Pro Gly Gln Ala Pro Arg Leu Leu Ile
        35                  40                  45 tat gat gca tcc agg agg gcc cct ggc atc cca gac agg ttc agt ggc     192
Tyr Asp Ala Ser Arg Arg Ala Pro Gly Ile Pro Asp Arg Phe Ser Gly
```

```
agt ggg tct ggg aca gac ttc act ctc acc att agc agc cta gag cct    240
Ser Gly Ser Gly Thr Asp Phe Thr Leu Thr Ile Ser Ser Leu Glu Pro
 65                  70                  75                  80 gaa gat ttc gca att tat tac tgt cag cat cgt tac acc tgg ctc tac    288
Glu Asp Phe Ala Ile Tyr Tyr Cys Gln His Arg Tyr Thr Trp Leu Tyr
                 85                  90                  95 act ttt ggc cag ggg acc aag ctg gag atc aaa                        321
Thr Phe Gly Gln Gly Thr Lys Leu Glu Ile Lys
            100                 105

<210> SEQ ID NO 110
<211> LENGTH: 107
<212> TYPE: PRT
<213> ORGANISM: Homo sapiens

<400> SEQUENCE: 110

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Asn Gln
            20                  25                  30

Phe Ala Trp Tyr Gln Gln Lys Pro Gly Gln Ala Pro Arg Leu Leu Ile
        35                  40                  45

Tyr Asp Ala Ser Arg Arg Ala Pro Gly Ile Pro Asp Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln His Arg Tyr Thr Trp Leu Tyr
                 85                  90                  95

Thr Phe Gly Gln Gly Thr Lys Leu Glu Ile Lys
            100                 105

<210> SEQ ID NO 111
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-302.31F11-PIMC VK variable kappa-light chain
      (VK) sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 111 gat att gtg atg act caa tca cca ctc tcc ctg ccc gtc gcc cct gga    48
Asp Ile Val Met Thr Gln Ser Pro Leu Ser Leu Pro Val Ala Pro Gly
 1               5                  10                  15 gag ccg gcc tcc atc tcc tgc agg tct agt cag agc ctc cta tac agt    96
Glu Pro Ala Ser Ile Ser Cys Arg Ser Ser Gln Ser Leu Leu Tyr Ser
            20                  25                  30
```

```
aat gga tac aac tat ttg gat tgg tac ctg cag aag cca ggg aag cct      144
Asn Gly Tyr Asn Tyr Leu Asp Trp Tyr Leu Gln Lys Pro Gly Lys Pro
         35                  40                  45 cca cag ctc ctg gtc tat ttg ggt tct gat cgg gcc tcc ggg gtc cct      192
Pro Gln Leu Leu Val Tyr Leu Gly Ser Asp Arg Ala Ser Gly Val Pro
 50                  55                  60 gac agg ttc agt ggc agt gga tca ggc aaa gat ttt aca ctg aac atc      240
Asp Arg Phe Ser Gly Ser Gly Ser Gly Lys Asp Phe Thr Leu Asn Ile
 65                  70                  75                  80 agc aga gtg gag gct gag gat gtt ggg gtt tat tac tgc atg caa ggt      288
Ser Arg Val Glu Ala Glu Asp Val Gly Val Tyr Tyr Cys Met Gln Gly
                 85                  90                  95 cta caa agt ccg tgg acg ttc ggc caa ggg acc aag gtg gaa atc aaa      336
Leu Gln Ser Pro Trp Thr Phe Gly Gln Gly Thr Lys Val Glu Ile Lys
            100                 105                 110

<210> SEQ ID NO 112
<211> LENGTH: 112
<212> TYPE: PRT
<213> ORGANISM: Homo sapiens

<400> SEQUENCE: 112

Asp Ile Val Met Thr Gln Ser Pro Leu Ser Leu Pro Val Ala Pro Gly
 1               5                  10                  15

Glu Pro Ala Ser Ile Ser Cys Arg Ser Ser Gln Ser Leu Leu Tyr Ser
                 20                  25                  30

Asn Gly Tyr Asn Tyr Leu Asp Trp Tyr Leu Gln Lys Pro Gly Lys Pro
         35                  40                  45

Pro Gln Leu Leu Val Tyr Leu Gly Ser Asp Arg Ala Ser Gly Val Pro
 50                  55                  60

Asp Arg Phe Ser Gly Ser Gly Ser Gly Lys Asp Phe Thr Leu Asn Ile
 65                  70                  75                  80

Ser Arg Val Glu Ala Glu Asp Val Gly Val Tyr Tyr Cys Met Gln Gly
                 85                  90                  95

Leu Gln Ser Pro Trp Thr Phe Gly Gln Gly Thr Lys Val Glu Ile Lys
            100                 105                 110

<210> SEQ ID NO 113
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION: NI-302.2A2-PIMC VK variable kappa-light chain
      (VK) sequence
<220> FEATURE:
<221> NAME/KEY: V_region
<222> LOCATION: (70)..(129)
<223> OTHER INFORMATION: complementarity determining region (CDR)
      VK-CDR1
<220> FEATURE:
<221> NAME/KEY: V_region
<222> LOCATION: (175)..(195)
<223> OTHER INFORMATION: complementarity determining region (CDR)
      VK-CDR2
<220> FEATURE:
<221> NAME/KEY: V_region
<222> LOCATION: (292)..(315)
<223> OTHER INFORMATION: complementarity determining region (CDR)
      VK-CDR3

<400> SEQUENCE: 113 gat att gtg atg act caa tca cca gac tcc ctg gct gtg tct ctg ggc       48
Asp Ile Val Met Thr Gln Ser Pro Asp Ser Leu Ala Val Ser Leu Gly
```

```
                1               5                   10                  15
       gag agg gcc acc atc aac tgc aag tcc agc cag agt ctt tta tac acc        96
       Glu Arg Ala Thr Ile Asn Cys Lys Ser Ser Gln Ser Leu Leu Tyr Thr
                        20                  25                  30 tcc aaa aat aag gac agt aag aac tac tta ggt tgg tac cag cag aaa       144
       Ser Lys Asn Lys Asp Ser Lys Asn Tyr Leu Gly Trp Tyr Gln Gln Lys
                    35                  40                  45 cca gga cag cct cct aag ctg ctc att tac tgg gca tct acc cgg gaa       192
       Pro Gly Gln Pro Pro Lys Leu Leu Ile Tyr Trp Ala Ser Thr Arg Glu
       50                  55                  60 tcc ggg gtc cct gac cga ttc agt ggc agc ggg tct ggg aca gat ttc       240
       Ser Gly Val Pro Asp Arg Phe Ser Gly Ser Gly Ser Gly Thr Asp Phe
       65                  70                  75                  80 act ctc acc atc agc agc ctg cag gct gag gat gtg gca gtt tat tac       288
       Thr Leu Thr Ile Ser Ser Leu Gln Ala Glu Asp Val Ala Val Tyr Tyr
                        85                  90                  95 tgt cag cag tat tat act act cct cag ttc ggc gga ggg acc aag gtg       336
       Cys Gln Gln Tyr Tyr Thr Thr Pro Gln Phe Gly Gly Gly Thr Lys Val
                    100                 105                 110 gaa atc aaa                                                           345
       Glu Ile Lys
               115

<210> SEQ ID NO 114
<211> LENGTH: 115
<212> TYPE: PRT
<213> ORGANISM: Homo sapiens

<400> SEQUENCE: 114

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Thr
            20                  25                  30

Ser Lys Asn Lys Asp Ser Lys Asn Tyr Leu Gly Trp Tyr Gln Gln Lys
        35                  40                  45

Pro Gly Gln Pro Pro Lys Leu Leu Ile Tyr Trp Ala Ser Thr Arg Glu
    50                  55                  60

Ser Gly Val Pro Asp Arg Phe Ser Gly Ser Gly Ser Gly Thr Asp Phe
65                  70                  75                  80

Thr Leu Thr Ile Ser Ser Leu Gln Ala Glu Asp Val Ala Val Tyr Tyr
                85                  90                  95

Cys Gln Gln Tyr Tyr Thr Thr Pro Gln Phe Gly Gly Gly Thr Lys Val
            100                 105                 110

Glu Ile Lys
        115

<210> SEQ ID NO 115
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-302.74C11-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
```

<222> LOCATION: (148)..(186)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 115

```
cag gtg cag ctg gtg caa tct ggg act gag gtg cag aag cct ggg gcc    48
Gln Val Gln Leu Val Gln Ser Gly Thr Glu Val Gln Lys Pro Gly Ala
1               5                   10                  15 tca gta aaa gtc tcc tgc aag gct tct gga tac agt ttc acc ggc tac    96
Ser Val Lys Val Ser Cys Lys Ala Ser Gly Tyr Ser Phe Thr Gly Tyr
                20                  25                  30 ttt ttg cac tgg gta cga cag gcc cct gga caa ggg ctt gag tgg atg    144
Phe Leu His Trp Val Arg Gln Ala Pro Gly Gln Gly Leu Glu Trp Met
            35                  40                  45 ggg tgg atc aac cct aac agt ggt gac aca aac tat gca gag aag ttt    192
Gly Trp Ile Asn Pro Asn Ser Gly Asp Thr Asn Tyr Ala Glu Lys Phe
        50                  55                  60 cgg ggc aga atc atc atg acc agg gac acg tct gtc agc aca gcc cac    240
Arg Gly Arg Ile Ile Met Thr Arg Asp Thr Ser Val Ser Thr Ala His
65                  70                  75                  80 atg gag ttg agc agc ctg aga ttt gac gac acg gcc cta tat tac tgt    288
Met Glu Leu Ser Ser Leu Arg Phe Asp Asp Thr Ala Leu Tyr Tyr Cys
                85                  90                  95 acg aga gag gcc cct gac ccg ggc gct gag acg gac gtc tgg ggc caa    336
Thr Arg Glu Ala Pro Asp Pro Gly Ala Glu Thr Asp Val Trp Gly Gln
                100                 105                 110 gga acc acg gtc acc gtc tcc tcg                                    360
Gly Thr Thr Val Thr Val Ser Ser
            115                 120
```

<210> SEQ ID NO 116
<211> LENGTH: 120
<212> TYPE: PRT
<213> ORGANISM: Homo sapiens

<400> SEQUENCE: 116

```
Gln Val Gln Leu Val Gln Ser Gly Thr Glu Val Gln Lys Pro Gly Ala
1               5                   10                  15

Ser Val Lys Val Ser Cys Lys Ala Ser Gly Tyr Ser Phe Thr Gly Tyr
                20                  25                  30

Phe Leu His Trp Val Arg Gln Ala Pro Gly Gln Gly Leu Glu Trp Met
            35                  40                  45

Gly Trp Ile Asn Pro Asn Ser Gly Asp Thr Asn Tyr Ala Glu Lys Phe
        50                  55                  60

Arg Gly Arg Ile Ile Met Thr Arg Asp Thr Ser Val Ser Thr Ala His
65                  70                  75                  80

Met Glu Leu Ser Ser Leu Arg Phe Asp Asp Thr Ala Leu Tyr Tyr Cys
                85                  90                  95

Thr Arg Glu Ala Pro Asp Pro Gly Ala Glu Thr Asp Val Trp Gly Gln
                100                 105                 110

Gly Thr Thr Val Thr Val Ser Ser
            115                 120
```

<210> SEQ ID NO 117
<211> LENGTH: 321
<212> TYPE: DNA

```
<213> ORGANISM: Homo sapiens
<220> FEATURE:
<221> NAME/KEY: CDS
<222> LOCATION: (1)..(321)
<223> OTHER INFORMATION: NI-302.74C11-PIMC VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 117 tcc tat gag ctg act cag cca ccc tcg gtg tca gtg tcc cca gga cag        48
Ser Tyr Glu Leu Thr Gln Pro Pro Ser Val Ser Val Ser Pro Gly Gln
1               5                   10                  15 acg gcc agg atc acc tgc tct gga gat gca gtg cca aag cag tat att        96
Thr Ala Arg Ile Thr Cys Ser Gly Asp Ala Val Pro Lys Gln Tyr Ile
            20                  25                  30 tat tgg tac cag cag aag cca ggc cag gcc cct att ctg gtg ata tat       144
Tyr Trp Tyr Gln Gln Lys Pro Gly Gln Ala Pro Ile Leu Val Ile Tyr
        35                  40                  45 aaa gac act cag agg cct tca ggg atc cct gag cga ttc tct ggc tcc       192
Lys Asp Thr Gln Arg Pro Ser Gly Ile Pro Glu Arg Phe Ser Gly Ser
50                  55                  60 aac tca ggg aca aca gtc acg ttg acc ata act ggc gtc cag gca gac       240
Asn Ser Gly Thr Thr Val Thr Leu Thr Ile Thr Gly Val Gln Ala Asp
65                  70                  75                  80 gac gag ggt gac tat tac tgt caa tca gca gac agt agt gct act tgg       288
Asp Glu Gly Asp Tyr Tyr Cys Gln Ser Ala Asp Ser Ser Ala Thr Trp
                85                  90                  95 gtg ttc ggc gga ggg acc aaa ttg acc gtc cta                           321
Val Phe Gly Gly Gly Thr Lys Leu Thr Val Leu
            100                 105

<210> SEQ ID NO 118
<211> LENGTH: 107
<212> TYPE: PRT
<213> ORGANISM: Homo sapiens

<400> SEQUENCE: 118

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Val Pro Lys Gln Tyr Ile
            20                  25                  30

Tyr Trp Tyr Gln Gln Lys Pro Gly Gln Ala Pro Ile Leu Val Ile Tyr
        35                  40                  45

Lys Asp Thr Gln Arg Pro Ser Gly Ile Pro Glu Arg Phe Ser Gly Ser
50                  55                  60

Asn Ser Gly Thr Thr Val Thr Leu Thr Ile Thr Gly Val Gln Ala Asp
65                  70                  75                  80

Asp Glu Gly Asp Tyr Tyr Cys Gln Ser Ala Asp Ser Ser Ala Thr Trp
                85                  90                  95

Val Phe Gly Gly Gly Thr Lys Leu Thr Val Leu
            100                 105
```

<210> SEQ ID NO 119
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.39G12-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 119

```
gag gtg cag ctg gtg gag tct ggg gga ggc ttg gtc cac cct tgg ggg      48
Glu Val Gln Leu Val Glu Ser Gly Gly Gly Leu Val His Pro Trp Gly
1               5                   10                  15 tcc ctg aga ctc tcc tgt gca gcc tct gga ttc agc gtc tct aat tac      96
Ser Leu Arg Leu Ser Cys Ala Ala Ser Gly Phe Ser Val Ser Asn Tyr
                20                  25                  30 gcc ata act tgg gtc cgc cgg gct cca ggg aag ggg ctg caa tat att     144
Ala Ile Thr Trp Val Arg Arg Ala Pro Gly Lys Gly Leu Gln Tyr Ile
            35                  40                  45 tca gta att tat cgt gat ggc agg aca tac tac gga gac tcc gtg agg     192
Ser Val Ile Tyr Arg Asp Gly Arg Thr Tyr Tyr Gly Asp Ser Val Arg
        50                  55                  60 ggc cgc ttc acc atc tct agg gac gat tcc aag aac act ctc tat ctt     240
Gly Arg Phe Thr Ile Ser Arg Asp Asp Ser Lys Asn Thr Leu Tyr Leu
65                  70                  75                  80 caa atg aac agc ctg aga ttt gag gac acg gct gtg tat tac tgt gcg     288
Gln Met Asn Ser Leu Arg Phe Glu Asp Thr Ala Val Tyr Tyr Cys Ala
                85                  90                  95 aga gcg cac ggc caa tat tac tat ggt gtg gac gtc tgg ggc caa gga     336
Arg Ala His Gly Gln Tyr Tyr Tyr Gly Val Asp Val Trp Gly Gln Gly
            100                 105                 110 acc acg gtc acc gtc tcc tcg                                         357
Thr Thr Val Thr Val Ser Ser
        115
```

<210> SEQ ID NO 120
<211> LENGTH: 119
<212> TYPE: PRT
<213> ORGANISM: Homo sapiens

<400> SEQUENCE: 120

```
Glu Val Gln Leu Val Glu Ser Gly Gly Gly Leu Val His Pro Trp Gly
1               5                   10                  15

Ser Leu Arg Leu Ser Cys Ala Ala Ser Gly Phe Ser Val Ser Asn Tyr
                20                  25                  30

Ala Ile Thr Trp Val Arg Arg Ala Pro Gly Lys Gly Leu Gln Tyr Ile
            35                  40                  45
```

```
Ser Val Ile Tyr Arg Asp Gly Arg Thr Tyr Tyr Gly Asp Ser Val Arg
    50                  55                  60

Gly Arg Phe Thr Ile Ser Arg Asp Asp Ser Lys Asn Thr Leu Tyr Leu
65                  70                  75                  80

Gln Met Asn Ser Leu Arg Phe Glu Asp Thr Ala Val Tyr Tyr Cys Ala
                85                  90                  95

Arg Ala His Gly Gln Tyr Tyr Tyr Gly Val Asp Val Trp Gly Gln Gly
            100                 105                 110

Thr Thr Val Thr Val Ser Ser
        115
```

```
<210> SEQ ID NO 121
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.39G12-PIMC VK variable kappa-light chain
      (VK) sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(303)
<223> OTHER INFORMATION: complementarity determining region (CDR)
      VK-CDR3

<400> SEQUENCE: 121 gac atc gtg atg acc cag tct cca ctc tcc ctg tcc gtc agc cct gga        48
Asp Ile Val Met Thr Gln Ser Pro Leu Ser Leu Ser Val Ser Pro Gly
1               5                   10                  15 gag ccg gcc tcc atc tcc tgc agg tct agt cag agc ctc cta cat agt        96
Glu Pro Ala Ser Ile Ser Cys Arg Ser Ser Gln Ser Leu Leu His Ser
            20                  25                  30 aat gga tac aac tat ttg gat tgg tac cgg cag aaa cca ggg cag tct       144
Asn Gly Tyr Asn Tyr Leu Asp Trp Tyr Arg Gln Lys Pro Gly Gln Ser
        35                  40                  45 cca cag ctc ctg atc tat ttg agt tct aat cgg ccc tcc ggg gtc cct       192
Pro Gln Leu Leu Ile Tyr Leu Ser Ser Asn Arg Pro Ser Gly Val Pro
    50                  55                  60 gat agg ttc agt gcc agt gga tca ggc aca gag ttc aca ctg caa atc       240
Asp Arg Phe Ser Ala Ser Gly Ser Gly Thr Glu Phe Thr Leu Gln Ile
65                  70                  75                  80 agc aga gtg gag gct gag gat gtt ggg gtt tat tac tgc atg caa tct       288
Ser Arg Val Glu Ala Glu Asp Val Gly Val Tyr Tyr Cys Met Gln Ser
                85                  90                  95 ctg caa acg ttc act ttc ggc gga ggg acc aag gtg gaa atc aaa           333
Leu Gln Thr Phe Thr Phe Gly Gly Gly Thr Lys Val Glu Ile Lys
            100                 105                 110

<210> SEQ ID NO 122
<211> LENGTH: 111
<212> TYPE: PRT
<213> ORGANISM: Homo sapiens

<400> SEQUENCE: 122
```

```
Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Arg Gln Lys Pro Gly Gln Ser
        35                  40                  45

Pro Gln Leu Leu Ile Tyr Leu Ser Ser Asn Arg Pro Ser Gly Val Pro
    50                  55                  60

Asp Arg Phe Ser Ala Ser Gly Ser Gly Thr Glu Phe Thr Leu Gln Ile
65                  70                  75                  80

Ser Arg Val Glu Ala Glu Asp Val Gly Val Tyr Tyr Cys Met Gln Ser
                85                  90                  95

Leu Gln Thr Phe Thr Phe Gly Gly Gly Thr Lys Val Glu Ile Lys
            100                 105                 110
```

<210> SEQ ID NO 123
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.11A4-PIMC VK variable kappa-light chain (VK) sequence
<220> FEATURE:
<221> NAME/KEY: V_region
<222> LOCATION: (70)..(105)
<223> OTHER INFORMATION: complementarity determining region (CDR) VK-CDR1
<220> FEATURE:
<221> NAME/KEY: V_region
<222> LOCATION: (151)..(171)
<223> OTHER INFORMATION: complementarity determining region (CDR) VK-CDR2
<220> FEATURE:
<221> NAME/KEY: V_region
<222> LOCATION: (268)..(291)
<223> OTHER INFORMATION: complementarity determining region (CDR) VK-CDR3

<400> SEQUENCE: 123

```
gaa att gtg ctg act cag tct cca ggc acc ctg tct ttg tct cca gga      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac ttc gcc tgg tac caa caa aaa cct ggc cag gct ccc agg ctc ctc     144
Tyr Phe Ala Trp Tyr Gln Gln Lys Pro Gly Gln Ala Pro Arg Leu Leu
        35                  40                  45 atc tat ggt acg tcc cgc agg gcc act gcc atc cca gac agg ttc agt     192
Ile Tyr Gly Thr Ser Arg Arg Ala Thr Ala Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa cag tat ggt agc tcg tgg     288
Pro Glu Asp Phe Ala Val Tyr Tyr Cys Gln Gln Tyr Gly Ser Ser Trp
                85                  90                  95 acg ttc ggc cca ggg acc aag gtg gaa atc aaa                         321
Thr Phe Gly Pro Gly Thr Lys Val Glu Ile Lys
            100                 105
```

<210> SEQ ID NO 124

```
<211> LENGTH: 107
<212> TYPE: PRT
<213> ORGANISM: Homo sapiens

<400> SEQUENCE: 124

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Thr Ser Arg Arg Ala Thr Ala Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Trp
                85                  90                  95

Thr Phe Gly Pro Gly Thr Lys Val Glu Ile Lys
            100                 105

<210> SEQ ID NO 125
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.22H9-PIMC VK variable kappa-light chain
      (VK) sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(303)
<223> OTHER INFORMATION: complementarity determining region (CDR)
      VK-CDR3

<400> SEQUENCE: 125 gat att gtg atg act caa tca cca ctc tcc ctg tcc gtc agc cct gga       48
Asp Ile Val Met Thr Gln Ser Pro Leu Ser Leu Ser Val Ser Pro Gly
1               5                   10                  15 gag ccg gcc tcc atc tcc tgc agg tct agt cag agc ctc cta cat agt       96
Glu Pro Ala Ser Ile Ser Cys Arg Ser Ser Gln Ser Leu Leu His Ser
            20                  25                  30 aat gga tac aac tat ttg gat tgg tac cgg cag aaa cca ggg cag tct      144
Asn Gly Tyr Asn Tyr Leu Asp Trp Tyr Arg Gln Lys Pro Gly Gln Ser
        35                  40                  45 cca caa ctc ctg atc tat ttg aat tct aat cgg gcc tcc ggg gtc cct      192
Pro Gln Leu Leu Ile Tyr Leu Asn Ser Asn Arg Ala Ser Gly Val Pro
50                  55                  60 gat agg ttc agt ggc agt gga tca ggc aca gag ttc aca ctg aca atc      240
Asp Arg Phe Ser Gly Ser Gly Ser Gly Thr Glu Phe Thr Leu Thr Ile
65                  70                  75                  80 agc aga gtg gag gct gag gat gtt ggg gtt tat tac tgc atg caa tct      288
Ser Arg Val Glu Ala Glu Asp Val Gly Val Tyr Tyr Cys Met Gln Ser
                85                  90                  95
```

```
ctg caa acg ttc act ttc ggc gga ggg acc aag gtg gaa atc aaa    333
Leu Gln Thr Phe Thr Phe Gly Gly Gly Thr Lys Val Glu Ile Lys
            100                 105                 110
```

<210> SEQ ID NO 126
<211> LENGTH: 111
<212> TYPE: PRT
<213> ORGANISM: Homo sapiens

<400> SEQUENCE: 126

```
Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Arg Gln Lys Pro Gly Gln Ser
        35                  40                  45

Pro Gln Leu Leu Ile Tyr Leu Asn Ser Asn Arg Ala Ser Gly Val Pro
    50                  55                  60

Asp Arg Phe Ser Gly Ser Gly Ser Gly Thr Phe Thr Leu Thr Ile
65                  70                  75                  80

Ser Arg Val Glu Ala Glu Asp Val Gly Val Tyr Tyr Cys Met Gln Ser
                85                  90                  95

Leu Gln Thr Phe Thr Phe Gly Gly Gly Thr Lys Val Glu Ile Lys
            100                 105                 110
```

<210> SEQ ID NO 127
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.44D7-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 127

```
gag gtg cag ctg gtg gag tct ggg gga ggc ttg gta cag cct ggg ggg    48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat    96
Ser Leu Arg Leu Ser Cys Ala Ala Ser Gly Phe Thr Phe Ser Ser Tyr
            20                  25                  30 gcc atg agt tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca ggt att ggt tat agt gat act agc aca tat tac gca gac tcc gtg    192
Ser Gly Ile Gly Tyr Ser Asp Thr Ser Thr Tyr Tyr Ala Asp Ser Val
    50                  55                  60 aag ggc cgc ttc acc gtc tcc aga gac att tcc aag aac acg ctg tat    240
Lys Gly Arg Phe Thr Val Ser Arg Asp Ile Ser Lys Asn Thr Leu Tyr
```

```
              65                  70                  75                  80
ctg caa atg aat agc ctg agg gcc gag gac acg gcc gta tat tac tgc          288
Leu Gln Met Asn Ser Leu Arg Ala Glu Asp Thr Ala Val Tyr Tyr Cys
                    85                  90                  95 gcg aaa ggt acc agg gac tat tac ggt atg gac gtc tgg ggc caa gga          336
Ala Lys Gly Thr Arg Asp Tyr Tyr Gly Met Asp Val Trp Gly Gln Gly
            100                 105                 110 acc acg gtc acc gtc tcc tcg                                              357
Thr Thr Val Thr Val Ser Ser
        115

<210> SEQ ID NO 128
<211> LENGTH: 119
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Tyr Ser Asp Thr Ser Thr Tyr Tyr Ala Asp Ser Val
    50                  55                  60

Lys Gly Arg Phe Thr Val Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Thr Arg Asp Tyr Tyr Gly Met Asp Val Trp Gly Gln Gly
            100                 105                 110

Thr Thr Val Thr Val Ser Ser
        115

<210> SEQ ID NO 129
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-302.78H12-PIMC VH variable heavy chain (VH)
      sequence
<220> FEATURE:
<221> NAME/KEY: V_region
<222> LOCATION: (91)..(108)
<223> OTHER INFORMATION: complementarity determining region (CDR)
      VH-CDR1
<220> FEATURE:
<221> NAME/KEY: V_region
<222> LOCATION: (151)..(198)
<223> OTHER INFORMATION: complementarity determining region (CDR)
      VH-CDR2
<220> FEATURE:
<221> NAME/KEY: V_region
<222> LOCATION: (295)..(348)
<223> OTHER INFORMATION: complementarity determining region (CDR)
      VH-CDR3

<400> SEQUENCE: 129 cag ctg cag ctg cag gag tcg ggc cca gga ctg gtg aag cct tcg gag          48
Gln Leu Gln Leu Gln Glu Ser Gly Pro Gly Leu Val Lys Pro Ser Glu
1               5                   10                  15 acc ctg tcc ctc acc tgt ctt gtc tct agt tac tcc atc agc aat ggt          96
Thr Leu Ser Leu Thr Cys Leu Val Ser Ser Tyr Ser Ile Ser Asn Gly
```

```
Thr Leu Ser Leu Thr Cys Leu Val Ser Ser Tyr Ser Ile Ser Asn Gly
            20                  25                  30 tac tac tgg ggc tgg att cgg cag ccc cca ggg aag ggg ctg gag tgg      144
Tyr Tyr Trp Gly Trp Ile Arg Gln Pro Pro Gly Lys Gly Leu Glu Trp
            35                  40                  45 att ggg agt atc tat cat aat ggg aac acc tat tac aac ccg tcc ctc      192
Ile Gly Ser Ile Tyr His Asn Gly Asn Thr Tyr Tyr Asn Pro Ser Leu
 50                  55                  60 aag agt cga gtc atc att tca gta gac acg tcc aag aac cag ttc tcc      240
Lys Ser Arg Val Ile Ile Ser Val Asp Thr Ser Lys Asn Gln Phe Ser
 65                  70                  75                  80 ctg aag ttg agg tct gtg acc gcc gca gac acg gcc gtg tac tac tgt      288
Leu Lys Leu Arg Ser Val Thr Ala Ala Asp Thr Ala Val Tyr Tyr Cys
            85                  90                  95 gcg atg cca agt gcc acc tat tat tat ggt tcg ggg act caa ttc cat      336
Ala Met Pro Ser Ala Thr Tyr Tyr Tyr Gly Ser Gly Thr Gln Phe His
            100                 105                 110 gcg ttt gat gtc tgg ggc caa ggg aca atg gtc acc gtc tct tcg          381
Ala Phe Asp Val Trp Gly Gln Gly Thr Met Val Thr Val Ser Ser
            115                 120                 125
```

<210> SEQ ID NO 130
<211> LENGTH: 127
<212> TYPE: PRT
<213> ORGANISM: Homo sapiens

<400> SEQUENCE: 130

```
Gln Leu Gln Leu Gln Glu Ser Gly Pro Gly Leu Val Lys Pro Ser Glu
 1               5                  10                  15

Thr Leu Ser Leu Thr Cys Leu Val Ser Ser Tyr Ser Ile Ser Asn Gly
            20                  25                  30

Tyr Tyr Trp Gly Trp Ile Arg Gln Pro Pro Gly Lys Gly Leu Glu Trp
            35                  40                  45

Ile Gly Ser Ile Tyr His Asn Gly Asn Thr Tyr Tyr Asn Pro Ser Leu
 50                  55                  60

Lys Ser Arg Val Ile Ile Ser Val Asp Thr Ser Lys Asn Gln Phe Ser
 65                  70                  75                  80

Leu Lys Leu Arg Ser Val Thr Ala Ala Asp Thr Ala Val Tyr Tyr Cys
            85                  90                  95

Ala Met Pro Ser Ala Thr Tyr Tyr Tyr Gly Ser Gly Thr Gln Phe His
            100                 105                 110

Ala Phe Asp Val Trp Gly Gln Gly Thr Met Val Thr Val Ser Ser
            115                 120                 125
```

<210> SEQ ID NO 131
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION: NI-302.15E8 VH variable heavy chain (VH) sequence
<220> FEATURE:
<221> NAME/KEY: V_region
<222> LOCATION: (91)..(105)
<223> OTHER INFORMATION: complementarity determining region (CDR) VH-CDR1
<220> FEATURE:
<221> NAME/KEY: V_region
<222> LOCATION: (148)..(201)
<223> OTHER INFORMATION: complementarity determining region (CDR) VH-CDR2

<220> FEATURE:
<221> NAME/KEY: V_region
<222> LOCATION: (298)..(351)
<223> OTHER INFORMATION: complementarity determining region (CDR)
    VH-CDR3

<400> SEQUENCE: 131

```
gag gtg cag ctg gtg gag tct ggg gga ggc ttg ata cag ccg ggg ggg       48
Glu Val Gln Leu Val Glu Ser Gly Gly Gly Leu Ile Gln Pro Gly Gly
1               5                   10                  15 tcc ctg aga ctc tcc tgt gca gtc tct gga ttc acc gtc agt agt tat       96
Ser Leu Arg Leu Ser Cys Ala Val Ser Gly Phe Thr Val Ser Ser Tyr
            20                  25                  30 agc atg aac tgg gtc cgc cag gct cca ggg aag ggg ctg gag tgg gtc      144
Ser Met Asn Trp Val Arg Gln Ala Pro Gly Lys Gly Leu Glu Trp Val
        35                  40                  45 tca tac act agt agt agc aga agt aat acc aaa aag tac gca gac tct      192
Ser Tyr Thr Ser Ser Ser Arg Ser Asn Thr Lys Lys Tyr Ala Asp Ser
50                  55                  60 gtg aag ggc cga ttc acc atc tct aga gac aat gcc agg aac tca ctc      240
Val Lys Gly Arg Phe Thr Ile Ser Arg Asp Asn Ala Arg Asn Ser Leu
65                  70                  75                  80 tat ctg caa atg aac agc ctg aga gac gag gac acg gct gtg tat tac      288
Tyr Leu Gln Met Asn Ser Leu Arg Asp Glu Asp Thr Ala Val Tyr Tyr
                85                  90                  95 tgt gcg aga gca ggg gac ttc ggg gag tta ctc act ggt gag ggg tat      336
Cys Ala Arg Ala Gly Asp Phe Gly Glu Leu Leu Thr Gly Glu Gly Tyr
            100                 105                 110 tac ggt atg gac gtc tgg ggc caa ggg acc acg gtc acc gtc tcc tcg      384
Tyr Gly Met Asp Val Trp Gly Gln Gly Thr Thr Val Thr Val Ser Ser
        115                 120                 125
```

<210> SEQ ID NO 132
<211> LENGTH: 128
<212> TYPE: PRT
<213> ORGANISM: Homo sapiens

<400> SEQUENCE: 132

```
Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Thr Val Ser Ser Tyr
            20                  25                  30

Ser Met Asn Trp Val Arg Gln Ala Pro Gly Lys Gly Leu Glu Trp Val
        35                  40                  45

Ser Tyr Thr Ser Ser Ser Arg Ser Asn Thr Lys Lys Tyr Ala Asp Ser
50                  55                  60

Val Lys Gly Arg Phe Thr Ile Ser Arg Asp Asn Ala Arg Asn Ser Leu
65                  70                  75                  80

Tyr Leu Gln Met Asn Ser Leu Arg Asp Glu Asp Thr Ala Val Tyr Tyr
                85                  90                  95

Cys Ala Arg Ala Gly Asp Phe Gly Glu Leu Leu Thr Gly Glu Gly Tyr
            100                 105                 110

Tyr Gly Met Asp Val Trp Gly Gln Gly Thr Thr Val Thr Val Ser Ser
        115                 120                 125
```

<210> SEQ ID NO 133
<211> LENGTH: 318
<212> TYPE: DNA
<213> ORGANISM: Homo sapiens
<220> FEATURE:
<221> NAME/KEY: CDS

```
<222> LOCATION: (1)..(318)
<223> OTHER INFORMATION: NI-302.15E8 VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(288)
<223> OTHER INFORMATION: complementarity determining region (CDR)
      VL-CDR3

<400> SEQUENCE: 133 tcc tat gag ctg act cag cca ccc tca gtg tcc gtg tcc cca gga cag       48
Ser Tyr Glu Leu Thr Gln Pro Pro Ser Val Ser Val Ser Pro Gly Gln
1               5                   10                  15 aca gcc acc atc acc tgc tcg gga gat gaa ttg ggg gat aaa tat gtt       96
Thr Ala Thr Ile Thr Cys Ser Gly Asp Glu Leu Gly Asp Lys Tyr Val
                20                  25                  30 ggt tgg tat caa cag aag cca ggc cag tcc cct ctg ctg gtc atc tat      144
Gly Trp Tyr Gln Gln Lys Pro Gly Gln Ser Pro Leu Leu Val Ile Tyr
            35                  40                  45 caa gat gcg aag cgg ccc tca ggg atc cct gag cga ttc tct ggc tcc      192
Gln Asp Ala Lys Arg Pro Ser Gly Ile Pro Glu Arg Phe Ser Gly Ser
        50                  55                  60 aac tct ggg aac aca gcc act ctg acc atc agc ggg acc cag gct atg      240
Asn Ser Gly Asn Thr Ala Thr Leu Thr Ile Ser Gly Thr Gln Ala Met
65                  70                  75                  80 gat gag gct gac tac tac tgt cag gcg tgg gac agc ggc acg atg gtt      288
Asp Glu Ala Asp Tyr Tyr Cys Gln Ala Trp Asp Ser Gly Thr Met Val
                85                  90                  95 ttc ggc gga ggg acc agg ctg acc gtc cta                              318
Phe Gly Gly Gly Thr Arg Leu Thr Val Leu
                100                 105

<210> SEQ ID NO 134
<211> LENGTH: 106
<212> TYPE: PRT
<213> ORGANISM: Homo sapiens

<400> SEQUENCE: 134

Ser Tyr Glu Leu Thr Gln Pro Pro Ser Val Ser Val Ser Pro Gly Gln
1               5                   10                  15

Thr Ala Thr Ile Thr Cys Ser Gly Asp Glu Leu Gly Asp Lys Tyr Val
                20                  25                  30

Gly Trp Tyr Gln Gln Lys Pro Gly Gln Ser Pro Leu Leu Val Ile Tyr
            35                  40                  45

Gln Asp Ala Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Gly Thr Met Val
                85                  90                  95

Phe Gly Gly Gly Thr Arg Leu Thr Val Leu
                100                 105
```

```
<210> SEQ ID NO 135
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-302.15D3 variable heavy chain (VH) sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(339)
<223> OTHER INFORMATION: complementarity determining region (CDR)
      VH-CDR3

<400> SEQUENCE: 135 gag gtg cag ctg gtg gag tct ggg gga gac tta gtt cag cct ggg ggg      48
Glu Val Gln Leu Val Glu Ser Gly Gly Asp Leu Val Gln Pro Gly Gly
1               5                   10                  15 tcc cta aga ctc tcc tgt gca gcc tct gga ttc acc ttc agt agc tac      96
Ser Leu Arg Leu Ser Cys Ala Ala Ser Gly Phe Thr Phe Ser Ser Tyr
            20                  25                  30 tgg atg cac tgg gtc cgc caa gct cca ggg aag ggt ctg gtg tgg gtc     144
Trp Met His Trp Val Arg Gln Ala Pro Gly Lys Gly Leu Val Trp Val
        35                  40                  45 tca cgt att agt aat gat ggc agt agc aaa acc tac gcg gac tcc gtg     192
Ser Arg Ile Ser Asn Asp Gly Ser Ser Lys Thr Tyr Ala Asp Ser Val
    50                  55                  60 aag ggc cga ttc acc atc tcc aga gac aac gcc aaa aac acg ctg tat     240
Lys Gly Arg Phe Thr Ile Ser Arg Asp Asn Ala Lys Asn Thr Leu Tyr
65                  70                  75                  80 ctg caa atg aac agt ctg aga gcc gag gac acg gct gtg tat tac tgt     288
Leu Gln Met Asn Ser Leu Arg Ala Glu Asp Thr Ala Val Tyr Tyr Cys
                85                  90                  95 gca ata ctt ggc gga tat tgt agt agt acc agt tgt cgt ccc ttt gac     336
Ala Ile Leu Gly Gly Tyr Cys Ser Ser Thr Ser Cys Arg Pro Phe Asp
            100                 105                 110 aac tgg ggc cag gga acc ctg gtc acc gtc tcc tcg                     372
Asn Trp Gly Gln Gly Thr Leu Val Thr Val Ser Ser
        115                 120

<210> SEQ ID NO 136
<211> LENGTH: 124
<212> TYPE: PRT
<213> ORGANISM: Homo sapiens

<400> SEQUENCE: 136

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Ser Asn Asp Gly Ser Ser Lys Thr Tyr Ala Asp Ser Val
    50                  55                  60

Lys Gly Arg Phe Thr Ile Ser Arg Asp Asn Ala Lys Asn Thr Leu Tyr
```

```
                    65                  70                  75                  80
Leu Gln Met Asn Ser Leu Arg Ala Glu Asp Thr Ala Val Tyr Tyr Cys
                        85                  90                  95

Ala Ile Leu Gly Gly Tyr Cys Ser Ser Thr Ser Cys Arg Pro Phe Asp
                100                 105                 110

Asn Trp Gly Gln Gly Thr Leu Val Thr Val Ser Ser
            115                 120

<210> SEQ ID NO 137
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-302.15D3 VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 137 cag tct gcc ctg act cag cct gcc tcc gtg tct ggg tct cct gga cag      48
Gln Ser Ala Leu Thr Gln Pro Ala Ser Val Ser Gly Ser Pro Gly Gln
1               5                   10                  15 tcg atc acc atc tcc tgc act gga acc agc agt gac gtt ggt gtt tat      96
Ser Ile Thr Ile Ser Cys Thr Gly Thr Ser Ser Asp Val Gly Val Tyr
            20                  25                  30 aac tat gtc tcc tgg tac caa caa cac cca ggc aaa gcc ccc aaa ctc     144
Asn Tyr Val Ser Trp Tyr Gln Gln His Pro Gly Lys Ala Pro Lys Leu
        35                  40                  45 atg att ttt gat gtc agt aat cgg ccc tca ggg att tct aat cgc ttc     192
Met Ile Phe Asp Val Ser Asn Arg Pro Ser Gly Ile Ser Asn Arg Phe
    50                  55                  60 tct ggc tcc aag tct ggc aac acg gcc tcc ctg acc atc tct ggg ctc     240
Ser Gly Ser Lys Ser Gly Asn Thr Ala Ser Leu Thr Ile Ser Gly Leu
65                  70                  75                  80 cag gct gag gac gag gct gat tat tac tgc agc tca tat aca agc agc     288
Gln Ala Glu Asp Glu Ala Asp Tyr Tyr Cys Ser Ser Tyr Thr Ser Ser
                85                  90                  95 gac act tgg gtg ttc ggc gga ggg acc aag ctg acc atc cta             330
Asp Thr Trp Val Phe Gly Gly Gly Thr Lys Leu Thr Ile Leu
            100                 105                 110

<210> SEQ ID NO 138
<211> LENGTH: 110
<212> TYPE: PRT
<213> ORGANISM: Homo sapiens

<400> SEQUENCE: 138

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Val Tyr
```

```
                    20                  25                  30

Asn Tyr Val Ser Trp Tyr Gln Gln His Pro Gly Lys Ala Pro Lys Leu
            35                  40                  45

Met Ile Phe Asp Val Ser Asn Arg Pro Ser Gly Ile Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Asp Thr Trp Val Phe Gly Gly Gly Thr Lys Leu Thr Ile Leu
            100                 105                 110

<210> SEQ ID NO 139
<211> LENGTH: 8
<212> TYPE: PRT
<213> ORGANISM: Artificial Sequence
<220> FEATURE:
<223> OTHER INFORMATION: Epitope of NI-302.33C11 antibody

<400> SEQUENCE: 139

Pro Pro Pro Pro Pro Pro Pro Pro
1               5

<210> SEQ ID NO 140
<211> LENGTH: 10
<212> TYPE: PRT
<213> ORGANISM: Artificial Sequence
<220> FEATURE:
<223> OTHER INFORMATION: Epitope of NI-302.63F3 antibody

<400> SEQUENCE: 140

Pro Gln Pro Pro Pro Gln Ala Gln Pro Leu
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Epitope of NI-302.31F11 antibody

<400> SEQUENCE: 141

Pro Pro Pro Gln Leu Pro Gln Pro Pro Pro
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Epitope of NI-302.2A2 antibody

<400> SEQUENCE: 142

Gln Ala Gln Pro Leu Leu Pro Gln Pro Gln Pro Pro Pro Pro Pro
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Epitope of NI302.15D3 antibody

<400> SEQUENCE: 143
```

Pro Pro Pro Gln Leu Pro Gln Pro Pro Gln Ala Gln Pro Leu
1               5                   10                  15

<210> SEQ ID NO 144
<211> LENGTH: 11
<212> TYPE: PRT
<213> ORGANISM: Artificial Sequence
<220> FEATURE:
<223> OTHER INFORMATION: Epitope of NI302.15E8 antibody

<400> SEQUENCE: 144

Lys Ala Phe Glu Ser Leu Lys Ser Phe Gln Gln
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Epitope of NI-302.35C1 antibody

<400> SEQUENCE: 145

Pro Pro Gly Pro Ala Val Ala Glu Glu Pro Leu His Arg Pro
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Epitope of NI-302.74C11 antibody

<400> SEQUENCE: 146

Pro Pro Pro Pro Pro Pro Pro Pro Pro Pro Pro
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Epitope of NI-302.15F9 antibody

<400> SEQUENCE: 147

Pro Pro Pro Pro Pro Pro Pro Pro Pro Pro Pro
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Epitope of NI-302.39G12 antibody

<400> SEQUENCE: 148

Pro Pro Pro Pro Pro Pro Pro Pro Pro Pro Pro
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Epitope of NI-302.11A4 antibody

<400> SEQUENCE: 149

Pro Pro Pro Pro Pro Pro Pro Pro Pro Pro Pro

```
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Epitope of NI-302.22H9 antibody

<400> SEQUENCE: 150

Pro Pro Pro Pro Pro Pro Pro Pro Pro Pro Pro
1               5                   10

<210> SEQ ID NO 151
<211> LENGTH: 8
<212> TYPE: PRT
<213> ORGANISM: Artificial Sequence
<220> FEATURE:
<223> OTHER INFORMATION: Epitope of NI-302.44D7 antibody

<400> SEQUENCE: 151

Pro Pro Pro Pro Pro Pro Pro Pro
1               5

<210> SEQ ID NO 152
<211> LENGTH: 11
<212> TYPE: PRT
<213> ORGANISM: Artificial Sequence
<220> FEATURE:
<223> OTHER INFORMATION: Epitope of NI-302.37C12 antibody

<400> SEQUENCE: 152

Pro Pro Pro Pro Pro Pro Pro Pro Pro Pro Pro
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Epitope of NI-302.55D8 antibody

<400> SEQUENCE: 153

Pro Pro Pro Pro Pro Pro Pro Pro Pro Pro Pro
1               5                   10

<210> SEQ ID NO 154
<211> LENGTH: 8
<212> TYPE: PRT
<213> ORGANISM: Artificial Sequence
<220> FEATURE:
<223> OTHER INFORMATION: Epitope of NI-302.7A8 antibody

<400> SEQUENCE: 154

Pro Pro Pro Pro Pro Pro Pro Pro
1               5

<210> SEQ ID NO 155
<211> LENGTH: 11
<212> TYPE: PRT
<213> ORGANISM: Artificial Sequence
<220> FEATURE:
<223> OTHER INFORMATION: Epitope of NI-302.78H12 antibody

<400> SEQUENCE: 155

Pro Pro Pro Pro Pro Pro Pro Pro Pro Pro Pro
1               5                   10
```

<210> SEQ ID NO 156
<211> LENGTH: 11
<212> TYPE: PRT
<213> ORGANISM: Artificial Sequence
<220> FEATURE:
<223> OTHER INFORMATION: Epitope of NI-302.71F6 antibody

<400> SEQUENCE: 156

Pro Pro Pro Pro Pro Pro Pro Pro Pro Pro Pro
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Epitope of NI-302.11H6 antibody

<400> SEQUENCE: 157

Pro Pro Pro Pro Pro Pro
1               5

<210> SEQ ID NO 158
<211> LENGTH: 8
<212> TYPE: PRT
<213> ORGANISM: Artificial Sequence
<220> FEATURE:
<223> OTHER INFORMATION: Epitope of NI-302.3D8 antibody

<400> SEQUENCE: 158

Pro Pro Pro Pro Pro Pro Pro Pro
1               5

<210> SEQ ID NO 159
<211> LENGTH: 6
<212> TYPE: PRT
<213> ORGANISM: Artificial Sequence
<220> FEATURE:
<223> OTHER INFORMATION: Epitope of NI-302.18A1 antibody

<400> SEQUENCE: 159

Pro Pro Pro Pro Pro Pro
1               5

<210> SEQ ID NO 160
<211> LENGTH: 6
<212> TYPE: PRT
<213> ORGANISM: Artificial Sequence
<220> FEATURE:
<223> OTHER INFORMATION: Epitope of NI-302.52C9 antibody

<400> SEQUENCE: 160

Pro Pro Pro Pro Pro Pro
1               5

<210> SEQ ID NO 161
<211> LENGTH: 8
<212> TYPE: PRT
<213> ORGANISM: Artificial Sequence
<220> FEATURE:
<223> OTHER INFORMATION: Epitope of NI-302.46C9 antibody

<400> SEQUENCE: 161

Pro Pro Pro Pro Pro Pro Pro Pro
1               5

<210> SEQ ID NO 162
<211> LENGTH: 15
<212> TYPE: PRT
<213> ORGANISM: Artificial Sequence
<220> FEATURE:
<223> OTHER INFORMATION: Alternative epitope of NI-302.63F3 antibody

<400> SEQUENCE: 162

Pro Pro Pro Gln Leu Pro Gln Pro Pro Gln Ala Gln Pro Leu
1               5                   10                  15

<210> SEQ ID NO 163
<211> LENGTH: 11
<212> TYPE: PRT
<213> ORGANISM: Artificial Sequence
<220> FEATURE:
<223> OTHER INFORMATION: Alternative epitope of NI-302.33C11 antibody

<400> SEQUENCE: 163

Pro Pro Pro Pro Pro Pro Pro Pro Pro Pro
1               5                   10

<210> SEQ ID NO 164
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-302.64E5-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(355)
<223> OTHER INFORMATION: complementarity determining region (CDR)
      VH-CDR2

<400> SEQUENCE: 164 gag gtg cag ctg gtg gag act ggg gga ggc ttg gta aag cct ggg ggg      48
Glu Val Gln Leu Val Glu Thr Gly Gly Gly Leu Val Lys Pro Gly Gly
1               5                   10                  15 tcc ctt aga ctc tcc tgt gca gcc tct gga ttc act ttc gac cag gcc      96
Ser Leu Arg Leu Ser Cys Ala Ala Ser Gly Phe Thr Phe Asp Gln Ala
            20                  25                  30 tgg atg agc tgg gtc cgc cag gtt cca ggg aag ggg ctg gag tgg gtt     144
Trp Met Ser Trp Val Arg Gln Val Pro Gly Lys Gly Leu Glu Trp Val
        35                  40                  45 ggc cgg att aaa acg aaa act gag ggt gaa gca aca gac tac gca gcg     192
Gly Arg Ile Lys Thr Lys Thr Glu Gly Glu Ala Thr Asp Tyr Ala Ala
    50                  55                  60 ccc gtg aga ggc aga ttc acc atc tca aga gat gat tca gaa gac acg     240
Pro Val Arg Gly Arg Phe Thr Ile Ser Arg Asp Asp Ser Glu Asp Thr
65                  70                  75                  80 gtg ttt ctg caa atg aac agc ctg aaa acc gag gac aca gcc ctg tat     288
Val Phe Leu Gln Met Asn Ser Leu Lys Thr Glu Asp Thr Ala Leu Tyr
                85                  90                  95 tac tgt acg tca acg gga gtc tta gca gca gct gtc gat gtc tac tgg     336

```
Tyr Cys Thr Ser Thr Gly Val Leu Ala Ala Val Asp Val Tyr Trp
            100                 105                 110 ggc cag gga acc ctg gtc acc gtc tcc tcg                          366
Gly Gln Gly Thr Leu Val Thr Val Ser Ser
        115                 120

<210> SEQ ID NO 165
<211> LENGTH: 122
<212> TYPE: PRT
<213> ORGANISM: Homo sapiens

<400> SEQUENCE: 165

Glu Val Gln Leu Val Glu Thr Gly Gly Gly Leu Val Lys Pro Gly Gly
1               5                   10                  15

Ser Leu Arg Leu Ser Cys Ala Ala Ser Gly Phe Thr Phe Asp Gln Ala
            20                  25                  30

Trp Met Ser Trp Val Arg Gln Val Pro Gly Lys Gly Leu Glu Trp Val
        35                  40                  45

Gly Arg Ile Lys Thr Lys Thr Glu Gly Glu Ala Thr Asp Tyr Ala Ala
    50                  55                  60

Pro Val Arg Gly Arg Phe Thr Ile Ser Arg Asp Asp Ser Glu Asp Thr
65                  70                  75                  80

Val Phe Leu Gln Met Asn Ser Leu Lys Thr Glu Asp Thr Ala Leu Tyr
                85                  90                  95

Tyr Cys Thr Ser Thr Gly Val Leu Ala Ala Val Asp Val Tyr Trp
            100                 105                 110

Gly Gln Gly Thr Leu Val Thr Val Ser Ser
        115                 120

<210> SEQ ID NO 166
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-302.64E5-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(355)
<223> OTHER INFORMATION: complementarity determining region (CDR)
      VH-CDR3

<400> SEQUENCE: 166 gag gtg cag ctg gtg gag tct ggg gga ggc ttg gta aag cct ggg ggg     48
Glu Val Gln Leu Val Glu Ser Gly Gly Gly Leu Val Lys Pro Gly Gly
1               5                   10                  15 tcc ctt aga ctc tcc tgt gca gcc tct gga ttc act ttc gac cag gcc     96
Ser Leu Arg Leu Ser Cys Ala Ala Ser Gly Phe Thr Phe Asp Gln Ala
            20                  25                  30 tgg atg agc tgg gtc cgc cag gtt cca ggg aag ggg ctg gag tgg gtt    144
Trp Met Ser Trp Val Arg Gln Val Pro Gly Lys Gly Leu Glu Trp Val
        35                  40                  45
```

```
ggc cgg att aaa acg aaa act gag ggt gaa gca aca gac tac gca gcg      192
Gly Arg Ile Lys Thr Lys Thr Glu Gly Glu Ala Thr Asp Tyr Ala Ala
 50                  55                  60 ccc gtg aga ggc aga ttc acc atc tca aga gat gat tca gaa gac acg      240
Pro Val Arg Gly Arg Phe Thr Ile Ser Arg Asp Asp Ser Glu Asp Thr
 65                  70                  75                  80 gtg ttt ctg caa atg aac agc ctg aaa acc gag gac aca gcc ctg tat      288
Val Phe Leu Gln Met Asn Ser Leu Lys Thr Glu Asp Thr Ala Leu Tyr
                     85                  90                  95 tac tgt acg tca acg gga gtc tta gca gca gct gtc gat gtc tac tgg      336
Tyr Cys Thr Ser Thr Gly Val Leu Ala Ala Ala Val Asp Val Tyr Trp
                100                 105                 110 ggc cag ggc acc ctg gtc acc gtc tcc tcg                              366
Gly Gln Gly Thr Leu Val Thr Val Ser Ser
                115                 120
```

<210> SEQ ID NO 167
<211> LENGTH: 122
<212> TYPE: PRT
<213> ORGANISM: Homo sapiens

<400> SEQUENCE: 167

```
Glu Val Gln Leu Val Glu Ser Gly Gly Leu Val Lys Pro Gly Gly
  1               5                  10                  15

Ser Leu Arg Leu Ser Cys Ala Ala Ser Gly Phe Thr Phe Asp Gln Ala
                 20                  25                  30

Trp Met Ser Trp Val Arg Gln Val Pro Gly Lys Gly Leu Glu Trp Val
             35                  40                  45

Gly Arg Ile Lys Thr Lys Thr Glu Gly Glu Ala Thr Asp Tyr Ala Ala
 50                  55                  60

Pro Val Arg Gly Arg Phe Thr Ile Ser Arg Asp Asp Ser Glu Asp Thr
 65                  70                  75                  80

Val Phe Leu Gln Met Asn Ser Leu Lys Thr Glu Asp Thr Ala Leu Tyr
                     85                  90                  95

Tyr Cys Thr Ser Thr Gly Val Leu Ala Ala Ala Val Asp Val Tyr Trp
                100                 105                 110

Gly Gln Gly Thr Leu Val Thr Val Ser Ser
                115                 120
```

<210> SEQ ID NO 168
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-302.64E5 VK  variable light-kappa chain (VK)
      sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 168

```
gac atc cag ttg acc cag tct cca gac tcc ctg gct gtg tct ctg ggc    48
Asp Ile Gln Leu Thr Gln Ser Pro Asp Ser Leu Ala Val Ser Leu Gly
1               5                   10                  15 gag agg gcc acc atg acc tgc aag tcc agc cag agt ctt ttc tac agt    96
Glu Arg Ala Thr Met Thr Cys Lys Ser Ser Gln Ser Leu Phe Tyr Ser
                20                  25                  30 tac aac aat gag aac tac tta gcc tgg tat cag cag aga cca gga cag   144
Tyr Asn Asn Glu Asn Tyr Leu Ala Trp Tyr Gln Gln Arg Pro Gly Gln
        35                  40                  45 cct cct aag ttg ctc att tac tgg gca tct acc cgg gaa tcc ggg gtc   192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc   240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa   288
Ile Ser Ser Leu Gln Ala Glu Asp Val Ala Val Tyr Tyr Cys Gln Gln
                85                  90                  95 tat tat agt act cct cag acg ttc ggc caa ggg acc aaa gtg gat atc   336
Tyr Tyr Ser Thr Pro Gln Thr Phe Gly Gln Gly Thr Lys Val Asp Ile
                100                 105                 110 aaa                                                               339
Lys

<210> SEQ ID NO 169
<211> LENGTH: 113
<212> TYPE: PRT
<213> ORGANISM: Homo sapiens

<400> SEQUENCE: 169

Asp Ile Gln Leu Thr Gln Ser Pro Asp Ser Leu Ala Val Ser Leu Gly
1               5                   10                  15

Glu Arg Ala Thr Met Thr Cys Lys Ser Ser Gln Ser Leu Phe Tyr Ser
                20                  25                  30

Tyr Asn Asn Glu Asn Tyr Leu Ala Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Gln Thr Phe Gly Gln Gly Thr Lys Val Asp Ile
                100                 105                 110

Lys

<210> SEQ ID NO 170
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-302.64E5-PIMC VK variable kappa-light chain
      (VK) sequence
<220> FEATURE:
<221> NAME/KEY: V_region
<222> LOCATION: (70)..(120)
<223> OTHER INFORMATION: complementarity determining region (CDR)
      VK-CDR1
<220> FEATURE:
```

```
<221> NAME/KEY: V_region
<222> LOCATION: (166)..(186)
<223> OTHER INFORMATION: complementarity determining region (CDR)
      VK-CDR2
<220> FEATURE:
<221> NAME/KEY: V_region
<222> LOCATION: (283)..(309)
<223> OTHER INFORMATION: complementarity determining region (CDR)
      VK-CDR3

<400> SEQUENCE: 170 gat att gtg atg act caa tca cca gac tcc ctg gct gtg tct ctg ggc      48
Asp Ile Val Met Thr Gln Ser Pro Asp Ser Leu Ala Val Ser Leu Gly
1               5                   10                  15 gag agg gcc acc atg acc tgc aag tcc agc cag agt ctt ttc tac agt      96
Glu Arg Ala Thr Met Thr Cys Lys Ser Ser Gln Ser Leu Phe Tyr Ser
            20                  25                  30 tac aac aat gag aac tac tta gcc tgg tat cag cag aga cca gga cag     144
Tyr Asn Asn Glu Asn Tyr Leu Ala Trp Tyr Gln Gln Arg Pro Gly Gln
        35                  40                  45 cct cct aag ttg ctc att tac tgg gca tct acc cgg gaa tcc ggg gtc     192
Pro Pro Lys Leu Leu Ile Tyr Trp Ala Ser Thr Arg Glu Ser Gly Val
50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct cag acg ttc ggc caa ggg acc aag gtg gaa atc     336
Tyr Tyr Ser Thr Pro Gln Thr Phe Gly Gln Gly Thr Lys Val Glu Ile
            100                 105                 110 aaa                                                                 339
Lys

<210> SEQ ID NO 171
<211> LENGTH: 113
<212> TYPE: PRT
<213> ORGANISM: Homo sapiens

<400> SEQUENCE: 171

Asp Ile Val Met Thr Gln Ser Pro Asp Ser Leu Ala Val Ser Leu Gly
1               5                   10                  15

Glu Arg Ala Thr Met Thr Cys Lys Ser Ser Gln Ser Leu Phe Tyr Ser
            20                  25                  30

Tyr Asn Asn Glu Asn Tyr Leu Ala Trp Tyr Gln Gln Arg Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Gln Thr Phe Gly Gln Gly Thr Lys Val Glu Ile
            100                 105                 110

Lys

<210> SEQ ID NO 172
<211> LENGTH: 357
<212> TYPE: DNA
<213> ORGANISM: Homo sapiens
```

```
<220> FEATURE:
<221> NAME/KEY: CDS
<222> LOCATION: (1)..(357)
<223> OTHER INFORMATION: NI-302.7D8-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 172 cag gtg cag ctg gtg caa tct gga tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac aac ttc aat aac tat      96
Ser Val Lys Val Ser Cys Lys Ala Ser Gly Tyr Asn Phe Asn Asn Tyr
            20                  25                  30 gcc atc aat tgg ttg cga cag gcc cct gga caa ggg ctt gag tgg atg     144
Ala Ile Asn Trp Leu Arg Gln Ala Pro Gly Gln Gly Leu Glu Trp Met
        35                  40                  45 gga tgg atc aac acc atc act ggg cac cca acg tat gcc cag ggc ttc     192
Gly Trp Ile Asn Thr Ile Thr Gly His Pro Thr Tyr Ala Gln Gly Phe
    50                  55                  60 aaa gga cga ttt gtc ttc tcc ttg gac acc tct gtc agc acg gca tat     240
Lys Gly Arg Phe Val Phe Ser Leu Asp Thr Ser Val Ser Thr Ala Tyr
65                  70                  75                  80 ctg cag atc agc agc cta aag cct gag gac act gcc gtc tat tac tgt     288
Leu Gln Ile Ser Ser Leu Lys Pro Glu Asp Thr Ala Val Tyr Tyr Cys
                85                  90                  95 gcg aga act tac agt aac tac ggc gaa ttt gac tac tgg ggc cag gga     336
Ala Arg Thr Tyr Ser Asn Tyr Gly Glu Phe Asp Tyr Trp Gly Gln Gly
            100                 105                 110 acc ctg gtc acc gtc tcc tcg                                         357
Thr Leu Val Thr Val Ser Ser
        115

<210> SEQ ID NO 173
<211> LENGTH: 119
<212> TYPE: PRT
<213> ORGANISM: Homo sapiens

<400> SEQUENCE: 173

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Asn Phe Asn Asn Tyr
            20                  25                  30

Ala Ile Asn Trp Leu Arg Gln Ala Pro Gly Gln Gly Leu Glu Trp Met
        35                  40                  45

Gly Trp Ile Asn Thr Ile Thr Gly His Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Pro Glu Asp Thr Ala Val Tyr Tyr Cys
```

```
                    85                  90                  95
Ala Arg Thr Tyr Ser Asn Tyr Gly Glu Phe Asp Tyr Trp Gly Gln Gly
                100                 105                 110

Thr Leu Val Thr Val Ser Ser
        115

<210> SEQ ID NO 174
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-302.7D8 VL  variable light-lambda chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(303)
<223> OTHER INFORMATION: complementarity determining region (CDR)
      VL-CDR3

<400> SEQUENCE: 174 cag tct gcc ctg act cag cct gcc tcc gtg tct ggg tct cgt gga cag       48
Gln Ser Ala Leu Thr Gln Pro Ala Ser Val Ser Gly Ser Arg Gly Gln
1               5                   10                  15 tcg atc acc atc tcc tgc act gga acc agc agt gat gtt gga agt tat       96
Ser Ile Thr Ile Ser Cys Thr Gly Thr Ser Ser Asp Val Gly Ser Tyr
                20                  25                  30 aac ctt gtc tcc tgg tac caa cag tac cca ggc aag gcc ccc aag ctc      144
Asn Leu Val Ser Trp Tyr Gln Gln Tyr Pro Gly Lys Ala Pro Lys Leu
            35                  40                  45 ata att cat gag ggc agt gag cgg ccc tca ggg gtt tct aat cgc ttc      192
Ile Ile His Glu Gly Ser Glu Arg Pro Ser Gly Val Ser Asn Arg Phe
        50                  55                  60 tct ggc tcc aag tct ggc aac acg gcc tcc ctg aca att tct ggg ctc      240
Ser Gly Ser Lys Ser Gly Asn Thr Ala Ser Leu Thr Ile Ser Gly Leu
65                  70                  75                  80 cag gct gag gac gag gct gat tat tac tgc tgc tca tat gca ggt act      288
Gln Ala Glu Asp Glu Ala Asp Tyr Tyr Cys Cys Ser Tyr Ala Gly Thr
                85                  90                  95 act act ttc gtg cta ttc ggc gga ggg acc aag ctg acc gtc ctc          333
Thr Thr Phe Val Leu Phe Gly Gly Gly Thr Lys Leu Thr Val Leu
                100                 105                 110

<210> SEQ ID NO 175
<211> LENGTH: 111
<212> TYPE: PRT
<213> ORGANISM: Homo sapiens

<400> SEQUENCE: 175

Gln Ser Ala Leu Thr Gln Pro Ala Ser Val Ser Gly Ser Arg Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln Tyr Pro Gly Lys Ala Pro Lys Leu
```

```
                35                  40                  45
Ile Ile His Glu Gly Ser Glu Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Thr
                 85                  90                  95

Thr Thr Phe Val Leu Phe Gly Gly Gly Thr Lys Leu Thr Val Leu
                100                 105                 110

<210> SEQ ID NO 176
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.72F10-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR2

<400> SEQUENCE: 176 gag gtg cag ctg gtg gag act ggg gga ggc ttc gta cag cct ggg ggg      48
Glu Val Gln Leu Val Glu Thr Gly Gly Gly Phe Val Gln Pro Gly Gly
 1               5                  10                  15 tcc ctg aga ctc tcc tgt gca gcc tct gga ttc aac ttc ggc agt tat      96
Ser Leu Arg Leu Ser Cys Ala Ala Ser Gly Phe Asn Phe Gly Ser Tyr
                 20                  25                  30 gcc atg agc tgg gtc cgc cag gct cca ggg aag gga ctg gag tgg gtg     144
Ala Met Ser Trp Val Arg Gln Ala Pro Gly Lys Gly Leu Glu Trp Val
             35                  40                  45 tca gat atc agt ggt att ggt agt aac aca tac tac gca gac tcc gtg     192
Ser Asp Ile Ser Gly Ile Gly Ser Asn Thr Tyr Tyr Ala Asp Ser Val
         50                  55                  60 aag ggc cgt ttc acc att tcc aga gac aat tcc gac aat acg ttg tac     240
Lys Gly Arg Phe Thr Ile Ser Arg Asp Asn Ser Asp Asn Thr Leu Tyr
 65                  70                  75                  80 ctg gac atg agc agc ctg aga gcc gag gac acg gcc aga tat tac tgt     288
Leu Asp Met Ser Ser Leu Arg Ala Glu Asp Thr Ala Arg Tyr Tyr Cys
                 85                  90                  95 gcg aag gat cga aag cgc agt ggc tgg tac gaa cag tgg ggc cag ggc     336
Ala Lys Asp Arg Lys Arg Ser Gly Trp Tyr Glu Gln Trp Gly Gln Gly
            100                 105                 110 acc ctg gtc acc gtc tcc tcg                                         357
Thr Leu Val Thr Val Ser Ser
        115

<210> SEQ ID NO 177
<211> LENGTH: 119
<212> TYPE: PRT
<213> ORGANISM: Homo sapiens
```

<400> SEQUENCE: 177

Glu Val Gln Leu Val Glu Thr Gly Gly Gly Phe Val Gln Pro Gly Gly
1               5                   10                  15

Ser Leu Arg Leu Ser Cys Ala Ala Ser Gly Phe Asn Phe Gly Ser Tyr
            20                  25                  30

Ala Met Ser Trp Val Arg Gln Ala Pro Gly Lys Gly Leu Glu Trp Val
        35                  40                  45

Ser Asp Ile Ser Gly Ile Gly Ser Asn Thr Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Asp Met Ser Ser Leu Arg Ala Glu Asp Thr Ala Arg Tyr Tyr Cys
                85                  90                  95

Ala Lys Asp Arg Lys Arg Ser Gly Trp Tyr Glu Gln Trp Gly Gln Gly
            100                 105                 110

Thr Leu Val Thr Val Ser Ser
            115

<210> SEQ ID NO 178
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-302.72F10-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 178 gag gtg cag ctg gtg gag tct ggg gga ggc ttc gta cag cct ggg ggg    48
Glu Val Gln Leu Val Glu Ser Gly Gly Gly Phe Val Gln Pro Gly Gly
1               5                   10                  15 tcc ctg aga ctc tcc tgt gca gcc tct gga ttc aac ttc ggc agt tat    96
Ser Leu Arg Leu Ser Cys Ala Ala Ser Gly Phe Asn Phe Gly Ser Tyr
            20                  25                  30 gcc atg agc tgg gtc cgc cag gct cca ggg aag gga ctg gag tgg gtg   144
Ala Met Ser Trp Val Arg Gln Ala Pro Gly Lys Gly Leu Glu Trp Val
        35                  40                  45 tca gat atc agt ggt att ggt agt aac aca tac tac gca gac tcc gtg   192
Ser Asp Ile Ser Gly Ile Gly Ser Asn Thr Tyr Tyr Ala Asp Ser Val
    50                  55                  60 aag ggc cgt ttc acc att tcc aga gac aat tcc gac aat acg ttg tac   240
Lys Gly Arg Phe Thr Ile Ser Arg Asp Asn Ser Asp Asn Thr Leu Tyr
65                  70                  75                  80 ctg gac atg agc agc ctg aga gcc gag gac acg gcc aga tat tac tgt   288
Leu Asp Met Ser Ser Leu Arg Ala Glu Asp Thr Ala Arg Tyr Tyr Cys
                85                  90                  95

```
gcg aag gat cga aag cgc agt ggc tgg tac gaa cag tgg ggc cag ggc     336
Ala Lys Asp Arg Lys Arg Ser Gly Trp Tyr Glu Gln Trp Gly Gln Gly
            100                 105                 110 acc ctg gtc acc gtc tcc tcg                                         357
Thr Leu Val Thr Val Ser Ser
        115
```

<210> SEQ ID NO 179
<211> LENGTH: 119
<212> TYPE: PRT
<213> ORGANISM: Homo sapiens

<400> SEQUENCE: 179

```
Glu Val Gln Leu Val Glu Ser Gly Gly Gly Phe Val Gln Pro Gly Gly
1               5                   10                  15

Ser Leu Arg Leu Ser Cys Ala Ala Ser Gly Phe Asn Phe Gly Ser Tyr
            20                  25                  30

Ala Met Ser Trp Val Arg Gln Ala Pro Gly Lys Gly Leu Glu Trp Val
        35                  40                  45

Ser Asp Ile Ser Gly Ile Gly Ser Asn Thr Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Asp Met Ser Ser Leu Arg Ala Glu Asp Thr Ala Arg Tyr Tyr Cys
                85                  90                  95

Ala Lys Asp Arg Lys Arg Ser Gly Trp Tyr Glu Gln Trp Gly Gln Gly
            100                 105                 110

Thr Leu Val Thr Val Ser Ser
        115
```

<210> SEQ ID NO 180
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.72F10 VK  variable light-kappa chain
      (VK) sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 180

```
gaa att gtg atg aca cag tct cca gcc acc ctg act ttg tct cca ggg     48
Glu Ile Val Met Thr Gln Ser Pro Ala Thr Leu Thr Leu Ser Pro Gly
1               5                   10                  15 gaa aga gcc acc ctc tcc tgc agg gcc agt cag agt att agc gcc tac     96
Glu Arg Ala Thr Leu Ser Cys Arg Ala Ser Gln Ser Ile Ser Ala Tyr
            20                  25                  30 tta ggc tgg tat caa caa aaa cct ggc cag gct ccc agg ctc ctc atc     144
Leu Gly Trp Tyr Gln Gln Lys Pro Gly Gln Ala Pro Arg Leu Leu Ile
        35                  40                  45
```

```
tat gat gca tcc att agg gcc act ggc att cca gac agg ttt agt ggc        192
Tyr Asp Ala Ser Ile Arg Ala Thr Gly Ile Pro Asp Arg Phe Ser Gly
    50                  55                  60 agt ggg tct ggg aca gac ttc act ctc acc atc agc agc cta gag cct        240
Ser Gly Ser Gly Thr Asp Phe Thr Leu Thr Ile Ser Ser Leu Glu Pro
65                  70                  75                  80 gaa gat tct gca gtt tat tac tgt cac cag cgt agc aag tgg cct ctt        288
Glu Asp Ser Ala Val Tyr Tyr Cys His Gln Arg Ser Lys Trp Pro Leu
                85                  90                  95 act ttc ggc gga ggg acc aag gtg gaa atc aaa                            321
Thr Phe Gly Gly Gly Thr Lys Val Glu Ile Lys
                100                 105

<210> SEQ ID NO 181
<211> LENGTH: 107
<212> TYPE: PRT
<213> ORGANISM: Homo sapiens

<400> SEQUENCE: 181

Glu Ile Val Met Thr Gln Ser Pro Ala Thr Leu Thr Leu Ser Pro Gly
1               5                   10                  15

Glu Arg Ala Thr Leu Ser Cys Arg Ala Ser Gln Ser Ile Ser Ala Tyr
            20                  25                  30

Leu Gly Trp Tyr Gln Gln Lys Pro Gly Gln Ala Pro Arg Leu Leu Ile
        35                  40                  45

Tyr Asp Ala Ser Ile Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Val Tyr Tyr Cys His Gln Arg Ser Lys Trp Pro Leu
                85                  90                  95

Thr Phe Gly Gly Gly Thr Lys Val Glu Ile Lys
                100                 105

<210> SEQ ID NO 182
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.72F10-PIMC VK variable kappa-light chain
      (VK) sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 182 gaa att gtg ctg act cag tct cca gcc acc ctg act ttg tct cca ggg         48
Glu Ile Val Leu Thr Gln Ser Pro Ala Thr Leu Thr Leu Ser Pro Gly
1               5                   10                  15 gaa aga gcc acc ctc tcc tgc agg gcc agt cag agt att agc gcc tac         96
```

```
                Glu Arg Ala Thr Leu Ser Cys Arg Ala Ser Gln Ser Ile Ser Ala Tyr
                                 20                  25                  30 tta ggc tgg tat caa caa aaa cct ggc cag gct ccc agg ctc ctc atc              144
Leu Gly Trp Tyr Gln Gln Lys Pro Gly Gln Ala Pro Arg Leu Leu Ile
             35                  40                  45 tat gat gca tcc att agg gcc act ggc att cca gac agg ttt agt ggc              192
Tyr Asp Ala Ser Ile Arg Ala Thr Gly Ile Pro Asp Arg Phe Ser Gly
 50                  55                  60 agt ggg tct ggg aca gac ttc act ctc acc atc agc agc cta gag cct              240
Ser Gly Ser Gly Thr Asp Phe Thr Leu Thr Ile Ser Ser Leu Glu Pro
 65                  70                  75                  80 gaa gat tct gca gtt tat tac tgt cac cag cgt agc aag tgg cct ctt              288
Glu Asp Ser Ala Val Tyr Tyr Cys His Gln Arg Ser Lys Trp Pro Leu
                 85                  90                  95 act ttc ggc gga ggg acc aag gtg gaa atc aaa                                  321
Thr Phe Gly Gly Gly Thr Lys Val Glu Ile Lys
            100                 105

<210> SEQ ID NO 183
<211> LENGTH: 107
<212> TYPE: PRT
<213> ORGANISM: Homo sapiens

<400> SEQUENCE: 183

Glu Ile Val Leu Thr Gln Ser Pro Ala Thr Leu Thr Leu Ser Pro Gly
1               5                   10                  15

Glu Arg Ala Thr Leu Ser Cys Arg Ala Ser Gln Ser Ile Ser Ala Tyr
                 20                  25                  30

Leu Gly Trp Tyr Gln Gln Lys Pro Gly Gln Ala Pro Arg Leu Leu Ile
             35                  40                  45

Tyr Asp Ala Ser Ile Arg Ala Thr Gly Ile Pro Asp Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Ser Ala Val Tyr Tyr Cys His Gln Arg Ser Lys Trp Pro Leu
                 85                  90                  95

Thr Phe Gly Gly Gly Thr Lys Val Glu Ile Lys
            100                 105

<210> SEQ ID NO 184
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-302.4A6-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 184
```

```
gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc gct tat        96
Ser Leu Arg Leu Ser Cys Ala Ala Ser Gly Phe Thr Phe Ser Ala Tyr
            20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
        35                  40                  45 tca act att agt ggt agt ggt ggt agt aca tac tac gca gac tcc gtg       192
Ser Thr Ile Ser Gly Ser Gly Gly Ser Thr Tyr Tyr Ala Asp Ser Val
    50                  55                  60 aag ggc cgg ttc tcc atc tcc aga gac aac tcc aaa aac acc ctg tat       240
Lys Gly Arg Phe Ser Ile Ser Arg Asp Asn Ser Lys Asn Thr Leu Tyr
65                  70                  75                  80 ctg caa atg aac agc ctg aga gcc gag gac acg gcc gta tat ttc tgt       288
Leu Gln Met Asn Ser Leu Arg Ala Glu Asp Thr Ala Val Tyr Phe Cys
                85                  90                  95 gcg aaa gtt acc acg gaa ctc tac ggt gct aac tcc tac tac tac tac       336
Ala Lys Val Thr Thr Glu Leu Tyr Gly Ala Asn Ser Tyr Tyr Tyr Tyr
            100                 105                 110 atg gac gtc tgg ggc aaa ggg acc acg gtc acc gtc tcc tcg                378
Met Asp Val Trp Gly Lys Gly Thr Thr Val Thr Val Ser Ser
        115                 120                 125

<210> SEQ ID NO 185
<211> LENGTH: 126
<212> TYPE: PRT
<213> ORGANISM: Homo sapiens

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Val Thr Thr Glu Leu Tyr Gly Ala Asn Ser Tyr Tyr Tyr Tyr
            100                 105                 110

Met Asp Val Trp Gly Lys Gly Thr Thr Val Thr Val Ser Ser
        115                 120                 125

<210> SEQ ID NO 186
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.4A6 VK  variable light-kappa chain (VK)
      sequence
<220> FEATURE:
<221> NAME/KEY: V_region
<222> LOCATION: (70)..(105)
<223> OTHER INFORMATION: complementarity determining region (CDR)
```

```
        VK-CDR1
<220> FEATURE:
<221> NAME/KEY: V_region
<222> LOCATION: (151)..(171)
<223> OTHER INFORMATION: complementarity determining region (CDR)
        VK-CDR2
<220> FEATURE:
<221> NAME/KEY: V_region
<222> LOCATION: (286)..(291)
<223> OTHER INFORMATION: complementarity determining region (CDR)
        VK-CDR3

<400> SEQUENCE: 186 gaa att gtg ttg aca cag tct cca ggc acc ctg tct ttg tct cca ggg       48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt gtc agc agg       96
Glu Arg Ala Thr Leu Ser Cys Arg Ala Ser Gln Ser Val Val Ser Arg
            20                  25                  30 tat tta gcc tgg tac cag caa aaa cct ggc cag gct ccc agg ctc ctc      144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80 cct gaa gat ttt gca atg tat tac tgt cag ctg tat ggt aac tca cag      288
Pro Glu Asp Phe Ala Met Tyr Tyr Cys Gln Leu Tyr Gly Asn Ser Gln
                85                  90                  95 acg ttc ggc cag ggg acc aag gtg gag atc aaa                          321
Thr Phe Gly Gln Gly Thr Lys Val Glu Ile Lys
                100                 105

<210> SEQ ID NO 187
<211> LENGTH: 107
<212> TYPE: PRT
<213> ORGANISM: Homo sapiens

<400> SEQUENCE: 187

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Val Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys Gln Leu Tyr Gly Asn Ser Gln
                85                  90                  95

Thr Phe Gly Gln Gly Thr Lys Val Glu Ile Lys
                100                 105

<210> SEQ ID NO 188
<211> LENGTH: 375
<212> TYPE: DNA
<213> ORGANISM: Homo sapiens
<220> FEATURE:
<221> NAME/KEY: CDS
<222> LOCATION: (1)..(375)
```

```
<223> OTHER INFORMATION: NI-302.12H2-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(342)
<223> OTHER INFORMATION: complementarity determining region (CDR)
      VH-CDR3

<400> SEQUENCE: 188 gag gtg cag ctg gtg cag tct ggg gga ggc ttg gta cag cct ggg ggg         48
Glu Val Gln Leu Val Gln Ser Gly Gly Gly Leu Val Gln Pro Gly Gly
1               5                   10                  15 tcc ctg aga ctt tcc tgt gaa gcc tct gga ttc acc ttt agc aac tat         96
Ser Leu Arg Leu Ser Cys Glu Ala Ser Gly Phe Thr Phe Ser Asn Tyr
            20                  25                  30 gcc atg ggc tgg gtc cgc cag gct cca ggg aag ggg ctg gag tgg gtc        144
Ala Met Gly Trp Val Arg Gln Ala Pro Gly Lys Gly Leu Glu Trp Val
        35                  40                  45 tca gta att agt ggt act ggt ggt agc aca tac tac gca gac tcc gtg        192
Ser Val Ile Ser Gly Thr Gly Gly Ser Thr Tyr Tyr Ala Asp Ser Val
    50                  55                  60 aag ggc cgg ttc acc atc tcc aga gac aat tcc atg aac acg ctg tat        240
Lys Gly Arg Phe Thr Ile Ser Arg Asp Asn Ser Met Asn Thr Leu Tyr
65                  70                  75                  80 ctg caa atg aac agc ccg aga gcc gac gac acg gcc gta tat tac tgt        288
Leu Gln Met Asn Ser Pro Arg Ala Asp Asp Thr Ala Val Tyr Tyr Cys
                85                  90                  95 gcg aaa gat ctg agg aag att agc ggt cct tta tac tac tac ggt atg        336
Ala Lys Asp Leu Arg Lys Ile Ser Gly Pro Leu Tyr Tyr Tyr Gly Met
            100                 105                 110 gac gtc tgg ggc caa ggg acc acg gtc acc gtc tcc tcg                    375
Asp Val Trp Gly Gln Gly Thr Thr Val Thr Val Ser Ser
        115                 120                 125

<210> SEQ ID NO 189
<211> LENGTH: 125
<212> TYPE: PRT
<213> ORGANISM: Homo sapiens

<400> SEQUENCE: 189

Glu Val Gln Leu Val Gln Ser Gly Gly Gly Leu Val Gln Pro Gly Gly
1               5                   10                  15

Ser Leu Arg Leu Ser Cys Glu Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Val Ile Ser Gly Thr Gly Gly Ser Thr Tyr Tyr Ala Asp Ser Val
    50                  55                  60

Lys Gly Arg Phe Thr Ile Ser Arg Asp Asn Ser Met Asn Thr Leu Tyr
65                  70                  75                  80

Leu Gln Met Asn Ser Pro Arg Ala Asp Asp Thr Ala Val Tyr Tyr Cys
                85                  90                  95

Ala Lys Asp Leu Arg Lys Ile Ser Gly Pro Leu Tyr Tyr Tyr Gly Met
```

```
                100                 105                 110
Asp Val Trp Gly Gln Gly Thr Thr Val Thr Val Ser Ser
        115                 120                 125

<210> SEQ ID NO 190
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-302.12H2-PIMC VH variable heavy chain (VH)
      sequence
<220> FEATURE:
<221> NAME/KEY: V_rehion
<222> LOCATION: (91)..(105)
<223> OTHER INFORMATION: complementarity determining region (CDR)
      VH-CDR1
<220> FEATURE:
<221> NAME/KEY: V_rehion
<222> LOCATION: (148)..(198)
<223> OTHER INFORMATION: complementarity determining region (CDR)
      VH-CDR2
<220> FEATURE:
<221> NAME/KEY: V_rehion
<222> LOCATION: (295)..(342)
<223> OTHER INFORMATION: complementarity determining region (CDR)
      VH-CDR3

<400> SEQUENCE: 190 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctt tcc tgt gaa gcc tct gga ttc acc ttt agc aac tat      96
Ser Leu Arg Leu Ser Cys Glu Ala Ser Gly Phe Thr Phe Ser Asn Tyr
            20                  25                  30 gcc atg ggc tgg gtc cgc cag gct cca ggg aag ggg ctg gag tgg gtc     144
Ala Met Gly Trp Val Arg Gln Ala Pro Gly Lys Gly Leu Glu Trp Val
        35                  40                  45 tca gta att agt ggt act ggt ggt agc aca tac tac gca gac tcc gtg     192
Ser Val Ile Ser Gly Thr Gly Gly Ser Thr Tyr Tyr Ala Asp Ser Val
    50                  55                  60 aag ggc cgg ttc acc atc tcc aga gac aat tcc atg aac acg ctg tat     240
Lys Gly Arg Phe Thr Ile Ser Arg Asp Asn Ser Met Asn Thr Leu Tyr
65                  70                  75                  80 ctg caa atg aac agc ccg aga gcc gac gac acg gcc gta tat tac tgt     288
Leu Gln Met Asn Ser Pro Arg Ala Asp Asp Thr Ala Val Tyr Tyr Cys
                85                  90                  95 gcg aaa gat ctg agg aag att agc ggt cct tta tac tac tac ggt atg     336
Ala Lys Asp Leu Arg Lys Ile Ser Gly Pro Leu Tyr Tyr Tyr Gly Met
            100                 105                 110 gac gtc tgg ggc caa ggg acc acg gtc acc gtc tcc tcg                 375
Asp Val Trp Gly Gln Gly Thr Thr Val Thr Val Ser Ser
        115                 120                 125

<210> SEQ ID NO 191
<211> LENGTH: 125
<212> TYPE: PRT
<213> ORGANISM: Homo sapiens

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Asn Tyr
            20                  25                  30
```

-continued

```
Ala Met Gly Trp Val Arg Gln Ala Pro Gly Lys Gly Leu Glu Trp Val
        35                  40                  45
Ser Val Ile Ser Gly Thr Gly Ser Thr Tyr Tyr Ala Asp Ser Val
 50                  55                  60
Lys Gly Arg Phe Thr Ile Ser Arg Asp Asn Ser Met Asn Thr Leu Tyr
 65                  70                  75                  80
Leu Gln Met Asn Ser Pro Arg Ala Asp Thr Ala Val Tyr Tyr Cys
                85                  90                  95
Ala Lys Asp Leu Arg Lys Ile Ser Gly Pro Leu Tyr Tyr Gly Met
            100                 105                 110
Asp Val Trp Gly Gln Gly Thr Thr Val Thr Val Ser Ser
        115                 120                 125
```

<210> SEQ ID NO 192
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-302.12H2 VK  variable light-kappa chain (VK)
      sequence
<220> FEATURE:
<221> NAME/KEY: V_region
<222> LOCATION: (70)..(105)
<223> OTHER INFORMATION: complementarity determining region (CDR)
      VK-CDR1
<220> FEATURE:
<221> NAME/KEY: V_region
<222> LOCATION: (151)..(171)
<223> OTHER INFORMATION: complementarity determining region (CDR)
      VK-CDR2
<220> FEATURE:
<221> NAME/KEY: V_region
<222> LOCATION: (268)..(294)
<223> OTHER INFORMATION: complementarity determining region (CDR)
      VK-CDR2

<400> SEQUENCE: 192

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc ggc      96
Glu Arg Ala Thr Leu Ser Cys Arg Ala Ser Gln Ser Val Ser Ser Gly
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc acc agg gcc act ggc atc cca gac agg ttc agt     192
Ile Tyr Gly Ala Ser Thr Arg Ala Thr Gly Ile Pro Asp Arg Phe Ser
 50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cac tat ggt gcc tca tcg     288
Pro Glu Asp Phe Ala Val Tyr Tyr Cys Gln His Tyr Gly Ala Ser Ser
                85                  90                  95 tac act ttt ggc cag ggg acc aag ctg gag atc aaa                     324
Tyr Thr Phe Gly Gln Gly Thr Lys Leu Glu Ile Lys
            100                 105
```

<210> SEQ ID NO 193
<211> LENGTH: 108
<212> TYPE: PRT
<213> ORGANISM: Homo sapiens

<400> SEQUENCE: 193

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ala Ser Ser
                85                  90                  95

Tyr Thr Phe Gly Gln Gly Thr Lys Leu Glu Ile Lys
            100                 105

<210> SEQ ID NO 194
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-302.8M1-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 194 gag gtc cag ctg gtg cag tct ggg gct gag gtg aag aag cct ggg gcc      48
Glu Val Gln Leu Val Gln Ser Gly Ala Glu Val Lys Lys Pro Gly Ala
1               5                   10                  15 tca gtg aaa gtt tcc tgc aag gca tcc gga tac acc ttc acc atc tac      96
Ser Val Lys Val Ser Cys Lys Ala Ser Gly Tyr Thr Phe Thr Ile Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga gga atc agc ccg agt ggt gcc cac aca atg tac gca cag aat ttc     192
Gly Gly Ile Ser Pro Ser Gly Ala His Thr Met Tyr Ala Gln Asn Phe
50                  55                  60 cag ggc aga gtc acc gtg acc agg gac acg tcc acg agc aca gtc tac     240
Gln Gly Arg Val Thr Val Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga ggg agc acg gtg act aac tat cga ccc ttt gac tac tgg ggc     336
Ala Arg Gly Ser Thr Val Thr Asn Tyr Arg Pro Phe Asp Tyr Trp Gly
            100                 105                 110

```
cag gga acc ctg gtc acc gtc tcc tcg                              363
Gln Gly Thr Leu Val Thr Val Ser Ser
        115                 120

<210> SEQ ID NO 195
<211> LENGTH: 121
<212> TYPE: PRT
<213> ORGANISM: Homo sapiens

<400> SEQUENCE: 195

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Tyr Met His Trp Val Arg Gln Ala Pro Gly Gln Gly Leu Glu Trp Met
        35                  40                  45

Gly Gly Ile Ser Pro Ser Gly Ala His Thr Met Tyr Ala Gln Asn Phe
    50                  55                  60

Gln Gly Arg Val Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Thr Val Thr Asn Tyr Arg Pro Phe Asp Tyr Trp Gly
            100                 105                 110

Gln Gly Thr Leu Val Thr Val Ser Ser
        115                 120

<210> SEQ ID NO 196
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-302.8M1-PIMC VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 196 cag gtg cag ctg gtg caa tct ggg gct gag gtg aag aag cct ggg gcc    48
Gln Val Gln Leu Val Gln Ser Gly Ala Glu Val Lys Lys Pro Gly Ala
1               5                   10                  15 tca gtg aaa gtt tcc tgc aag gca tcc gga tac acc ttc acc atc tac    96
Ser Val Lys Val Ser Cys Lys Ala Ser Gly Tyr Thr Phe Thr Ile Tyr
            20                  25                  30 tat atg cac tgg gtg cga cag gcc cct gga caa ggg ctt gag tgg atg   144
Tyr Met His Trp Val Arg Gln Ala Pro Gly Gln Gly Leu Glu Trp Met
        35                  40                  45 gga gga atc agc ccg agt ggt gcc cac aca atg tac gca cag aat ttc   192
Gly Gly Ile Ser Pro Ser Gly Ala His Thr Met Tyr Ala Gln Asn Phe
```

```
                      50                  55                  60
cag ggc aga gtc acc gtg acc agg gac acg tcc acg agc aca gtc tac       240
Gln Gly Arg Val Thr Val Thr Arg Asp Thr Ser Thr Ser Thr Val Tyr
 65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                 85                  90                  95 gcg aga ggg agc acg gtg act aac tat cga ccc ttt gac tac tgg ggc       336
Ala Arg Gly Ser Thr Val Thr Asn Tyr Arg Pro Phe Asp Tyr Trp Gly
            100                 105                 110 cag ggc acc ctg gtc acc gtc tcc tcg                                   363
Gln Gly Thr Leu Val Thr Val Ser Ser
        115                 120

<210> SEQ ID NO 197
<211> LENGTH: 121
<212> TYPE: PRT
<213> ORGANISM: Homo sapiens

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
                20                  25                  30

Tyr Met His Trp Val Arg Gln Ala Pro Gly Gln Gly Leu Glu Trp Met
            35                  40                  45

Gly Gly Ile Ser Pro Ser Gly Ala His Thr Met Tyr Ala Gln Asn Phe
        50                  55                  60

Gln Gly Arg Val Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Thr Val Thr Asn Tyr Arg Pro Phe Asp Tyr Trp Gly
            100                 105                 110

Gln Gly Thr Leu Val Thr Val Ser Ser
        115                 120

<210> SEQ ID NO 198
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-302.8M1 VK variable light-kappa chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 198 gac atc cag atg acc cag tct cca tcc tcc ctg tct gca tct gta gga       48
```

```
Asp Ile Gln Met Thr Gln Ser Pro Ser Ser Leu Ser Ala Ser Val Gly
1               5                   10                  15 gac aga gtc act atc act tgc cgg gcg agt cag gac att agc aat tat        96
Asp Arg Val Thr Ile Thr Cys Arg Ala Ser Gln Asp Ile Ser Asn Tyr
            20                  25                  30 tta gcc tgg tat cag cag aaa cca ggg aaa gtt cct aaa ctc ctg atc        144
Leu Ala Trp Tyr Gln Gln Lys Pro Gly Lys Val Pro Lys Leu Leu Ile
            35                  40                  45 ttt gct gca tcc act ttg caa tca ggg gtc ccg tct cgg ttc ggt ggc        192
Phe Ala Ala Ser Thr Leu Gln Ser Gly Val Pro Ser Arg Phe Gly Gly
    50                  55                  60 agt gga tct ggg aca gat ttc act ctc acc atc agc agc ctg cag cct        240
Ser Gly Ser Gly Thr Asp Phe Thr Leu Thr Ile Ser Ser Leu Gln Pro
65                  70                  75                  80 gaa gat gtt gca act tat tac tgt caa aac tat aac agt ggc cct ccg        288
Glu Asp Val Ala Thr Tyr Tyr Cys Gln Asn Tyr Asn Ser Gly Pro Pro
                85                  90                  95 cct ttc ggc cct ggg acc aaa gtg gat atc aaa                            321
Pro Phe Gly Pro Gly Thr Lys Val Asp Ile Lys
                100                 105

<210> SEQ ID NO 199
<211> LENGTH: 107
<212> TYPE: PRT
<213> ORGANISM: Homo sapiens

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
            35                  40                  45

Phe Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Gly Pro Pro
                85                  90                  95

Pro Phe Gly Pro Gly Thr Lys Val Asp Ile Lys
                100                 105

<210> SEQ ID NO 200
<211> LENGTH: 10
<212> TYPE: PRT
<213> ORGANISM: Artificial Sequence
<220> FEATURE:
<223> OTHER INFORMATION: Epitope recognized by NI-302.64E5

<400> SEQUENCE: 200

Pro Gln Pro Pro Gln Ala Gln Pro Leu
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Epitope recognized by NI-302.7D8

<400> SEQUENCE: 201
```

-continued

```
Gln Gln Gln Gln Gln Gln Gln Pro Pro Pro
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Epitope recognized by NI-302.72F10

<400> SEQUENCE: 202

Pro Pro Pro Gly Pro Ala Val Ala Glu Glu Pro Leu His
1               5                   10

<210> SEQ ID NO 203
<211> LENGTH: 15
<212> TYPE: PRT
<213> ORGANISM: Artificial Sequence
<220> FEATURE:
<223> OTHER INFORMATION: peptide 1 for determination of antibody binding
      epitope

<400> SEQUENCE: 203

Gln Gln Gln Gln Gln Gln Gln Pro Pro Pro Pro Pro Pro Pro
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: peptide 2 for determination of antibody binding
      epitope

<400> SEQUENCE: 204

Gln Gln Pro Pro Pro Pro Pro Pro Pro Pro Pro Pro Gln Leu
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: peptide 3 for determination of antibody binding
      epitope

<400> SEQUENCE: 205

Pro Pro Pro Pro Pro Pro Pro Pro Gln Leu Pro Gln Pro Pro
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: peptide 4 for determination of antibody binding
      epitope

<400> SEQUENCE: 206

Leu Pro Gln Pro Gln Pro Pro Pro Pro Pro Pro Pro Pro Pro
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: PPPPPPPPPPPGPAVA
```

```
<400> SEQUENCE: 207

Pro Pro Pro Pro Pro Pro Pro Pro Pro Gly Pro Ala Val Ala
1               5                   10                  15

<210> SEQ ID NO 208
<211> LENGTH: 10
<212> TYPE: PRT
<213> ORGANISM: Artificial Sequence
<220> FEATURE:
<223> OTHER INFORMATION: consensus sequence 1

<400> SEQUENCE: 208

Pro Pro Pro Pro Pro Pro Pro Pro Pro Pro
1               5                   10

<210> SEQ ID NO 209
<211> LENGTH: 15
<212> TYPE: PRT
<213> ORGANISM: Artificial Sequence
<220> FEATURE:
<223> OTHER INFORMATION: peptide 6 for determination of antibody binding
      epitope

<400> SEQUENCE: 209

Pro Pro Pro Gln Leu Pro Gln Pro Pro Gln Ala Gln Pro Leu
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: peptide 7 for determination of antibody binding
      epitope

<400> SEQUENCE: 210

Pro Gln Pro Pro Gln Ala Gln Pro Leu Leu Pro Gln Pro Gln
1               5                   10                  15

<210> SEQ ID NO 211
<211> LENGTH: 88
<212> TYPE: PRT
<213> ORGANISM: Artificial Sequence
<220> FEATURE:
<223> OTHER INFORMATION: HD21

<400> SEQUENCE: 211

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Pro Pro Pro Pro Pro Pro Pro Pro Pro Pro
        35                  40                  45

Pro Gln Leu Pro Gln Pro Pro Gln Ala Gln Pro Leu Leu Pro Gln Pro
    50                  55                  60

Pro Gln Pro Pro Pro Pro Pro Pro Pro Pro Gly Pro Ala Val
65                  70                  75                  80

Ala Glu Glu Pro Leu His Arg Pro
                85

<210> SEQ ID NO 212
<211> LENGTH: 102
<212> TYPE: PRT
```

```
<213> ORGANISM: Artificial Sequence
<220> FEATURE:
<223> OTHER INFORMATION: HD35

<400> SEQUENCE: 212

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Gln Gln Gln Gln Gln Gln Gln Gln
        35                  40                  45

Gln Gln Gln Gln Pro Pro Pro Pro Pro Pro Pro Pro Pro Gln
50                      55                  60

Leu Pro Gln Pro Pro Gln Ala Gln Pro Leu Leu Pro Gln Pro Gln
65                      70                  75                  80

Pro Pro Pro Pro Pro Pro Pro Pro Gly Pro Ala Val Ala Glu
                85                  90                  95

Glu Pro Leu His Arg Pro
            100

<210> SEQ ID NO 213
<211> LENGTH: 116
<212> TYPE: PRT
<213> ORGANISM: Artificial Sequence
<220> FEATURE:
<223> OTHER INFORMATION: HD49

<400> SEQUENCE: 213

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln
                20                  25                  30

Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln
50                      55                  60

Gln Gln Pro Pro Pro Pro Pro Pro Pro Pro Pro Gln Leu Pro
65                      70                  75                  80

Gln Pro Pro Gln Ala Gln Pro Leu Leu Pro Gln Pro Gln Pro Pro
                85                  90                  95

Pro Pro Pro Pro Pro Pro Pro Gly Pro Ala Val Ala Glu Glu Pro
                100                 105                 110

Leu His Arg Pro
        115

<210> SEQ ID NO 214
<211> LENGTH: 8
<212> TYPE: PRT
<213> ORGANISM: Artificial Sequence
<220> FEATURE:
<223> OTHER INFORMATION: consensus sequence 2

<400> SEQUENCE: 214

Pro Pro Pro Pro Pro Pro Pro Pro
1               5

<210> SEQ ID NO 215
<211> LENGTH: 15
<212> TYPE: PRT
<213> ORGANISM: Artificial Sequence
```

```
<220> FEATURE:
<223> OTHER INFORMATION: peptide 8 for determination of antibody binding
      epitope

<400> SEQUENCE: 215

Pro Pro Pro Gly Pro Ala Val Ala Glu Glu Pro Leu His Arg Pro
1               5                   10                  15

<210> SEQ ID NO 216
<211> LENGTH: 10
<212> TYPE: PRT
<213> ORGANISM: Artificial Sequence
<220> FEATURE:
<223> OTHER INFORMATION: consensus sequence 3

<400> SEQUENCE: 216

Pro Pro Pro Pro Pro Pro Pro Pro Gln Leu
1               5                   10

<210> SEQ ID NO 217
<211> LENGTH: 11
<212> TYPE: PRT
<213> ORGANISM: Artificial Sequence
<220> FEATURE:
<223> OTHER INFORMATION: consensus sequence 4

<400> SEQUENCE: 217

Pro Pro Pro Pro Pro Pro Pro Pro Pro Pro Pro
1               5                   10

<210> SEQ ID NO 218
<211> LENGTH: 15
<212> TYPE: PRT
<213> ORGANISM: Artificial Sequence
<220> FEATURE:
<223> OTHER INFORMATION: peptide 9 for determination of antibody binding
      epitope

<400> SEQUENCE: 218

Ala Ala Pro Pro Pro Pro Pro Pro Pro Ala Ala Ala Ala Ala
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: peptide 10 for determination of antibody
      binding epitope

<400> SEQUENCE: 219

Ala Ala Pro Pro Pro Pro Pro Pro Pro Pro Pro Ala Ala Ala
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: peptide 11 for determination of antibody
      binding epitope

<400> SEQUENCE: 220

Pro Pro Pro Pro Pro Pro Pro Pro Pro Pro Pro Ala Ala Ala
1               5                   10                  15

<210> SEQ ID NO 221
```

```
<211> LENGTH: 15
<212> TYPE: PRT
<213> ORGANISM: Artificial Sequence
<220> FEATURE:
<223> OTHER INFORMATION: peptide 12 for determination of antibody
      binding epitope

<400> SEQUENCE: 221

Ala Ala Pro Pro Pro Pro Pro Pro Ala Ala Ala Ala Ala Ala Ala
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: peptide 13 for determination of antibody
      binding epitope

<400> SEQUENCE: 222

Ala Ala Pro Pro Pro Pro Pro Pro Pro Ala Ala Ala Ala Ala
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: consensus sequence 5

<400> SEQUENCE: 223

Pro Pro Pro Pro Pro Pro Pro Pro Gln Leu Pro Gln Pro Pro Pro
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: peptide 14 for determination of antibody
      binding epitope

<400> SEQUENCE: 224

Gln Ala Gln Pro Leu Leu Pro Gln Pro Gln Pro Pro Pro Pro Pro
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: peptide 15 for determination of antibody
      binding epitope

<400> SEQUENCE: 225

Glu Lys Leu Met Lys Ala Phe Glu Ser Leu Lys Ser Phe Gln Gln
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: peptide 16 for determination of antibody
      binding epitope

<400> SEQUENCE: 226

Lys Ala Phe Glu Ser Leu Lys Ser Phe Gln Gln Gln Gln Gln Gln
```

<210> SEQ ID NO 227
<211> LENGTH: 15
<212> TYPE: PRT
<213> ORGANISM: Artificial Sequence
<220> FEATURE:
<223> OTHER INFORMATION: peptide 17 for determination of antibody
      binding epitope

<400> SEQUENCE: 227

Gln Gln Gln Gln Gln Gln Gln Gln Gln Gln Gln Gln Pro Pro Pro
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: peptide 18 for determination of antibody
      binding epitope

<400> SEQUENCE: 228

Pro Pro Pro Pro Pro Gly Pro Ala Val Ala Glu Glu Pro Leu His
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: peptide 19 for determination of antibody
      binding epitope

<400> SEQUENCE: 229

Pro Pro Pro Gly Pro Ala Val Ala Glu Glu Pro Leu His Arg Pro
1               5                   10                  15

<210> SEQ ID NO 230
<211> LENGTH: 151
<212> TYPE: PRT
<213> ORGANISM: Artificial Sequence
<220> FEATURE:
<223> OTHER INFORMATION: NIV-1022 (72F10H)

<400> SEQUENCE: 230

Glu Val Gln Leu Val Glu Thr Gly Gly Gly Phe Val Gln Pro Gly Gly
1               5                   10                  15

Ser Leu Arg Leu Ser Cys Ala Ala Ser Gly Phe Asn Phe Gly Ser Tyr
            20                  25                  30

Ala Met Ser Trp Val Arg Gln Ala Pro Gly Lys Gly Leu Glu Trp Val
        35                  40                  45

Ser Asp Ile Ser Gly Ile Gly Ser Asn Thr Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Asp Met Ser Ser Leu Arg Ala Glu Asp Thr Ala Arg Tyr Tyr Cys
                85                  90                  95

Ala Lys Asp Arg Lys Arg Ser Gly Trp Tyr Glu Gln Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

```
            130                 135                 140
Gly Cys Leu Val Lys Asp Tyr
145                 150

<210> SEQ ID NO 231
<211> LENGTH: 155
<212> TYPE: PRT
<213> ORGANISM: Artificial Sequence
<220> FEATURE:
<223> OTHER INFORMATION: NIV-526 (33C11H)

<400> SEQUENCE: 231

Glu Val Gln Leu Val Glu Ser Gly Gly Val Val Gln Pro Gly Asn
1               5                   10                  15

Ser Leu Arg Leu Ser Cys Ala Ala Ser Gly Phe Arg Phe Ser Asp Phe
                20                  25                  30

Gly Met His Trp Val Arg Gln Ala Pro Gly Lys Gly Leu Glu Trp Leu
            35                  40                  45

Ala Leu Ile Trp Tyr Asp Gly Gly Tyr Lys Tyr Tyr Ala Asp Ser Val
        50                  55                  60

Lys Gly Arg Phe Thr Ile Ser Arg Asp Asn Ser Lys Asn Thr Met Phe
65                  70                  75                  80

Leu Gln Met Asn Ser Leu Arg Ala Glu Asp Thr Ala Val Tyr Tyr Cys
                85                  90                  95

Ala Thr His Leu Glu Tyr Cys Ser Arg Thr Thr Cys Tyr Leu Gly His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr
145                 150                 155

<210> SEQ ID NO 232
<211> LENGTH: 153
<212> TYPE: PRT
<213> ORGANISM: Artificial Sequence
<220> FEATURE:
<223> OTHER INFORMATION: NIV-559 (35C1H)

<400> SEQUENCE: 232

Glu Val Gln Leu Val Glu Ser Gly Gly Asn Leu Val Gln Pro Gly Gly
1               5                   10                  15

Ser Leu Arg Leu Ser Cys Thr Ala Ser Gly Phe Thr Phe Ser Ile Thr
                20                  25                  30

Ala Leu Ser Trp Val Arg Gln Ala Pro Glu Lys Gly Pro Gln Trp Val
            35                  40                  45

Ser Ala Ile Thr Gly Asn Ala Tyr Gly Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Ile Tyr Tyr Cys
                85                  90                  95

Val Lys Gly Ile Ala Ser Asp Ser Ser Gly Tyr Ser Ala Phe Trp Gly
            100                 105                 110

Pro Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr
145                 150

<210> SEQ ID NO 233
<211> LENGTH: 151
<212> TYPE: PRT
<213> ORGANISM: Artificial Sequence
<220> FEATURE:
<223> OTHER INFORMATION: NIV-641 (31F11H)

<400> SEQUENCE: 233

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Thr
            20                  25                  30

Tyr Met Ser Trp Val Arg Gln Ala Pro Gly Lys Gly Leu Glu Cys Val
        35                  40                  45

Ser Val Ile Phe Ser Gly Ala Asp Thr Tyr Tyr Ala Asp Ser Val Lys
    50                  55                  60

Gly Arg Phe Thr Val Ser Arg Asp Asn Ser Lys Asn Thr Leu Phe Leu
65                  70                  75                  80

Gln Met Asn Ser Leu Arg Val Glu Asp Thr Ala Thr Tyr Tyr Cys Val
                85                  90                  95

Arg His Tyr Tyr Gly Ser Asp Leu Pro Ser Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr
145                 150

<210> SEQ ID NO 234
<211> LENGTH: 151
<212> TYPE: PRT
<213> ORGANISM: Artificial Sequence
<220> FEATURE:
<223> OTHER INFORMATION: NIV-873 (52C9H)

<400> SEQUENCE: 234

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Val Ser Asp Thr
            20                  25                  30

Tyr Met Ser Trp Val Arg Gln Ala Pro Gly Lys Gly Leu Glu Trp Val
        35                  40                  45

Ser Gly Ile His Ala Gly Gly Glu Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Arg Leu Thr Pro Glu Asp Thr Ala Val Phe Tyr Cys Ala
                85                  90                  95

Arg His Tyr Tyr Gly Asn Asp Asp Asp Thr Asp Tyr Trp Gly Gln Gly
            100                 105                 110

Thr Leu Val Thr Val Ser Ser Ala Ser Thr Lys Gly Pro Ser Val Phe
        115                 120                 125
```

-continued

```
Pro Leu Ala Pro Ser Ser Lys Ser Thr Ser Gly Gly Thr Ala Ala Leu
    130                 135                 140

Gly Cys Leu Val Lys Asp Tyr
145                 150

<210> SEQ ID NO 235
<211> LENGTH: 158
<212> TYPE: PRT
<213> ORGANISM: Artificial Sequence
<220> FEATURE:
<223> OTHER INFORMATION: NIV-1059 (4A6H)

<400> SEQUENCE: 235

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Val Thr Thr Glu Leu Tyr Gly Ala Asn Ser Tyr Tyr Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr
145                 150                 155

<210> SEQ ID NO 236
<211> LENGTH: 151
<212> TYPE: PRT
<213> ORGANISM: Artificial Sequence
<220> FEATURE:
<223> OTHER INFORMATION: NIV-561 (44D7H)

<400> SEQUENCE: 236

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Tyr Ser Asp Thr Ser Thr Tyr Tyr Ala Asp Ser Val
    50                  55                  60

Lys Gly Arg Phe Thr Val Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Arg Asp Tyr Tyr Gly Met Asp Val Trp Gly Gln Gly
            100                 105                 110

Thr Met Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr
145                 150

<210> SEQ ID NO 237
<211> LENGTH: 158
<212> TYPE: PRT
<213> ORGANISM: Artificial Sequence
<220> FEATURE:
<223> OTHER INFORMATION: NIV-1074 (12H2H)

<400> SEQUENCE: 237

Cys Glu Val Gln Leu Val Gln Ser Gly Gly Gly Leu Val Gln Pro Gly
1               5                  10                  15

Gly Ser Leu Arg Leu Ser Cys Glu Ala Ser Gly Phe Thr Phe Ser Asn
            20                  25                  30

Tyr Ala Met Gly Trp Val Arg Gln Ala Pro Gly Lys Gly Leu Glu Trp
        35                  40                  45

Val Ser Val Ile Ser Gly Thr Gly Gly Ser Thr Tyr Tyr Ala Asp Ser
50                  55                  60

Val Lys Gly Arg Phe Thr Ile Ser Arg Asp Asn Ser Met Asn Thr Leu
65                  70                  75                  80

Tyr Leu Gln Met Asn Ser Pro Arg Ala Asp Asp Thr Ala Val Tyr Tyr
                85                  90                  95

Cys Ala Lys Asp Leu Arg Lys Ile Ser Gly Pro Leu Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr
145                 150                 155

<210> SEQ ID NO 238
<211> LENGTH: 155
<212> TYPE: PRT
<213> ORGANISM: Artificial Sequence
<220> FEATURE:
<223> OTHER INFORMATION: NIV-845 (6N9H)

<400> SEQUENCE: 238

Glu Val Gln Leu Val Glu Ser Gly Gly Asp Leu Val Gln Pro Gly Gly
1               5                  10                  15

Ser Leu Arg Leu Ser Cys Val Val Ser Gly Phe Thr Phe Ser Ser Tyr
            20                  25                  30

Ala Met Thr Trp Val Arg Gln Ala Pro Gly Lys Gly Leu Ala Trp Val
        35                  40                  45

Ser Thr Ile Ser Ala Thr Gly Gly Ser Thr Phe Tyr Thr Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Asp Asp Thr Ala Ile Tyr Tyr Cys
                85                  90                  95

Val Lys Asp Leu Phe Gly Val Asp Thr Ser Tyr Tyr Gly Met Asp Val
            100                 105                 110
```

```
Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr
145                 150                 155

<210> SEQ ID NO 239
<211> LENGTH: 151
<212> TYPE: PRT
<213> ORGANISM: Artificial Sequence
<220> FEATURE:
<223> OTHER INFORMATION: NIV-843 (3D8H)

<400> SEQUENCE: 239

Glu Val Gln Leu Val Gln Ser Gly Gly Gly Leu Val Gln Pro Gly Gly
1               5                   10                  15

Ser Leu Arg Leu Ser Cys Glu Ala Ser Gly Phe Ile Phe Lys Thr Tyr
            20                  25                  30

Ala Met Ser Trp Val Arg Gln Leu Pro Gly Arg Gly Leu Glu Trp Val
        35                  40                  45

Ser Ala Ile Ser Ala Thr Gly Gly Ser Thr Phe Tyr Ala Glu Ser Val
    50                  55                  60

Lys Gly Arg Leu Thr Ile Ser Arg Asp Thr Ala Lys Asn Thr Val Tyr
65                  70                  75                  80

Leu Gln Met Asn Asn Leu Arg Ala Glu Asp Thr Ala Met Tyr Tyr Cys
                85                  90                  95

Ala Lys Gly Ser Thr Ala Val Tyr Leu Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr
145                 150

<210> SEQ ID NO 240
<211> LENGTH: 151
<212> TYPE: PRT
<213> ORGANISM: Artificial Sequence
<220> FEATURE:
<223> OTHER INFORMATION: NIV-429 (37C12H-PIMC)

<400> SEQUENCE: 240

Glu Val Gln Leu Val Glu Ser Gly Gly Gly Leu Val Gln Pro Gly Gly
1               5                   10                  15

Ser Leu Arg Leu Ser Cys Val Ala Ser Ala Leu Thr Val Thr Asn Ser
            20                  25                  30

Gln Met Thr Trp Val Arg Arg Ala Pro Gly Arg Gly Leu Glu Trp Val
        35                  40                  45

Ser Val Ile Tyr Thr Ser Gly Ser Ala Tyr Tyr Ala Asp Ser Val Lys
    50                  55                  60

Gly Arg Phe Thr Ile Ser Arg Asp Asn Ser Lys Asn Thr Val Phe Leu
65                  70                  75                  80

Gln Met Asn Ser Leu Arg Val Glu Asp Thr Ala Val Tyr Tyr Cys Ala
                85                  90                  95

Lys Gly Pro Ser Ala Tyr Tyr Tyr Gly Leu Asp Leu Trp Gly Gln Gly
            100                 105                 110
```

```
Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr
145                 150

<210> SEQ ID NO 241
<211> LENGTH: 151
<212> TYPE: PRT
<213> ORGANISM: Artificial Sequence
<220> FEATURE:
<223> OTHER INFORMATION: NIV-593

```
                    100                 105                 110
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr
145                 150

<210> SEQ ID NO 243
<211> LENGTH: 154
<212> TYPE: PRT
<213> ORGANISM: Artificial Sequence
<220> FEATURE:
<223> OTHER INFORMATION: NIV-599 (11A4H)

<400> SEQUENCE: 243

Cys Glu Val Gln Leu Val Glu Ser Gly Gly Gly Leu Ile Gln Pro Gly
1               5                   10                  15

Gly Ser Leu Arg Leu Ser Cys Ala Ala Ser Gly Phe Pro Val Ser Ser
            20                  25                  30

Ser Tyr Met Ser Trp Val Arg Gln Ala Pro Gly Glu Gly Leu Glu Trp
        35                  40                  45

Val Ser Val Leu Tyr Arg Asp Gly Asp Thr Tyr Tyr Ala Asp Ser Val
    50                  55                  60

Gln Gly Arg Phe Thr Ile Ser Arg Asp Asn Ser Gln Asn Thr Phe Tyr
65                  70                  75                  80

Leu Gln Met Asn Ser Leu Lys Ala Glu Asp Thr Ala Val Tyr Tyr Cys
                85                  90                  95

Ala Gly Asp Arg Arg Ser Ser His Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr
145                 150

<210> SEQ ID NO 244
<211> LENGTH: 151
<212> TYPE: PRT
<213> ORGANISM: Artificial Sequence
<220> FEATURE:
<223> OTHER INFORMATION: NIV-1057 (7D8H)

<400> SEQUENCE: 244

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Asn Phe Asn Asn Tyr
            20                  25                  30

Ala Ile Asn Trp Leu Arg Gln Ala Pro Gly Gln Gly Leu Glu Trp Met
        35                  40                  45

Gly Trp Ile Asn Thr Ile Thr Gly His Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Pro Glu Asp Thr Ala Val Tyr Tyr Cys
                85                  90                  95
```

```
Ala Arg Thr Tyr Ser Asn Tyr Gly Glu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr
145                 150
```

<210> SEQ ID NO 245
<211> LENGTH: 151
<212> TYPE: PRT
<213> ORGANISM: Artificial Sequence
<220> FEATURE:
<223> OTHER INFORMATION: NIV-795 (63F3H)

<400> SEQUENCE: 245

```
Gln Val Gln Leu Val Gln Ser Gly Ser Ala Phe Lys Lys Pro Gly Thr
1               5                   10                  15

Ser Val Lys Val Ser Cys Lys Ala Ser Gly Tyr Thr Phe Glu Thr Arg
            20                  25                  30

Ser Met Asn Trp Val Arg Gln Ala Pro Gly Gln Gly Leu Glu Tyr Met
        35                  40                  45

Gly Trp Ile Asn Thr Asn Thr Gly Asn Arg Thr Tyr Val Gln Ala Phe
    50                  55                  60

Arg Gly Arg Phe Val Phe Ser Leu Asp Thr Ser Val Ser Thr Ala Tyr
65                  70                  75                  80

Leu Gln Ile Ser Asn Leu Lys Thr Glu Asp Thr Ala Val Tyr Tyr Cys
                85                  90                  95

Ala Arg Gly Ala Gly Gly Tyr Trp Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr
145                 150
```

<210> SEQ ID NO 246
<211> LENGTH: 153
<212> TYPE: PRT
<213> ORGANISM: Artificial Sequence
<220> FEATURE:
<223> OTHER INFORMATION: NIV-1061 (8M1H)

<400> SEQUENCE: 246

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Tyr Met His Trp Val Arg Gln Ala Pro Gly Gln Gly Leu Glu Trp Met
        35                  40                  45

Gly Gly Ile Ser Pro Ser Gly His Thr Met Tyr Ala Gln Asn Phe
    50                  55                  60

Gln Gly Arg Val Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Gly Ser Thr Val Thr Asn Tyr Arg Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr
145                 150

<210> SEQ ID NO 247
<211> LENGTH: 158
<212> TYPE: PRT
<213> ORGANISM: Artificial Sequence
<220> FEATURE:
<223> OTHER INFORMATION: NIV-634 (55D8H)

<400> SEQUENCE: 247

Gln Val Gln Leu Val Gln Ser Gly Ser Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Arg Ile Asn Pro Asn Asn Gly Gly Thr Asn Tyr Ala Gln Asn Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Gly Gly Glu Leu Leu Arg Glu Gly Gly Tyr His Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr
145                 150                 155

<210> SEQ ID NO 248
<211> LENGTH: 152
<212> TYPE: PRT
<213> ORGANISM: Artificial Sequence
<220> FEATURE:
<223> OTHER INFORMATION: NIV-636 (74C11H)

<400> SEQUENCE: 248

Glu Val Gln Leu Val Gln Ser Gly Thr Glu Val Gln Lys Pro Gly Ala
1               5                   10                  15

Ser Val Lys Val Ser Cys Lys Ala Ser Gly Tyr Ser Phe Thr Gly Tyr
            20                  25                  30

Phe Leu His Trp Val Arg Gln Ala Pro Gly Gln Gly Leu Glu Trp Met
        35                  40                  45

Gly Trp Ile Asn Pro Asn Ser Gly Asp Thr Asn Tyr Ala Glu Lys Phe
    50                  55                  60

Arg Gly Arg Ile Ile Met Thr Arg Asp Thr Ser Val Ser Thr Ala His
65                  70                  75                  80

Met Glu Leu Ser Ser Leu Arg Phe Asp Asp Thr Ala Leu Tyr Tyr Cys
```

```
                85                  90                  95
Thr Arg Glu Ala Pro Asp Pro Gly Ala Glu Thr Asp Val Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr
145                 150

<210> SEQ ID NO 249
<211> LENGTH: 153
<212> TYPE: PRT
<213> ORGANISM: Artificial Sequence
<220> FEATURE:
<223> OTHER INFORMATION: NIV-799 (11H6H)

<400> SEQUENCE: 249

Glu Val Gln Leu Val Gln Ser Gly Ala Val Met Lys Lys Pro Gly Asp
1               5                   10                  15
Ser Val Arg Val Ser Cys Arg Ala Ser Thr Tyr Ser Phe Ser Thr Tyr
            20                  25                  30
Ser Phe Thr Trp Val Arg Gln Val Pro Gly Gln Gly Leu Glu Trp Met
        35                  40                  45
Gly Trp Ile Ser Ala Tyr Asn Gly His Thr Asn Tyr Val Asp Ser Phe
    50                  55                  60
Gln Gly Arg Leu Thr Leu Thr Thr Asp Thr Ser Ala

```
Lys Leu Ser Ser Val Thr Ala Ala Asp Thr Ala Met Tyr Phe Cys Ala
                85                  90                  95

Arg Gly Tyr Ser Tyr Asp Pro Lys Tyr Tyr Phe Asp Ser Trp Ser Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr
145                 150
```

<210> SEQ ID NO 251
<211> LENGTH: 159
<212> TYPE: PRT
<213> ORGANISM: Artificial Sequence
<220> FEATURE:
<223> OTHER INFORMATION: NIV-638 (78H12H)

<400> SEQUENCE: 251

```
Gln Val Gln Leu Gln Glu Ser Gly Pro Gly Leu Val Lys Pro Ser Glu
1               5                   10                  15

Thr Leu Ser Leu Thr Cys Leu Val Ser Ser Tyr Ser Ile Ser Asn Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Asn Gly Asn Thr Tyr Tyr Asn Pro Ser Leu
    50                  55                  60

Lys Ser Arg Val Ile Ile Ser Val Asp Thr Ser Lys Asn Gln Phe Ser
65                  70                  75                  80

Leu Lys Leu Arg Ser Val Thr Ala Ala Asp Thr Ala Val Tyr Tyr Cys
                85                  90                  95

Ala Met Pro Ser Ala Thr Tyr Tyr Gly Ser Gly Thr Gln Phe His
            100                 105                 110

Ala Phe Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr
145                 150                 155
```

<210> SEQ ID NO 252
<211> LENGTH: 155
<212> TYPE: PRT
<213> ORGANISM: Artificial Sequence
<220> FEATURE:
<223> OTHER INFORMATION: NIV-857 (46C9H)

<400> SEQUENCE: 252

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Val Ser Ser Gly
            20                  25                  30

Ala Tyr Tyr Trp Ser Trp Ile Arg Gln Pro Ala Gly Lys Arg Leu Glu
        35                  40                  45

Trp Ile Gly Arg Val Tyr Pro Thr Trp Ser Asn Tyr Asn Pro Ser
    50                  55                  60

Leu Glu Ser Arg Val Thr Ile Ser Leu Asp Thr Ser Asn Asn Gln Phe
65                  70                  75                  80
```

```
Ser Leu Lys Leu Thr Ser Leu Thr Ala Ala Asp Thr Ala Val Tyr Tyr
                85                  90                  95

Cys Ala Arg Glu Ala Pro Gly Asp Tyr Asp Ala Ala Pro Leu Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr
145                 150                 155

<210> SEQ ID NO 253
<211> LENGTH: 152
<212> TYPE: PRT
<213> ORGANISM: Artificial Sequence
<220> FEATURE:
<223> OTHER INFORMATION: NIV-835 (18A1H)

<400> SEQUENCE: 253

Gln Leu Gln Leu Gln Glu Ser Gly Pro Gly Leu Val Lys Pro Ser Glu
1               5                   10                  15

Ala Leu Ser Leu Thr Cys Thr Val Ser Gly Gly Ser Ile Thr Thr Asp
            20                  25                  30

Tyr Tyr Tyr Trp Gly Trp Ile Arg Gln Ser Pro Gly Lys Gly Leu Glu
        35                  40                  45

Trp Val Gly Thr Ile Tyr Phe Gly Gly Ala Thr Tyr Tyr Asn Pro Ser
    50                  55                  60

Leu Arg Asn Arg Val Ser Ile Ser Val As

```
65                  70                  75                  80

Thr Val Phe Leu Gln Met Asn Ser Leu Lys Thr Glu Asp Thr Ala Leu
                85                  90                  95

Tyr Tyr Cys Thr Ser Thr Gly Val Leu Ala Ala Ala Val Asp Val Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr
145                 150                 155

<210> SEQ ID NO 255
<211> LENGTH: 154
<212> TYPE: PRT
<213> ORGANISM: Artificial Sequence
<220> FEATURE:
<223> OTHER INFORMATION: NIV-893 (8F1H)

<400> SEQUENCE: 255

Glu Val Gln Leu Val Glu Ser Gly Gly Gly Leu Val Lys Pro Gly Gly
1               5                   10                  15

Ser Leu Thr Ile Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly His Ile Arg Thr Gln Ala Glu Gly Gly Thr Ser Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ile Pro Pro Pro Tyr Tyr Tyr Tyr Tyr Gly Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr
145                 150

<210> SEQ ID NO 256
<211> LENGTH: 152
<212> TYPE: PRT
<213> ORGANISM: Artificial Sequence
<220> FEATURE:
<223> OTHER INFORMATION: NIV-520 (15F9H)

<400> SEQUENCE: 256

Glu Val Gln Leu Val Glu Ser Gly Gly Gly Leu Val Thr Pro Gly Gly
1               5                   10                  15

Ser Leu Arg Leu Ser Cys Glu Ala Ser Gly Phe Leu Phe Lys Asn Ser
            20                  25                  30

Ser Met Asn Trp Val Arg Gln Thr Pro Gly Lys Gly Leu Glu Trp Val
        35                  40                  45

Ser Ser Ile Asp Thr Ser Ala Thr Asn Tyr Lys Tyr Tyr Ala Asp Ser
    50                  55                  60
```

```
Val Lys Gly Arg Phe Thr Ile Ser Arg Asp Asp Ala Thr Asn Ser Leu
 65                  70                  75                  80

Tyr Leu Gln Met Asn Ser Leu Arg Ala Asp Asp Thr Ala Thr Tyr Tyr
                 85                  90                  95

Cys Ala Arg Gly Tyr Tyr Thr Pro Arg Asp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr
145                 150

<210> SEQ ID NO 257
<211> LENGTH: 156
<212> TYPE: PRT
<213> ORGANISM: Artificial Sequence
<220> FEATURE:
<223> OTHER INFORMATION: NIV-597 (7A8H)

<400> SEQUENCE: 257

Cys Glu Val Gln Leu Val Glu Ser Gly Gly Gly Ser Val Gln Pro Gly
  1               5                  10                  15

Gly Ser Leu Arg Leu Ser Cys Val Ala Ser Gly Phe Ile Phe Arg Asn
             20                  25                  30

Ser Trp Met Thr Trp Val Arg Gln Asp Pro Gly Lys Gly Leu Glu Trp
         35                  40                  45

Val Ala Asn Ile Lys Glu Asp Gly Ser Arg Thr Tyr Tyr Val Asp Ser
 50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Ala Arg Gly Asp Tyr Asn Ser Gly Ile Tyr Tyr Phe Pro Gly Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr
145                 150                 155

<210> SEQ ID NO 258
<211> LENGTH: 150
<212> TYPE: PRT
<213> ORGANISM: Artificial Sequence
<220> FEATURE:
<223> OTHER INFORMATION: NIV-972 (2A2H)

<400> SEQUENCE: 258

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Trp Met Asn Trp Val Arg Gln Ala Pro Gly Lys Gly Leu Glu Trp Val
         35                  40                  45

Ala Asn Ile Lys Pro Asp Gly Ser Asp Lys Tyr Tyr Val Asp Ser Val
 50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Asp Gly Ser Gly Trp Asn Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr
145             150

<210> SEQ ID NO 259
<211> LENGTH: 155
<212> TYPE: PRT
<213> ORGANISM: Artificial Sequence
<220> FEATURE:
<223> OTHER INFORMATION: NIV-1058 (7D8L)

<400> SEQUENCE: 259

Gln Ser Ala Leu Thr Gln Pro Ala Ser Val Ser Gly Ser Arg Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln Tyr Pro Gly Lys Ala Pro Lys Leu
        35                  40                  45

Ile Ile His Glu Gly Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Thr Thr Phe Val Leu Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala
145                 150                 155

<210> SEQ ID NO 260
<211> LENGTH: 154
<212> TYPE: PRT
<213> ORGANISM: Artificial Sequence
<220> FEATURE:
<223> OTHER INFORMATION: NIV-564 (71F6L)

<400> SEQUENCE: 260

Gln Ser Ala Leu Thr Gln Pro Ala Ser Val Ser Gly Ser Pro Gly Gln
1               5                   10                  15

Ala Ile Thr Ile Ser Cys Thr Gly Thr Ser Ser Asp Ile Gly Ser Tyr
            20                  25                  30

Asp Phe Val Ser Trp Tyr Gln Gln Asp Pro Gly Lys Ala Pro Lys Val
        35                  40                  45

Ile Ile Tyr Gly Val Asn Lys Arg Pro Ser Gly Val Ser Asn Arg Phe

```
                    50                  55                  60

Ser Gly Ser Lys Ser Gly Asn Thr Ala Ser Leu Thr Ile Ser Gly Leu
 65                  70                  75                  80

Gln Ala Asp Asp Glu Ala Asp Tyr Tyr Cys Cys Ser Tyr Ala Gly Ser
                     85                  90                  95

Thr Thr Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala
145                 150

<210> SEQ ID NO 261
<211> LENGTH: 153
<212> TYPE: PRT
<213> ORGANISM: Artificial Sequence
<220> FEATURE:
<223> OTHER INFORMATION: NIV-894 (8F1L)

<400> SEQUENCE: 261

Gln Ser Ala Leu Thr Gln Pro Ala Ser Val Ser Gly Ser Pro Gly Gln
 1               5                  10                  15

Ser Ile Thr Ile Ser Cys Thr Gly Ala Ser Ser Asp Val Gly Thr Tyr
                20                  25                  30

Asp Leu Val Ser Trp Tyr Gln Gln His Pro Gly Lys Ala Pro Lys Leu
            35                  40                  45

Ile Ile Tyr Glu Val Asn Lys Arg Pro Ser Gly Val Ser Tyr Arg Phe
        50                  55                  60

Ser Ala Ser Lys Ser Ala Asn Thr Ala Ser Leu Thr Ile Ser Gly Leu
 65                  70                  75                  80

Gln Ala Glu Asp Glu Ala Glu Tyr Tyr Cys Cys Ser Tyr Ala Gly Tyr
                 85                  90                  95

Ser Thr Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala
145                 150

<210> SEQ ID NO 262
<211> LENGTH: 155
<212> TYPE: PRT
<213> ORGANISM: Artificial Sequence
<220> FEATURE:
<223> OTHER INFORMATION: NIV-639 (78H12L)

<400> SEQUENCE: 262

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Arg Asp Val Gly Asn Tyr
                20                  25                  30

Asn Tyr Val Ser Trp Tyr Gln Gln His Pro Gly Glu Val Pro Lys Leu
            35                  40                  45
```

Ile Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Glu Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala
145                 150                 155

<210> SEQ ID NO 263
<211> LENGTH: 156
<212> TYPE: PRT
<213> ORGANISM: Artificial Sequence
<220> FEATURE:
<223> OTHER INFORMATION: NIV-635 (55D8L)

<400> SEQUENCE: 263

Gln Ser Val Leu Thr Gln Pro Pro Ser Val Ser Gly Ala Pro Gly Gln
1               5                   10                  15

Arg Val Thr Ile Ser Cys Thr Gly Asn Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Phe Asp Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asn Tyr His Cys Gln Ser Tyr Asp Asn Ser
                85                  90                  95

Leu Ser Gly Ser Trp Val Phe Gly Gly Gly Thr Lys Leu Thr Val Leu
            100                 105                 110

Ser Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala
145                 150                 155

<210> SEQ ID NO 264
<211> LENGTH: 151
<212> TYPE: PRT
<213> ORGANISM: Artificial Sequence
<220> FEATURE:
<223> OTHER INFORMATION: NIV-637 (74C11L)

<400> SEQUENCE: 264

Gln Ser Val Leu Thr Gln Pro Pro Ser Val Ser Val Ser Pro Gly Gln
1               5                   10                  15

Thr Ala Arg Ile Thr Cys Ser Gly Asp Ala Val Pro Lys Gln Tyr Ile
            20                  25                  30

Tyr Trp Tyr Gln Gln Lys Pro Gly Gln Ala Pro Ile Leu Val Ile Tyr
        35                  40                  45

Lys Asp Thr Gln Arg Pro Ser Gly Ile Pro Glu Arg Phe Ser Gly Ser
 50                  55                  60

Asn Ser Gly Thr Thr Val Thr Leu Thr Ile Thr Gly Val Gln Ala Asp
 65                  70                  75                  80

Asp Glu Gly Asp Tyr Tyr Cys Gln Ser Ala Asp Ser Ser Ala Thr Trp
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala
145                 150

<210> SEQ ID NO 265
<211> LENGTH: 154
<212> TYPE: PRT
<213> ORGANISM: Artificial Sequence
<220> FEATURE:
<223> OTHER INFORMATION: NIV-562 (44D7L)

<400> SEQUENCE: 265

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
             20                  25                  30

Tyr Tyr Pro Ser Trp Tyr Gln Gln Thr Pro Gly Arg Ala Pro Arg Thr
         35                  40                  45

Leu Ile Tyr Ser Thr Asn Thr Arg Ser Ser Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Phe Met Gly Ser
                 85                  90                  95

Gly Ile Gly Val Phe Gly Gly Gly Thr Arg Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala
145                 150

<210> SEQ ID NO 266
<211> LENGTH: 154
<212> TYPE: PRT
<213> ORGANISM: Artificial Sequence
<220> FEATURE:
<223> OTHER INFORMATION: NIV-800 (11H6L)

<400> SEQUENCE: 266

Gln Thr Val Val Thr Gln Glu Pro Thr Phe Ser Val Ser Pro Gly Gly
 1               5                  10                  15

Thr Val Thr Leu Thr Cys Ala Leu Arg Phe Gly Ser Val Ser Ser Ser
             20                  25                  30

Tyr Tyr Pro Ser Trp Phe Gln Gln Thr Pro Gly Gln Ala Pro Arg Thr

```
        35                  40                  45

Leu Ile Tyr Ser Thr Asn Thr Arg Ser Ser Gly Val Pro Ala Arg Phe
    50                  55                  60

Ser Gly Ser Ile Leu Gly Asn Lys Ala Ala Leu Thr Ile Ala Gly Ala
65                  70                  75                  80

Gln Ala Asn Asp Glu Ala Asp Tyr Tyr Cys Val Leu Tyr Met Gly Ser
                85                  90                  95

Gly Ile Gly Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala
145                 150

<210> SEQ ID NO 267
<211> LENGTH: 150
<212> TYPE: PRT
<213> ORGANISM: Artificial Sequence
<220> FEATURE:
<223> OTHER INFORMATION: NIV-1023 (72F10K)

<400> SEQUENCE: 267

Glu Ile Val Met Thr Gln Ser Pro Ala Thr Leu Thr Leu Ser Pro Gly
1               5                   10                  15

Glu Arg Ala Thr Leu Ser Cys Arg Ala Ser Gln Ser Ile Ser Ala Tyr
            20                  25                  30

Leu Gly Trp Tyr Gln Gln Lys Pro Gly Gln Ala Pro Arg Leu Leu Ile
        35                  40                  45

Tyr Asp Ala Ser Ile Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Val Tyr Tyr Cys His Gln Arg Ser Lys Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val
145                 150

<210> SEQ ID NO 268
<211> LENGTH: 157
<212> TYPE: PRT
<213> ORGANISM: Artificial Sequence
<220> FEATURE:
<223> OTHER INFORMATION: NIV-1071 (64E5K)

<400> SEQUENCE: 268

Cys Asp Ile Gln Leu Thr Gln Ser Pro Asp Ser Leu Ala Val Ser Leu
1               5                   10                  15

Gly Glu Arg Ala Thr Met Thr Cys Lys Ser Ser Gln Ser Leu Phe Tyr
            20                  25                  30
```

```
Ser Tyr Asn Asn Glu Asn Tyr Leu Ala Trp Tyr Gln Gln Arg Pro Gly
            35                  40                  45

Gln Pro Pro Lys Leu Leu Ile Tyr Trp Ala Ser Thr Arg Glu Ser Gly
 50                  55                  60

Val Pro Asp Arg Phe Ser Gly Ser Gly Ser Gly Thr Asp Phe Thr Leu
 65                  70                  75                  80

Thr Ile Ser Ser Leu Gln Ala Glu Asp Val Ala Val Tyr Tyr Cys Gln
                85                  90                  95

Gln Tyr Tyr Ser Thr Pro Gln Thr Phe Gly Gln Gly Thr Lys Val Asp
                100                 105                 110

Ile Lys Arg Thr Val Ala Ala Pro Ser Val Phe Ile Phe Pro Pro Ser
                115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val
145                 150                 155

<210> SEQ ID NO 269
<211> LENGTH: 156
<212> TYPE: PRT
<213> ORGANISM: Artificial Sequence
<220> FEATURE:
<223> OTHER INFORMATION: NIV-796 (63F3K)

<400> SEQUENCE: 269

Asp Ile Gln Met Thr Gln Ser Pro Asp Ser Leu Ala Val Ser Leu Gly
 1               5                  10                  15

Glu Arg Ala Thr Ile Asn Cys Lys Ser Asn Gln Ser Leu Phe Tyr Ser
                20                  25                  30

Ser Asn Asn Asn Asn Tyr Leu Ala Trp Tyr Gln His Lys Ser Gly Gln
            35                  40                  45

Pro Pro Lys Leu Leu Val Tyr Trp Gly Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Ile Tyr Tyr Cys His Gln
                85                  90                  95

Tyr Tyr His Asn Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val
145                 150                 155

<210> SEQ ID NO 270
<211> LENGTH: 158
<212> TYPE: PRT
<213> ORGANISM: Artificial Sequence
<220> FEATURE:
<223> OTHER INFORMATION: NIV-973 (2A2K)

<400> SEQUENCE: 270

Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Thr
                20                  25                  30
```

```
Ser Lys Asn Lys Asp Ser Lys Asn Tyr Leu Gly Trp Tyr Gln Gln Lys
        35                  40                  45

Pro Gly Gln Pro Pro Lys Leu Leu Ile Tyr Trp Ala Ser Thr Arg Glu
    50                  55                  60

Ser Gly Val Pro Asp Arg Phe Ser Gly Ser Gly Ser Gly Thr Asp Phe
65                  70                  75                  80

Thr Leu Thr Ile Ser Ser Leu Gln Ala Glu Asp Val Ala Val Tyr Tyr
                85                  90                  95

Cys Gln Gln Tyr Tyr Thr Thr Pro Gln Phe Gly Gly Gly Thr Lys Val
                100                 105                 110

Glu Ile Lys Arg Thr Val Ala Ala Pro Ser Val Phe Ile Phe Pro Pro
            115                 120                 125

Ser Asp Glu Gln Leu Lys Ser Gly Thr Ala Ser Val Val Cys Leu Leu
        130                 135                 140

Asn Asn Phe Tyr Pro Arg Glu Ala Lys Val Gln Trp Lys Val
145                 150                 155

<210> SEQ ID NO 271
<211> LENGTH: 154
<212> TYPE: PRT
<213> ORGANISM: Artificial Sequence
<220> FEATURE:
<223> OTHER INFORMATION: NIV-430 (37C12-PIMC)

<400> SEQUENCE: 271

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val
145                 150

<210> SEQ ID NO 272
<211> LENGTH: 155
<212> TYPE: PRT
<213> ORGANISM: Artificial Sequence
<220> FEATURE:
<223> OTHER INFORMATION: NIV-836 (18A1K)

<400> SEQUENCE: 272

Glu Ile Val Leu Thr Gln Ser Pro Leu Ser Val Pro Val Thr Pro Gly
1               5                   10                  15

Glu Pro Ala Ser Ile Ser Cys Arg Ser Ser Gln Ser Leu Leu His Asn
```

-continued

```
                    20                  25                  30
Asn Gly Tyr Asn Tyr Leu Asp Trp Tyr Leu Lys Lys Pro Gly Gln Ser
                35                  40                  45
Pro Gln Leu Leu Ile Tyr Leu Gly Ser Thr Arg Ala Ser Gly Val Pro
            50                  55                  60
Asp Arg Phe Ser Ala Ser Gly Ser Gly Thr Asp Phe Thr Leu Glu Ile
65                  70                  75                  80
Ser Arg Val Glu Ala Glu Asp Val Gly Val Tyr Tyr Cys Met Gln Ala
                85                  90                  95
Leu Gln Thr Pro Pro Thr Phe Gly Arg Gly Thr Lys Val Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val
145                 150                 155
```

<210> SEQ ID NO 273
<211> LENGTH: 155
<212> TYPE: PRT
<213> ORGANISM: Artificial Sequence
<220> FEATURE:
<223> OTHER INFORMATION: NIV-874 (52C9K)

<400> SEQUENCE: 273

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Val Gln Lys Pro Gly Gln Ser
            35                  40                  45
Pro Gln Leu Leu Ile Tyr Leu Gly Ser Thr Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Leu Gln Ala
                85                  90                  95
Gln Gln Ile Pro Trp Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val
145                 150                 155
```

<210> SEQ ID NO 274
<211> LENGTH: 155
<212> TYPE: PRT
<213> ORGANISM: Artificial Sequence
<220> FEATURE:
<223> OTHER INFORMATION: NIV-642 (31F11K)

<400> SEQUENCE: 274

```
Asp Val Val Met Thr Gln Ser Pro Leu Ser Leu Pro Val Ala Pro Gly
1               5                   10                  15
```

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Lys Pro
        35                  40                  45

Pro Gln Leu Leu Val Tyr Leu Gly Ser Asp Arg Ala Ser Gly Val Pro
    50                  55                  60

Asp Arg Phe Ser Gly Ser Gly Ser Gly Lys Asp Phe Thr Leu Asn Ile
65                  70                  75                  80

Ser Arg Val Glu Ala Glu Asp Val Gly Val Tyr Tyr Cys Met Gln Gly
                85                  90                  95

Leu Gln Ser Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val
145                 150                 155

<210> SEQ ID NO 275
<211> LENGTH: 154
<212> TYPE: PRT
<213> ORGANISM: Artificial Sequence
<220> FEATURE:
<223> OTHER INFORMATION: NIV-594 (22H9K)

<400> SEQUENCE: 275

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Arg Gln Lys Pro Gly Gln Ser
        35                  40                  45

Pro Gln Leu Leu Ile Tyr Leu Asn Ser Asn Arg Ala Ser Gly Val Pro
    50                  55                  60

Asp Arg Phe Ser Gly Ser Gly Ser Gly Thr Glu Phe Thr Leu Thr Ile
65                  70                  75                  80

Ser Arg Val Glu Ala Glu Asp Val Gly Val Tyr Tyr Cys Met Gln Ser
                85                  90                  95

Leu Gln Thr Phe Thr Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val
145                 150

<210> SEQ ID NO 276
<211> LENGTH: 154
<212> TYPE: PRT
<213> ORGANISM: Artificial Sequence
<220> FEATURE:
<223> OTHER INFORMATION: NIV-596 (39G12K)

<400> SEQUENCE: 276

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Arg Gln Lys Pro Gly Gln Ser
            35                  40                  45

Pro Gln Leu Leu Ile Tyr Leu Ser Ser Asn Arg Pro Ser Gly Val Pro
    50                  55                  60

Asp Arg Phe Ser Ala Ser Gly Ser Gly Thr Glu Phe Thr Leu Gln Ile
65                  70                  75                  80

Ser Arg Val Glu Ala Glu Asp Val Gly Val Tyr Tyr Cys Met Gln Ser
                85                  90                  95

Leu Gln Thr Phe Thr Phe Gly Gly Gly Thr Lys Val Asp Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val
145                 150

<210> SEQ ID NO 277
<211> LENGTH: 155
<212> TYPE: PRT
<213> ORGANISM: Artificial Sequence
<220> FEATURE:
<223> OTHER INFORMATION: NIV-521 (15F9K)

<400> SEQUENCE: 277

Asp Val Val Met Thr Gln Ser Pro Gln Thr Leu Ser Val Ser Leu Gly
1               5                   10                  15

Gln Ala Ala Ser Ile Ser Cys Arg Ser Ser Gln Ser Leu Leu Tyr Arg
            20                  25                  30

Asp Asn Asn Thr Tyr Leu Asn Trp Phe His Gln Arg Pro Gly Gln Ser
            35                  40                  45

Pro Arg Arg Leu Ile Tyr Arg Ala Ser Asp Arg Asp Ser Gly Val Pro
    50                  55                  60

Asp Arg Phe Ser Gly Gly Gly Ser Gly Thr Asp Phe Thr Leu Lys Ile
65                  70                  75                  80

Ser Gly Val Glu Ala Glu Asp Val Gly Thr Tyr Tyr Cys Met Gln Gly
                85                  90                  95

Thr His Trp Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val
145                 150                 155

<210> SEQ ID NO 278
<211> LENGTH: 156
<212> TYPE: PRT
<213> ORGANISM: Artificial Sequence
<220> FEATURE:
<223> OTHER INFORMATION: NIV-598 (7A8K)

<400> SEQUENCE: 278

Cys Asp Val Val Met Thr Gln Ser Pro Leu Ser Leu Pro Val Thr Leu

```
                1               5                   10                  15
Gly Gln Pro Ala Ser Ile Ser Cys Arg Ser Ser Gln Ser Leu Val Tyr
                20                  25                  30

Ser Asp Gly Asn Thr Tyr Leu Asn Trp Phe Gln Gln Arg Pro Gly Gln
                35                  40                  45

Ser Pro Arg Arg Leu Ile Tyr Lys Val Ser Asn Arg Asp Ser Gly Val
        50                  55                  60

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Ile Tyr Tyr Cys Met Gln
                85                  90                  95

Gly Thr His Trp Pro Gly Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val
145                 150                 155

<210> SEQ ID NO 279
<211> LENGTH: 150
<212> TYPE: PRT
<213> ORGANISM: Artificial Sequence
<220> FEATURE:
<223> OTHER INFORMATION: NIV-1062 (8M1Ka)

<400> SEQUENCE: 279

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ala Trp Tyr Gln Gln Lys Pro Gly Lys Val Pro Lys Leu Leu Ile
                35                  40                  45

Phe Ala Ala Ser Thr Leu Gln Ser Gly Val Pro Ser Arg Phe Gly Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Gly Pro Pro
                85                  90                  95

Pro Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val
145                 150

<210> SEQ ID NO 280
<211> LENGTH: 150
<212> TYPE: PRT
<213> ORGANISM: Artificial Sequence
<220> FEATURE:
<223> OTHER INFORMATION: NIV-844 (3D8K)

<400> SEQUENCE: 280
```

```
Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Arg Asn Phe
            20                  25                  30

Leu Ala Trp Ile Gln Gln Lys Pro Gly Lys Pro Pro Lys Ser Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Phe Tyr Asn Tyr Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val
145                 150
```

<210> SEQ ID NO 281
<211> LENGTH: 150
<212> TYPE: PRT
<213> ORGANISM: Artificial Sequence
<220> FEATURE:
<223> OTHER INFORMATION: NIV-858 (46C9K)

<400> SEQUENCE: 281

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser His Tyr
            20                  25                  30

Leu Asn Trp Tyr Arg Gln Lys Pro Gly Lys Ala Pro Gln Leu Val Ile
            35                  40                  45

Tyr Ala Ala Ser Ser Leu Gln Ser Glu Val Pro Ser Arg Phe Ser Gly
50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val
145                 150
```

<210> SEQ ID NO 282
<211> LENGTH: 150
<212> TYPE: PRT
<213> ORGANISM: Artificial Sequence
<220> FEATURE:
<223> OTHER INFORMATION: NIV-527 (33C11K)

<400> SEQUENCE: 282

```
Asp Ile Gln Leu Thr Gln Ser Pro Ser Phe Leu Ser Ala Ser Val Gly
1               5                   10                  15

Asp Thr Val Thr Phe Thr Cys Arg Ala Ser Gln Gly Ile Ser Asp Tyr
                20                  25                  30

Leu Ala Trp Phe Gln Lys Pro Gly Ile Ala Pro Lys Leu Leu Ile
                35                  40                  45

Tyr Ala Ala Ser Thr Leu Gln Thr Gly Val Pro Ser Arg Phe Ser Gly
50                      55                  60

Ser Gly Ser Gly Thr Glu Phe Thr Leu Thr Ile Arg Ser Leu Gln Ser
65                  70                  75                  80

Glu Asp Phe Gly Thr Tyr Tyr Cys Gln Gln Leu Lys Thr Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val
145                 150

<210> SEQ ID NO 283
<211> LENGTH: 150
<212> TYPE: PRT
<213> ORGANISM: Artificial Sequence
<220> FEATURE:
<223> OTHER INFORMATION: NIV-560 (35C1K)

<400> SEQUENCE: 283

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asn Gln
                20                  25                  30

Phe Ala Trp Tyr Gln Gln Lys Pro Gly Gln Ala Pro Arg Leu Leu Ile
                35                  40                  45

Tyr Asp Ala Ser Ar

<400> SEQUENCE: 284

```
Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Val Ser Arg
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Met Tyr Tyr Cys Gln Leu Tyr Gly Asn Ser Gln
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val
145 150
```

<210> SEQ ID NO 285
<211> LENGTH: 152
<212> TYPE: PRT
<213> ORGANISM: Artificial Sequence
<220> FEATURE:
<223> OTHER INFORMATION: NIV-1075 (12H2K)

<400> SEQUENCE: 285

```
Cys Glu Ile Val Leu Thr Gln Ser Pro Gly Thr Leu Ser Leu Ser Pro
1 5 10 15

Gly Glu Arg Ala Thr Leu Ser Cys Arg Ala Ser Gln Ser Val Ser Ser
20 25 30

Gly Tyr Leu Ala Trp Tyr Gln Gln Lys Pro Gly Gln Ala Pro Arg Leu
35 40 45

Leu Ile Tyr Gly Ala Ser Thr Arg Ala Thr Gly Ile Pro Asp Arg Phe
50 55 60

Ser Gly Ser Gly Ser Gly Thr Asp Phe Thr Leu Thr Ile Ser Arg Leu
65 70 75 80

Glu Pro Glu Asp Phe Ala Val Tyr Tyr Cys Gln His Tyr Gly Ala Ser
85 90 95

Ser Tyr Thr Phe Gly Gln Gly Thr Lys Leu Glu Ile Lys Arg Thr Val
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val
145 150

<210> SEQ ID NO 286
<211> LENGTH: 151
<212> TYPE: PRT
<213> ORGANISM: Artificial Sequence
<220> FEATURE:
<223> OTHER INFORMATION: NIV-846 (6N9K)

```
<400> SEQUENCE: 286

Glu Ile Val Leu Thr Gln Ser Pro Gly Thr Leu Ser Leu Ser Pro Gly
1               5                   10                  15

Glu Arg Ala Thr Leu Ser Cys Arg Pro Ser Gln Ser Val Ser Gly Arg
            20                  25                  30

Tyr Val Ala Trp Tyr Gln Gln Lys Pro Gly Gln Ala Pro Arg Leu Leu
        35                  40                  45

Phe Tyr Ala Ala Ser Asn Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ala Ser Ser
                85                  90                  95

Tyr Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val
145                 150

<210> SEQ ID NO 287
<211> LENGTH: 151
<212> TYPE: PRT
<213> ORGANISM: Artificial Sequence
<220> FEATURE:
<223> OTHER INFORMATION: NIV-600 (11A4K)

<400> SEQUENCE: 287

Cys Glu Ile Val Met Thr Gln Ser Pro Gly Thr Leu Ser Leu Ser Pro
1               5                   10                  15

Gly Glu Arg Ala Thr Leu Ser Cys Arg

HUMAN-DERIVED ANTI-HUNTINGTIN (HTT) ANTIBODIES AND USES THEREOF

FIELD OF THE INVENTION

The present invention generally relates to antibody-based therapy of Huntington's disease (HD) associated with Huntingtin (HTT). In particular, the present invention relates to novel molecules specifically binding to human HTT and/or antigens thereof, particularly human-derived antibodies as well as HTT-binding fragments, synthetic and biotechnological derivatives thereof, which are useful in the treatment of diseases and conditions induced by such pathogenic HTT isoforms.

In addition, the present invention relates to pharmaceutical and diagnostic compositions comprising such HTT-binding molecules, antibodies and mimics thereof valuable both as a diagnostic tool to identify diseases and/or disorders associated with HTT aggregation and as a passive vaccination strategy for treating disorders related to diseases associated with HTT amyloidosis.

BACKGROUND OF THE INVENTION

Huntington's disease (HD) is an autosomal dominant neurological amyloidogenic disease. 5 to 10 individuals per 100,000 individuals are affected with this autosomal disease. However, the prevalence in the US is much higher, studies have shown that under 200,000 US individuals 50% have the risk of developing HD, in particular 30,000 patients are registered in the US while only 100,000 patients are registered worldwide.

HD, as shown in several studies, results from a trinucleotide CAG repeat expansion in the Huntingtin (HTT) gene, in particular in exon 1 of the HTT gene located on chromosome 4 (MacDonald et al., Cell 72, (1993), 971-983), which is translated into a polyglutamine (polyQ) stretch in the HTT protein. HD occurs when the polyQ tract exceeds a threshold of 35-40 glutamine residues in length with a strong inverse correlation between repeat length and age-of-onset of disease. This polyQ stretch leads to a misfolding and aggregation of HTT in several regions, e.g. neurons and glial cells. With increasing age an accumulation of the HTT aggregates takes place leading to degeneration of the striatal GABAergic neurons and cortical pyramidal neurons. Symptoms of the HTT misfolding and aggregation include involuntary movements, lack of motor coordination, depression, cognitive decline such as memory loss and/or dementia.

Since 1993 when the HD mutation was identified the understanding of the pathophysiology and molecular biology of the disease has significantly improved. Medicaments such as e.g. Xenazine® (tetrabenazine, Lundbeck) a hexahydro-dimethoxy-benzoquinolizine derivative VMAT2 inhibitor had been designed for symptomatic treatment targeting involuntary muscle movements.

In addition, gene silencing approaches such as RNA interference (RNAi) have been suggested as potential therapies. In particular, the use of siRNA directed against HTT gene in a HD mouse model (R6/2) was shown to inhibit mutant HTT gene expression, see e.g. Warby et al., Am. J. Hum Genet. 84 (2009), 351-366 and Olshina et al., Biological Chemistry 285 (2010), 21807-21816. However, one limitation of this method lies in the difficulty to introduce sufficient amount of siRNA into the target cells or tissues as shown by e.g. Boudreau et al. (Brain Research 1338 (2010), 112-121). Furthermore this approach may face safety liabilities as a continued need for the expression of Huntingtin was suggested by gene deletions studies in animal models and cultured cells (Dragatsis et al., Nat. Genet. 26 (2000), 300-306; Gauthier et al., Cell. 118 (2004), 127-138; Zuccato et al., Nat. Genet. 35 (2003), 76-83).

Therefore, there is a need for novel therapeutic strategies an efficacious and safe therapy of diseases associated with HTT aggregation which preferably directly interfere with amyloid formation by mutant HTT.

This technical problem is solved by the embodiments characterized in the claims and described further below and illustrated in the Examples and Figures.

SUMMARY OF THE INVENTION

The present invention provides anti-huntingtin (HTT) antibodies and equivalent HTT-binding molecules for use in the prophylactic or therapeutic treatment of diseases and conditions associated with HTT amyloidosis. More specifically, therapeutically useful human-derived antibodies as well as HTT-binding fragments, synthetic and biotechnological derivatives thereof that recognize mutated and/or aggregated forms of HTT are provided.

In particular, experiments performed in accordance with the present invention were successful in the recombinant cloning and production of human-derived monoclonal HTT-specific antibodies which are specific for mutated and/or aggregated HTT species and/or fragments thereof. The human subjects being the source of the B cells from which the cDNA encoding the variable domain of human-derived monoclonal anti-HTT antibodies, respectively, have been isolated, were healthy donors. However, in another embodiment of the present invention, the source of the B cells from which the human-derived monoclonal anti-HTT antibodies and the cDNA encoding their variable domain, respectively, might be isolated are HD patients carrying trinucleotide CAG repeat expansion in the HTT gene and being either symptom-free or displaying an unusually slow progressing or stable disease course or alternatively displaying typical clinical features of Huntington's disease. Furthermore, as demonstrated in the Examples, the antibodies of the present invention are capable of attenuating dendritic spine loss, improve behavioral performance during task-specific training and enhance sensorimotor ability in a mouse model of HD. Therefore, it is prudent to expect that the human monoclonal anti-HTT antibodies of the present invention and derivatives thereof besides being non-immunogenic also exhibit a therapeutically beneficial effect in human.

As described in the background section, hitherto the pathogenesis of HD has been tried block by intracellular approaches such as RNA interference (RNAi); see also, e.g., Stanek et al., Human Gene Therapy 25 (2014), 461-474 for silencing mutant Huntingtin by Adeno-associated virus-mediated RNA interference. With respect to an immunotherapeutic approach the intracellular expression of single-chain antibody fragments (scFv), i.e. intrabodies which are devoid of the constant region of immunoglobulins such as of the IgG class has been explored in the last decade; see, e.g., supra and Butler et al., Prog Neurobiol. 97 (2012), for engineered intracellular scFv and single-domain (dAb; nanobody) antibody therapies to counteract mutant huntingtin and related toxic intracellular proteins.

For example, Lecerf et al., Proc. Nat. Acad. Sci. 98 (2001), 4764-4769 describe a single-chain variable region fragment (scFv) antibody specific for the 17 N terminal residues of huntingtin, adjacent to the polyglutamine in HD exon 1 selected from a large human phage display. A corresponding scFv antibody, scFv-C4 comprising a lambda variable light ($V_L$) chain (Kvam et al., PLoS One 4 (2009), e5727; GenBank accession number ACA53373) is described to have some neuro-protective effect in B6.CgHDR6/1 transgenic mice, a HD mouse model, which however weakened both with severity of disease at time of injection. In order to improve the steady-level of the intrabody and to direct N-terminal htt exon 1 (httex1) protein fragments bound by scFv-C4 to the proteasome for degradation in order to prevent them from aggregation the PEST signal sequence of Mouse Ornithine Decarboxylase (mODC) mODC has been fused to the scFv-C4 antibody; see Butler and Messer, PLoS One 6 (2011), e29199. No in vivo experiments have been reported yet.

Also the group of Khoshnan et al. was aiming at the development of intrabody-based therapeutics for HD and inter alia describe anti-huntingtin scFv antibodies derived from mouse monoclonal antibodies binding the epitopes polyglutamine (polyQ), polyproline (polyP), and anti-C terminus and their effects upon intracellular expression on mutant huntingtin aggregation and toxicity; see, e.g., Ko et al., Brain Research 56 (2001), 319-329, Khoshnan et al., Proc. Nat. Acad. Sci 99 (2002), 1002-1007 and Legleiter et al., J. Biol. Chem. 284 (2009), 21647-21658 and their patent application US 2003/0232052 A1. In the US application, also a "human" scFv antibody denoted "hMW9" is described to have been isolated from a human scFvs phage library using recombinant mutant huntingtin protein. However, in contrast to mouse monoclonal derived scFv MW1, MW2, MW7 and MW8 no sequence data are provided for hMW9 which hitherto has also never been reported again.

Colby et al., Proc. Nat. Acad. Sci. 342 (2004), 901-912 describe the development of a human light chain variable domain ($V_L$) intracellular antibody specific for the amino terminus of Huntingtin via yeast surface display of a non-immune human antibody library. This single-domain intrabody consisting only of the lambda light chain domain of the original scFv was described to inhibit huntingtin aggregation in a cell-free in vitro assay as well as in a mammalian cell culture model of HD; see also to corresponding international application WO 2005/052002. Again, no in vivo experiments have been reported yet.

Hence, apparently current intrabody based approaches either did not extend over cell-based assays or had not been proven to be successful in animal models of HD yet, at least not in long term experiments. In particular, intrabodies reveal several limitations in-vivo such as their potential toxicity due to intracellular/intranuclear accumulation of intrabody-antigen complexes or the limited distribution of for example viral delivery into large brain volumes in humans; see, e.g., Butler et al., Prog. Neurobiol. 97 (2012), 190-204 and Sothwell et al., J. Neurosci. 29 (2009), 13589-13602. Furthermore, a general drawback of intracellular approaches is the problem of addressing the antibody and its encoding vector DNA, respectively, to the desired cells and, if exogenously applied the inconvenient administration regimen, for example intrastriatal injections; see, e.g., Snyder-Keller et al., Neuropathol. Exp. Neurol. 69 (2010), 1078-1085. In addition, general concerns with respect to gene therapy and the use of viral vectors remain.

In contrast, the experiments performed in accordance with the present invention demonstrate for the first time that full-length IgG antibodies directed against different epitopes of huntingtin upon systemic administration can be successfully delivered to the brain (Example 24 and FIG. 18) and that the antibodies of the present invention are capable of attenuating dendritic spine loss, improve behavioral performance during task-specific training and enhance sensorimotor ability in a mouse model of HD (Example 34 and FIG. 34).

Therefore, as illustrated in the Examples, the anti-HTT antibody or an HTT-binding fragment, synthetic or biotechnological derivative thereof is preferably of the IgG class, which as generally known and described herein comprises two identical variable heavy ($V_H$) chain polypeptides and two identical variable light ($V_L$) chain polypeptides, and a constant region and domain, respectively, i.e. at least one or all of the constant domains of the light chain (CL) and the heavy chain (CH1, CH2 or CH3). Put in other words, in one aspect of the present invention recombinantly expressed bivalent antibodies specific for Huntingtin and aggregated forms, fragments, peptides and derivatives thereof are provided suitable for use in the treatment or in in vivo diagnosis of huntingtin and disorders associated therewith, which are characterized by the presence of an immunoglobulin constant region. As described herein further below the immunoglobulin may be of any class such as IgG, IgM, IgA IgG, or IgE and corresponding immunoglobulin subclasses (isotypes), e.g., IgG1, IgG2, IgG3, IgG4, IgA1. Preferably however, the antibody is of the human IgG subtype.

In addition, as also further explained herein, the human-derived antibodies of the present invention are characterized by comprising at least one or more CDR of human origin, i.e. being encoded by a cDNA derived from human memory B cells, and preferably wherein the $V_H$ and/or $V_L$ chain are of human memory B cell origin too. The constant region or any domain thereof if human may be of the same or different origin as the CDR(s) and the $V_H$ and/or $V_L$ chain, respectively.

In this context, unless stated otherwise or clear from context reference herein to the antibody of the present invention includes the human-derived antibodies illustrated in the Examples as well as HTT-binding fragments, synthetic and biotechnological derivatives thereof.

As can be further noted form the prior art approaches of providing intrabodies derived from human scFvs phage library almost always scFcvs were obtained with a light chain variable region of Vlamda origin; see Kvam et al. and Colby et al., supra. In contrast, more than 90% of the human-derived antibodies of the present invention use a Vkappa light chain, which also applies to antibodies NI-302.31F11 and NI-302.35C1 illustrated in Example 24 to be capable of penetrating the brain upon systemic administration and in Example 34 (NI-302.35C1) to have beneficial effects on behavioral performance and motor-related tasks of mice in a HD animal model. Therefore, it is tempting to speculate that antibodies having a Vkappa light chain might have superior properties over antibodies having a light chain of Vlamda origin. Therefore, in a preferred embodiment of the antibody of the present invention the light chain variable region is of Vkappa origin.

As illustrated in the Examples and Figures, the anti-HTT-antibody, HTT-binding fragment, synthetic and biotechnological variant thereof binds to different regions of the HTT exon 1 protein which shows the "toxic" alteration as described above, i.e. the expanded, unstable trinucleotide repeat, as shown in the Examples. In particular, the antibody of the present invention recognizes a polyP-region, a polyQ/polyP-region, the P-rich-region, the C terminal-region or the N-terminal region of HTT exon 1 protein. The epitopes of the subject antibodies illustrated in the Examples are summarized in FIG. 20. As mentioned in the background section, HD occurs when the polyQ tract exceeds a threshold of 35-40 glutamine residues in length due to an aggregation of HTT. Accordingly, as shown in Example 3, aggregated and soluble HTT exon 1 proteins with 21, 35 or 49 polyQ repeats were generated and the binding of the identified antibodies tested. In the following these constructs will be denoted HDX with X being the number of Qs, e.g. HTT exon 1 with 21 polyQ repeats will be denoted HD21. Therefore, unless specifically indicated otherwise the term HTT means HTT exon1 and the soluble HTT refers to the corresponding GST-fusion proteins.

In a preferred embodiment of the present invention, the anti-HTT antibody or HTT-binding fragment, synthetic or biotechnological derivative thereof is capable of preferentially binding aggregated or misfolded forms of HTT. As described in e.g. Legleiter et al., JBC 285 (19) (2010), 14777-14790 and demonstrated in the Examples the aggregation of HDX proteins in terms of speed and seize increases with the number of Qs.

In a particularly preferred embodiment of the present invention, the anti-HTT antibody or HTT-binding fragment, synthetic or biotechnological derivative thereof demonstrates the immunological binding characteristics of an antibody characterized by any one of the variable regions $V_H$ and/or $V_L$ as set forth in FIG. 1. Preferably, the variable region of the antibody comprises at least one complementarity determining region (CDR) of the $V_H$ and/or $V_L$ of the variable regions, i.e. pair of $V_H$ and $V_L$ chain as set forth in FIG. 1A to 1AU, wherein one or more amino acid substitutions are permitted as long as binding specificity of the resultant antibody compared to the subject antibody comprising the corresponding pair of $V_H$ and $V_L$ chain as set forth in FIG. 1A to 1AU as illustrated in the Examples, e.g. as summarized in FIG. 20 remains unaffected in kind, i.e. epitope specificity and $EC_{50}$ values in the same order of magnitude for the indicated antigen, preferably in the range of at least 50%, more preferably 25% and most preferably at least 10% identical value. Preferably, one, two or all three CDRs of the $V_H$ and $V_L$ chain contain at least one amino acid at a corresponding position which is conserved (i.e. being the same or a conservative substitute amino acid) in at least about 20%, preferably about 40%, more preferably about 50% and most preferably about 75% in the $V_H$ and $V_L$ chain amino acid sequences, respectively, of the subject antibodies which recognize the same type of HTT epitope, i.e. poly-P, P-rich, C-terminus or N-terminus. For example, sequence alignment of the subject antibodies reveals the predominant presence of one or two tyrosines (Y) in CDRH1; see FIG. 36. Similar conserved amino acid can be identified in the other CDRs as well.

In a further embodiment of the present invention, the anti-HTT antibody or HTT-binding fragment, synthetic or biotechnological derivative thereof is a bispecific antibody. Thus, the antibody of the present invention may be capable of recognizing at least two distinct epitopes either on the same or on different antigens. For example, while a first antigen-binding site, i.e. variable domain may be specific for HTT and preferably comprises a variable region of any one of the subject antibodies illustrated in the appended Examples and Figures, the second antigen-binding site may be specific for a different, preferably also neurotoxic protein and comprise a variable region of corresponding antibody. Hence, protein misfolding and aggregation is a major hallmark of neurodegenerative disorders such as Alzheimer's disease (AD), Parkinson's disease (PD) and HD. Tough until recently, the consensus was that each aggregation-prone protein was characteristic of each disorder [α-synuclein (α-syn)/PD, mutant huntingtin (HTT)/HD, Tau and amyloid beta peptide/AD], growing evidence indicates that aggregation-prone proteins can actually co-aggregate and modify each other's behavior and toxicity, suggesting that this process may also contribute to the overlap in clinical symptoms across different diseases; see, e.g., for co-aggregation of α-syn and mutant HTT Poças et al., Hum. Mol. Genet. 24 (2015), 1898-1907.

Thus, in one embodiment of the present invention the anti-HTT antibody or HTT-binding fragment, synthetic or biotechnological derivative thereof is a bispecific antibody which is capable of binding HTT and a protein associated with a neurodegenerative disorder, in particular in the brain, preferably selected from the group consisting of α-synuclein, Tau, amyloid beta peptide, SOD1, C9orf72, and TDP-43; see, e.g., Blokhuis et al., Acta Neuropathol. 125 (2013), 777-794. Human-derived monoclonal antibodies against the mentioned proteins are known in the art; see, e.g., international application WO2008/081008 for anti-abeta antibody, WO2010/069603 for anti-α-synuclein antibody; WO2012/049570 for anti-tau antibody; WO2012/080518 for anti-SOD1 antibody; WO2012/113775 for anti-ankyrin antibody; WO2013/061163 for anti-TDP-43 antibody and European patent application EP 14 187 180.6 and its subsequent international application for C9orf72. Bi- and multispecific antibodies can be generated by methods well known in the art, for example by chemical recombination of monoclonal immunoglobulin G1 fragments as described, e.g., by Brennan et al., Science. 229 (1985), 81-83, or recombinant simultaneously co-expression of the appropriate heavy and light chain and corresponding pairing; see, e.g., Lewis et al., Nature Biotechnology 32 (2014), 191-198; for review see, e.g., Kontermann, mAbs 4 (2012), 182-197 and Kontermann and Brinkmann, Drug Discovery Today 20 (2015), 838-847.

Alternatively, or in addition the bi- or multi-specific antibody comprises at least a first and second antigen-binding site, i.e. variable domain specific for two distinct epitopes of HTT, preferably wherein one or both variable regions are derived from any one of the subject antibodies illustrated in the appended Examples and Figures, and as further described herein. Thus, in a preferred embodiment the bispecific antibody of the present invention comprises two binding sites/domains of an antibody which recognizes a polyP-region, a polyQ/polyP-region, the P-rich-region, the C terminal-region, the N-terminal region or a conformational epitope of HTT exon 1 protein. The epitopes of the subject antibodies illustrated in the Examples are summarized in FIG. 20. Accordingly, in one embodiment the bispecific antibody of the present invention recognizes at least two different epitopes depicted in FIG. 20 and has the combined binding specificities of the cognate subject antibody, respectively.

The antigen-binding fragment of any one the subject antibodies disclosed herein can be a single chain Fv fragment, an F(ab') fragment, an F(ab) fragment, and an F(ab')2 fragment, or any other antigen-binding fragment. However, as mentioned in a particularly preferred embodiment, the antibody or HTT-binding fragment, synthetic or biotechnological derivative thereof is a human IgG isotype antibody and comprises at least part of the constant region. Alternatively, the antibody is a chimeric human-rodent or rodentized antibody such as murine or murinized, rat or ratinized antibody, the rodent versions being particularly useful for diagnostic methods and studies in animals.

Furthermore, the present invention relates to compositions comprising the antibody of the present invention or antigen-binding fragment, synthetic or biotechnological derivative thereof and to immunotherapeutic and immunodiagnostic methods using such compositions in the prevention, diagnosis or treatment of diseases and/or disorders associated with HTT amyloidosis, wherein an effective amount of the composition is administered to a patient in need thereof.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in FIG. 1. Preferably, the polynucleotide is a cDNA.

Accordingly, the present invention also encompasses vectors comprising said polynucleotides and host cells transformed therewith as well as their use for the production of an antibody and equivalent binding molecules which are specific for HTT and preferably are capable of binding mutated and/or aggregated HTT species or fragments thereof. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies. Hence, the present invention also relates to the use of the cDNA, vector and host cell described herein and illustrated in the Examples for the production of an anti-HTT antibody, in particular human-derived anti-HTT antibody or a biotechnological derivative thereof.

Furthermore, disclosed herein are compositions and methods that can be used to identify HTT, in particular mutated and/or aggregated HTT species or fragments in vitro, e.g. in samples and/or in vivo. The disclosed anti-HTT antibodies and binding fragments thereof can be used to screen human blood, plasma, serum, saliva, peritoneal fluid, cerebrospinal fluid ("CSF"), and urine for the presence of HTT and/or mutated and/or aggregated HTT species or fragments thereof in samples, for example, by using ELISA-based or surface adapted assay. In one embodiment the present invention relates to a method of diagnosing or monitoring the progression of a disease and/or disorder related to mutated and/or aggregated HTT species or fragments thereof in a subject, the method comprising determining the presence of mutated, and/or aggregated HTT species or fragments in a sample from the subject to be diagnosed with at least one antibody of the present invention or an HTT-binding molecule and/or binding molecules for mutated and/or aggregated HTT species or fragments having substantially the same binding specificities of any one thereof, wherein the presence of mutated and/or aggregated HTT species or fragments is indicative of the disorder.

Accordingly, the present invention also relates to a method of preparing a pharmaceutical composition for use in the treatment of a disorder associated with or caused by HTT aggregates, the method comprising:

(a) expressing the cDNA of the present invention and/or culturing the host cell of the present invention under appropriate culture conditions suitable for the production of the anti-HTT antibody, in particular human-derived anti-HTT antibody or a biotechnological derivative thereof;

(b) purifying the antibody, biotechnological derivative or immunoglobulin chain(s) thereof from a reaction mixture and the culture, respectively, to pharmaceutical grade; and (c) admixing the antibody or biotechnological derivative thereof with a pharmaceutically acceptable carrier.

Furthermore, in one embodiment of the present invention the anti-HTT antibodies and HTT-binding molecules comprising at least one CDR of an antibody of the present invention are provided for the preparation of a composition for in vivo detection (also called in vivo imaging) of or targeting a therapeutic and/or diagnostic agent to HTT, in particular mutated and/or aggregated HTT species or fragments in the human or animal body. The methods and compositions disclosed herein can aid in diseases and/or disorders associated with HTT aggregation or amyloidosis and characterized, e.g., by the occurrence of aggregated forms of HTT and can be used to monitor disease progression and therapeutic efficacy of the therapy provided to the subject, for example in in vivo imaging related diagnostic methods. In one embodiment the in vivo detection (imaging) comprises scintigraphy, positron emission tomography (PET), single photon emission tomography (SPECT), near infrared (NIR) optical imaging or magnetic resonance imaging (MRI).

Hence, it is a particular object of the present invention to provide methods for treating, diagnosing or preventing a disease and/or disorder associated with HTT amyloidosis. The methods comprise administering an effective concentration of a preferably human antibody or antibody derivative to the subject where the antibody targets HTT or fragments thereof, preferably mutated and/or aggregated or misfolded HTT species or fragments thereof.

In a further aspect the present invention provides a peptide having an epitope of HTT, preferably of mutated and/or aggregated HTT species or fragments thereof specifically recognized by an antibody of the present invention. Said peptide comprises or consists of an amino acid sequence as indicated below in the detailed description and in the Examples or a modified sequence thereof in which one or more amino acids are substituted, deleted and/or added. Additionally, the present invention provides a method for diagnosing diseases and/or disorders associated with HTT amyloidosis in a subject, comprising a step of determining the presence of an antibody that binds to said peptide in a biological sample of said subject.

Further embodiments of the present invention will be apparent from the description and Examples that follow.

BRIEF DESCRIPTION OF THE DRAWINGS

FIG. 1: Amino acid sequences of the variable regions of human antibodies NI-302.33C11, NI-302.63F3, NI-302.35C1, NI-302.31F11, NI-302.2A2, NI-302.6N9, NI-302.74C11, NI-302.15F9, NI-302.39G12, NI-302.11A4, NI-302.22H9, NI-302.44D7, NI-302.37C12, NI-302.55D8, NI-302.7A8, NI-302.78H12, NI-302.71F6, NI-302.11H6, NI-302.3D8, NI-302.18A1, NI-302.8F1, NI-302.52C9, NI-302.46C9, NI-302.15E8, NI-302.15D3, NI-302.64E5, NI-302.7D8, NI-302.72F10, NI-302.12H2, NI-302.8M1 and NI-302.4A6. Framework (FR) and complementarity determining regions (CDRs) are indicated with the CDRs being underlined. The Kabat numbering scheme was used (cf. www.bioinf.org.uk/abs/).

Figure 2:
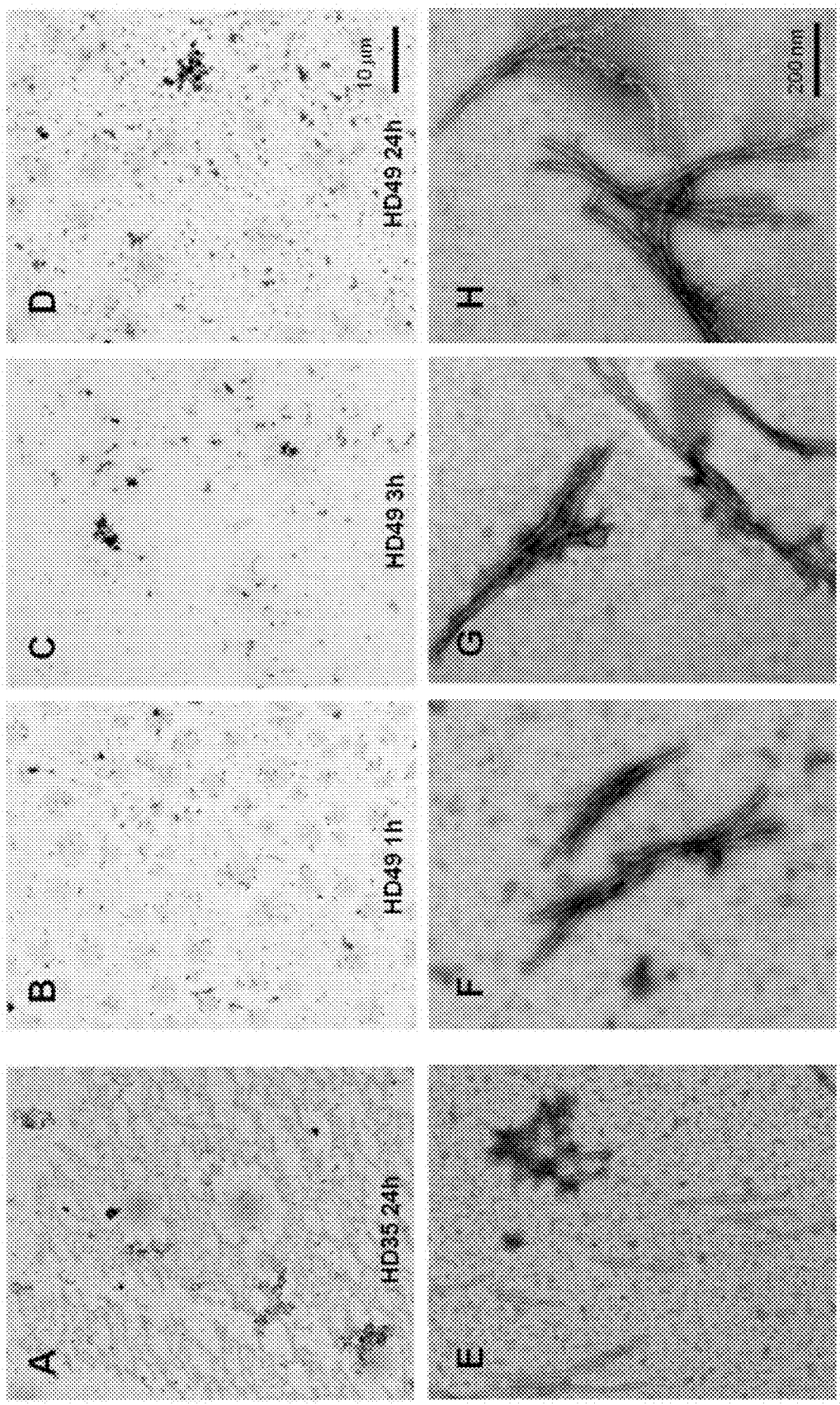
FIG. 2: Characterization of Huntingtin (HTT) exon 1 proteins and aggregates. (A) Cloning of GST-HttEx1Q21 (GST-HD21), GST-HttEx1Q35 (GST-HD35) and GST-HttEx1Q49 (GST-HD49) expression constructs; (B)

Coomassie dye staining upon SDS-PAGE of purified GST only (lane 1), GST-HttExon1Q21 (GST-HD21, lane 2), GST-HttExon1Q35 (GST-HD35, lane 3) and GST-HttExon1Q49 (GST-HD49, lane 4) proteins showing good purity but also some additional bands; (C) Characterization of in vitro HD21, HD35 and HD49 time-resolved in vitro aggregation reactions by dot-blot (left) and filter retardation analysis (right) with polyclonal HD-1 antibody as detection antibody. Aggregation reactions of HD35 at 24 hours or HD49 reactions after 3 hours show aggregates larger than the pore size of 0.2 μm detectable by HD-1 in the filter retardation assay analysis; (D) Characterization of in vitro HD35 and HD49 preparations by electron microscopy. Aggregation reactions of HD35 after 24 hours [A, E] or HD49 reactions after 1 hour [B, F], 3 hours [C, G] or 24 hours [D, H]. Overview pictures [A-D] with 1'000× magnification and detailed structures [E-H] at 66'000× magnification.

Figure 3:
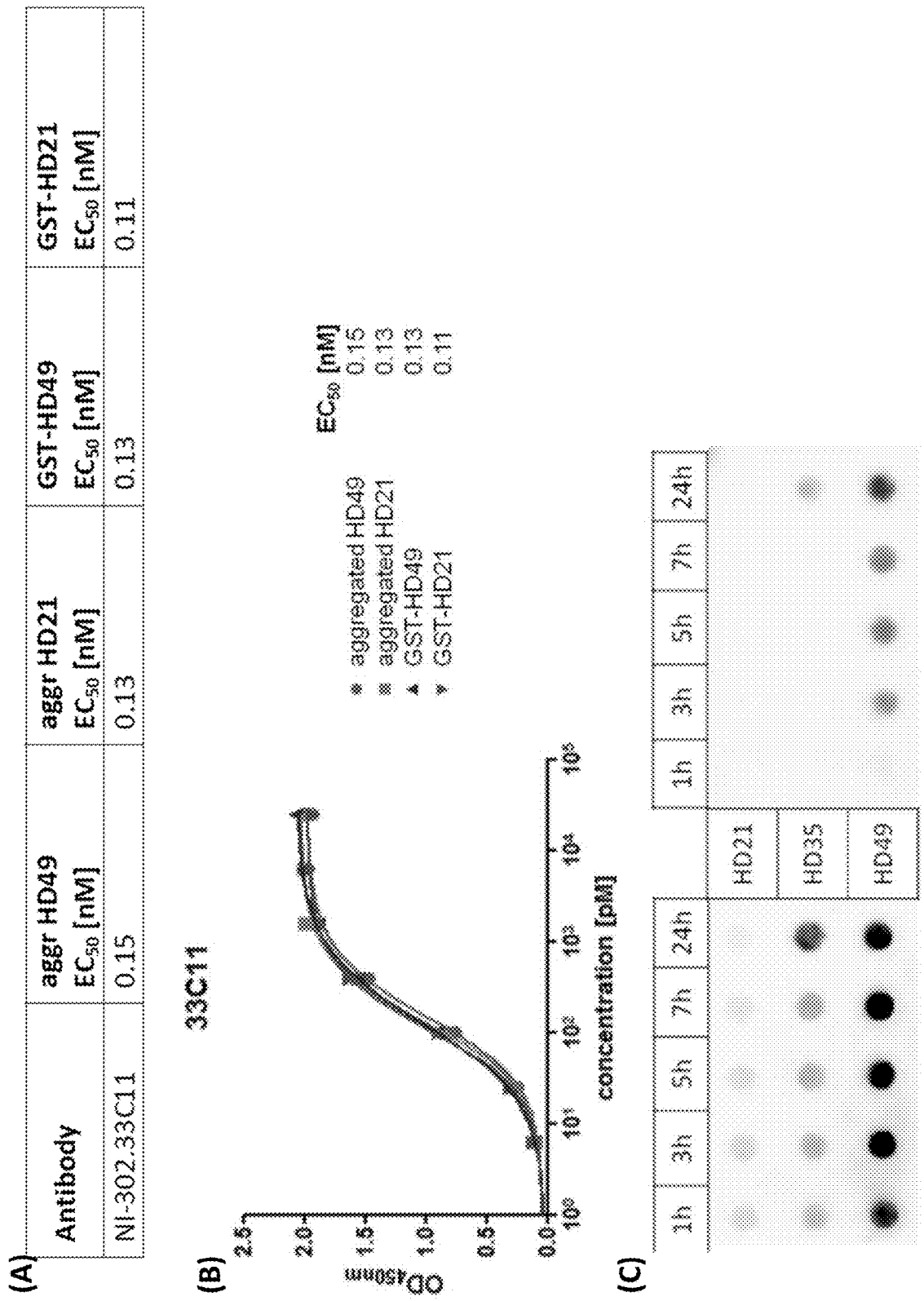

FIG. 3: Characterization of the binding affinity of anti-polyP domain-binding antibody NI-302.33C11. (A) NI-302.33C11 binding affinity for different HTT species determined by direct ELISA; (B) NI-302.33C11 $EC_{50}$ determinations for aggregated HD49 (●), aggregated HD21 (■), soluble GST-HD49 (▲) and GST-HD21 (▼) Htt Exon 1 proteins using direct ELISA. NI-302.33C11 antibody binds with similar $EC_{50}$ values to all four species; and (C) NI-302.33C11 binding analysis to HTT aggregates on in vitro HD21, HD35 and HD49 time-resolved in vitro aggregation reactions by dot-blot (left) and filter retardation assay (right) with preferential binding to later (aggregated) reactions of HD35 and HD49 in the dot-blot assays and aggregates of HD35 and HD49 in the filter retardation assay.

FIG. 4: Determination of NI-302.33C11 antibody binding epitope by scan of overlapping peptides. At the top: pepscan image after NI-302.33C11 antibody hybridization. Below: graphical overviews of peptides sequences bound by NI-302.33C11 antibody. Overlapping amino acids between peptides (putative binding epitope) being recognized by the NI-302.33C11 antibody are highlighted in bold in the consensus sequences. The HRP-conjugated donkey anti-human IgG Fcγ detection antibody alone does not bind any linear huntingtin peptide.

Figure 5:
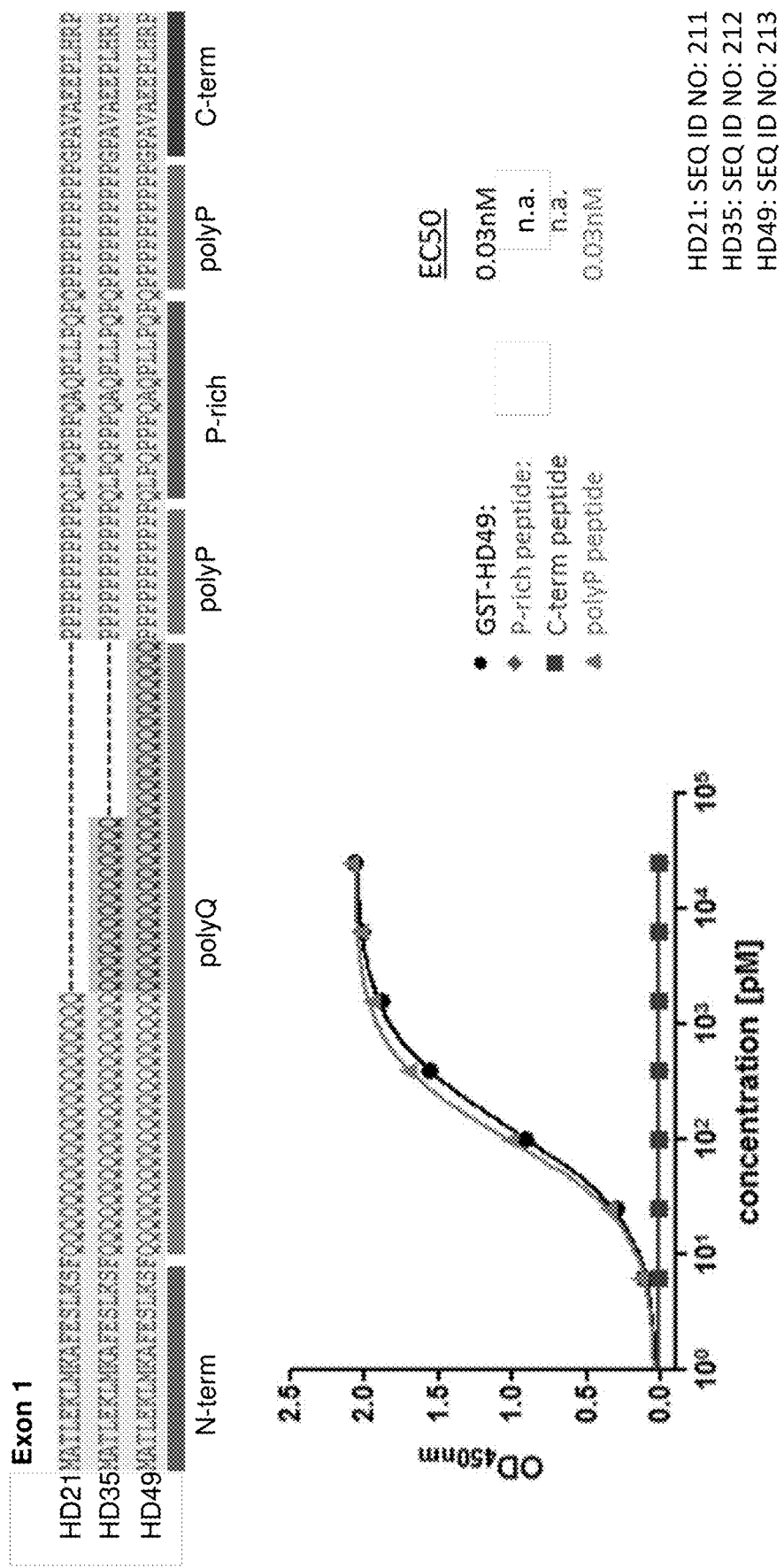

FIG. 5: NI-302.33C11 binds to the polyP-domain of HTT. $EC_{50}$ determinations for GST-HD49 (●), BSA-coupled P-rich domain peptide (♦), BSA-coupled C-terminal peptide (■) or BSA-coupled polyP peptide (▲) using direct ELISA.

Figure 6:
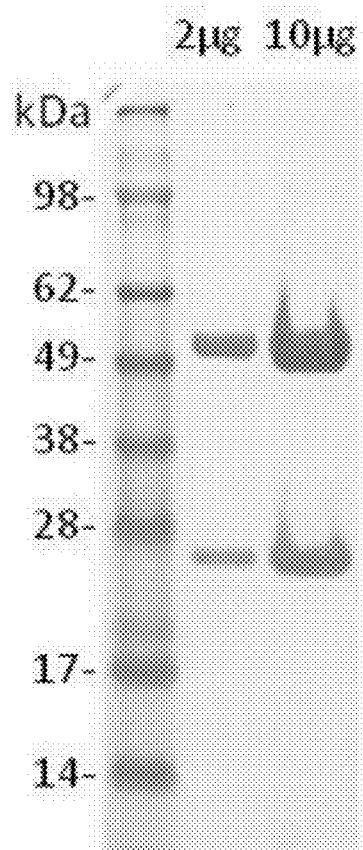

FIG. 6: Characterization of the purity and integrity as well as the binding specificity of NI-302.33C11 antibody. SDS-PAGE analysis followed by Coomassie staining of 2 and 10 μg recombinant human NI-302.33C11 anti-polyP domain antibody.

Figure 7:
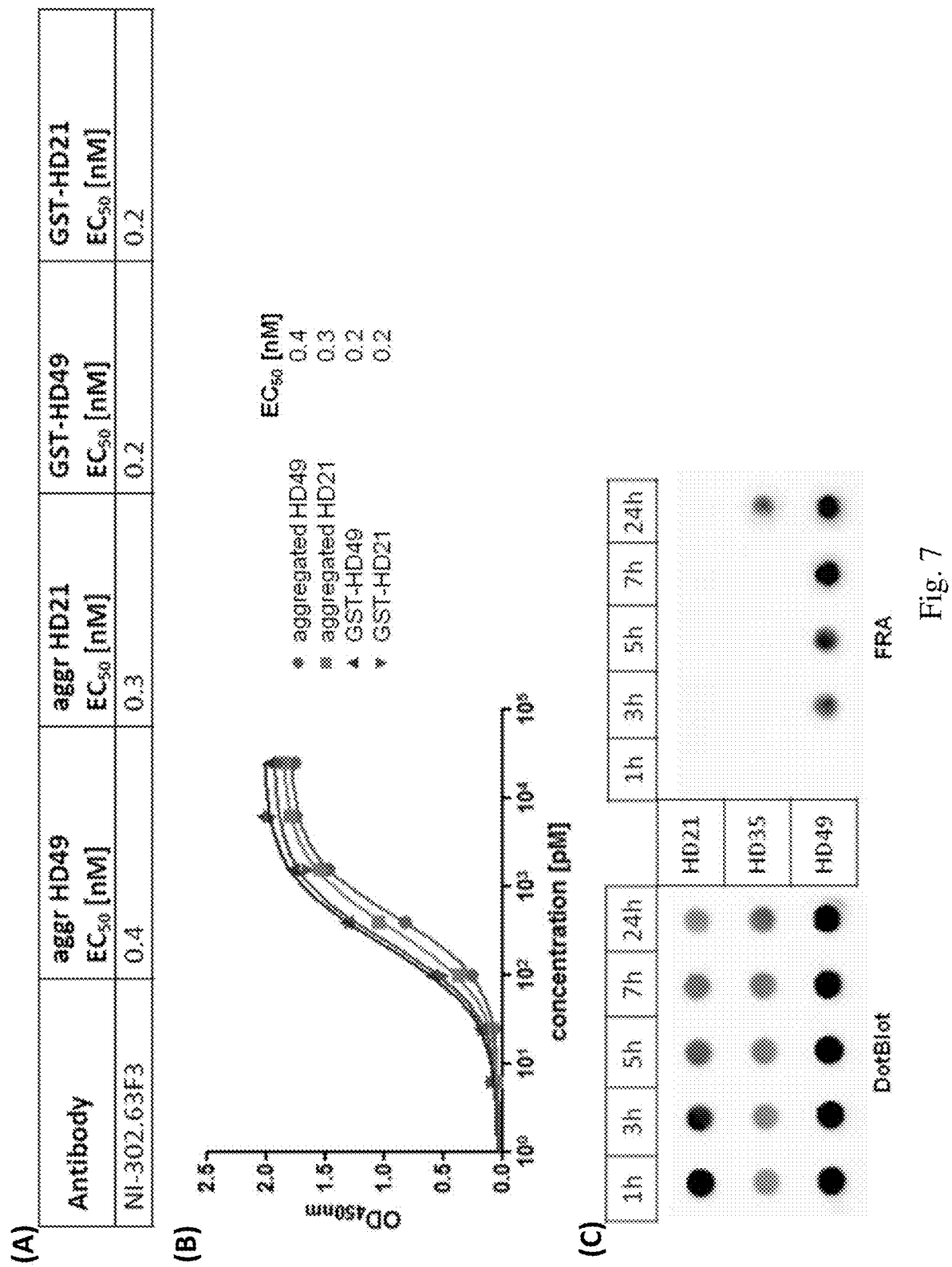

FIG. 7: Characterization of binding affinity of anti-proline-rich domain antibody NI302.63F3. (A) NI-302.63F3 binding affinity for different HTT species determined by direct ELISA; (B) NI-302.63F3 $EC_{50}$ determinations for aggregated HD49 (●), aggregated HD21 (■), soluble GST-HD49 (▲) and GST-HD21 (▼) Htt Exon 1 proteins using direct ELISA. NI-302.63F3 antibody has a similar $EC_{50}$ values to all four species; (C) Characterization of antibody NI-302.63F3 on in vitro HD21, HD35 and HD49 time-resolved in vitro aggregation reactions by dot-blot (left) and filter retardation assay (right) with preferential binding to huntingtin with expanded polyQ tracts (HD49>HD35) in the dot-blot assays and aggregates of HD35 and HD49 in the filter retardation assay.

FIG. 8: Determination of NI-302.63F3 antibody binding epitope by scan of overlapping peptides. At the top: pepscan image after NI-302.63F3 antibody hybridization. Below: graphical overviews of peptides sequences bound by NI-302.63F3 antibody. Overlapping amino acids between peptides (putative binding epitope) being recognized by the NI-302.63F3 antibody are highlighted in bold in the consensus sequences. The HRP-conjugated donkey anti-human IgG Fcγ detection antibody alone does not bind any linear huntingtin peptide.

Figure 9:
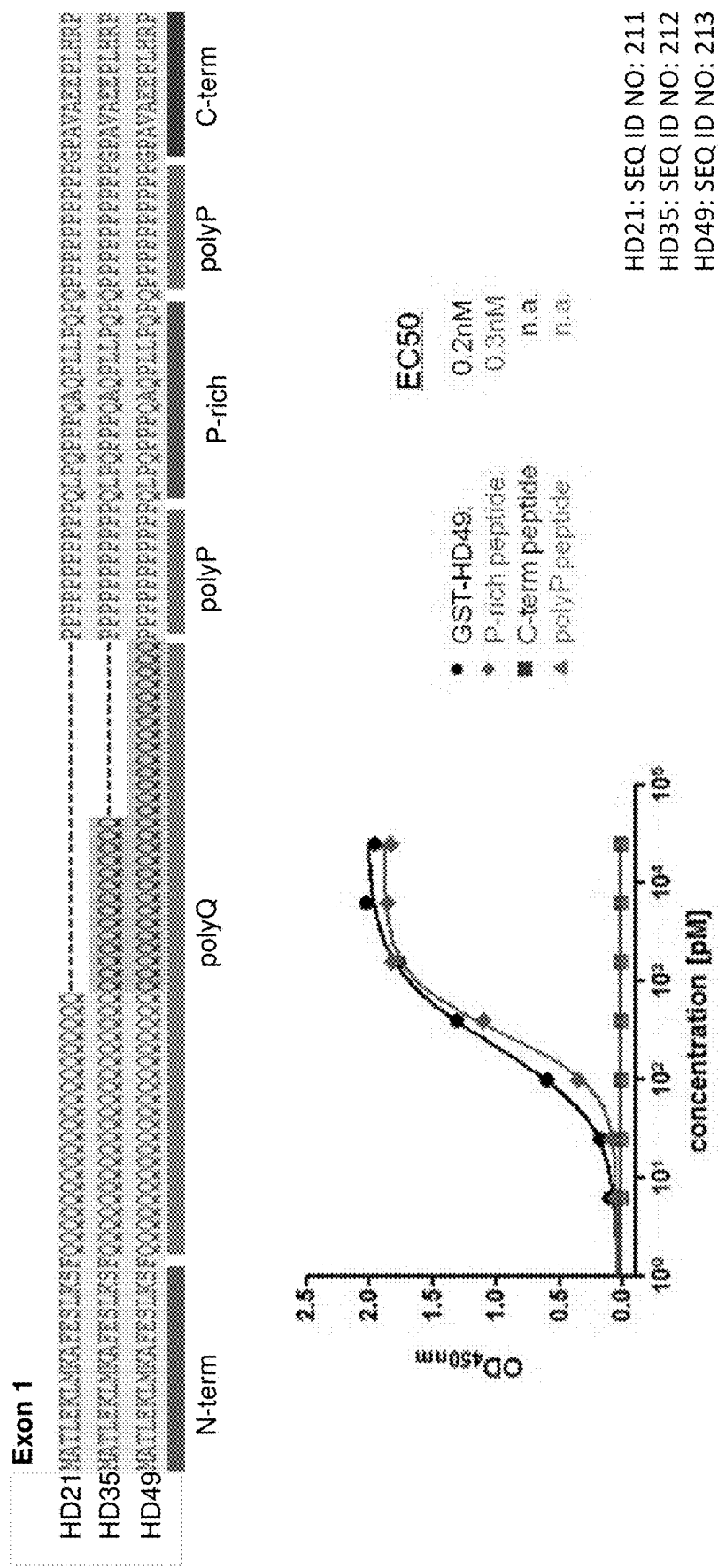

FIG. 9: NI-302.63F3 binds to the P-rich domain of HTT. $EC_{50}$ determinations for GST-HD49 (●), BSA-coupled P-rich domain peptide (♦), BSA-coupled C-terminal peptide (■) or BSA-coupled polyP peptide (▲) using direct ELISA.

Figure 10:
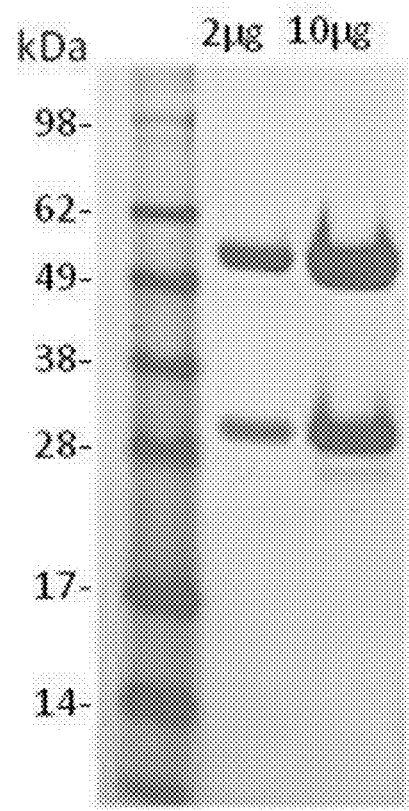

FIG. 10: Characterization of the purity and integrity as well as the binding specificity of NI-302.63F3 antibody. SDS-PAGE analysis followed by Coomassie staining of 2 and 10 μg recombinant human NI-302.63F3 anti-proline-rich domain antibody.

Figure 11:
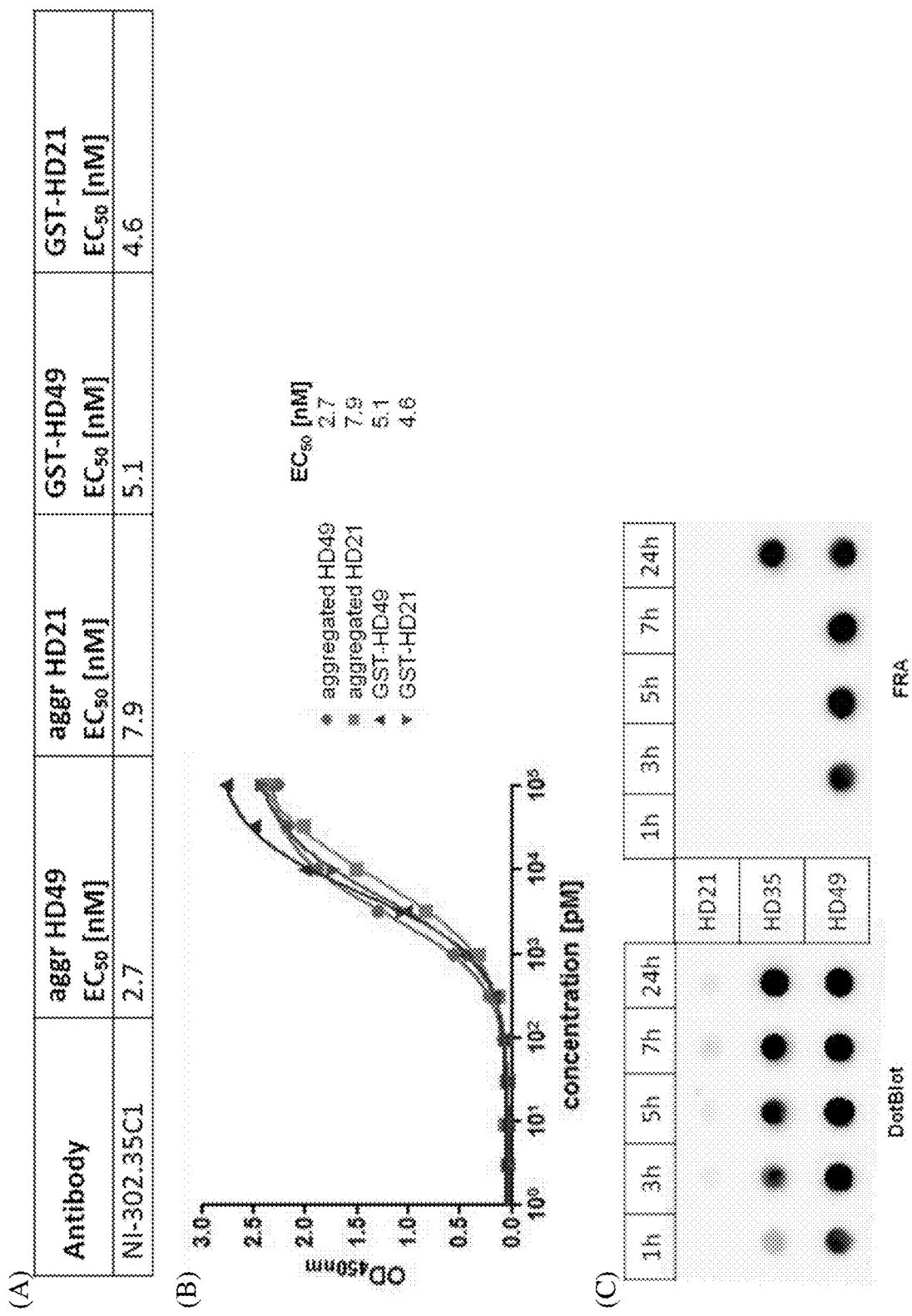

FIG. 11: Characterization of the binding affinity of anti-C-terminal domain-binding antibody NI 302.35C1. (A) NI-302.35C1 binding affinity for different HTT species determined by direct ELISA; (B) NI-302.35C1 $EC_{50}$ determinations for aggregated HD49 (●), aggregated HD21 (■), soluble GST-HD49 (▲) and GST-HD21 (▼) Htt Exon 1 proteins using direct ELISA; (C) Characterization of antibody NI-302.35C1 on in vitro HD21, HD35 and HD49 time-resolved in vitro aggregation reactions by dot-blot (left) and filter retardation assay (right) with preferential binding to later (aggregated) reactions of HD35 and HD49 in the dot-blot assays and aggregates of HD35 and HD49 in the filter retardation assay.

Figure 12:
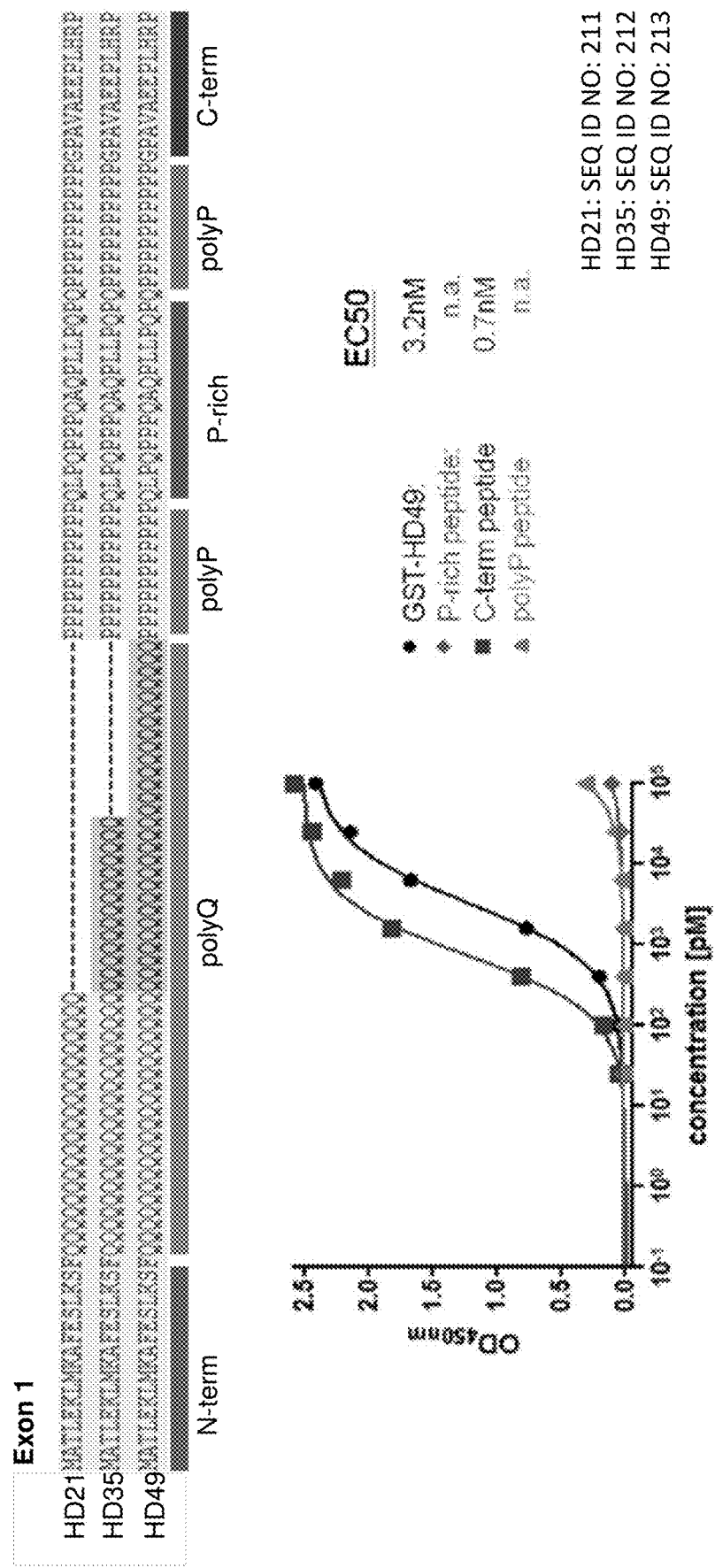

FIG. 12: NI-302.35C1 binds to the BSA-coupled C-terminal domain peptide of HTT. $EC_{50}$ determinations for GST-HD49 (●), BSA-coupled P-rich domain peptide (♦), BSA-coupled C-terminal peptide (■) or BSA-coupled polyP peptide (▲) using direct ELISA.

Figure 13:
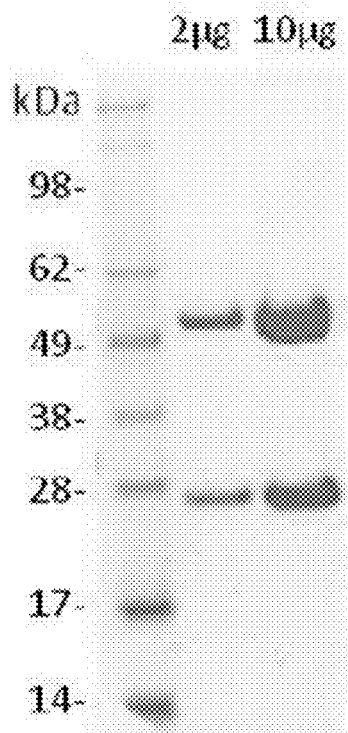

FIG. 13: Characterization of the purity and integrity as well as the binding specificity of NI-302.35C1 antibody. SDS-PAGE analysis followed by Coomassie staining of 2 and 10 μg recombinant human NI-302 anti-C-terminal domain antibody.

Figure 14:
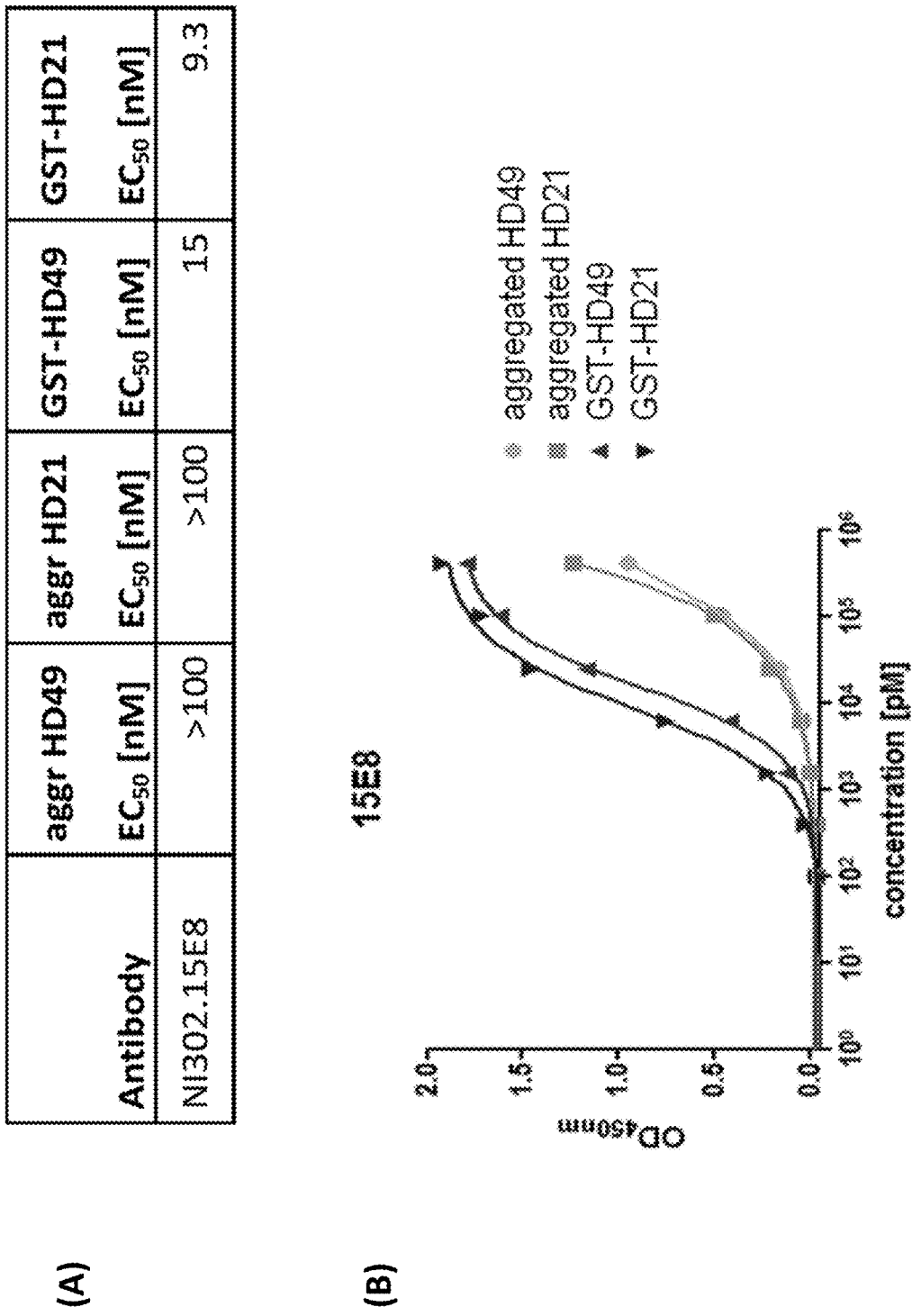

FIG. 14: Characterization of binding affinity of anti-N-terminal domain antibody NI302.15E8. (A) NI-302.15E8 binding affinity for different HTT species determined by direct ELISA; (B) NI-302.15E8 $EC_{50}$ determinations for aggregated HD49 (●), aggregated HD21 (■), soluble GST-HD49 (▲) and GST-HD21 (▼) Htt Exon 1 proteins using direct ELISA. NI-302.15E8 antibody has a higher affinity binding $EC_{50}$ values to non-aggregated species.

Figure 15:
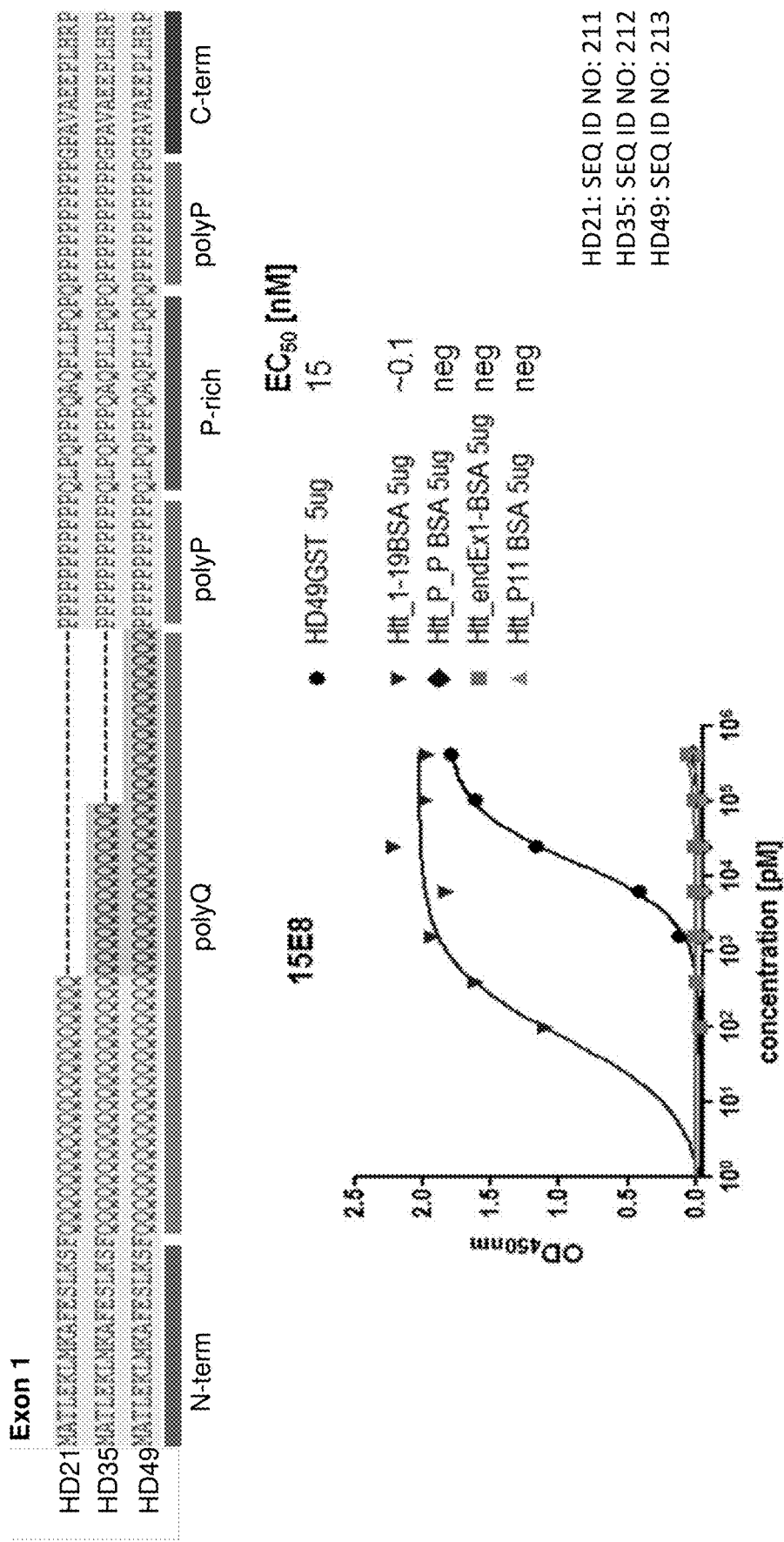

FIG. 15: NI-302.15E8 binds to the BSA-coupled N-terminal domain peptide of HTT. $EC_{50}$ determinations for GST-HD49 (●), BSA-coupled N-terminal peptide (▼) BSA-coupled P-rich domain peptide (♦), BSA-coupled C-terminal peptide (■) or BSA-coupled polyP peptide (▲) using direct ELISA.

Figure 16:
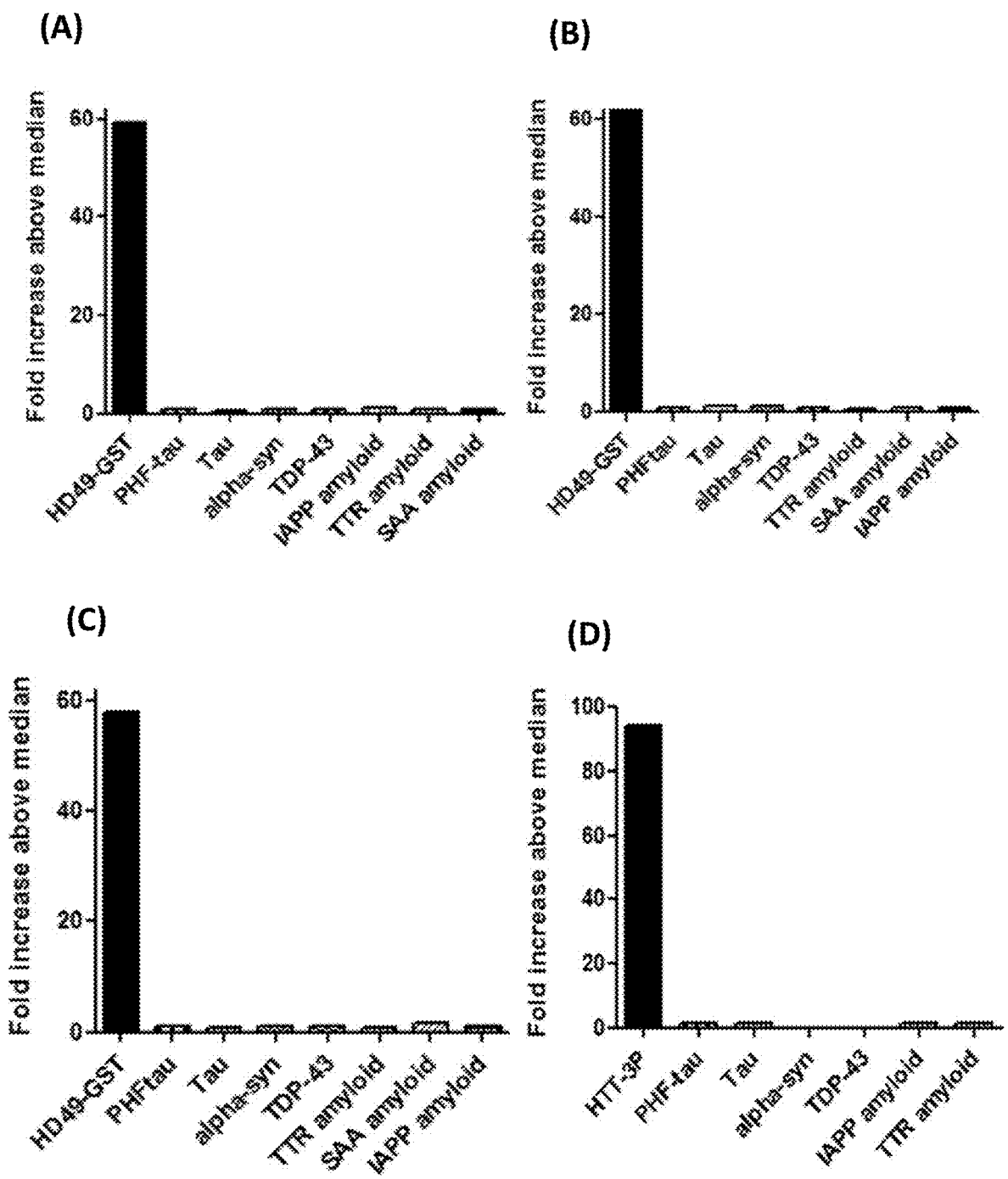

FIG. 16: Target specificity analysis by direct ELISA. NI-302 antibodies (A) NI-302.33C11, (B) NI-302.63F3, and (C) NI-302.35C1 and (D) NI-302.15E8 do not bind unrelated aggregating protein targets as shown in the binding specificity analysis by direct ELISA.

Figure 17:
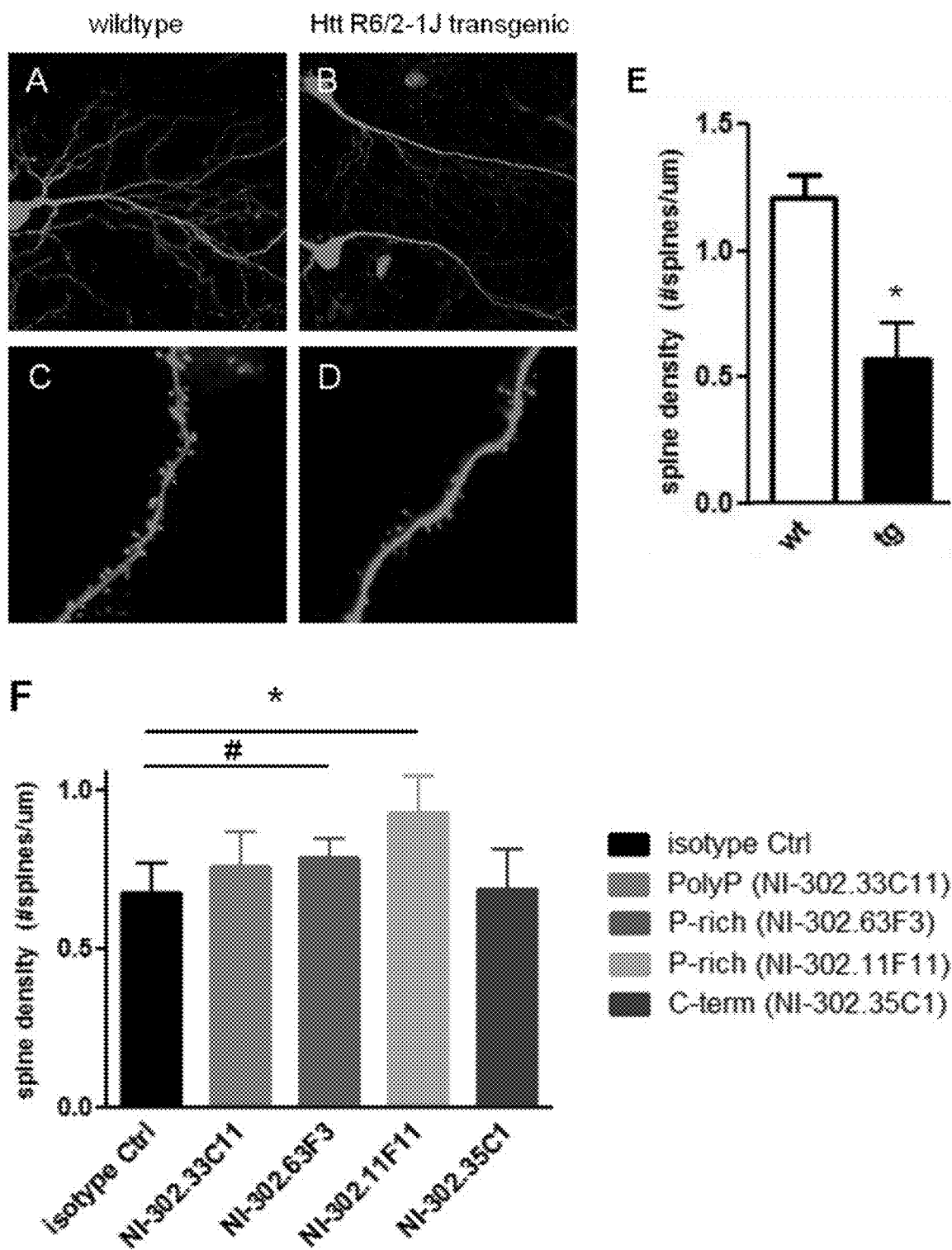

FIG. 17: Spine density is significantly reduced in hippocampal slice cultures of Tg(HDexon1)62Gpb/1J transgenic mice compared to non-transgenic littermates. (A-D) Overview of GFP positive hippocampal neurons of non-transgenic littermates (A, C) vs. Tg(HDexon1)62Gpb/1J mice (B, D), showing a single dendrite with the individual spines at higher magnification (C, D). (E) Significant reduction of dendritic spine density in transgenic vs. wildtype animals (n=3-7 slices per group from 2 wt or 3 transgenic animals). (F) Attenuation of dendritic spine density loss by antibodies NI-302.11F11 and 302.63F3 in slices of transgenic mice. (n=8-13 slices per group from a total of 12 transgenic animals). Data represent the mean±SEM. *p<0.05 (MWU), #p=0.05.

Figure 18:
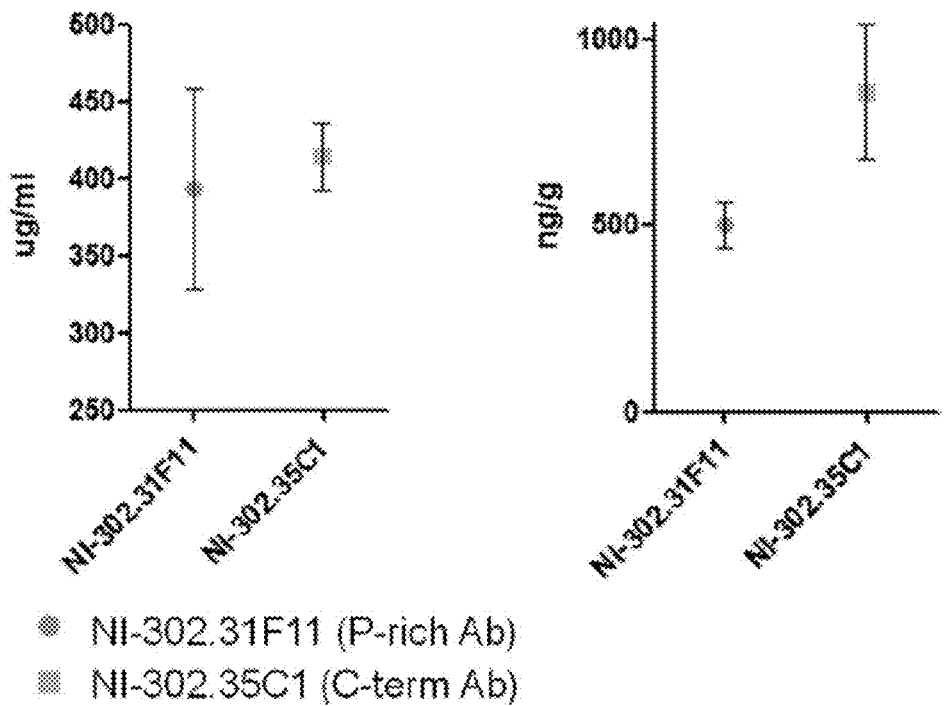

FIG. 18: Penetration of NI-302 antibodies in the brain of R6/1 animal model. (A) Mean NI-302.31F11 (●) and NI-302.35C1 (■) plasma and brain drug levels in R6/1 transgenic animals after a single intraperitoneal injection of 50 mg/kg. Data represent the mean±SEM. n=3 for each group; (B) Plasma and brain drug levels of individual mice after a single dose of 50 mg/kg.

Figure 19:
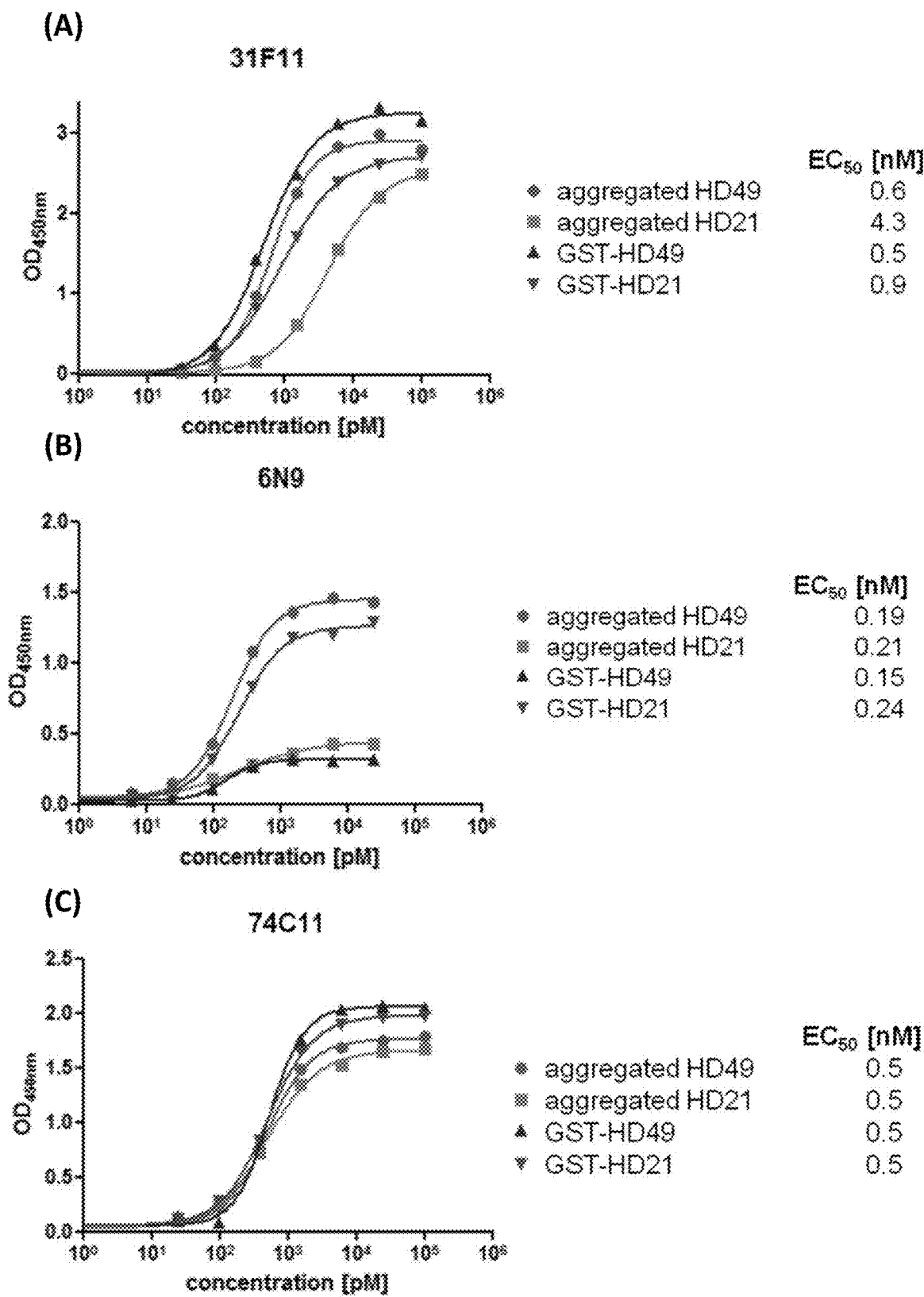
Figure 19:
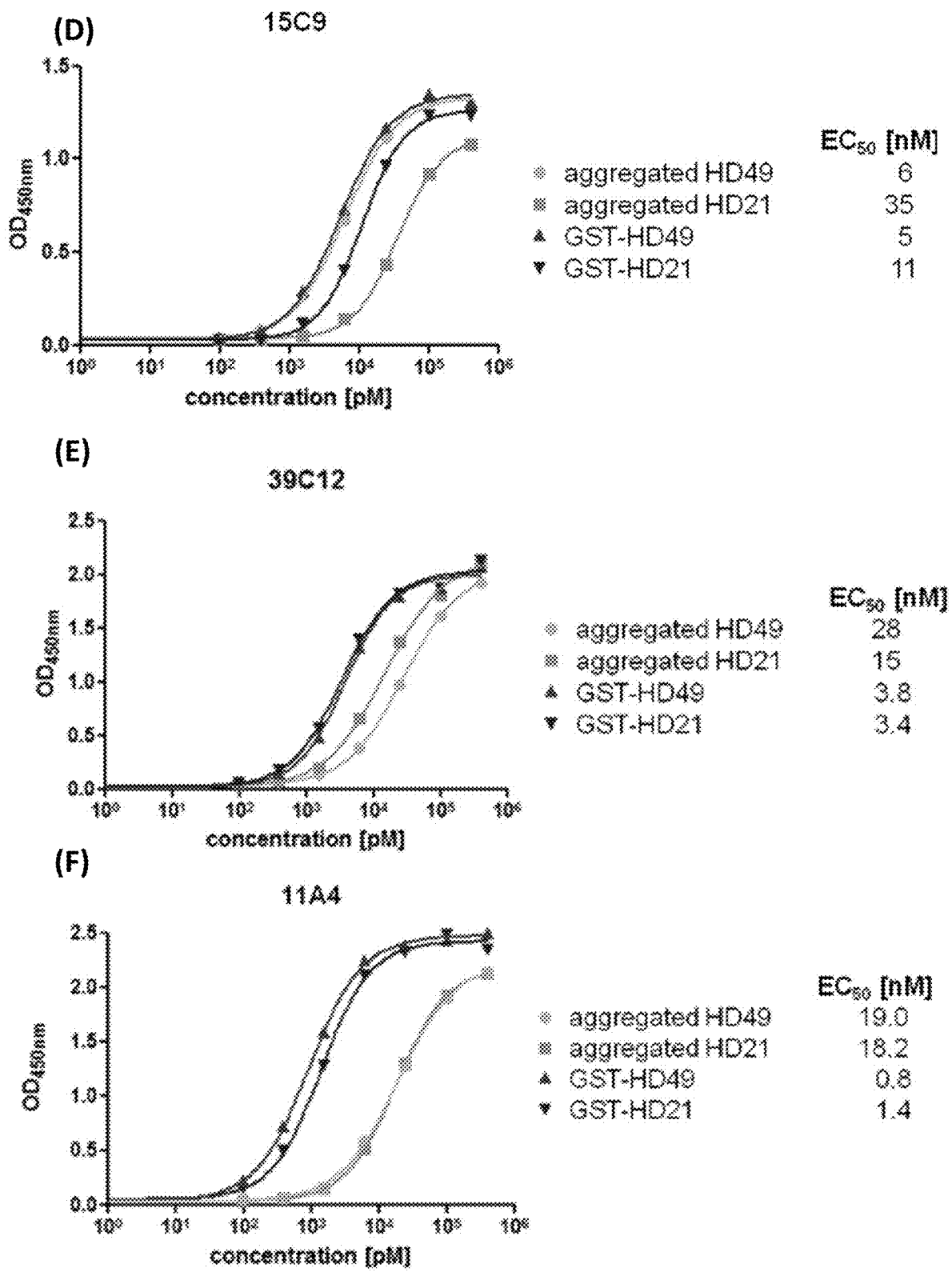
Figure 19:
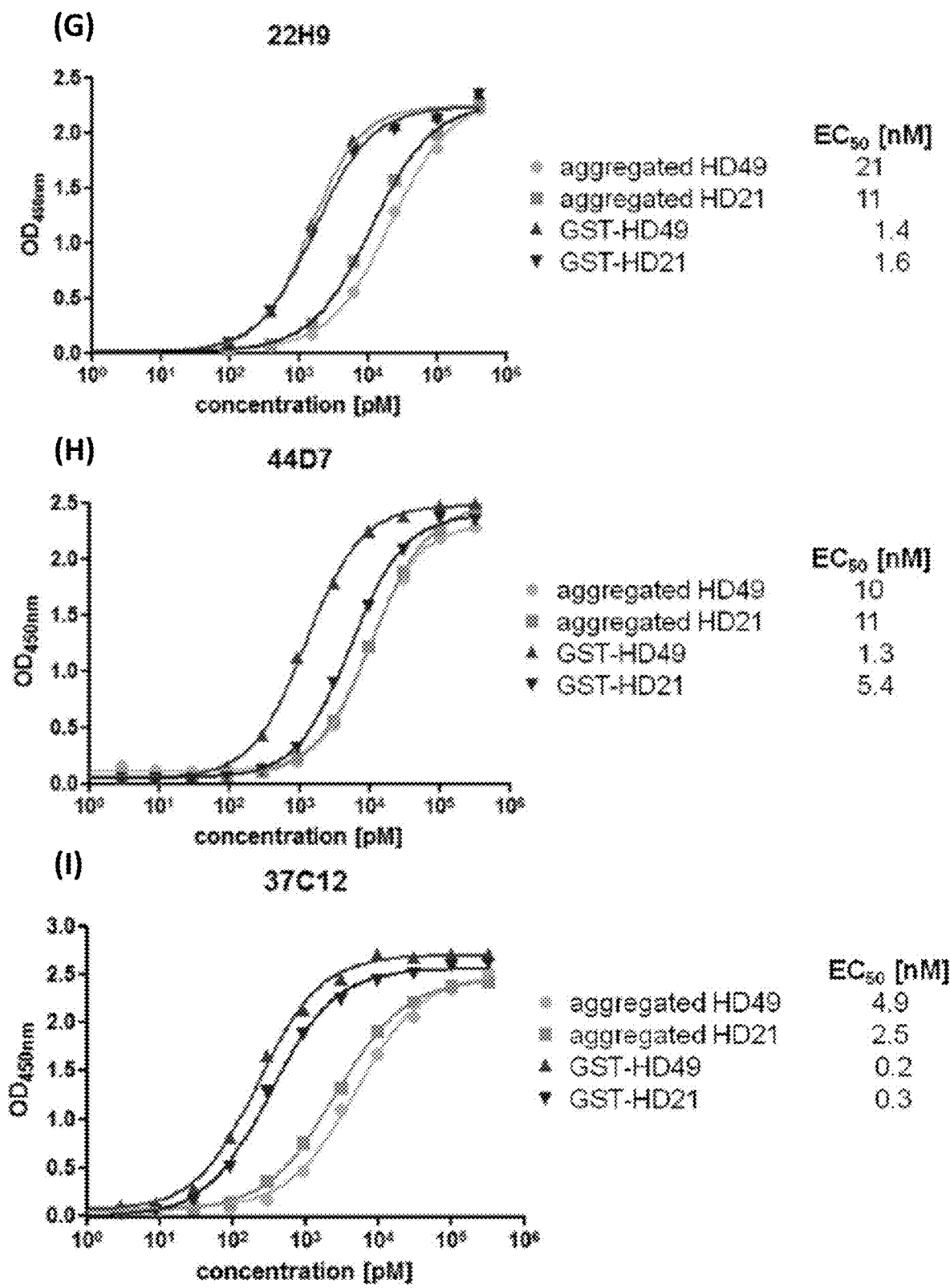
Figure 19:
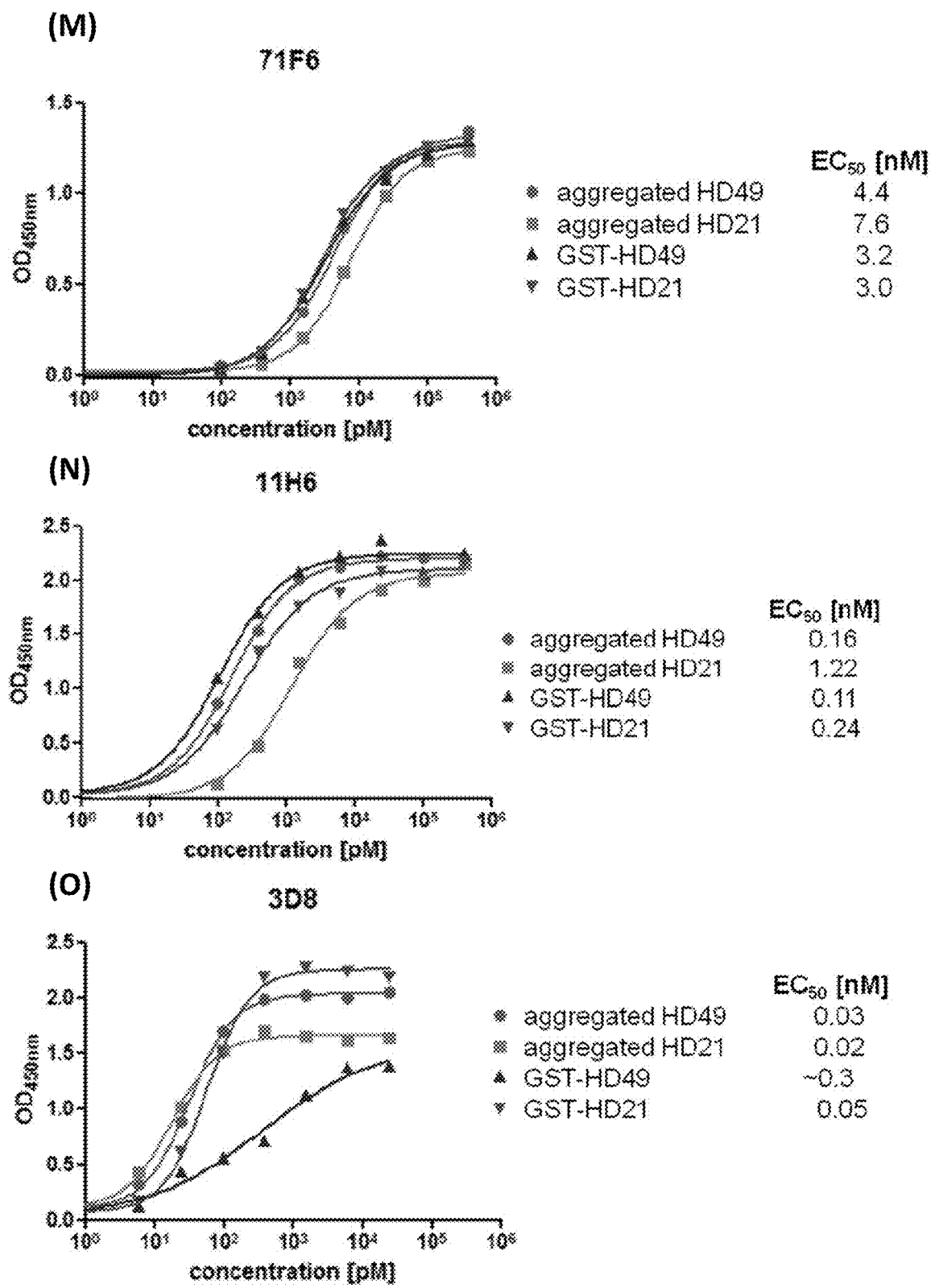
Figure 19:
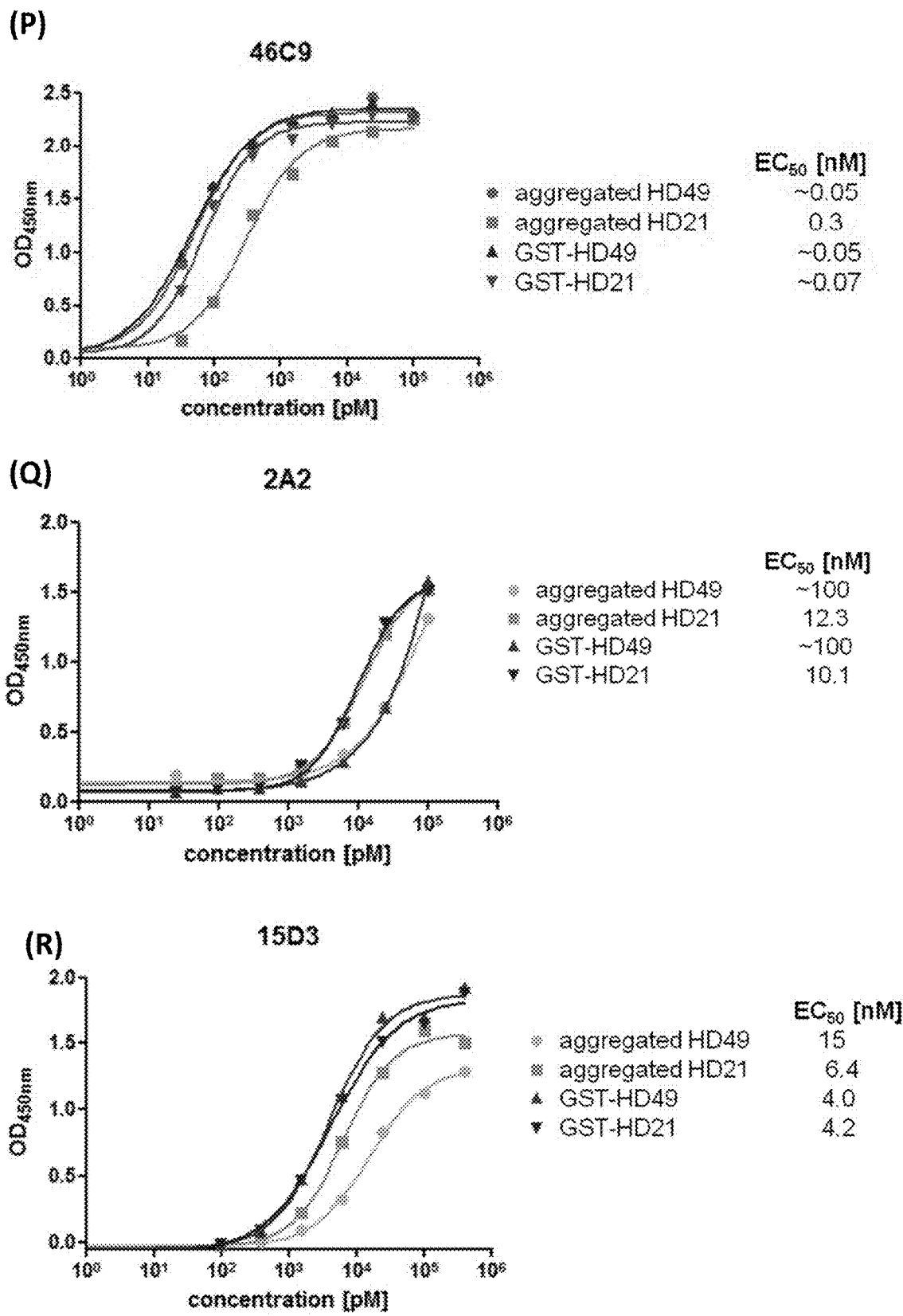

FIG. 19: $EC_{50}$ determinations of human-derived HTT antibodies for aggregated HD49 (●), aggregated HD21 (■), soluble GST-HD49 (▲) and GST-HD21 (▼) Htt Exon 1 proteins using direct ELISA. (A): antibody NI-302.31F11; (B): antibody NI-302.6N9; (C): antibody NI-302.74C11; (D): antibody NI-302.15C9; (E): antibody NI-302.39C12; (F): antibody NI-302.11A4; (G): antibody NI-302.22H9; (H): antibody NI-302.44D7; (I): antibody NI-302.37C12; (J): antibody NI-302.55D8; (K): antibody NI-302.7A8; (L): antibody NI-302.78H12; (M): antibody NI-302.71F6; (N): antibody NI-302.11H6; (O): antibody NI-302.3D8; (P): antibody NI-302.46C9; (Q): antibody NI-302.2A2; (R): antibody NI-302.15D3. Some antibodies (e.g. NI-302.37C12 (I), NI-302.55D8 (J), NI-302.11A4 (F) or NI-302.22H9 (G)) seem to have preferred binding to uncut GST-HTT protein suggesting that these antibodies preferentially recognize uncut soluble GST-HD constructs whereas some antibodies (e.g. NI-302.74C11 (C) or NI-302.71F6 (M)) showed high affinity binding with similar EC-values to all HTT preparation suggesting that they bind to an epitope that is similar exposed in aggregated and uncut HTT exon 1 constructs in the ELISA assay.

FIG. 20: Characterization of binding affinity by direct ELISA. Binding affinity to the different HTT proteins of human-derived HTT-specific antibodies FIG. 21: Characterization of antibody NI-302.44D7, NI-302.37C12, NI-302.15F9 and NI-302.71F6 on in vitro HD21, HD35 and HD49 time-resolved in vitro aggregation reactions by dot-blot (left) and filter retardation assay (right) with preferential binding in particular NI-302.15F9 and NI-302.71F6 to later (aggregated) reactions of HD35 and HD49 in the dot-blot assays and SDS stable aggregates of HD35 and HD49 in the filter retardation assay.

Figure 22:
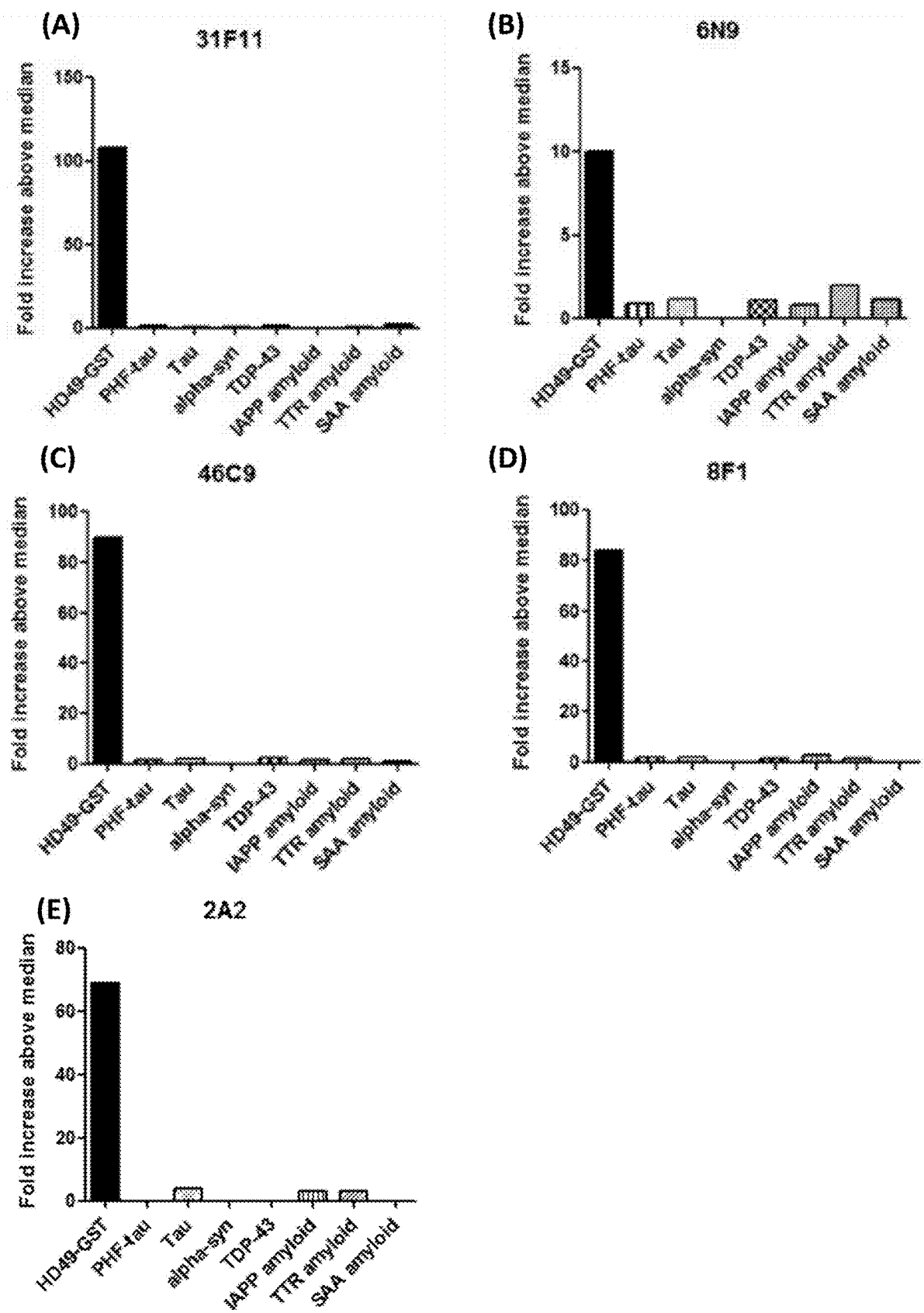
Figure 22:
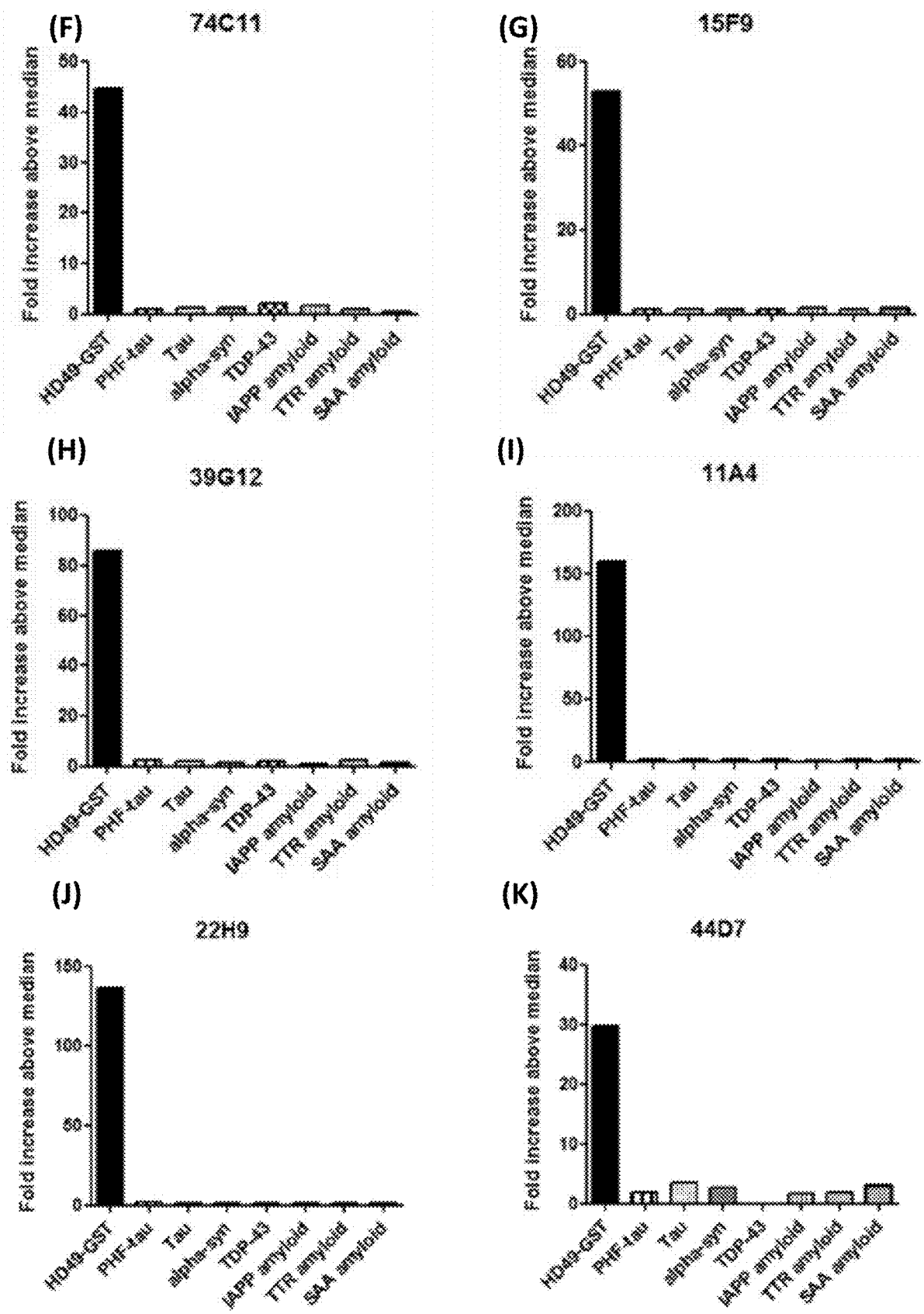
Figure 22:
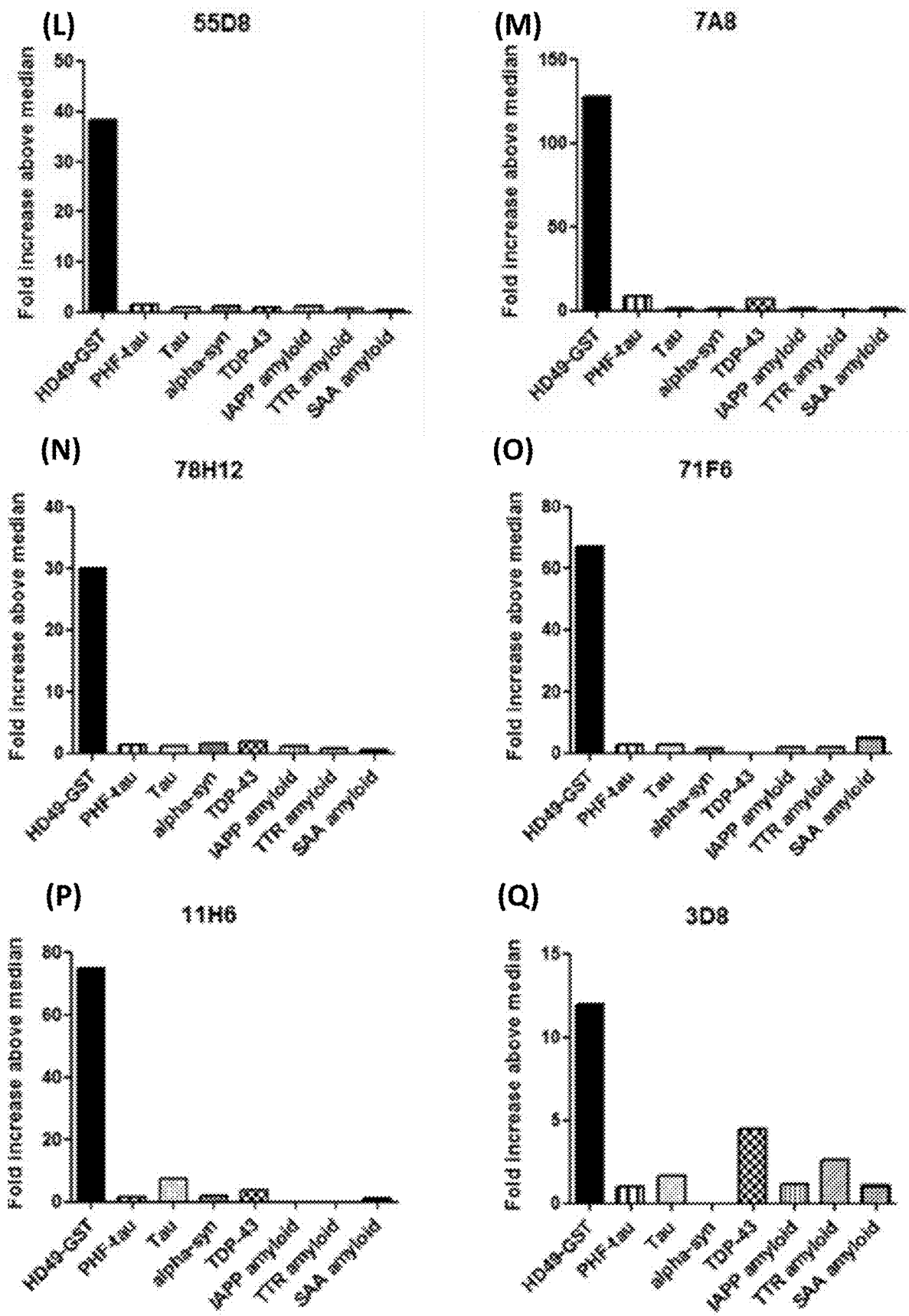
Figure 23:
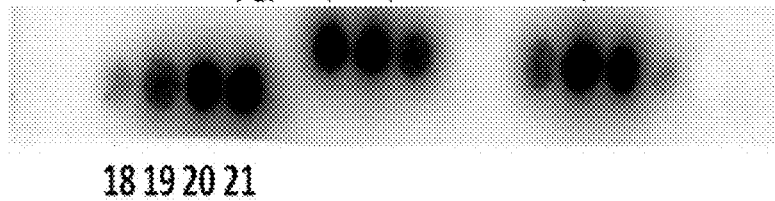

FIG. 22: Target specificity analysis by direct ELISA. NI-302 antibodies (A) NI-302.31F11, (B) NI-302.6N9, (C) NI-302.46C9, (D) NI-302.8F1, (E) NI-302.2A2, (F) NI-302.74C11, (G) NI-302.15F9, (H) NI-302.39G12, (I) NI-302.11A4, (J) NI-302.22H9, (K) NI-302.44D7, (L) NI-302.55D8, (M) NI-302.7A8, (N) NI-302.78H12, (O) NI-302.71F6, (P) NI-302.11H6, and (Q) NI-302.3D8 do not bind unrelated aggregating protein targets as shown in the binding specificity analysis by direct ELISA FIG. 23: Determination of NI-302 antibody binding epitope by scan of overlapping peptides. At the top: pepscan image after NI-302 antibody hybridization. Below: graphical overviews of peptides sequences and NI-302 antibody binding score to the single peptides are shown. Overlapping amino acids between peptides (putative binding epitope) being recognized by the NI-302 antibody are highlighted in gray in the consensus sequences. The HRP-conjugated donkey anti-human IgG Fcγ detection antibody alone does not bind any linear huntingtin peptide. (A) NI-302.31F11 1 µg/ml on a 21 spot membrane, (B) NI-302.74C11 1 µg/ml on a 16 spot membrane, (C) NI-302.15F9 1 µg/ml on a 16 spot membrane, (D) NI-302.39G12 1 µg/ml on a 16 spot membrane, (E) NI-302.11A4 1 µg/ml on a 16 spot membrane, (F) NI-302.22H9 1 µg/ml on a 16 spot membrane, (G) NI-302.44D7 1 µg/ml on a 16 spot membrane, (H) NI-302.37C12 1 µg/ml on a 16 spot membrane, (I) NI-302.55D8 1 µg/ml on a 16 spot membrane, (J) NI-302.7A8 1 µg/ml on a 21 spot membrane, (K) NI-302.78H12 1 µg/ml on a 16 spot membrane, (L) NI-302.71F6 1 µg/ml on a 16 spot membrane, (M) NI-302.11H6 1 µg/ml on a 21 spot membrane, (N) NI-302.18A11 µg/ml on a 21 spot membrane, (O) NI-302.3D8 1 µg/ml on a 21 spot membrane, (P) NI-302.46C9 1 µg/ml on a 21 spot membrane and (Q) NI-302.52C9 1 µg/ml on a 21 spot membrane, (R) NI-302.2A2 1 µg/ml on a 21 spot membrane, (S) NI-302.15E8 1 µg/ml on a 21 spot membrane and (T) NI-302.15D3 1 µg/ml on a 21 spot membrane.

Figure 24:
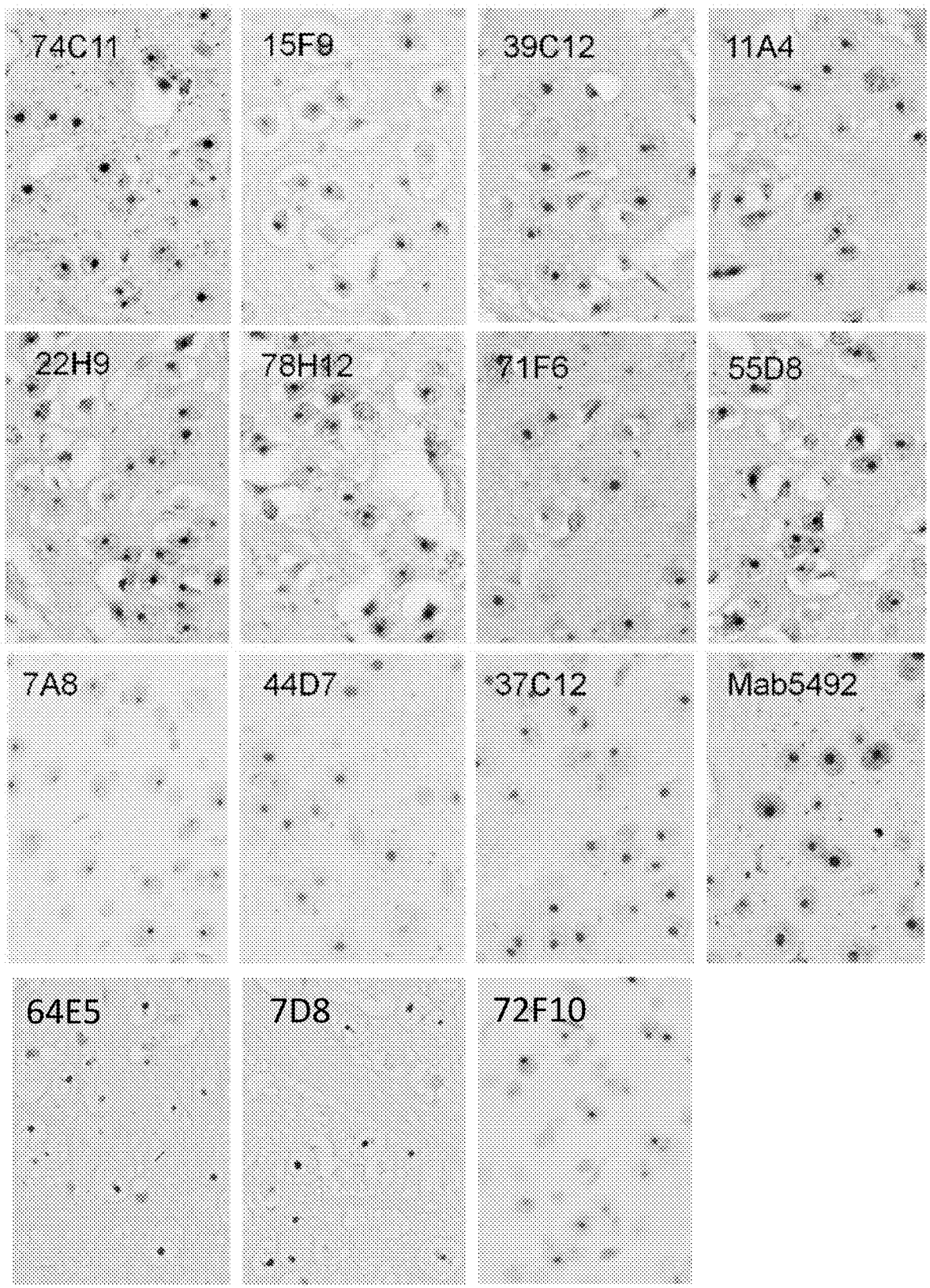

FIG. 24: Immunohistochemical analysis of NI-302 antibodies reveals prominent staining of neuronal intranuclear inclusions in striatal neurons of late disease stage Tg(HDexon1)62Gpb/1J transgenic animals at 5 nM (74C11, 39C12, 11A4, 22H9, 78H12, 37C12, 7D8, 72F10), or 50 nM concentrations (15F9, 71F6, 55D8, 44D7, 7A8, 64E5). Mab5492 is a commercially available N-terminal HTT antibody.

Figure 25:
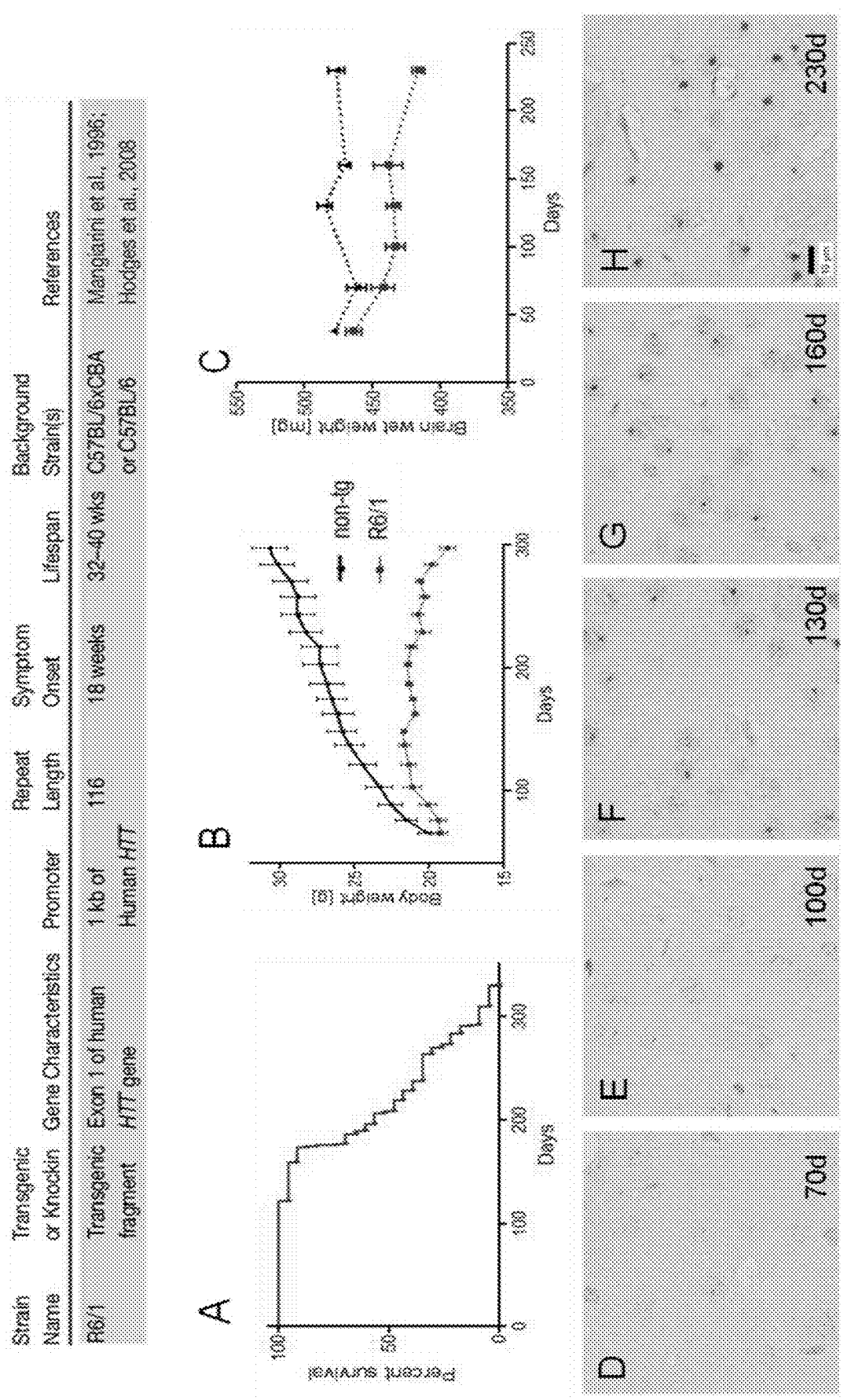

FIG. 25: Basic characterization of R6/1 transgenic mouse model Tg(HDexon1)61Gpb/J. (A) Survival curve, (B) body weight curve and (C) total brain wet weight during the disease progression of this animal model. (D-H) Characterization of appearance of neuronal intranuclear inclusions with disease progression in the striatum by staining with NI-302.33C11 HTT antibody.

Figure 26:
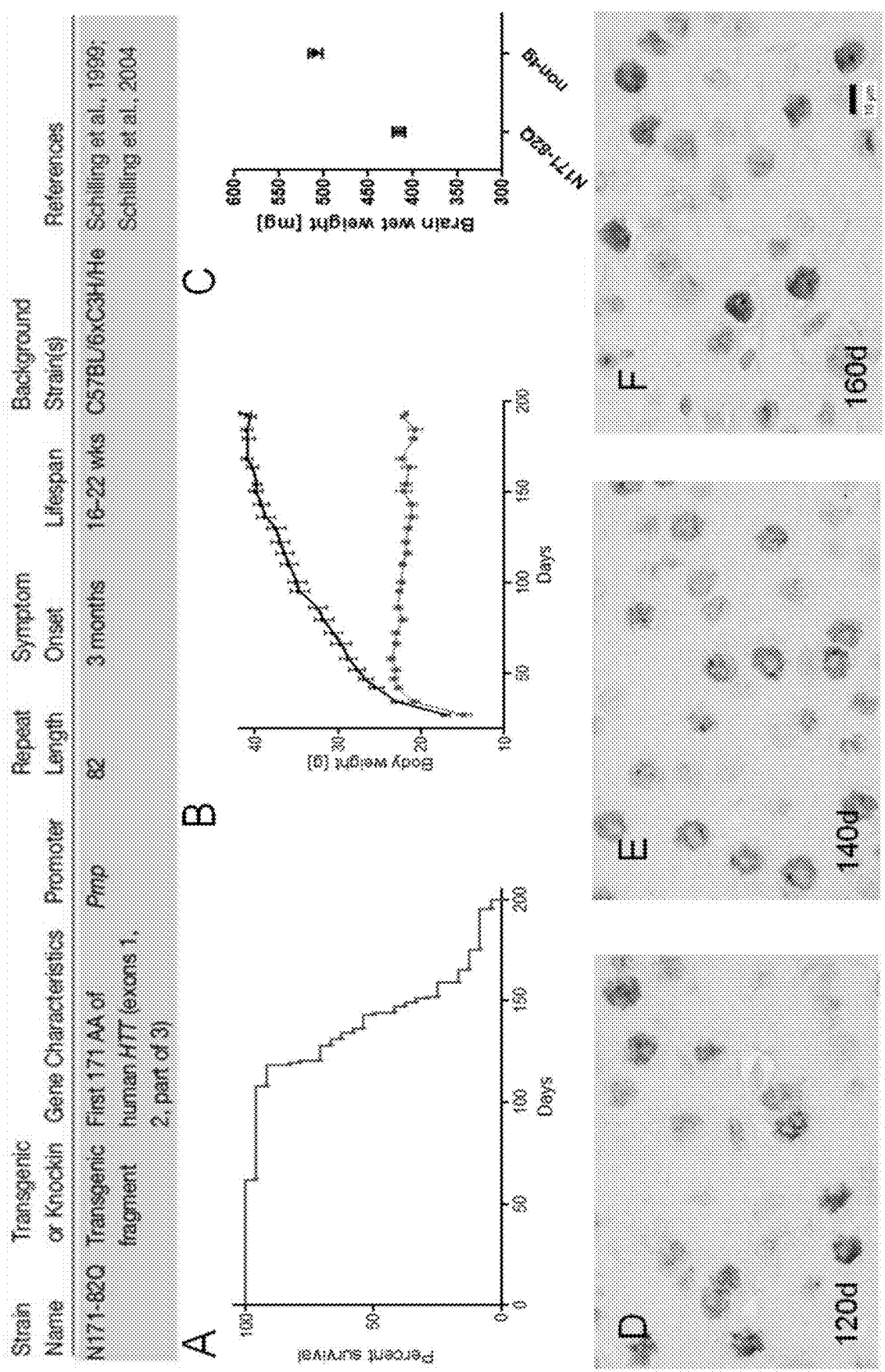

FIG. 26: Basic characterization of B6C3-Tg(HD82G1n) 81Dbo/J (N171-82Q) transgenic mouse model. (A) Survival curve, (B) body weight curve during the disease progression and (C) total brain wet weight at end stage of this animal model. (D-F) Characterization of appearance of neuronal intranuclear inclusions with disease progression in the striatum by staining with Mab5492 HTT antibody.

Figure 27:
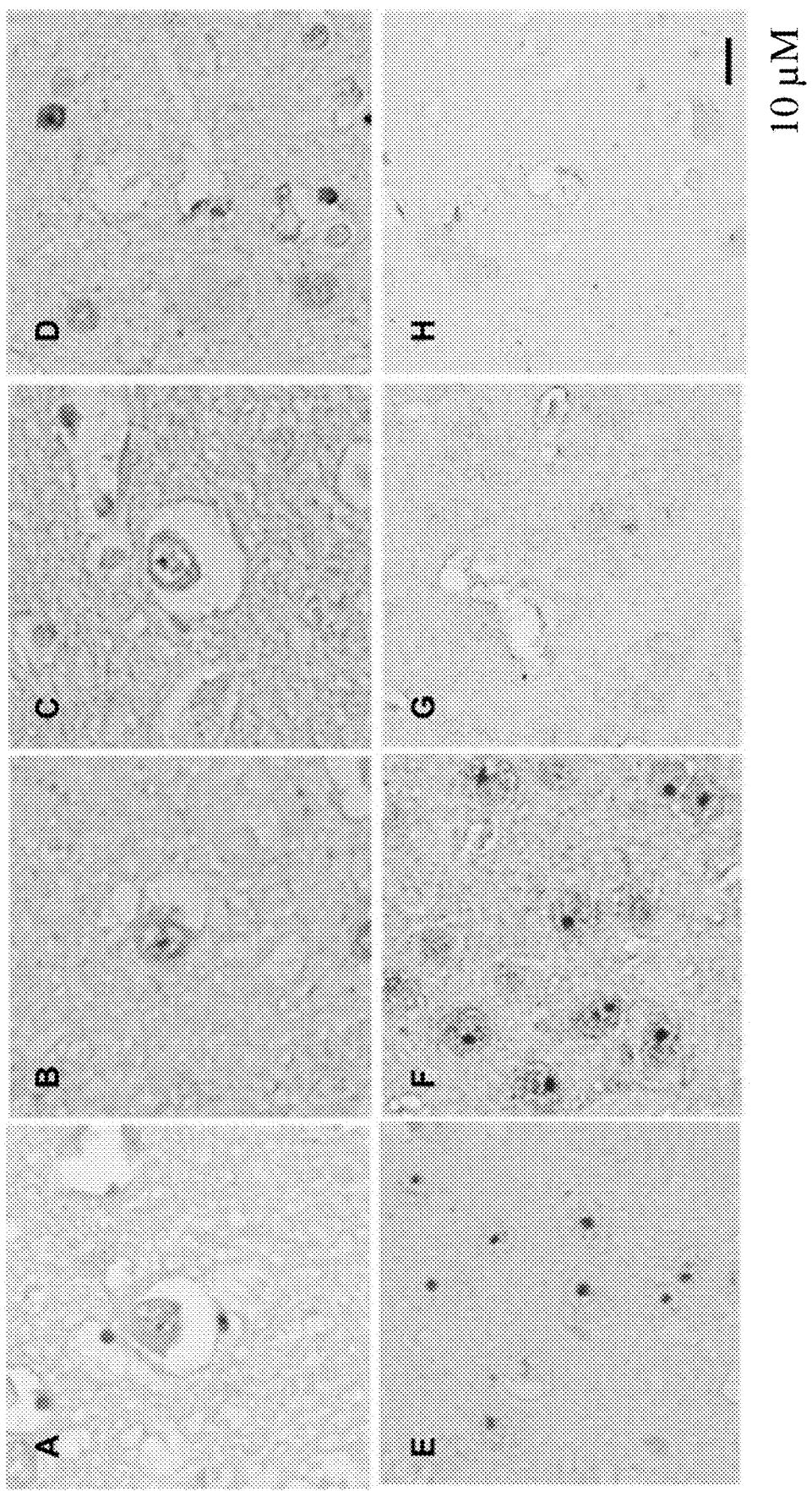

FIG. 27: Immunohistochemical analysis with 50 nM of NI-302.33C11(polyP-epitope) shows staining of neuronal intranuclear inclusions in cortical neurons of four different Huntington Disease patients (A-D) and in striatal neurons of 270 day old, late disease stage B6.Cg-Tg(HDexon1)61Gpb/ J) transgenic animals at 1 (E) and 5 nM (F) concentration. No staining is detected in non-transgenic littermates (G), if primary antibody is omitted during the staining (H) or if tissue of non-Huntington Disease controls is stained with 50 nM of NI-302.33C11.

Figure 28:
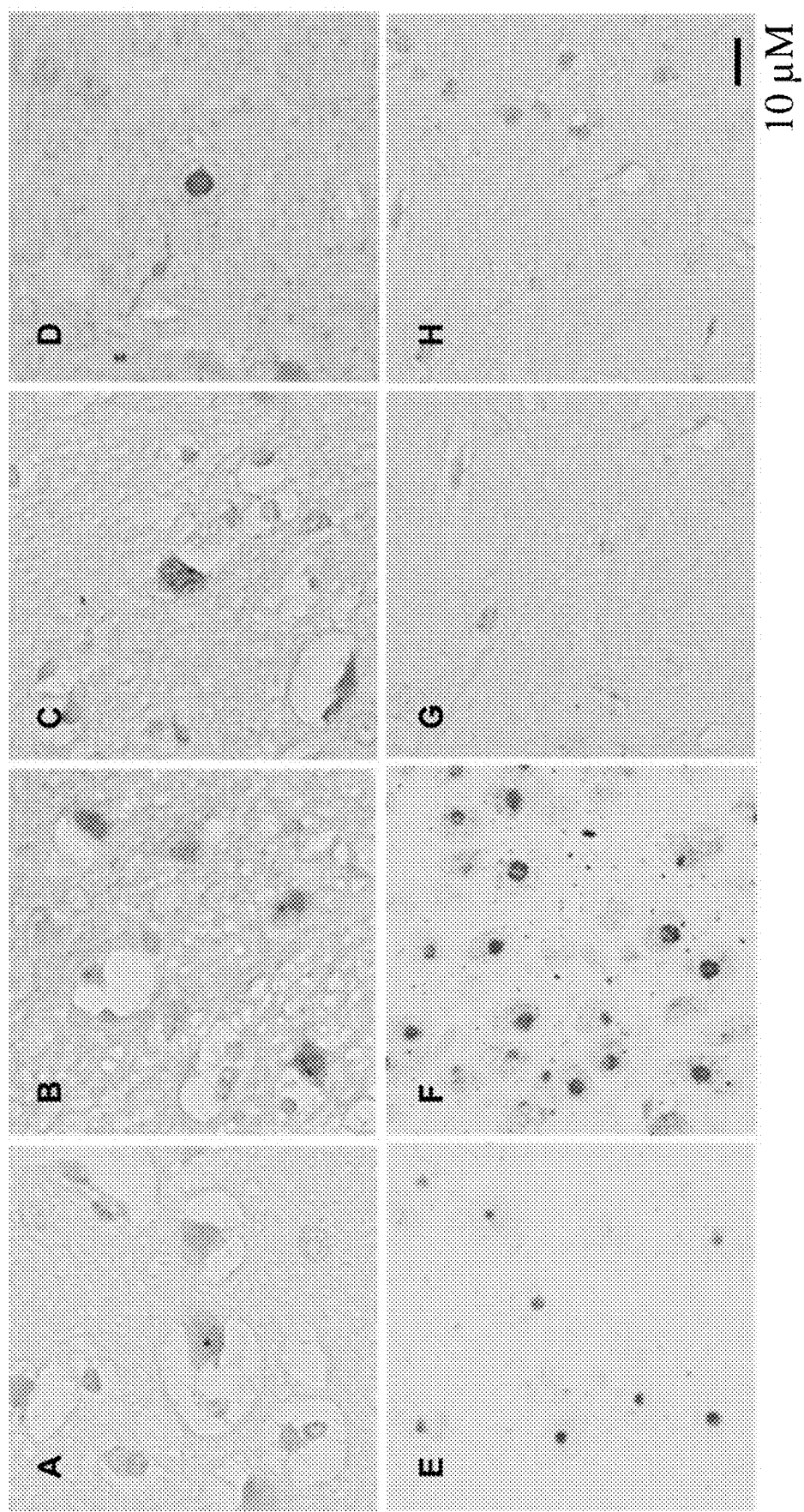

FIG. 28: Immunohistochemical analysis with 50 nM of NI-302.63F3 (P-rich domain epitope) shows staining of neuronal intranuclear inclusions (A-C) and staining of some neurites (D) of cortical neurons of four different Huntington Disease patients (A-D) and in striatal neurons of 270 day old, late disease stage B6.Cg-Tg(HDexon1)61Gpb/J) transgenic animals at 1 (E) and 50 nM (F) concentration. No staining is detected in non-transgenic littermates (G), if primary antibody is omitted during the staining (H) or if tissue of non-Huntington Disease controls is stained with 50 nM of NI-302.63F3.

Figure 29:
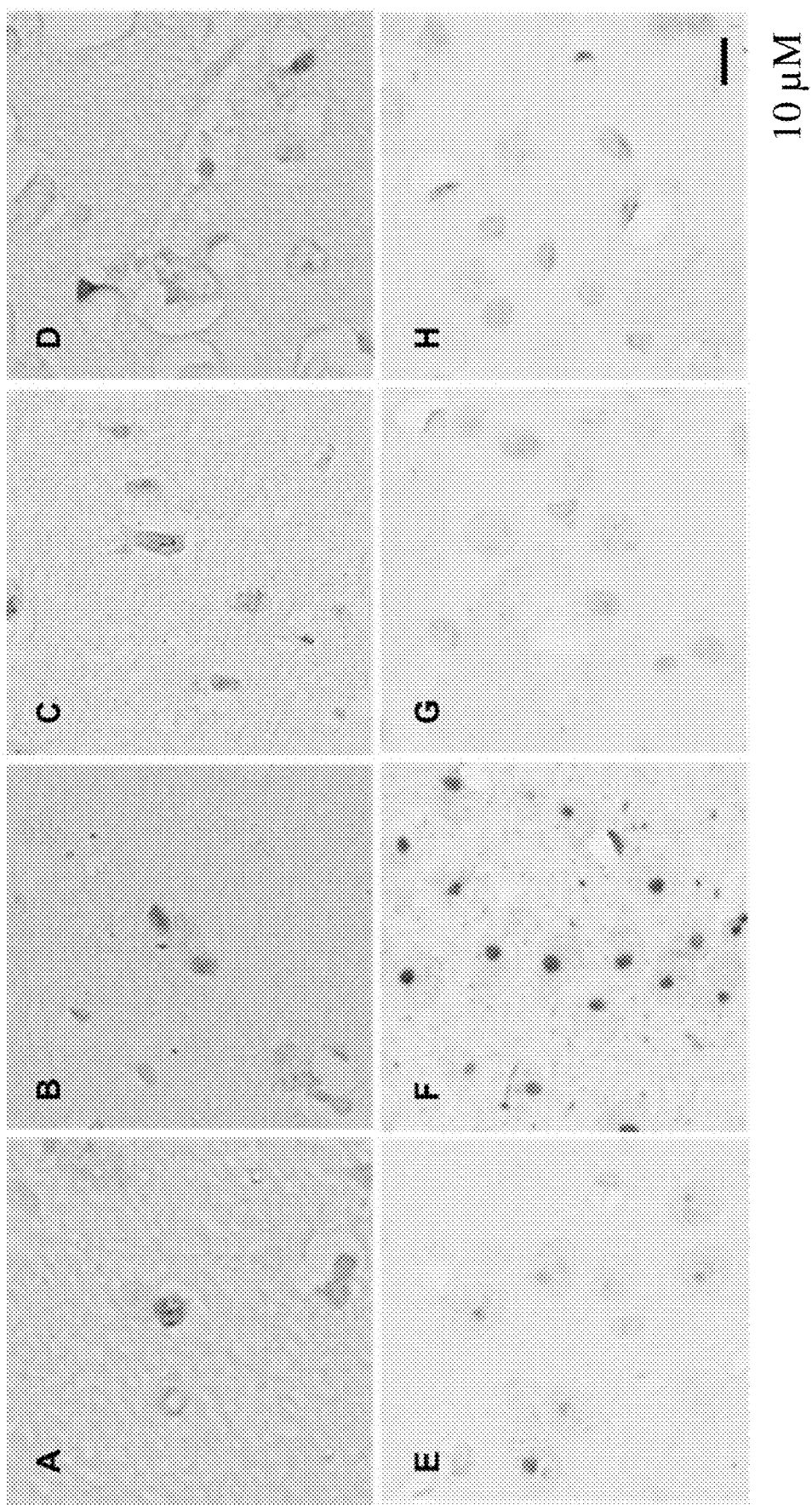

FIG. 29: Immunohistochemical analysis with 100 nM of NI-302.35C1 (end Exon 1 epitope) shows staining of neuronal intranuclear inclusions (A-C) and staining of some neurites (D) of cortical neurons of four different Huntington Disease patients (A-D) and in striatal neurons of 270 day old, late disease stage B6.Cg-Tg(HDexon1)61Gpb/J) transgenic animals at 1 (E) and 50 nM (F) concentration. No staining is detected in non-transgenic littermates (G), if primary antibody is omitted during the staining (H) or if tissue of non-Huntington Disease controls is stained with 100 nM of NI-302.35C1.

Figure 30:
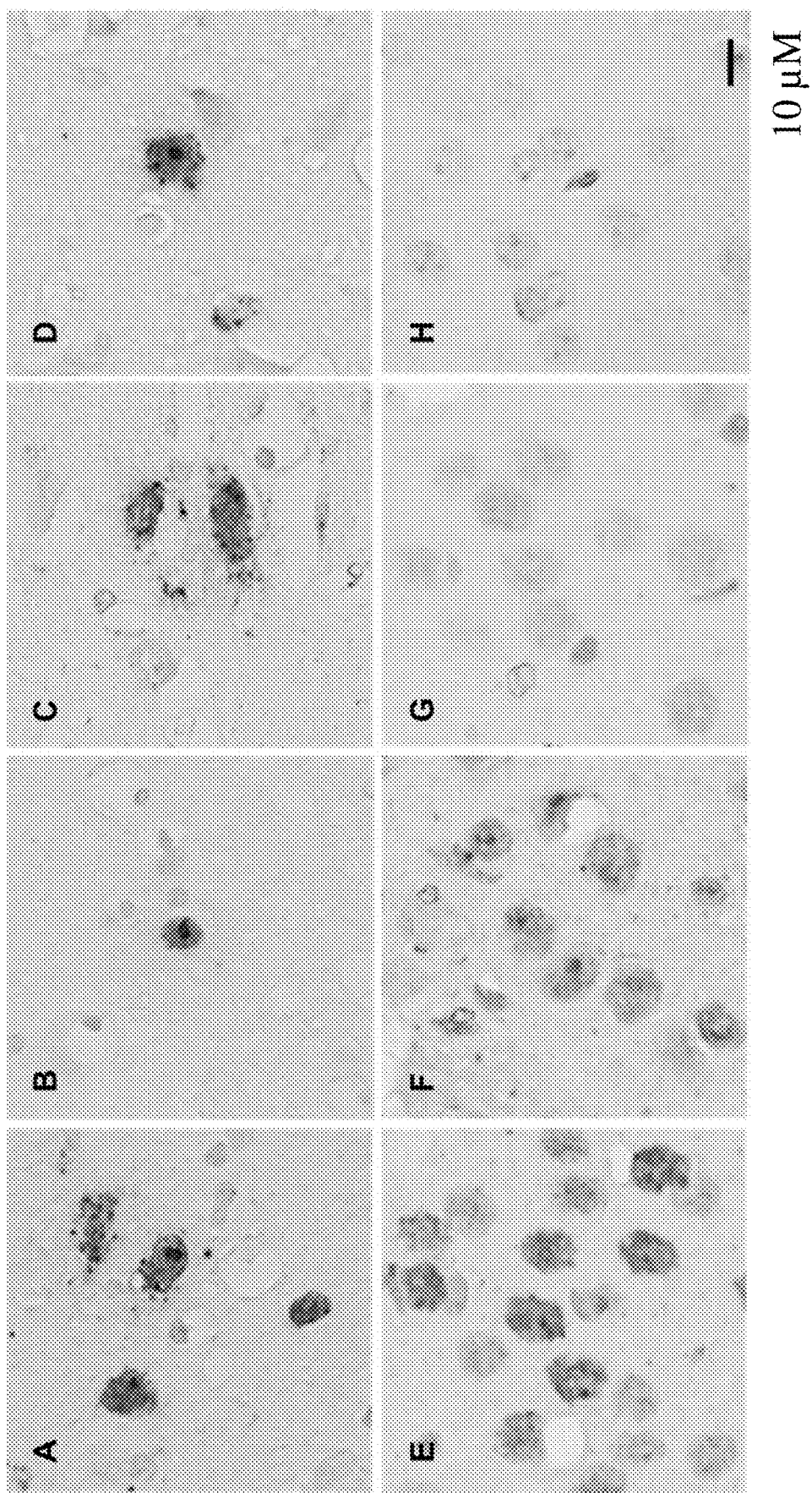

FIG. 30: Immunohistochemical analysis with commercially available anti-polyQ antibody Mab1574 (1:2000, Chemicon) shows staining of neuronal intranuclear and cytoplasmic inclusions and staining of some neurites (A, D) of cortical neurons of four different Huntington Disease patients (A-D) and in striatal neurons of presymptomatic, 150 day old (E) and 270 day old (F), late disease stage B6.Cg-Tg(HDexon1)61Gpb/J) transgenic animals. No staining is detected in non-transgenic littermates (G), if primary antibody is omitted during the staining (H) or if tissue of non-Huntington Disease controls is stained with Mab 1574.

Figure 31:
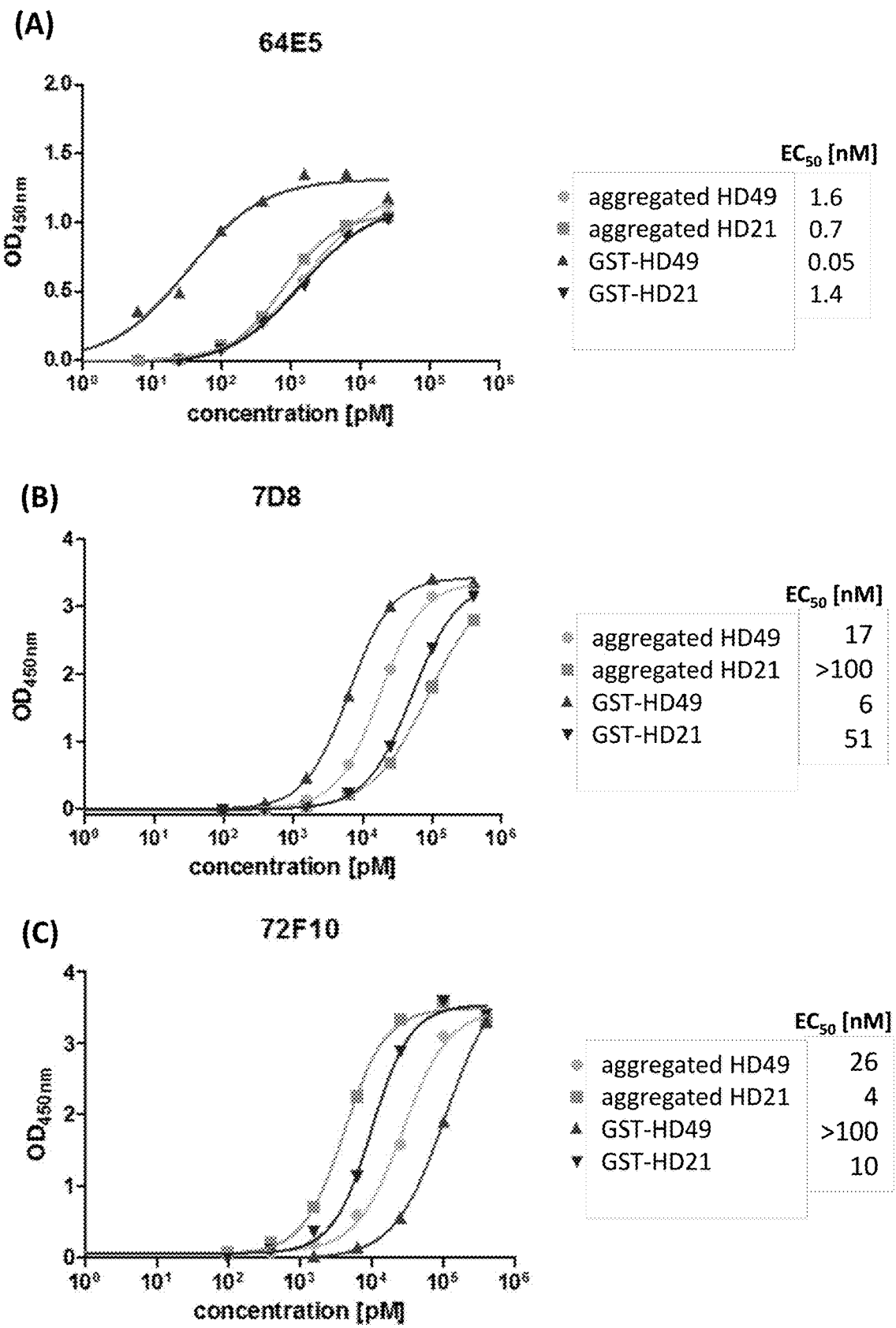

FIG. 31: $EC_{50}$ determinations of human-derived HTT antibodies for aggregated HD49 (●), aggregated HD21 (■), soluble GST-HD49 (▲) and GST-HD21 (▼) Htt Exon 1 proteins using direct ELISA. Some antibodies (e.g. NI-302.64E5 (A) or NI-302.7D8 (B)) seem to have preferred binding to uncut GST-HD49 protein suggesting that these antibodies preferentially recognize uncut soluble GST-HD constructs containing longer polyQ repeats. Antibody NI-302.72F10 (C) shows preference to HD21 constructs and some antibodies (e.g. NI-302.4A6 (D), NI-302.12H2 (E) or NI-302.8M1 (F)) showed high affinity binding with similar EC-values to all HTT preparation suggesting that they bind to an epitope that is similar exposed in aggregated and uncut HTT exon 1 constructs in the ELISA assay.

FIG. 32: Characterization of antibody (A) NI-302.64E5, (B) NI-302.7D8, (C) NI-302.72F10, (D) NI-302.4A6, (E) NI-30212H2, (F) NI-302.8M1 and (G) NI-302.33C11 (as control) on in vitro HD21, HD35 and HD49 time-resolved in vitro aggregation reactions by dot-blot (left) and filter retardation assay (right) with preferential binding in particular of NI-302.64E5 and NI-302.72F10 to later (aggregated) reactions of HD35 and/or HD49 in the dot-blot assays and SDS stable aggregates of HD35 and HD49 in the filter retardation assay.

Figure 33:
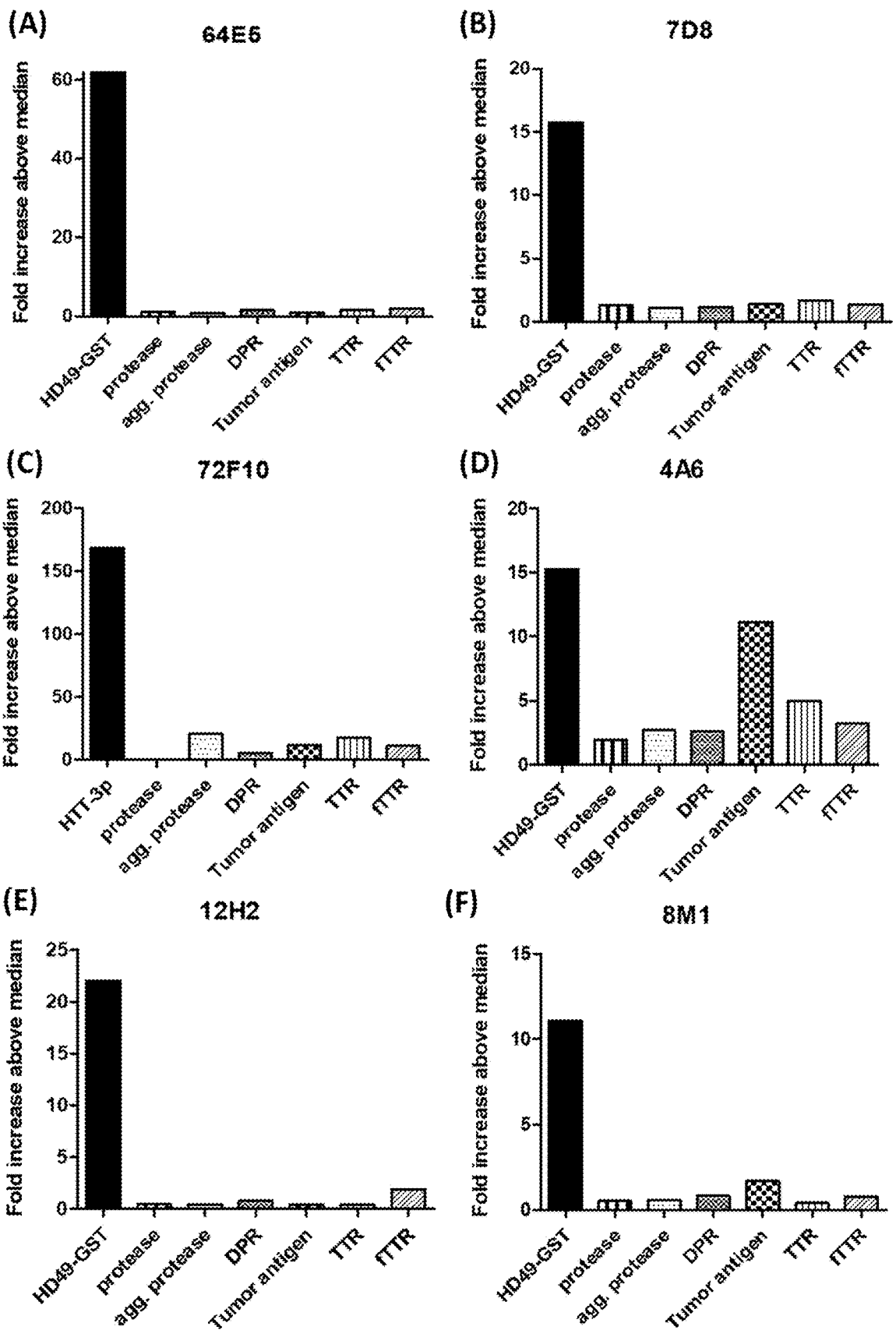

FIG. 33: Target specificity analysis by direct ELISA. NI-302 antibodies (A) NI-302.64E5, (B) NI-302.7D8, (C) NI-302.72F10, (E) NI-302.12H2 and (F) NI-302.8M1 do not bind unrelated aggregating protein targets as shown in the binding specificity analysis by direct ELISA, except (D) NI-302.4A6 which shows some binding to p53.

Figure 34:
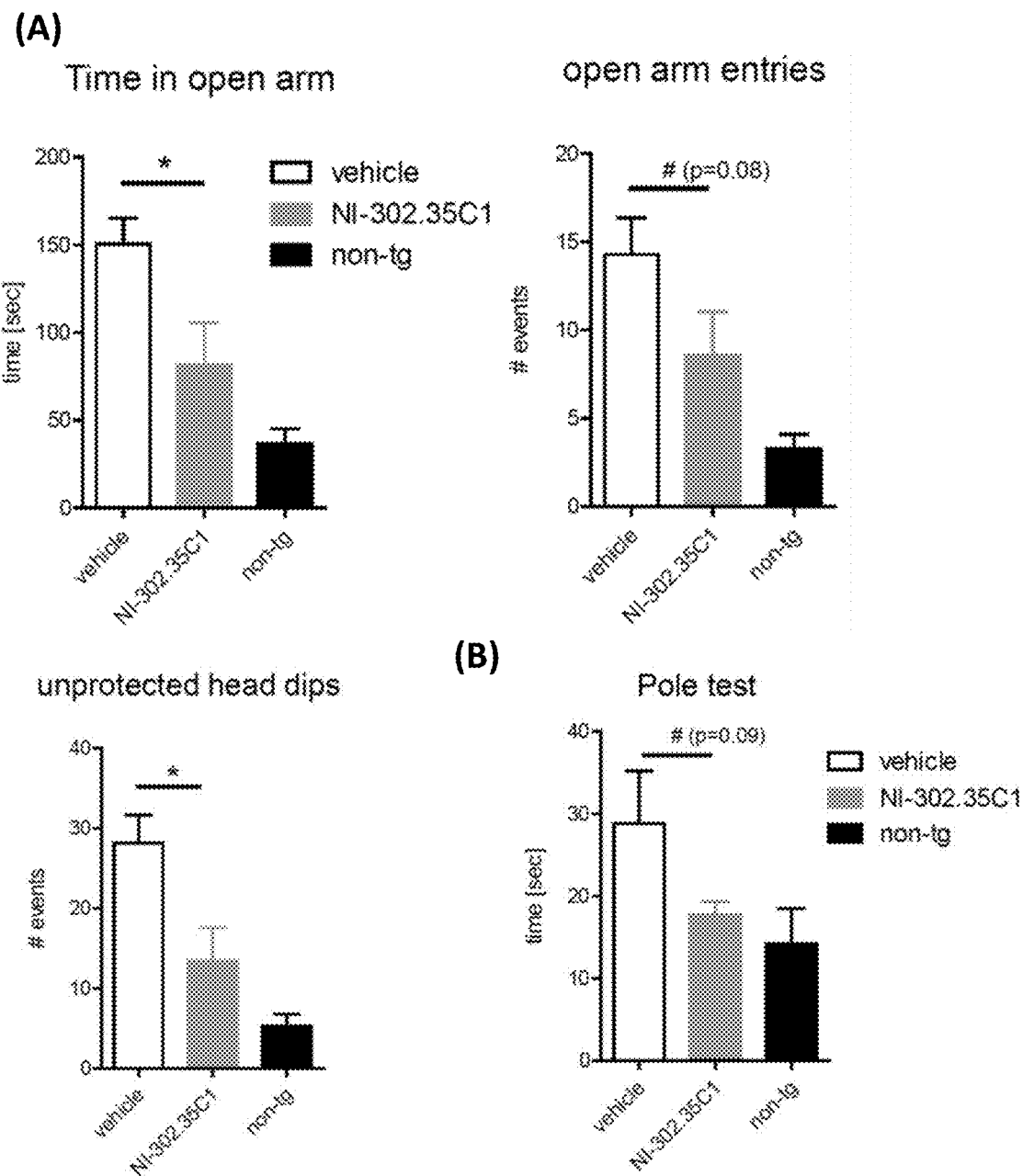

FIG. 34: Study of C-terminal domain-binding antibody NI 302.35C1 on behavioral performance during task-specific training and sensorimotor ability in a mice model of HD. (A) The plus-maze analysis was used to investigate the level of anxiety in the R6/1 mice. At 6 months of age, NI-302.35C1 treated R6/1 animals spend less time in the open arms, entered the open arms less frequently and did less unprotected head dips on the open arm compared to vehicle treated R6/1 animals. Hence the NI-302.35C1 treated R6/1 mice displayed a more anxious phenotype, comparable to the non-transgenic littermates. (B) NI-302.35C1 treated R6/1 animal showed an improved performance in the pole test compared to vehicle treated R6/1 animals reaching levels similar to non-transgenic animals.

FIG. 35 Determination of NI-302 antibody binding epitope by scan of overlapping peptides. At the top: pepscan image after NI-302 antibody hybridization. Below: graphical overviews of peptides sequences are shown. Overlapping amino acids between peptides (putative binding epitope) being recognized by the NI-302 antibody are shown in the consensus sequence below. The HRP-conjugated donkey anti-human IgG Fcγ detection antibody alone does not bind any linear huntingtin peptide. (A) NI-302.64E5, (B) NI-302.7D8, (C) NI-302.72F10, (D) NI-302.4A6, (E) NI-302.12H2, (F) NI-302.8M1 all antibodies at 1 µg/ml on the 21 spot membrane.

Figure 36:
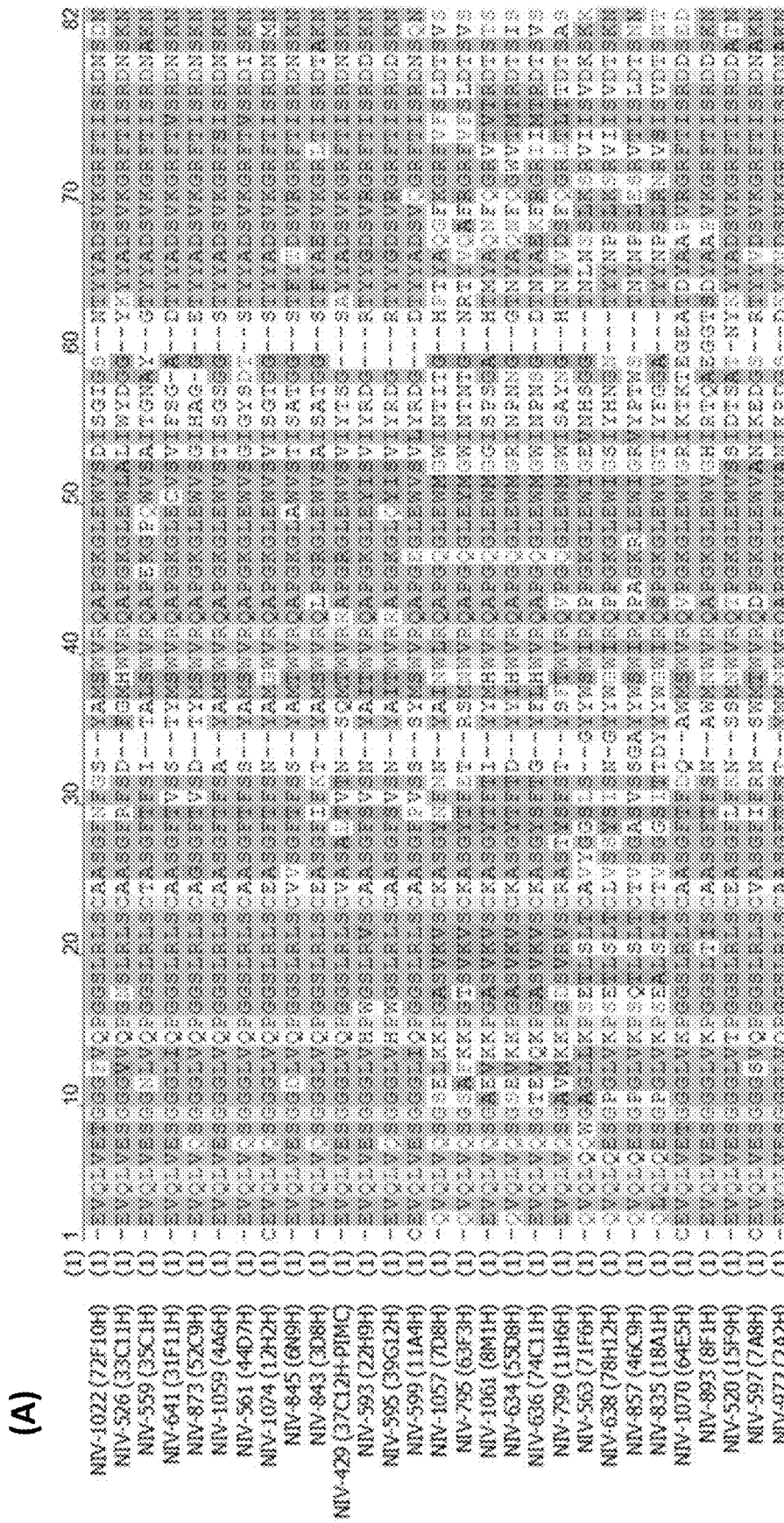
Figure 36:
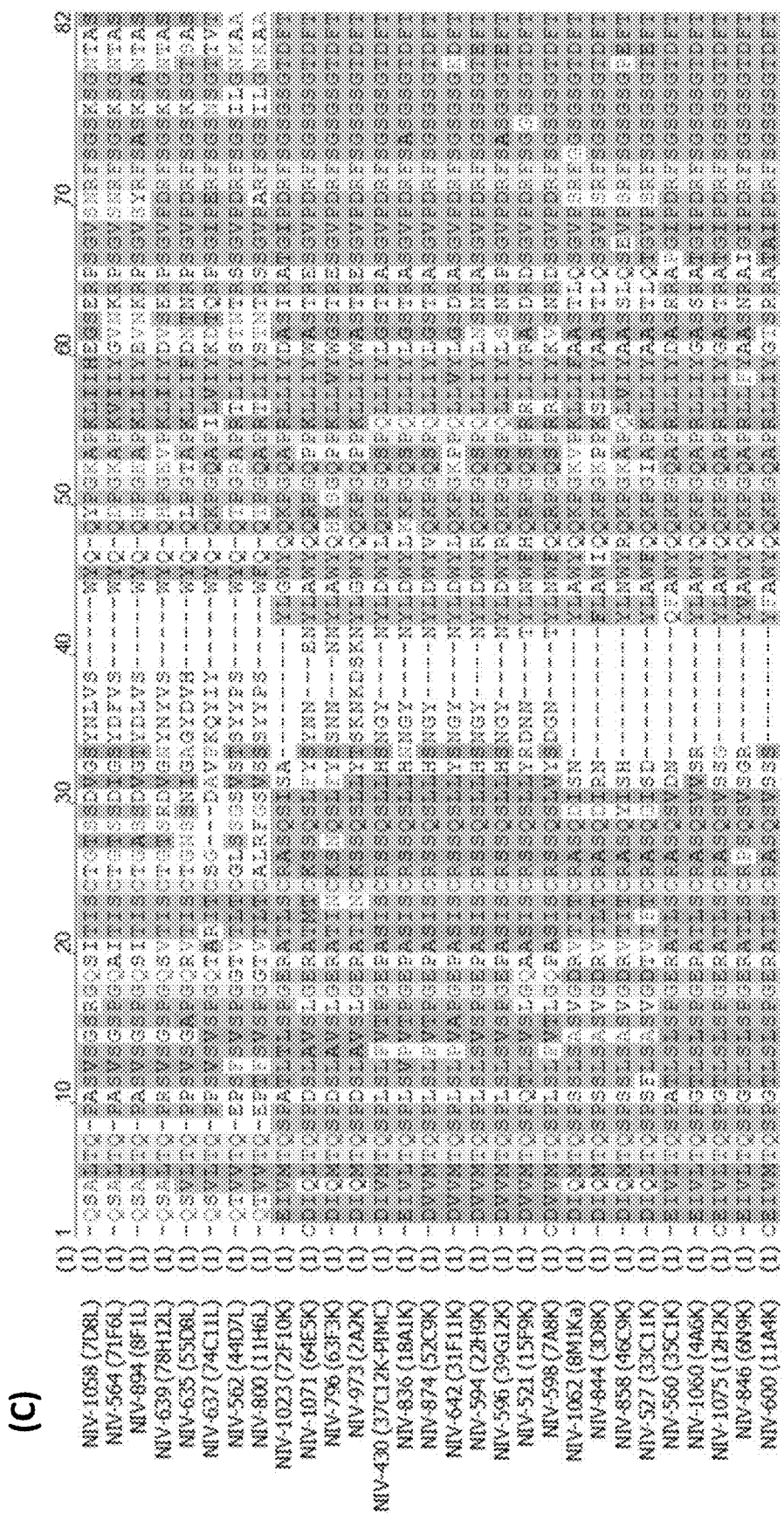

FIG. 36 Amino acid sequence alignment of the CDRs in the $V_H$ and $V_L$ or $V_K$ chains of NI-302 antibodies. Each sequence was checked in terms of conserved amino acids, segments, or other motifs revealing an accumulation of tyrosines in the CDRs.

DETAILED DESCRIPTION OF THE INVENTION

The present invention generally relates to immunotherapy and non-invasive methods for the detection of diseases and/or disorders as well as conditions associated with the presence of pathologic, often mutant and/or aggregated forms of huntingtin (HTT). More specifically, the present invention relates to recombinant human-derived monoclonal antibodies and HTT-binding fragments, synthetic and biotechnological derivatives thereof, which have been generated based on sequence information obtained from selected human donor populations and are capable of binding to such HTT isoforms and antigens thereof. The recombinant human-derived monoclonal antibody of the present invention is advantageously characterized by specifically binding to mutated and/or aggregated HTT species and/or fragments thereof allowing a targeting for treatment and/or diagnosis of pathological altered HTT species. Due to their human derivation, the resulting recombinant antibodies of the present invention can be reasonably expected to be efficacious and safe as therapeutic agent, and highly specific as a diagnostic reagent for the detection of pathological HTT without giving false positives.

In addition, the present invention relates to the human monoclonal antibody and any derivatives thereof described herein for use in the treatment of patients either alone or with other agents utilized for symptoms associated with HTT amyloidosis, wherein the antibody of the present invention and any of its derivatives is designed to be administered concomitantly with the agent suppressing side effects or sequentially before or after administration of the same. In this context, the anti-HTT antibody and HTT-binding fragment of the present invention are preferably substantially non-immunogenic in human. In one embodiment of the present invention, pharmaceutical compositions are provided comprising both a human monoclonal antibody of the present invention or any derivatives thereof and one or more drug utilized for symptoms associated with HTT amyloidosis.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

Huntingtin (HTT), also known as IT15 is a disease gene linked to Huntington's disease (HD), a neurodegenerative disorder characterized by loss of striatal neurons. It is thought that HD is caused by an expanded, unstable trinucleotide repeat in the HTT gene, which translates as a polyglutamine repeat in the protein product. A fairly broad range in the number of trinucleotide repeats has been identified in normal controls, and repeat numbers in excess of 35-40 have been described as pathological. The HTT locus (NG_009378.1; 4830 to 174286; NCBI RefSeqGene) is large, spanning 180 kb and consisting of 67 exons.

In this context, it has been demonstrated that an N-terminal fragment of mutant HTT, i.e. exon 1 protein of the HTT gene, with an expanded CAG repeat represents the "toxic" species of HTT which is sufficient to cause aggregation and a progressive neurological phenotype in transgenic mice; see, e.g., Mangiarini et al., Cell 87 (1996), 493-506 and Ross et al., Lancet Neurol. 10 (2011), 83-98, DiFiglia et al, Science 277 (1997), 1990-1993, Gutekunst et al., J Neurosci 19(7) (1999), 2522-2534.

Unless stated otherwise, by "specifically recognizing HTT", "antibody specific to/for HTT" and "anti-HTT antibody" antibodies are meant which specifically, generally, and collectively bind to HTT, wherein HTT refer to different forms the HTT including but not limited to the native form of HTT as well as other forms of HTT, e.g. pathologically altered HTT, such as mutated, misfolded and/or aggregated HTT. Provided herein are human-derived antibodies selective for full-length and/or fragments and/or mutated, misfolded and/or aggregated forms of HTT.

If not specifically indicated otherwise, the term "HTT", is used interchangeably to specifically refer to the different forms of huntingtin (HTT). The term "HTT" is also used to generally identify other conformers of HTT, for example, pathologically altered forms of HTT such as misfolded and/or aggregated forms of HTT. Furthermore, unless specifically indicated otherwise the term HTT in particular means HTT exon1 and the soluble HTT refers to the corresponding GST-fusion proteins. The term "HTT" is also used to refer collectively to all types and forms of HTT, such as mutated HTT. Added letters in front of the terms, e.g. HTT, are used to indicate the organism the particular ortholog is originating from, e.g. hHTT for human HTT or mHTT for murine origin.

The anti-HTT antibodies disclosed herein specifically bind HTT and epitopes thereof and to various conformations of HTT and epitopes thereof. For example, disclosed herein are antibodies that specifically bind pathologically altered HTT species or fragments thereof, such as mutated, misfolded, and/or aggregated forms of HTT or fragments thereof. The term (pathologically) mutated, misfolded, and/or aggregated/aggregates of HTT is used interchangeable to specifically refer to the aforementioned forms. The term (pathological) "aggregated forms" or "aggregates" as used herein describes the products of an accumulation or cluster formation due to HTT erroneous/pathological interaction with one another. These aggregates, accumulations or cluster forms may be, substantially consist or consist of both HTT and/or HTT fragments and of non-fibrillar oligomers and/or fibrillar oligomers and fibrils thereof. As used herein, reference to an antibody that "specifically binds", "selectively binds", or "preferentially binds" HTT refers to an antibody that does not bind other unrelated proteins. In one example, a HTT antibody disclosed herein can bind HTT or an epitope thereof and show no binding above about 2 times background for other proteins. In a preferred embodiment, the antibody of the present invention does not substantially recognize unrelated amyloid-forming proteins selected from the group consisting of paired helical filament (PHF)-tau, TAU, alpha-synuclein, transactive response DNA binding protein 43 (TDP43), islet amyloid polypeptide (TAPP), transthyrethin (TTR), serum amyloid A (SAA); see Examples 8, 13, 18 and 31. An antibody that "specifically binds" or "selectively binds" a HTT conformer refers to an antibody that does not bind all conformations of HTT, i.e., does not bind at least one other HTT conformer. For example, disclosed herein are antibodies that can preferentially bind to mutated and/or aggregated forms of HTT both in vitro and in tissues obtained from patients with diseases and/or disorders associated with HTT amyloidosis or with a risk to develop diseases and/or disorders associated with HTT amyloidosis. In another embodiment of the present invention the antibodies of the present invention specifically targets different regions of the HTT exon 1; see, e.g., FIGS. 5, 9, 12, 14, 15. Since the anti-HTT antibodies of the present invention have been isolated from human subjects, they may also be called "human auto-antibodies" or "human-derived antibodies" in order to emphasize that those antibodies were indeed expressed initially by the subjects and are not synthetic constructs generated, for example, by means of human immunoglobulin expressing phage libraries or xenogeneic antibodies generated in a transgenic animal expressing part of the human immunoglobulin repertoire which hitherto represented one common method for trying to provide human-like antibodies. On the other hand, the human-derived antibody of the present invention may be denoted synthetic, recombinant, and/or biotechnological in order distinguish it from human serum antibodies per se, which may be purified via protein A or affinity column.

However, a particular advantage of the therapeutic approach of the present invention lies in the fact that the antibodies of the present invention are derived from B cells or B memory cells from healthy human subjects with no signs of a disease showing the occurrence of, or related to misfolded/aggregated HTT and thus are, with a certain probability, capable of preventing a clinically manifest disease related to misfolded/aggregated HTT, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target HTT molecules by means of somatic variation of the variable regions of the antibody. The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-HTT antibodies of the present invention, both its target structure-specific efficiency as therapeutic agent and its decreased probability of side effects significantly increase its clinical probability of success.

In contrast, antibodies derived from cDNA library's or phage displays are artificial molecules such as a humanized antibody which is still of murine origin and thus foreign to the human body. Therefore the clinical utility and efficacy of the therapeutic antibodies can be limited by the production of anti-drug antibodies (ADAs), which can influence the efficacy and pharmacokinetics of the antibodies and sometimes lead to serious side effects, see e.g. Igawa et al., MAbs. 3 (2011), 243-252. In particular, humanized antibodies or antibodies generated with recent human-antibody-generation technologies are in contrast to the human-derived antibodies such as those of the present invention prone to induce an antibody response and these human-like antibodies derived from e.g. phage display such as adalimumab have been reported to induce ADA production, see, e.g., Mansour, Br. J. Ophthalmol 91 (2007), 274-276 and Igawa et al., MAbs. 3 (2011), 243-252. Therefore, human-derived antibodies which are not prone to undesired immune response are more beneficial for the patient than artificial molecules derived from libraries or displays.

The term "peptide" is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

Polypeptides:

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Included as polypeptides of the present invention are fragments, derivatives, analogs or variants of the foregoing polypeptides and any combinations thereof as well. The terms "fragment," "variant," "derivative", and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to HTT, variants, derivatives or analogs of either of them. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

Furthermore, the terms "fragment," "variant," "derivative", and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of HTT specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of Similarity and/or Identity of Molecules:

"Similarity" between two peptides is determined by comparing the amino acid sequence of one peptide to the sequence of a second peptide; see Example 35 as well as FIG. 36. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Be, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution.

The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (blast.ncbi.nlm.nih.gov/Blast.cgi).

The determination of percent identity or similarity is performed with the standard parameters of the BLASTn programs for BLAST polynucleotide searches and BLASTp programs for BLAST protein search, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse ß-glucuronidase.

A "binding molecule" as used in the context of the present invention relates primarily to antibodies, and fragments thereof, but may also refer to other non-antibody molecules that bind to HTT including but not limited to hormones, receptors, ligands, ankyrins, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively. As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to HTT is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides.

This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Unless human-derived monoclonal antibodies or an antigen-binding fragment, synthetic or biotechnological derivative thereof as particularly preferred embodiments of the present are referred to, antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')₂, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are HTT binding fragments which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human-derived monoclonal antibody isolated from a human, wherein the B cell expressing the antibody is isolated from a human and in turn the antibody or preferably the cDNA encoding the variable domain and optionally the cDNA for the cognate constant domain. Optionally, the framework region of the human antibody is aligned and adopted in accordance with the pertinent human germ line variable region sequences in the database; see, e.g., Vbase (vbase.mrc-cpe.cam.ac.uk/) (www.vbase2.org/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural HTT in its relevant conformation in the human body, (ii) having protected the individual or is at least significant for the presence of HTT, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote a HTT binding molecule which is of human origin, i.e. which has been isolated from a human cell such as a B cell or hybridoma thereof or the cDNA of which has been directly cloned from mRNA of a human cell, for example a human memory B cell. A human antibody is still "human", i.e. human-derived even if amino acid substitutions are made in the antibody, e.g., to improve binding characteristics. In this context, contrary to humanized antibodies and otherwise human-like antibodies, see also the discussion infra, the human-derived antibodies of the present invention are characterized by comprising CDRs which have been seen by human body and therefore are substantially devoid of the risk of being immunogenic. Therefore, the antibody of the present invention may still be denoted human-derived if at least one, preferably two and most preferably all three CDRs of one or both the variable light and heavy chain of the antibody are derived from the human antibodies illustrated herein.

In one embodiment the human-derived antibodies of the present invention comprises heterologous regions compared to the natural occurring antibodies, e.g. amino acid substitutions in the framework region, constant region exogenously fused to the variable region, different amino acids at the C- or N-terminal ends and the like.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al. are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man. As used herein, the term "rodentized antibody" or "rodentized immunoglobulin" refers to an antibody comprising one or more CDRs from a human antibody of the present invention; and a human framework region that contains amino acid substitutions and/or deletions and/or insertions that are based on a rodent antibody sequence. When referred to rodents, preferably sequences originating in mice and rats are used, wherein the antibodies comprising such sequences are referred to as "murinized" or "ratinized" respectively. The human immunoglobulin providing the CDRs is called the "parent" or "acceptor" and the rodent antibody providing the framework changes is called the "donor". Constant regions need not be present, but if they are, they are usually substantially identical to the rodent antibody constant regions, i.e. at least about 85% to 90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized light chain variable region and/or a murinized heavy chain variable region. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. The above explanations in respect of "murinized" antibodies apply analogously for "rodentized" antibodies, such as "ratinized antibodies", wherein rat sequences are used instead of the murine.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

As used herein, the term "bispecific" or "bifunctional" antibody molecule is an antibody molecule that has two different epitope/antigen binding sites, and accordingly has binding specificities for two different target epitopes. These two epitopes may be epitopes of the same antigen or of different antigens. In contrast thereto a "bivalent antibody" may have binding sites of identical antigenic specificity. Methods of making a bispecific antibody are known in the art, e.g. chemical conjugation of two different monoclonal antibodies as illustrated in Example 36 or for example, also chemical conjugation of two antibody fragments, for example, of two Fab fragments (Brennan et al., Science 229 (1985), 81-83; Nitta et al., Eur. J. Immunol. 19 (1989), 1437-1441; Glennie et al., J. Immunol. 139 (1987), 2367-2375; Jung et al., Eur. J. Immunol., 21 (1991), 2431-2435). Alternatively, bispecific antibodies are made recombinantly (Gruber et al., J. Immunol. 152 (1994), 5368-5374; Kurucz et al., J. Immunol. 154 (1995), 4576-4582; Mallender and Voss, J. Biol. Chem. 269 (1994), 199-206). Traditionally, the recombinant production of bispecific antibodies is based on the co-expression of two immunoglobulin heavy chain-light chain pairs, where the two heavy chains have different binding specificities. Because of the random assortment of heavy and light chains, a potential mixture of ten different antibody structures are produced of which only one has the desired binding specificity (Milstein and Cuello, Nature 305 (1983), 537-540; Lanzavecchia and Scheidegger, Eur. J. Immunol. 17 (1987), 105-111. An alternative approach involves fusing the variable domains with the desired binding specificities to heavy chain constant region including at least part of the hinge region, CH2 and CH3 regions. In one embodiment the CH1 region containing the site necessary for light chain binding is present in at least one of the fusions. DNA encoding these fusions, and if desired the light chains are inserted into separate expression vectors and are then co-transfected into a suitable host organism. It is possible though to insert the coding sequences for two or all three chains into one expression vector.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of HTT, in particular of a N-terminal, polyP region, P-rich region or the C-terminal region of exon 1.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind HTT or a fragment, variant or specific conformation thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind HTT or a fragment, variant or specific conformation thereof with an off rate (k(off)) less than or equal to $5 \times 10^4$ sec$^{-1}$, $10^4$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein may be said to bind HTT or a fragment, variant or specific conformation thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind HTT or a fragment, variant or specific conformation thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to HTT and/or mutated, misfolded, and/or aggregated HTT species and/or fragments thereof.

Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-13}$ M, $10^{-13}$ M, $5 \times 10^{-13}$ M, $10^{-13}$ M, $5 \times 10^{-14}$ M, $10^{-14}$ M, $5 \times 10^{-15}$ M, $10^{-15}$ M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 μl buffer (20 mM Tris, pH. 7.5, 0.5% Nonidet, 1 mM EDTA, 1 mM PMSF, 0.1 M NaCl, IX Sigma Protease Inhibitor, and IX Sigma Phosphatase Inhibitors 1 and 2). The suspension can be kept on ice for 20 min. with intermittent vortexing. After spinning at 15,000×g for 5 min at about 4° C., aliquots of supernatant can be stored at about −70° C.

Diseases:

Unless stated otherwise, the terms "disorder" and "disease" are used interchangeably herein and comprise any undesired physiological change in a subject, an animal, an isolated organ, tissue or cell/cell culture.

Huntington's disease (HD) is an autosomal dominant, progressive neurodegenerative disorder characterized by the expansion of a CAG trinucleotide repeat within the huntingtin (HTT) gene (Huntington's Disease Collaborative Research Group, Cell 72(6) (1993), 971-983), wherein the pathogenic threshold of this expansion is approximately 37 repeats, whereas fewer repeats below this number do not result in pathogenesis, see e.g. Trottier et al., Nature 378 (6555) (1995), 403-406. The expansion of the CAG trinucleotide repeat results in an expanded polyglutamine (Poly-Gln, Poly-Q) tract in the amino terminus of the huntingtin protein (HTT), which is associated with the aggregation of HTT. However, the precise mechanism leading to the accumulation of HTT and its associated symptoms has not been elucidated so far.

Studies have shown that both flanking regions of the polyglutamine (Poly-Q) tract, i.e. amino-terminal region consisting of an amphipathic alpha-helical targeting domain and the carboxy-terminal region characterized by two proline tracts (Poly-P region) and a leucine-proline-rich tract (P-rich region) seem to be critical in mediating the toxicity of the mutated HTT, see e.g. Caron et al., PNAS 110 (2013), 14610-14615.

The mechanism contributing to the pathological symptoms of HD, such as hyperkinesia, hypokinesia, mental and movement disorders including disturbances of affect and the drive, lack of motor persistence, thoughtless and impulsive behavior, resignation and depression, disorders of visual information processing, subcortical dementia, loss of cognitive abilities, disorientation and paucity of speech, delusions, restlessness of the arms, legs, face, head and the trunk, choreic hyperkinesis, dysarthria, dysphagia, anarthria, dystonias, has not been elucidated so far. Possible mechanisms include but are not limited to a reduced flexibility of the hinge region due to the expanded Poly-Q tract of HTT as well as to proteases which lead to the formation of different HTT fragments due to the expanded Poly-Q tract.

Since the antibodies of the present invention have been shown to be therapeutically effective in a HD mouse model, see e.g. Example 24 and FIG. 17 as well as Example 34 and FIG. 34 and in addition are capable of binding to HTT amyloids in tissue sections from HD patients, see e.g. Example 31 and FIG. 27-30, the human-derived antibodies and biotechnological derivatives thereof are useful in both the treatment and diagnosis of HD and the above-mentioned symptoms. Therefore, in one embodiment of the present invention the antibodies of the present invention, binding molecules having substantially the same binding specificities of any one thereof, the polynucleotides, the vectors or the cells of the present invention are used for preparation of a pharmaceutical or diagnostic composition for prophylactic and/or therapeutic treatment of HD, in particular HTT amyloidosis diseases and/or disorders, for monitoring disease progression and/or treatment response, and for the diagnosis of diseases associated with HTT amyloidosis.

Treatment:

As used herein, the terms "treat" or "treatment" refer to both therapeutic treatment and prophylactic or preventative measures, wherein the object is to prevent or slow down (lessen) an undesired physiological change or disorder, such as the development of cardiac deficiency. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals;

and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal", is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols 2nd Edition by Robinson et al., Humana Press, Totowa, N.J., USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533.

II. Antibodies of the Present Invention

The present invention generally relates to human-derived anti-HTT antibodies and HTT-binding fragments thereof, which preferably demonstrate the immunological binding characteristics and/or biological properties as outlined for the antibodies illustrated in the Examples. In accordance with the present invention human monoclonal antibodies specific for HTT were cloned from B cells of a pool of healthy human subjects. However, in another embodiment of the present invention, the human monoclonal anti-HTT antibodies might also be cloned from B cells of patients showing symptoms of a disease and/or disorder associated with HTT amyloidosis.

In the course of the experiments performed in accordance with the present invention, antibodies present in the conditioned media of cultured human memory B cell were evaluated for their capacity to bind to HTT and to more than 10 other proteins including bovine serum albumin (BSA); see Examples 8, 13, 18, 31 and 33. Only the B-cell supernatants able to bind to the HTT protein but not to any of the other proteins in the screen were selected for further analysis, including determination of the antibody class and light chain subclass. The selected B-cells were then processed for antibody cloning.

In brief, this consisted in the extraction of messenger RNAs from the selected B-cells, retro-transcription by RT-PCR, amplification of the antibody-coding regions by PCR, cloning into plasmid vectors and sequencing. Selected human antibodies were then produced by recombinant expression in HEK293 or CHO cells and purification, and subsequently characterized for their capacity to bind human HTT protein. The combination of various tests, e.g. recombinant expression of the antibodies in HEK293 or CHO cells and the subsequent characterization of their binding specificities towards human HTT protein, and their distinctive binding to pathologically mutated and/or aggregated forms thereof confirmed that for the first time human antibodies have been cloned that are highly specific for HTT and distinctively recognize and selectively bind the pathologically aggregated forms of HTT protein. In some cases, mouse chimeric antibodies were also generated on the basis of the variable domains of the human antibodies of the present invention.

Thus, the present invention generally relates to recombinant human-derived monoclonal anti-HTT antibodies and HTT-binding fragments, synthetic and biotechnological derivatives and variants thereof. In one embodiment of the invention, the antibody is capable of binding human HTT.

In one embodiment of the present invention the antibody specifically binds an epitope in a polyP-region of HTT, which comprises the amino acid sequence PPPPPPPP (NI-302.33C11; NI-302.44D7; NI-302.7A8; NI-302.3D8; NI-302.46C9) (SEQ ID Nos. 139, 151, 154, 158, 161), amino acid sequence PPPPPP (NI-302.11H6, NI-302.18A1, NI-302.52C9 (SEQ ID Nos.: 157, 159, 160), amino acid sequence PPPPPPPPPP (NI-302.74C11, NI-302.15F9, NI-302.39G12, NI-302.11A4, NI-302.22H9, NI-302.37C12, NI-302.55D8, NI-302.78H12, NI-302.71F6 (SEQ ID Nos.: 146, 147, 148, 149, 150, 152, 153, 155, 156), an epitope in the P-rich-region which comprises the amino acid sequence PQPPPQAQPL (NI-302.63F3 SEQ ID No. 140, NI-302.64E5 SEQ ID No. 200), the amino acid sequence PPPQLPQPPP (NI-302.31F11, SEQ ID No. 141), the amino acid sequence QAQPLLPQPQPPPPP (NI-302.2A2; SEQ ID No. 142), or the amino acid sequence PPPQLPQPPPQAQPL (NI302.15D3; SEQ ID No. 143), an epitope in the C-terminal region which comprise the amino acid sequence PPGPAVAEEPLHRP (NI-302.35C1, SEQ ID No. 145) or PPPGPAVAEEPLH (NI-302.72F10, SEQ ID No. 202), an epitope in the N-terminal region which comprises the amino acid sequence KAFESLKSFQ (NI-NI-302.15E8, SEQ ID No. 144) or an epitope in the P/Q-rich-region which comprises the amino acid sequence QQQQQQQQQPPP (NI-302.7D8 SEQ ID No. 201), or a conformational epitope.

In another embodiment, the present invention is directed to an anti-HTT antibody, or antigen-binding fragment, variant or biotechnological derivatives thereof, where the antibody specifically binds to the same epitope in a polyP-region of HTT as a reference antibody selected from the group consisting of NI-302.33C11, NI-302.74C11, NI-302.15F9, NI-302.39G12, NI-302.11A4, NI-302.22H9, NI-302.44D7, NI-302.37C12, NI-302.55D8, NI-302.7A8, 302.78H12, NI-302.71F6, NI-302.11H6, NI-302.3D8, NI-302.18A1, NI-302.8F1, NI-302.52C9, NI-302.46C9. Epitope mapping identified a sequence within the polyP-region of human HTT including amino acids PPPPPPPPPP (SEQ ID Nos.: 146, 147, 148, 149, 150, 152, 153, 155, 156) as the unique linear epitope recognized by antibodies NI-302.74C11, NI-302.15F9, NI-302.39G12, NI-302.11A4, NI-302.22H9, NI-302.37C12, NI-302.55D8, NI-302.78H12, NI-302.71F6 of this invention. Additionally, epitope mapping identified a sequence within the polyP-region of human HTT including amino acids PPPPPPPP (SEQ ID Nos. 139, 151, 154, 158, 161) as the unique linear epitope recognized by antibodies NI-302.33C11, NI-302.44D7, NI-302.7A8, NI-302.3D8, NI-302.46C9 of this invention, and amino acids PPPPPP (SEQ ID Nos.: 157, 159, 160) as the unique linear epitope recognized by antibodies NI-302.11H6, NI-302.18A1, NI-302.52C9 of this invention. Therefore, in one embodiment the antibody of the present invention is provided, wherein the antibody specifically binds to an epitope in a polyP-region of HTT, which comprises the amino acid sequence PPPPPPPPPP (SEQ ID Nos.: 146, 147, 148, 149, 150, 152, 153, 155, 156), PPPPPPPP (SEQ ID Nos. 139, 151, 154, 158, 161), or PPPPPP (SEQ ID Nos.: 157, 159, 160).

In one embodiment, the present invention is directed to an anti-HTT antibody, or antigen-binding fragment, variant or biotechnological derivatives thereof, where the antibody specifically binds to the same epitope in the P-rich region of HTT as a reference antibody selected from the group consisting of NI-302.63F3, NI-302.31F11, NI-302.2A2, and NI-302.15D3. Epitope mapping identified a sequence within the P-rich-region of human HTT including amino acids PQPPPQAQPL (SEQ ID No. 140) as the unique linear epitope recognized by antibody NI-302.63F3 of this invention, PPPQLPQPPP (SEQ ID No. 141), as the unique linear epitope recognized by antibody NI-302.31F11 of this invention, PPPQLPQPPP (SEQ ID No. 141), as the unique linear epitope recognized by antibody NI-302.31F11 of this invention, QAQPLLPQPQPPPPP (SEQ ID No. 142) as the unique linear epitope recognized by antibody NI-302.2A2, PPPQLPQPPPQAQPL (SEQ ID No. 143) as the unique linear epitope recognized by antibody NI302.15D3, PQPPPQAQPL as the unique linear epitope recognized by antibody NI302.64E5. Therefore, in one embodiment the antibody of the present invention is provided, wherein the antibody specifically binds to an epitope in the P-rich-region of HTT which comprises the amino acid sequence PQPPPQAQPL (SEQ ID No. 140), PPPQLPQPPP (SEQ ID No. 141), QAQPLLPQPQPPPPP (SEQ ID No. 142), PPPQLPQPPPQAQPL (SEQ ID No. 143).

In another embodiment the present invention is directed to an anti-HTT antibody, or antigen-binding fragment, variant or biotechnological derivatives thereof, wherein the antibody specifically binds to the same epitope in the polyQ/polyP-region of HTT as reference antibody NI-302.7D8. Epitope mapping identified a sequence within the Q/P-rich-region of human HTT including amino acids QQQQQQQPPP (SEQ ID No. 201) as the unique linear epitope recognized by antibody NI-302.7D8 of this invention. Therefore, in one embodiment the antibody of the present invention is provided, wherein the antibody specifically binds to an epitope in in the polyQ/polyP-region of HTT which comprises the amino acid sequence QQQQQQQPPP (SEQ ID No. 201)

In one embodiment, the present invention is directed to an anti-HTT antibody, or antigen-binding fragment, variant or biotechnological derivatives thereof, where the antibody specifically binds to the same epitope in the C-terminal region of HTT as a reference antibody selected from the group consisting of NI-302.35C1. Epitope mapping identified a sequence within the C-terminal region of human HTT including amino acids PPGPAVAEEPLHRP (SEQ ID No. 145) as the unique linear epitope recognized by antibody NI-302.35C1 of this invention. Therefore, in one embodiment the antibody of the present invention is provided, wherein the antibody specifically binds to an epitope in in the C-terminal region of HTT which comprises the amino acid sequence PPGPAVAEEPLHRP (SEQ ID No. 145).

In a further embodiment, the present invention is directed to an anti-HTT antibody, or antigen-binding fragment, variant or biotechnological derivatives thereof, where the antibody specifically binds to the same epitope in the C-terminal region of HTT as reference antibody NI-302.72F10. Epitope mapping identified a sequence within the C-terminal region of human HTT including amino acids PPPGPAVAEEPLH (SEQ ID No. 202) as the unique linear epitope recognized by antibody NI-302.72F10 of this invention. Therefore, in one embodiment the antibody of the present invention is provided, wherein the antibody specifically binds to an epitope in in the C-terminal region of HTT which comprises the amino acid sequence PPPGPAVAEEPLH (SEQ ID No. 202).

In another embodiment, the present invention is directed to an anti-HTT antibody, or antigen-binding fragment, variant or biotechnological derivatives thereof, where the antibody specifically binds to the same epitope in the N-terminal region of HTT as reference antibody NI-302.15E8. Epitope mapping identified a sequence within the N-terminal region of human HTT including amino acids KAFESLKSFQ (SEQ ID No. 144) as the unique linear epitope recognized by antibody NI-302.15E8 of this invention. Therefore, in one embodiment the antibody of the present invention is provided, wherein the antibody specifically binds to an epitope in in the N-terminal region of HTT which comprises the amino acid sequence KAFESLKSFQ (SEQ ID No. 144).

In one embodiment, the present invention is directed to an anti-HTT antibody, or antigen-binding fragment, variant or biotechnological derivatives thereof, where the antibody specifically binds to the same epitope of HTT exon 1 as a reference antibody selected from the group consisting of NI-302.6N9, NI-302.4A6, NI-302.12H2 or NI-302.8M1 which have been shown not to bind to linear peptides of HTT exon 1 but aggregated HTT exon 1 proteins with 21 or 49 polyQ (HD21 and HD49) with high affinity and an $EC_{50}$ value in the subnanomolar range; see, e.g., Example 25 and FIG. 20 for overview. Therefore, in one preferred embodiment the antibody of the present invention specifically binds aggregated forms of HTT, in particular protein aggregates derived from HTT exon 1 with an $EC_{50}$ value of below 1 nM, preferably below 0.1 nM and most preferably below 0.01 nM.

Furthermore, without intending to be bound by initial experimental observations as demonstrated in the Examples and shown in Figures, the human monoclonal NI-302.33C11, NI-302.63F3, NI-302.35C1, NI-302.31F11, NI-302.6N9, NI-302.46C9, NI-302.8F1, NI-302.74C11, NI-302.15F9, NI-302.39G12, NI-302.11A4, NI-302.22H9, NI-302.44D7, NI-302.55D8, NI-302.7A8, NI-302.78H12, NI-302.71F6, NI-302.11H6, NI-302.3D8, and NI.302-64E5 and NI.302-72F10 anti-HTT antibodies of the present invention are preferably characterized in specifically binding to pathological mutated and/or aggregated HTT and to substantially smaller affinity recognizing HTT in the physiological form, see e.g. Examples 7, 13, 18 and FIGS. 3, 7, 11, 21, 32. Hence, the present invention provides a set of human anti-HTT antibodies with binding properties particularly useful for diagnostic and therapeutic purposes. Thus, in one embodiment the present invention provides antibodies which are capable of specifically binding pathologically aggregated forms of HTT. However, in addition or alternatively, the antibodies of the present invention which are capable to bind to a polyP-region or a P-rich region of HTT exon 1 may be also utilized in other applications. In particular, these antibodies are not limited to HTT but can also bind to other targets showing also a polyP-tract or a P-rich region.

In one embodiment, the antibody of the present invention exhibits the binding properties of the exemplary NI-302.33C11, NI-302.63F3, NI-302.35C1, NI.302-7D8 and NI.302-72F10 antibodies as described in the Examples. The anti-HTT antibody of the present invention preferentially recognizes pathologically altered HTT, such as mutated and/or aggregated HTT species and fragments thereof rather than physiological HTT. Thus, in one embodiment, the antibody of the present invention does not substantially recognize physiological HTT species.

The term "does not substantially recognize" when used in the present application to describe the binding affinity of a molecule of a group comprising an antibody, a fragment thereof or a binding molecule for a specific target molecule, antigen and/or conformation of the target molecule and/or antigen means that the molecule of the aforementioned group binds said molecule, antigen and/or conformation with a binding affinity which is at least 2-fold, 3-fold, 4-fold, 5-fold, 6-fold, 7-fold, 8-fold or 9-fold less than the binding affinity of the molecule of the aforementioned group for binding another molecule, antigen and/or conformation. Very often the dissociation constant (KD) is used as a measure of the binding affinity. Sometimes, it is the $EC_{50}$ on a specific assay as for example an ELISA assay that is used as a measure of the binding affinity. Preferably the term "does not substantially recognize" when used in the present application means that the molecule of the aforementioned group binds said molecule, antigen and/or conformation with a binding affinity which is at least or 10-fold, 20-fold, 50-fold, 100-fold, 1000-fold or 10000-fold less than the binding affinity of said molecule of the aforementioned group for binding to another molecule, antigen and/or conformation.

As described above, the aggregation of HTT in HD is suggested to occur due to an extension of the poly-glutamine tract within the HTT exon 1. In particular, it has been shown that HD mainly occurs in patients having a threshold over the 35-40 glutamine residues in length in the HTT. Accordingly, as shown in Example 3, aggregated and soluble construct of HTT exon 1 with 21, 35 or 49 polyQ repeats were generated in order to identify the utility of the anti-HTT-antibodies of the present invention to specifically bind to pathological altered HTT.

The term HDX as used in the following describes the HTT constructs which were generated in accordance with Example 3. Particularly the X denotes the number of glutamine repeats (Qs), e.g. HTT exon 1 protein with 21 polyQ repeats will be denoted HD21.

Utilizing the constructs as described in the Examples, it could be shown that the anti-HTT antibody of the present invention in addition, or alternatively, binds to pathologically, disease causing and/or mutated and/or aggregated forms of human HTT. In this context, the binding affinities may be in the range as shown for the exemplary NI-302.33C11, NI-302.63F3, NI-302.35C1, NI-302.31F11, NI-302.6N9, NI-302.46C9, NI-302.8F1, NI-302.74C11, NI-302.15F9, NI-302.39G12, NI-302.11A4, NI-302.22H9, NI-302.44D7, NI-302.55D8, NI-302.7A8, NI-302.78H12, NI-302.71F6, NI-302.11H6, and NI-302.3D8 antibodies in FIG. 3(A), 7(A), 11(A), 14(A), respective FIGS. 19, 20 and 31, i.e. having half maximal effective concentrations ($EC_{50}$) of about 1 pM to 250 nM, preferably an $EC_{50}$ of about 25 pM to 50 nM, most preferably an $EC_{50}$ of about 0.05 nM to 30 nM for human aggregated HD49-HTT and aggregated recombinant HD49-HTT, or an $EC_{50}$ of about 0.05 nM to 5 nM for human aggregated HD21-HTT and aggregated recombinant HD21-HTT.

In particular, the anti-HTT antibody, binding fragment or biotechnological derivative thereof has a binding affinity corresponding to an $EC_{50}$ value of ≤20 nM, preferably ≤10 nM and most preferably ≤1 nM for binding aggregated HD49 HTT and/or of ≤40 nM, preferably ≤10 nM and most preferably ≤1 nM for binding HD21 HTT; see FIGS. 3, 7, 11, 19 and 31.

HTT aggregation associated with the development of HD is most frequently associated with poly-glutamine (polyQ) tracts of >35 repeats. As shown in the present invention, the anti-HTT antibodies described herein showed high binding efficiency to HD tracts with higher repetitions, see e.g. Examples 7, 13, 18, 31 and 33. Therefore, in one embodiment of the present invention the anti-HTT antibody, HTT-binding molecule, fragment, synthetic or biotechnological variant thereof binds to HTT with expanded poly-glutamine (Q) tract. In a preferred embodiment it binds to HTT with more than 35 repeats. In a particular preferred embodiment of the present invention, the antibody binds to HTT with expanded poly-glutamine (Q) tract consisting of 49 (HD49) repeats over 35 repeats (HD35) and more over 21 repeats (HD21).

However, in accordance with the present invention also anti-HTT antibodies, HTT-binding molecules, fragments, synthetic or biotechnological variants thereof binding to poly-glutamine (polyQ) tracts under 35 (HD35) are described. Therefore, in one embodiment of the present invention, the antibody, binding molecule or variants thereof binds to HTT showing "normal" polyQ tracts. In particular, the antibody is capable of binding to HTT with polyQ tracts <35 repeats (HD35).

Some antibodies are able to bind to a wide array of biomolecules, e.g., proteins. As the skilled artisan will appreciate, the term specific is used herein to indicate that other biomolecules than HTT proteins or fragments thereof do not significantly bind to the antigen-binding molecule, e.g., one of the antibodies of the present invention. Preferably, the level of binding to a biomolecule other than HTT results in a binding affinity which is at most only 20% or less, 10% or less, only 5% or less, only 2% or less or only 1% or less (i.e. at least 5, 10, 20, 50 or 100 fold lower, or anything beyond that) of the affinity to HTT, respectively; see e.g., FIG. 20.

In one embodiment, the anti-HTT antibody of the present invention binds preferentially to aggregated forms of HTT and/or fragments, derivatives, fibrils and/or oligomers thereof. In another embodiment the anti-HTT antibody of the present invention preferentially binds to both native HTT and pathologically mutated and/or aggregated forms of HTT.

In a further embodiment of the present invention, the anti-HTT antibody or HTT-binding fragment, synthetic or biotechnological derivative thereof is a bispecific antibody. Thus, the antibody of the present invention may be capable of recognizing at least two distinct epitopes either on the same or on different antigens; see also, supra.

In one embodiment, at least one binding site/domain of the bispecific antibody specifically recognizes an epitope in a polyP-region of HTT, which comprises the amino acid sequence PPPPPPPP (NI-302.33C11; NI-302.44D7; NI-302.7A8; NI-302.3D8; NI-302.46C9) (SEQ ID Nos. 139, 151, 154, 158, 161), amino acid sequence PPPPPP (NI-302.11H6, NI-302.18A1, NI-302.52C9 (SEQ ID Nos.: 157, 159, 160), amino acid sequence PPPPPPPPPP (NI-302.74C11, NI-302.15F9, NI-302.39G12, NI-302.11A4, NI-302.22H9, NI-302.37C12, NI-302.55D8, NI-302.78H12, NI-302.71F6 (SEQ ID Nos.: 146, 147, 148, 149, 150, 152, 153, 155, 156), an epitope in the P-rich-region which comprises the amino acid sequence PQPPPQAQPL (NI-302.63F3 SEQ ID No. 140, NI-302.64E5 SEQ ID No. 200), the amino acid sequence PPPQLPQPPP (NI-302.31F11, SEQ ID No. 141), the amino acid sequence QAQPLLPQPQPPPPP (NI-302.2A2; SEQ ID No. 142), or the amino acid sequence PPPQLPQPPPQAQPL (NI302.15D3; SEQ ID No. 143), an epitope in the C-terminal region which comprise the amino acid sequence PPGPA-VAEEPLHRP (NI-302.35C1, SEQ ID No. 145) or PPPGPA-VAEEPLH (NI-302.72F10, SEQ ID No. 202), an epitope in the N-terminal region which comprises the amino acid sequence KAFESLKSFQ (NI-302.15E8, SEQ ID No. 144), an epitope in the P/Q-rich-region which comprises the amino acid sequence QQQQQQQQQPPP (NI-302.7D8 SEQ ID No. 201), or a conformational epitope recognized by any one of antibodies NI-302.6N9, NI-302.4A6, NI-302.12H2 or NI-302.8M1.

As mentioned before, accumulation of polyglutamine (poly-Gln, polyQ)-containing HTT protein aggregates in neuronal intranuclear inclusions is a hallmark of the progressive neurodegenerative disorder Huntington's disease (HD). Electron micrographs of these aggregates revealed fibrillar structures showing a closely related morphology as in B-amyloid fibrils in Alzheimer's disease, see e.g. Caughey et al., Trends Cell Biol. 7 (1997), 56-62 and Caputo et al., Arch. Biochem. Biophys. 292 (1992), 199-205, suggesting that HD, wherein degenerative process primarily involves medium spiny striatal neurons and cortical neurons leading to dysfunction and subsequently neuronal loss, tissue damage due to excitotoxicity, mitochondrial damage, free radicals, and possibly also inflammatory mechanisms including microglia activation and further progressive nature of symptoms, are a result of toxic amyloid fibrillogenesis. Therefore, in one embodiment the antibody of the present invention is useful for the treatment of Huntingtion's disease (HD) and symptoms thereof.

So far, intracellularly expressed antibodies (intrabodies) have been described and considered as therapeutic tools in HD which perturb the HTT function, see e.g. Ali et al. in Neurobiology of Huntington's Disease: Applications to Drug Discovery, Lo et al., Chapter 10, CRC Press (2011). Although these intrabodies showed a positive effect on the aggregation and cell death induced by HTT in cell based assays, see e.g. Khoshnan et al., Proc Natl Acad Sci USA. 99 (2002), 1002-1007, one disadvantage in their therapeutic utility is the route of administration. In particular, the preferred method for the delivery of the therapeutic intrabodies to the brain is a viral vector-based gene therapy. However, a major disadvantage of using this kind of administration is among other the high host immunogenicity. Therefore, non-viral methods utilizing other routes of administration as are preferably used in the therapeutic or diagnostic approaches. The antibodies of the present invention have been shown to attenuate the dendritic spine density loss upon addition to the culture medium, i.e. extracellularly. Therefore, in contrast to the intrabodies described before, the antibodies of the present invention can be expected to be efficacious following therapeutically preferred administration routes. Accordingly, in one embodiment of the present invention the antibody is administered by a subcutaneous injection (s.c.), intravenous injection (i.v.), intramuscular injection (i.m.), intraperitoneal (i.p.), intrathecal, jet injection, wherein the radius of action is not limited to the intracellular expression of the antibody.

As already mentioned before, and as shown in Example 24 and FIG. 17 the therapeutic utility of the antibodies of the present invention has been shown. In particular, it has been shown that the anti-HTT antibodies of the present invention are capable of attenuating the dendritic spine density loss. Therefore, in one embodiment of the present invention the ant-HTT antibody, the HTT-binding fragment, synthetic or biotechnological derivative thereof leads to an attenuation of spine density loss.

Furthermore, the therapeutic utility of the antibodies of the present invention has been demonstrated in Example 34 and FIG. 34. In particular, it has been shown that the anti-HTT antibodies of the present invention improve behavioral recovery during task-specific training and enhance loco-motor ability. Therefore, in one embodiment of the present invention the ant-HTT antibody, the HTT-binding fragment, synthetic or biotechnological derivative thereof leads to an improvement of behavioral performance during task-specific training and enhancement of sensorimotor ability.

The present invention is also drawn to an antibody, or antigen-binding fragment, variant or derivatives thereof, where the antibody comprises an antigen-binding domain identical to that of an antibody selected from the group consisting of NI-302.33C11, NI-302.63F3, NI-302.35C1, NI-302.31F11, NI-302.2A2, NI-302.6N9, NI-302.74C11, NI-302.15F9, NI-302.39G12, NI-302.11A4, NI-302.22H9, NI-302.44D7, NI-302.37C12, NI-302.55D8, NI-302.7A8, NI-302.78H12, NI-302.71F6, NI-302.11H6, NI-302.3D8, NI-302.18A1, NI-302.8F1, NI-302.52C9, NI-302.46C9, NI-302.15E8, NI-302.15D3, NI-302.64E5, NI-302.7D8, NI-302.72F10, NI-302.12H2, NI-302.8M1 and NI-3024A6.

The present invention further exemplifies several binding molecules, e.g., antibodies and binding fragments thereof, recognizing a polyP-region of HTT, which may be characterized by comprising in their variable region, e.g., binding domain at least one complementarity determining region (CDR) of the $V_H$ and/or $V_L$ variable region comprising any one of the amino acid sequences depicted in FIG. 1. The corresponding nucleotide sequences encoding the above-identified variable regions are set forth in Table II below. Exemplary sets of CDRs of the above amino acid sequences of the $V_H$ and/or $V_L$ region are depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3. Therefore, in one embodiment the antibody of the present invention or a HTT-binding fragment thereof is provided comprising in its variable region at least one complementarity determining region (CDR) as depicted in FIG. 1 and/or one or more CDRs thereof comprising one or more amino acid substitutions.

Further the present invention exemplifies several binding molecules, e.g., antibodies and binding fragments thereof, recognizing the P-rich region of HTT which may be characterized by comprising in their variable region, e.g., binding domain at least one complementarity determining region (CDR) of the $V_H$ and/or $V_L$ variable region comprising any one of the amino acid sequences depicted in FIG. 1. The corresponding nucleotide sequences encoding the above-identified variable regions are set forth in Table III below. Exemplary sets of CDRs of the above amino acid sequences of the $V_H$ and/or $V_L$ region are depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3. Therefore, in one embodiment the antibody of the present invention or a HTT-binding fragment thereof is provided comprising in its variable region at least one complementarity determining region (CDR) as depicted in FIG. 1 and/or one or more CDRs thereof comprising one or more amino acid substitutions.

The present invention in addition exemplifies several binding molecules, e.g., antibodies and binding fragments thereof, recognizing the C-terminal region of HTT which may be characterized by comprising in their variable region, e.g., binding domain at least one complementarity determining region (CDR) of the $V_H$ and/or $V_L$ variable region comprising any one of the amino acid sequences depicted in FIG. 1. The corresponding nucleotide sequences encoding the above-identified variable regions are set forth in Table IV below. Exemplary sets of CDRs of the above amino acid sequences of the $V_H$ and/or $V_L$ region are depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3. Therefore, in one embodiment the antibody of the present invention or a HTT-binding fragment thereof is provided comprising in its variable region at least one complementarity determining region (CDR) as depicted in FIG. 1 and/or one or more CDRs thereof comprising one or more amino acid substitutions.

Additionally, the present invention exemplifies several binding molecules, e.g., antibodies and binding fragments thereof, recognizing the N-terminal-region of HTT which may be characterized by comprising in their variable region, e.g., binding domain at least one complementarity determining region (CDR) of the $V_H$ and/or $V_L$ variable region comprising any one of the amino acid sequences depicted in FIG. 1. The corresponding nucleotide sequences encoding the above-identified variable regions are set forth in Table VI below. Exemplary sets of CDRs of the above amino acid sequences of the $V_H$ and/or $V_L$ region are depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3. Therefore, in one embodiment the antibody of the present invention or a HTT-binding fragment thereof is provided comprising in its variable region at least one complementarity determining region (CDR) as depicted in FIG. 1 and/or one or more CDRs thereof comprising one or more amino acid substitutions.

In one embodiment, the antibody of the present invention is any one of the antibodies comprising an amino acid sequence of the $V_H$ and/or $V_L$ region as depicted in FIG. 1 or a $V_H$ and/or $V_L$ region thereof comprising one or more amino acid substitutions. Preferably, the antibody of the present invention is characterized by the preservation of the cognate pairing of the heavy and light chain as was present in the human B-cell.

In a further embodiment of the present invention the anti-HTT antibody, HTT-binding fragment, synthetic or biotechnological variant thereof can be optimized to have appropriate binding affinity to the target and pharmacokinetic properties. Therefore, at least one amino acid in the CDR or variable region, which is prone to modifications selected from the group consisting of glycosylation, oxidation, deamination, peptide bond cleavage, iso-aspartate formation and/or unpaired cysteine is substituted by a mutated amino acid that lack such alteration or wherein at least one carbohydrate moiety is deleted or added chemically or enzymatically to the antibody. Examples for amino acid optimization can be found in Table VII, wherein antibodies showing primer-induced alterations are shown. Additional modification optimizing the antibody properties are described in Gavel et al., Protein Engineering 3 (1990), 433-442 and Helenius et al., Annu. Rev. Biochem. 73 (2004), 1019-1049.

Alternatively, the antibody of the present invention is an antibody or antigen-binding fragment, derivative or variant thereof, which competes for binding to HTT with at least one of the antibodies having the $V_H$ and/or $V_L$ region as depicted in FIG. 1.

The antibody with at least one antibody having the $V_H$ and/or $V_L$ region as depicted in FIG. 1 competing for binding to HTT may be further characterized in a dot blot assay and/or filter retardation, as described in Example 6, 13, 18, 31 and/or 32. Therefore, in one embodiment of the present invention the antibody binds to HTT, preferably to HTT with an expanded poly-Q tract consisting of 49 (HD49) repeats in a dot blot assay and/or filter retardation.

Experimental results provided in FIGS. 3, 7, 11, 21, 22 as well as FIGS. 32 and 33, and Examples 6, 7, 13, 18, 26 and 32 suggest that some of the anti-HTT antibodies of the present invention preferentially bind to disease causing mutated and/or aggregated forms of human anti-HTT over the other amyloid forming proteins. In one embodiment thus, the antibody of the present invention preferentially recognizes mutated and/or aggregated HTT and/or fragment and/or derivatives thereof over other amyloid forming proteins.

In one embodiment of the present invention the anti-HTT antibody, HTT-binding fragment, synthetic or biotechnological derivative thereof does preferentially recognize mutated, aggregated and/or soluble forms of HTT over physiological HTT.

The antibody of the present invention may be human, in particular for therapeutic applications. Alternatively, the antibody of the present invention is a rodent, rodentized or chimeric rodent-human antibody, preferably a murine, murinized or chimeric murine-human antibody or a rat, ratinized or chimeric rat-human antibody which are particularly useful for diagnostic methods and studies in animals. In one embodiment the antibody of the present invention is a chimeric rodent-human or a rodentized antibody. Furthermore, in one embodiment, the chimeric antibody of the present invention, i.e. comprising the variable domains of a human antibody and generic murine light and heavy constant domains bind with a high affinity to human HTT. Preferably, the binding affinity of chimeric antibodies is similar to their human counterparts.

In one embodiment the antibody of the present invention is provided by cultures of single or oligoclonal B-cells that are cultured and the supernatant of the culture which contains antibodies produced by said B-cells, is screened for presence and affinity of anti-HTT antibodies therein. The screening process comprises screening for binding to native monomeric, fibrillar or non-fibrillar aggregates like oligomers of hHTT derived from a synthetic full-length hHTT peptide or e.g. purified from human plasma or recombinant expression.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-HTT antibody of the present invention is unique and no other antibody which is capable of binding to the epitope recognized by the human monoclonal antibody of the present invention exists. A further indication for the uniqueness of the antibodies of the present invention is the fact that, as indicated in FIGS. 19, 20, 24, and 27 to 29, antibodies of the present invention bind epitopes that are specific for the mutated and/or aggregated forms of HTT, which as indicated above, are of particular pathological relevance and may not be obtainable by the usual processes for antibody generation, such as immunization or in vitro library screenings.

Therefore, in one embodiment the present invention also extends generally to anti-HTT antibodies and HTT-binding molecules which compete with the human monoclonal antibody of the present invention for specific binding to HTT. The present invention is more specifically directed to an antibody, or antigen-binding fragment, variant or derivatives thereof, where the antibody specifically binds to the same epitope in a polyP-region of HTT as a reference antibody selected from the group consisting of NI-302.33C11, NI-302.74C11, NI-302.15F9, NI-302.39G12, NI-302.11A4, NI-302.22H9, NI-302.44D7, NI-302.37C12, NI-302.55D8, NI-302.7A8, NI-302.71F6, NI-302.11H6, NI-302.3D8, NI-302.18A1, NI-302.8F1, NI-302.52C9, NI-302.78H12 and NI-302.46C9. Further, in one embodiment the present invention is more specifically directed to an antibody, or antigen-binding fragment, variant or derivatives thereof, where the antibody specifically binds to the same epitope in the P-rich-region of HTT as a reference antibody selected from the group consisting of NI-302.63F3, NI-302.31F11, NI-302.2A2, NI-302.15D3 and/or NI-302.64E5. In another embodiment the present invention is directed to an antibody, or antigen-binding fragment, variant or derivatives thereof, which binds to the same epitope in the C-terminal-region of HTT as a reference antibody selected from the group consisting of NI-302.35C1 and/or NI.302-72F10. In a further embodiment the present invention is directed to an antibody, or antigen-binding fragment, variant or derivatives thereof, which binds to the same epitope in the N-terminal-region of HTT as a reference antibody selected from the group consisting of NI-302.15E8. In another embodiment the present invention is directed to an antibody, or antigen-binding fragment, variant or derivatives thereof, which binds to the same epitope of HTT as a reference antibody selected from the group consisting of NI-302.6N9, NI-320.12H2, NI-302.8M1 and/or NI-302.4A6. In one embodiment the present invention is directed to an antibody, or antigen-binding fragment, variant or derivatives thereof, which binds to the same epitope of HTT as reference antibody NI-302.7D8.

In a preferred embodiment the present invention also extends generally to anti-HTT antibodies and HTT-binding molecules which compete with the human monoclonal antibody of the present invention for specific binding to mutated and/or aggregated HTT species or fragments thereof, as shown in Examples 7, 13, 18, 31 and 33 as well as FIGS. 7, 13, 19 and 31. The present invention is therefore, more specifically also directed to an antibody, or antigen-binding fragment, variant or derivatives thereof, where the antibody specifically binds to the same epitope in a polyP-region of mutated and/or aggregated HTT species or fragments thereof as a reference antibody selected from the group consisting of NI-302.74C11, NI-302.15F9, NI-302.39G12, NI-302.11A4, NI-302.22H9, NI-302.37C12, NI-302.55D8, NI-302.78H12, NI-302.71F6, NI-302.33C11, NI-302.44D7, NI-302.7A8, NI-302.3D8, NI-302.46C9, NI-302.11H6, NI-302.18A1, NI-302.52C9, and/or NI-302.8F1. Further, in one embodiment the present invention is more specifically directed to an antibody, or antigen-binding fragment, variant or derivatives thereof, where the antibody specifically binds to the same epitope in the P-rich-region of mutated and/or aggregated HTT species or fragments thereof as a reference antibody selected from the group consisting of NI-302.63F3, NI-302.31F11, NI-302.2A2, NI-302.15D3 and/or NI-302.64E5. In another embodiment the present invention is directed to an antibody, or antigen-binding fragment, variant or derivatives thereof, which binds to the same epitope in the C-terminal-region of mutated and/or aggregated HTT species or fragments thereof as a reference antibody selected from the group consisting of NI-302.35C1 and/or NI.302-72F10. In a further embodiment the present invention is directed to an antibody, or antigen-binding fragment, variant or derivatives thereof, which binds to the same epitope in the N-terminal-region of mutated and/or aggregated HTT species or fragments thereof as a reference antibody selected from the group consisting of NI-302.15E8. In another embodiment the present invention is directed to an antibody, or antigen-binding fragment, variant or derivatives thereof, which binds to the same epitope of HTT as a reference antibody selected from the group consisting of NI-302.6N9, NI-320.12H2, NI-302.8M1 and/or NI-302.4A6. In one embodiment the present invention is directed to an antibody, or antigen-binding fragment, variant or biotechnological derivative thereof, which binds to the same epitope of HTT as reference antibody NI-302.7D8.

Competition between antibodies is determined by an assay in which the immunoglobulin under test inhibits specific binding of a reference antibody to a common antigen, such as HTT. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al., Molec. Immunol. 25 (1988), 7-15 and Moldenhauer et al., Scand. J. Immunol. 32 (1990), 77-82. Typically, such an assay involves the use of purified HTT or mutated and/or aggregated HTT, such as oligomers and/or fibrils thereof bound to a solid surface or cells bearing either of these, an unlabeled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. Preferably, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-302.33C11, NI-302.63F3, NI-302.35C1, NI-302.31F11, NI-302.2A2, NI-302.6N9, NI-302.74C11, NI-302.15F9, NI-302.39G12, NI-302.11A4, NI-302.22H9, NI-302.44D7, NI-302.37C12, NI-302.55D8, NI-302.7A8, NI-302.78H12, NI-302.71F6, NI-302.11H6, NI-302.3D8, NI-302.18A1, NI-302.8F1, NI-302.52C9, NI-302.46C9, NI-302.15E8, NI-302.64E5, NI-302.7D8, NI-302.72F10, NI-302.12H2, NI-302.8M1 and/or NI-302.4A6 from binding to HTT.

The present invention is further drawn to an antibody, or antigen-binding fragment, variant or derivatives thereof, where the antibody competitively inhibits a reference antibody selected from the group consisting of NI-302.74C11, NI-302.15F9, NI-302.39G12, NI-302.11A4, NI-302.22H9, NI-302.37C12, NI-302.55D8, NI-302.78H12, NI-302.71F6, NI-302.33C11, NI-302.44D7, NI-302.7A8, NI-302.3D8, NI-302.46C9, NI-302.11H6, NI-302.18A1, NI-302.52C9, NI-302.8F1, NI-302.63F3, NI-302.31F11, NI-302.2A2, NI302.15D3, NI-302.35C1, NI-302.6N9, NI-302.7D8 and/or NI-302.72F10 from binding to mutated and/or aggregated HTT species or fragments thereof.

In a preferred embodiment the antibody, the binding of an antibody, binding fragment, synthetic or biotechnological variant thereof, to HTT, preferably to HTT with an expanded poly-Q tract consisting of 49 (HD49) repeats can be measured in a dot blot assay and/or filter retardation as described in the Examples, in particular in 7, 13, 18, 31 and/or 33.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 1 respectively. While FIG. 1 shows $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 1.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1 respectively. In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1 respectively, except for one, two, three, four, five, or six amino acid substitutions in any one $V_H$-CDR. In certain embodiments the amino acid substitutions are conservative.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 1 respectively. While FIG. 1 shows $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1 respectively. In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1 respectively, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO 89/09622. Methods for the production of humanized antibodies are described in, e.g., European application EP-A1 0 239 400 and international application WO 90/07861. Further sources of antibodies to be utilized in accordance with the present invention are so-called xenogeneic antibodies. The general principle for the production of xenogeneic antibodies such as human-like antibodies in mice is described in, e.g., international applications WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see e.g. international application WO 88/09344. In one embodiment therefore, the antibody of the present invention is provided, which is selected from the group consisting of a single chain Fv fragment (scFv), a F(ab') fragment, a F(ab) fragment, and a F(ab')2 fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO 00/30680 for corresponding technical details.

The antibodies of the present invention may also include additional modifications which optimize their therapeutic potential. These modifications comprise but are not limited to modifications to the amino acid sequence of the antibody (e.g., the variable regions) and post-translational modifications. Post-translational modifications (PTMs) are chemical modifications that play a key role in functional proteomics, because they regulate activity, localization and interaction with other cellular molecules such as proteins, nucleic acids, lipids, and cofactors. Therefore, the optimization of the antibodies may provide several advantages such as an improved stability during storage as well as pharmacokinetics and/or pharmacodynamics profile such as the in vivo or in vitro circulating time of the antibody, increased solubility, stability, increased affinity to the target, decreased off-rate, an improved effector function of the constant region (Fc region) and safety profile of the antibody, such as a decreased immunogenicity, or reduced susceptibility to post-translational modifications, as shown e.g. in Igawa et al., MAbs 3 (2011), 243-52. Accordingly, in one embodiment of the present invention the anti-HTT antibody, HTT-binding fragment, synthetic or biotechnological variant thereof can be optimized, wherein at least one amino acid in the CDR or variable region, which is prone to modifications including but are not limited to acetylation, acylation, ADP-ribosylation, amidation, deamidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, isomerization, demethylation, formation of covalent cross-links, formation of cysteine, formation of pyroglutamate, formylation, γ-carboxylation, glycosylation, GPI anchor formation, hydroxylation, hydrolysis, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, "Proteins: Structures and Molecular Properties," 2nd eds., Freeman and Co., N.Y., 1992; "Postranslational Covalent Modification of Proteins," Johnson, eds., Academic Press, New York, 1983; Seifter et al., Meth. Enzymol. 182 (1990), 626-646; Rattan et al., Ann. NY. Acad. Sei. 663 (1992) 48-62) is substituted by a mutated amino acid that lack such alteration or wherein at least one carbohydrate moiety is deleted or added chemically or enzymatically to the antibody. In a preferred embodiment the modifications are selected from the group consisting of glycosylation, oxidation, deamination, peptide bond cleavage, iso-aspartate formation and/or unpaired cysteine. Additional modification that optimize the utility of the HTT-antibodies or binding molecules as a therapeutic agent are well known in the art and described e.g. in Igawa et al., MAbs 3 (2011), 243-52 which disclosure content is incorporated herein. Means of adding or deleting carbohydrate moieties can be achieved chemically or enzymatically and is described in detail in e.g. Berg et al. "Biochemistry" 5th eds W H Freeman, New York 2002; WO 87/05330; Aplin et al., CRC Crit. Rev. Biochem., 22 (1981), 259-306; Hakimuddin et al., Arch. Biochem. Biophys., 259 (1987), 10-52; Edge et al., Anal. Biochem., 118 (1981), 131; Thotakura et al., Meth. Enzymol. 138. (1987), 350.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the anti-HTT antibodies and/or antibodies capable of binding mutated and/or aggregated HTT species and/or fragments thereof of the present invention and displays the mentioned properties, i.e. which specifically recognizes HTT and/or mutated and/or aggregated HTT species and/or fragments thereof. Such antibodies and binding molecules can be tested for their binding specificity and affinity by ELISA and immunohistochemistry as described herein, see, e.g., the Examples. These characteristics of the antibodies and binding molecules can be tested by Western Blot as well.

As an alternative to obtaining immunoglobulins directly from the culture of B cells or memory B cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in FIG. 1.

Binding molecules, e.g., antibodies, or antigen-binding fragments, synthetic or biotechnological variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of HTT aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO 2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing HTT localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as HTT localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences binding to HTT as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration. Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced", i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO 98/52976 and WO 00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., HTT-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press (1986), 59-103. It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and $F(ab')_2$ fragments may be produced recombinantly or by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In one embodiment, an antibody of the invention comprises at least one CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an $IgG_1$ human constant domain, see, e.g., international applications WO 02/060955 and WO 02/096948A2. This vector is engineered to delete the CH2 domain and provide a synthetic vector expressing a domain deleted $IgG_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase HTT localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to HTT. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind HTT and/or mutated and/or aggregated HTT species and/or fragments thereof).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of HTT and/or mutated and/or aggregated HTT species and/or fragments thereof) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single-stranded and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes. DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In this context, the present invention also relates to a polynucleotide encoding at least the binding domain or variable region of an immunoglobulin chain of the antibody of the present invention. In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90%, or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90%, or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 1.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90%, or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90%, or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 1.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 1.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90%, or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-HTT antibody and/or antibody recognizing a polyP-region in the HTT and/or mutated and/or aggregated HTT species and/or fragments thereof as depicted in and Table II. Additionally, in one embodiment the polynucleotide comprises, consists essentially of, or consists of a nucleic acid having a polynucleotide sequence of the $V_H$ or $V_L$ region of an anti-HTT antibody and/or antibody recognizing the P-rich-region in the HTT and/or mutated and/or aggregated HTT species and/or fragments thereof as depicted in and Table III and/or further recognizing the C-terminal region in the HTT and/or mutated and/or aggregated HTT species and/or fragments thereof as depicted in and Table IV and/or further recognizing the Q/P-rich region of HTT and/or mutated and/or aggregated HTT species and/or fragments thereof as depicted in Table VII. In addition, in one embodiment the polynucleotide comprises, consists essentially of, or consists of a nucleic acid having a polynucleotide sequence of the $V_H$ or $V_L$ region of an anti-HTT antibody and/or antibody recognizing the HTT and/or mutated and/or aggregated HTT species and/or fragments thereof as depicted in and Table V. Furthermore, in one embodiment the polynucleotide comprises, consists essentially of, or consists of a nucleic acid having a polynucleotide sequence of the $V_H$ or $V_L$ region of an anti-HTT antibody and/or antibody recognizing the N-terminal region in the HTT and/or mutated and/or aggregated HTT species and/or fragments thereof as depicted in and Table VI. In addition, in one embodiment the polynucleotide comprises, consists essentially of, or consists of a nucleic acid having a polynucleotide sequence of the $V_H$ or $V_L$ region of an anti-HTT antibody and/or antibody recognizing the HTT and/or mutated and/or aggregated HTT species and/or fragments thereof as depicted in and Table V. Additionally or alternatively, in one embodiment the polynucleotide comprises, consists essentially of, or consists of a nucleic acid having a polynucleotide sequence of the $V_H$ or $V_L$ region of an anti-HTT antibody and/or antibody as depicted in and Table VIII.

In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-HTT antibody and/or fragments thereof as depicted in Table II, III, IV, V, VI, VII or VIII.

TABLE II

Nucleotide sequences of the $V_H$ and $V_L$ region of antibodies recognizing an epitope of a polyP-region of HTT, i.e exon 1 in aggregated form.

| Antibody | Nucleotide sequences of variable heavy ($V_H$) and variable light ($V_L$) chains |
|---|---|
| NI-302.33C11-$V_H$ | GAGGTGCAGCTGGTGGAGTCTGGGGGAGGCGTTGTCCAGCCTGGGAACTCC CTGAGACTCTCCTGTGCAGCGTCTGGATTCAGGTTCAGTGACTTTGGCATGC ACTGGGTCCGCCAGGCTCCAGGCAAGGGACTGGAGTGGCTGGCACTTATAT GGTATGATGGAGGGTATAAGTACTATGCAGACTCCGTGAAGGGCCGATTCA CCATCTCCAGAGACAATTCCAAGAATACGATGTTTCTACAAATGAACAGCCT GAGAGCCGAGGACACGGCTGTTTATTACTGTGCGACCCACCTAGAATATTGC AGTAGAACCACCTGCTATCTCGGCCACTGGGGCCAGGGAACCCTGGTCACC GTCTCCTCG SEQ ID NO: 1 |
| NI-302.33C11-$V_K$ | GACATCCAGTTGACCCAGTCTCCGTCCTTCCTATCTGCGTCTGTGGGAGACA CAGTCACCTTCACTTGCCGGGCCAGTCAGGGCATTAGCGATTATTTAGCCTG GTTTCAGCAGAAACCAGGGATTGCCCCTAAGCTCCTGATCTATGCTGCGTCC ACTTTGCAAACCGGGGTCCCATCAAGGTTCAGCGGCAGTGGATCTGGGACA GAATTCACTCTCACAATCCGCAGCCTGCAGTCTGAAGATTTTGGAACTTATT ACTGTCAGCAGCTTAAAACTTACCCGTACACTTTTGGCCAGGGGACCAAGGT GGAAATCAAA SEQ ID NO: 3 |
| NI-302.74C11-$V_H$ | GAGGTGCAGCTGGTGCAGTCTGGGACTGAGGTGCAGAAGCCTGGGGCCTCA GTAAAAGTCTCCTGCAAGGCTTCTGGATACAGTTTCACCGGCTACTTTTTGC ACTGGGTACGACAGGCCCCTGGACAAGGGCTTGAGTGGATGGGGTGGATCA ACCCTAACAGTGGTGACACAAACTATGCAGAGAAGTTTCGGGGCAGAATCA TCATGACCAGGGACACGTCTGTCAGCACAGCCCACATGGAGTTGAGCAGCC TGAGATTTGACGACACGGCCCTATATTACTGTACGAGAGAGGCCCCTGACCC GGGCGCTGAGACGGACGTCTGGGGCCAAGGGACCACGGTCACCGTCTCCTC G SEQ ID NO: 25 |
| NI-302.74C11-$V_L$ | CAGTCTGTGCTGACTCAGCCACCCTCGGTGTCAGTGTCCCCAGGACAGACGG CCAGGATCACCTGCTCTGGAGATGCAGTGCCAAAGCAGTATATTTATTGGTA CCAGCAGAAGCCAGGCCAGGCCCCTATTCTGGTGATATATAAAGACACTCA GAGGCCTTCAGGGATCCCTGAGCGATTCTCTGGCTCCAACTCAGGGACAACA GTCACGTTGACCATAACTGGCGTCCAGGCAGACGACGAGGGTGACTATTAC TGTCAATCAGCAGACAGTAGTGCTACTTGGGTGTTCGGCGGAGGGACCAAA TTGACCGTCCTA SEQ ID NO: 27 |
| NI-302.15F9-$V_H$ | GAGGTGCAGCTGGTGGAGTCTGGGGGAGGCCTGGTCACGCCGGGGGGGTCC CTGAGACTCTCGTGTGAGGCCTCTGGATTTCTCTTCAAGAATTCTAGCATGA ACTGGGTCCGTCAGACTCCGGGGAAGGGGCTGGAGTGGGTCTCGTCCATTG ACACTTCTGCTACAAATTATAAGTATTATGCAGACTCTGTGAAGGGCCGATT TACCATCTCCAGGGATGACGCCACCAACTCTCTCTATCTGCAAATGAATAGC |

TABLE II-continued

Nucleotide sequences of the $V_H$ and $V_L$ region of antibodies recognizing an epitope of a polyP-region of HTT, i.e exon 1 in aggregated form.

| Antibody | Nucleotide sequences of variable heavy ($V_H$) and variable light ($V_L$) chains |
|---|---|
|  | CTGCGAGCCGACGACACGGCTACTTATTACTGTGCGCGAGGTTATTATACCC<br>CCCGGGACTTTGACTACTGGGGCCAGGGCACCCTGGTCACCGTCTCCTCG<br>SEQ ID NO: 29 |
| NI-302.15F9-$V_K$ | GATGTTGTGATGACTCAGTCTCCACAGACCCTGTCCGTCAGCCTTGGACAGG<br>CGGCCTCCATCTCCTGCAGGTCGAGTCAAAGCCTCTTGTATCGTGATAACAA<br>CACATACTTGAATTGGTTTCACCAGAGGCCAGGCCAATCTCCAAGGCGCCTC<br>ATTTATAGGGCTTCTGACCGGGACTCTGGGGTCCCAGACAGATTCAGCGGCG<br>GTGGGTCAGGCACTGATTTCACATTGAAAATCAGTGGAGTGGAGGCTGAAG<br>ATGTTGGCACTTATTACTGCATGCAAGGAACACACTGGCCTCGGACGTTCGG<br>CCAAGGGACCAAGGTGGAGATCAAA SEQ ID NO: 31 |
| NI-302.39G12-$V_H$ | GAGGTGCAGCTGGTGCAGTCTGGGGGAGGCTTGGTCCACCCTTGGGGGTCC<br>CTGAGACTCTCCTGTGCAGCCTCTGGATTCAGCGTCTCTAATTACGCCATAA<br>CTTGGGTCCGCCGGGCTCCAGGGAAGGGGCTGCAATATATTTCAGTAATTTA<br>TCGTGATGGCAGGACATACTACGGAGACTCCGTGAGGGGCCGCTTCACCAT<br>CTCTAGGGACGATTCCAAGAACACTCTCTATCTTCAAATGAACAGCCTGAGA<br>TTTGAGGACACGGCTGTGTATTACTGTGCGAGAGCGCACGGCCAATATTACT<br>ATGGTGTGGACGTCTGGGGCCAAGGGACCACGGTCACCGTCTCCTCG<br>SEQ ID NO: 33 |
| NI-302.39G12-$V_K$ | GATGTTGTGATGACTCAGTCTCCACTCTCCCTGTCCGTCAGCCCTGGAGAGC<br>CGGCCTCCATCTCCTGCAGGTCTAGTCAGAGCCTCCTACATAGTAATGGATA<br>CAACTATTTGGATTGGTACCGGCAGAAACCAGGGCAGTCTCCACAGCTCCTG<br>ATCTATTTGAGTTCTAATCGGCCCTCCGGGGTCCCTGATAGGTTCAGTGCCA<br>GTGGATCAGGCACAGAGTTCACACTGCAAATCAGCAGAGTGGAGGCTGAGG<br>ATGTTGGGGTTTATTACTGCATGCAATCTCTGCAAACGTTCACTTTCGGCGG<br>AGGGACCAAAGTGGATATCAAA SEQ ID NO: 35 |
| NI-302.11A4-$V_H$ | GAGGTGCAGCTGGTGGAGTCTGGAGGAGGCTTGATCCAGCCGGGGGGGTCC<br>CTGAGACTCTCCTGTGCAGCCTCTGGGTTCCCCGTCAGTAGCAGTTACATGA<br>GCTGGGTCCGCCAGGCTCCAGGAGAGGGGCTGGAGTGGGTCTCAGTTCTTTA<br>TAGAGACGGTGACACATACTACGCAGACTCCGTGCAGGGCCGATTCACCAT<br>CTCCAGAGACAATTCCCAGAACACGTTCTATCTTCAAATGAACAGCCTGAAA<br>GCCGAGGACACGGCCGTGTATTACTGTGCGGGTGATAGAAGGTCGTCACAC<br>TACTATTACGGTATGGACGTCTGGGGCCAGGGGACCACGGTCACCGTCTCCT<br>CG SEQ ID NO: 37 |
| NI-302.11A4-$V_K$ | GAAATTGTGATGACACAGTCTCCAGGCACCCTGTCTTTGTCTCCAGGAGAAA<br>GAGCCACCCTCTCCTGCAGGGCCAGTCAGAGTGTTAGCAGCAGCTACTTCGC<br>CTGGTACCAACAAAAACCTGGCCAGGCTCCCAGGCTCCTCATCTATGGTACG<br>TCCCGCAGGGCCACTGCCATCCCAGACAGGTTCAGTGGCAGTGGGTCTGGG<br>ACAGACTTCACTCTCACCATCAGCAGACTGGAGCCTGAAGATTTTGCAGTGT<br>ATTACTGTCAACAGTATGGTAGCTCGTGGACGTTCGGCCCAGGGACCAAGGT<br>GGAGATCAAA SEQ ID NO: 39 |
| NI-302.22H9-$V_H$ | GAGGTGCAGCTGGTGGAGTCTGGGGGAGGCTTGGTCCACCCTTGGGGGTCC<br>CTGAGAGTCTCCTGTGCAGCCTCTGGATTCAGCGTCTCTAATTACGCCATAA<br>CTTGGGTCCGCCAGGCTCCAGGGAAGGGGCTGGAATATATTTCAGTGATTTA<br>TCGTGATGGCAGGACATACTACGGAGACTCCGTGAGGGGCCGCTTCACCAT<br>CTCTAGGGACGATTCCAAGAACACTATCTATCTTCAAATGAACAGCCTGAGA<br>TTTGAGGACACGGCTGTGTATTACTGTGCGAGAGCGCACGGCCAATATTATT<br>ATGGTGTGGACGTCTGGGGCCAAGGGACCACGGTCACCGTCTCCTCG<br>SEQ ID NO 41: |
| NI-302.22H9-$V_K$ | GATGTTGTGATGACTCAGTCTCCACTCTCCCTGTCCGTCAGCCCTGGAGAGC<br>CGGCCTCCATCTCCTGCAGGTCTAGTCAGAGCCTCCTACATAGTAATGGATA<br>CAACTATTTGGATTGGTACCGGCAGAAACCAGGGCAGTCTCCACAACTCCTG<br>ATCTATTTGAATTCTAATCGGGCCTCCGGGGTCCCTGATAGGTTCAGTGGCA<br>GTGGATCAGGCACAGAGTTCACACTGACAATCAGCAGAGTGGAGGCTGAGG<br>ATGTTGGGGTTTATTACTGCATGCAATCTCTGCAAACGTTCACTTTCGGCGG<br>AGGGACCAAGGTGGAGATCAAA SEQ ID NO: 43 |
| NI-302.44D7-$V_H$ | GAGGTGCAGCTGGTGCAGTCTGGGGGAGGCTTGGTACAGCCTGGGGGGTCC<br>CTGAGACTCTCCTGTGCAGCCTCTGGATTCACCTTTAGCAGCTATGCCATGA<br>GTTGGGTCCGCCAGGCTCCAGGGAAGGGGCTGGAGTGGGTCTCAGGTATTG<br>GTTATAGTGGATACTAGCACATATTACGCAGACTCCGTGAAGGGCCGCTTCAC<br>CGTCTCCAGAGACATTTCCAAGAACACGCTGTATCTGCAAATGAATAGCCTG<br>AGGGCCGAGGACACGGCCGTATATTACTGCGCGAAAGGTACCAGGGACTAT<br>TACGGTATGGACGTCTGGGGCCAAGGGACAATGGTCACCGTCTCTTCG<br>SEQ ID NO: 45 |
| NI-302.44D7-$V_K$ | CAGACTGTGGTGACTCAGGAGCCATCGTTCTCAGTGTCCCCTGGAGGGACAG<br>TCACACTCACTTGTGGCTTGAGTTCTGGCTCAGTTTCTACTAGTTACTACCCC |

TABLE II-continued

Nucleotide sequences of the V_H and V_L region of antibodies recognizing an epitope of a polyP-region of HTT, i.e exon 1 in aggregated form.

| Antibody | Nucleotide sequences of variable heavy (V_H) and variable light (V_L) chains |
|---|---|
| | AGCTGGTACCAGCAGACCCCAGGCCGGGCTCCACGCACGCTCATCTACAGC<br>ACAAACACTCGCTCTTCTGGGGTCCCTGATCGCTTCTCTGGCTCCATCCTTGG<br>GAACAAGGCTGCCCTCACCATCACGGGGCCCAGGCAGATGATGAATCTGA<br>TTATTACTGTGTGCTGTTTATGGGTAGTGGCATTGGGGTGTTCGGCGGAGGG<br>ACCAGGCTGACCGTCCTA SEQ ID NO: 47 |
| NI-302.37C12-V_H | GAGGTGCAGCTGGTGGAGTCTGGTGGAGGCTTGGTCCAGCCTGGGGGGTCC<br>CTGAGACTCTCTTGTGTTGCCTCTGCACTCACCGTCACTAACAGCCAAATGA<br>CCTGGGTCCGCCGGGCTCCAGGGAGGGGGTTGGAGTGGGTCTCAGTTATTTA<br>CACCAGTGGTAGTGCATACTACGCAGACTCCGTGAAGGGCAGATTCACCAT<br>CTCCAGAGACAATTCCAAGAACACAGTGTTTCTTCAAATGAACAGCCTGAG<br>AGTCGAAGACACGGCTGTGTATTACTGTGCGAAAGGCCCCATCAGCCTATTAT<br>TACGGTTTGGACCTTTGGGGCCAAGGGACCACGGTCACCGTCTCCTCG<br>SEQ ID NO: 49 |
| NI-302.37C12-V_K | GATATTGTGATGACTCAATCACCACTCTCCCTGCCCGTCACCCCTGGAGAGC<br>CGGCCTCCATCTCCTGCAGGTCTAGTCAGAGCCTCCTGCATAGTAATGGATA<br>CAACTATTTGGATTGGTACCTGCAGAAGCCGGGGCAGTCTCCACAGCTCCTG<br>ATCTATTTGGGTTCTACTCGGGCCTCCGGGGTCCCTGACAGGTTCAGTGGCA<br>GTGGATCAGGCACAGATTTTACACTGAAGATCAGCAGAGTGGAGGCTGAGG<br>ATGTTGGGGTTTATTACTGCATGCAAGGTCTACAGACGTACACTTTTGGCCA<br>GGGGACCAAGCTGGAGATCAAA SEQ ID NO: 51 |
| NI-302.55D8-V_H | CAGGTGCAGCTGGTGCAGTCTGGGTCTGAGGTGAAGAAGCCTGGGGCCTCA<br>GTGAAGGTCTCCTGCAAGGCTTCTGGATACACCTTCACCGACTACTATATAC<br>ACTGGGTGCGACAGGCCCCTGGACAAGGGCTTGAGTGGATGGGACGGATCA<br>ACCCTAACAATGGTGGCACAAACTATGCACAGAACTTTCAGGGCTGGGTCA<br>CCATGACCAGGGACACGTCCATCAGCACAGCCTACATGGAGCTCAGCAGAC<br>TGAGATCTGACGACACGGCCGTCTATTACTGTGCGAGAGTGGGGGCGAGC<br>TGCTACGAGAAGGCGGCTATCACTACTACATGGACGTCTGGGGCAAGGGGA<br>CCACGGTCACCGTCTCCTCG SEQ ID NO: 53 |
| NI-302.55D8-V_L | CAGTCTGTGTTGACGCAGCCGCCCTCAGTGTCTGGGGCCCCAGGGCAGAGG<br>GTCACCATCTCCTGCACTGGGAACAGCTCCAACATCGGGGCAGGTTATGATG<br>TACACTGGTACCAGCAGCTTCCAGGAACAGCCCCCAAACTCCTCATCTTTGA<br>TAATACCAATCGGCCCTCAGGGGTCCCTGACCGATTCTCTGCTCCAAGTCT<br>GGCACCTCAGCCTCCCTGGCCATCACTGGGCTCCAGGCTGAGGATGAGGCTA<br>ATTATCACTGCCAGTCCTATGACAACAGCCTGAGTGGTTCTTGGGTGTTCGG<br>CGGAGGGACCAAGCTGACCGTCCTA SEQ ID NO: 55 |
| NI-302.7A8-V_H | GAGGTGCAGCTGGTGGAGTCTGGGGGAGGCTCGGTCCAGCCTGGGGGGTCC<br>CTGAGACTCTCCTGTGTAGCCTCTGGATTCATATTTAGAAACAGTTGGATGA<br>CCTGGGTCCGCCAGGATCCAGGGAAGGGGCTGGAGTGGGTGGCCAACATAA<br>AGGAAGATGGAAGTCGGACATACTATGTGGACTCTGTGAAGGGCCGATTCA<br>CCATCTCCAGAGACAACGCCAAGAACTCACTGTATCTGCAGATGAACAGCC<br>TGAGAGCCGAGGACACGGCTGTATATTACTGTGCGAGAGGAGATTATAATT<br>CGGGCATCTATTACTTTCCCGGGGACTACTGGGGCCAGGGCACCCTGGTCAC<br>CGTCTCCTCG SEQ ID NO: 57 |
| NI-302.7A8-V_K | GATGTTGTGATGACTCAGTCTCCACTCTCCCTGCCCGTCACCCTTGGACAGC<br>CGGCCTCCATCTCCTGTAGGTCTAGTCAAAGCCTCGTATACAGTGATGGAAA<br>CACCTACTTGAATTGGTTTCAGCAGAGGCCAGGCCAGTCTCCAAGGCGCCTC<br>ATTTATAAGGTTTCTAACCGGGACTCTGGGGTCCCAGACAGATTCAGCGGCA<br>GTGGGTCAGGCACTGATTTCACACTGAGAATCAGCAGGGTGGAGGCTGAGG<br>ATGTTGGCATTTATTACTGCATGCAAGGTACACACTGGCCTGGGACGTTCGG<br>CCAAGGGACCAAGGTGGAGATCAAA SEQ ID NO: 59 |
| NI-302.78H12-V_H | CAGGTGCAGCTGCAGGAGTCGGGCCCAGGACTGGTGAAGCCTTCGGAGACC<br>CTGTCCCTCACCTGTCTTGTCTCTAGTTACTCCATCAGCAATGGTTACTACTG<br>GGGCTGGATTCGGCAGCCCCAGGGAAGGGGCTGGAGTGGATTGGGAGTAT<br>CTATCATAATGGGAACACCTATTACAACCCGTCCCTCAAGAGTCGAGTCATC<br>ATTTCAGTAGACACGTCCAAGAACCAGTTCTCCCTGAAGTTGAGGTCTGTGA<br>CCGCCGCAGACACGGCCGTGTACTACTGTGCGATGCCAAGTGCCACCTATTA<br>TTATGGTTCGGGGACTCAATTCCATGCGTTTGATGTCTGGGGCCAAGGGACC<br>ACGGTCACCGTCTCCTCG SEQ ID NO: 61 |
| NI-302.78H12-V_L | CAGTCTGCCCTGACTCAGCCTCGCTCAGTGTCCGGGTCTCCTGGACAGTCAG<br>TCACCATCTCCTGCACTGGAACCAGCAGAGATGTTGGTAATTATAACTATGT<br>CTCCTGGTACCAACAACACCCAGGCGAAGTCCCCAAACTCATAATTTATGAT<br>GTCAGTGAGCGGCCCTCAGGGGTCCCTGATCGCTTCTCTGGCTCCAAGTCTG<br>GCAACACGGCCTCGCTGACCATCTCTGGGCTCCAGGCTGAGGATGAGGCTG<br>ACTATTACTGCTGCTCATATGCTGGCAGTTACACCTTCGAGGTATTTGGCGG<br>AGGGACCAAGCTGACCGTCCTA SEQ ID NO: 63 |

TABLE II-continued

Nucleotide sequences of the V_H and V_L region of antibodies recognizing an epitope of a polyP-region of HTT, i.e exon 1 in aggregated form.

| Antibody | Nucleotide sequences of variable heavy (V_H) and variable light (V_L) chains |
| --- | --- |
| NI-302.71F6-V_H | CAGGTGCAGCTACAGCAGTGGGGCGCAGGACTATTGAAGCCTTCGGAGACC CTGTCCCTCACGTGCGCTGTCTATGGTGGGTCCCTCAGTGGTTACTACTGGA GCTGGATCCGCCAGCCCCCAGGGAAGGGGCTGGAGTGGATAGGGGAAGTCA ATCATAGTGGAGGCACCAACCTCAATTCGTCCCTCAAGAGTCGAGTCATCAT TTCAGTAGACAAGTCCAAGAAGCAGTTCTCCCTGAAACTGAGCTCTGTGACC GCCGCGGACACGGCTATGTACTTCTGTGCGAGAGGATACAGCTATGACCCA AAATACTACTTTGACTCCTGGAGCCAGGGCACCCTGGTCACCGTCTCCTCG SEQ ID NO: 65 |
| NI-302.71F6-V_L | CAGTCTGCCCTGACTCAGCCTGCCTCCGTGTCTGGGTCTCCTGGACAGGCGA TCACCATCTCCTGCACTGGAACCAGTAGTGATATTGGGAGTTATGATTTTGT CTCCTGGTACCAGCAGGACCCAGGCAAAGCCCCCAAAGTCATTATTTATGGG GTCAATAAGCGGCCCTCAGGGGTTTCTAATCGCTTCTCTGGCTCCAAGTCTG GCAACACGGCCTCCCTGACAATCTCTGGACTCCAGGCTGACGACGAGGCTG ATTATTACTGCTGCTCATATGCTGGTAGTACCACTTGGGTGTTCGGCGGAGG GACCAAACTGACCGTCCTA SEQ ID NO: 67 |
| NI-302.11H6-V_H | GAGGTGCAGCTGGTGCAGTCTGGAGCTGTGATGAAGAAGCCTGGAGACTCA GTGAGGGTCTCCTGCAGGGCTTCTACTTACAGCTTTTCCACCTATAGTTTCAC CTGGGTGCGACAGGTCCCTGGACAAGGCCTTGAGTGGATGGGATGGATCAG CGCTTATAATGGTCACACAAACTATGTAGACAGCTTCCAGGGCAGACTCACG TTGACCACAGACACATCCGCGAGTACAGCGTACATGGAACTGAGGAGCCTC AGATCTGACGACACGGCCATCTATTATTGTGCGGCTGTAGACACCACTTACT ACTATTACGGCATGGACGTCTGGGGCCAAGGCACCCTGGTCACCGTCTCCTC G SEQ ID NO: 69 |
| NI-302.11H6-V_L | CAGACTGTGGTGACTCAGGAGCCAACGTTCTCAGTGTCCCCTGGAGGGACA GTCACACTCACTTGTGCCTTGAGGTTTGGCTCAGTCTCTAGTAGCTACTATCC CAGCTGGTTCCAGCAGACCCCAGGCCAGGCTCCACGCACGCTCATCTACAGC ACAAACACCCGCTCTTCGGGGGTCCCTGCTCGATTCTCTGGCTCCATTCTTGG GAACAAAGCTGCCCTCACCATCGCGGGGGCCCAGGCAAATGATGAGGCTGA CTATTACTGTGCTGTATATGGGTAGTGAATCGGGGTGGTGTTCGGCGGAGGG ACCAAGTTGACCGTCCTA SEQ ID NO: 71 |
| NI-302.3D8-V_H | GAGGTGCAGCTGGTGCAGTCTGGGGGAGGCTTGGTACAGCCTGGGGGGTCC CTGAGACTCTCTTGTGAAGCCTCCGGATTCATCTTTAAAACCTATGCCATGA GCTGGGTCCGCCAGCTTCCCGGGAGGGGGCTGGAATGGGTCTCAGCTATAA GTGCCACTGGTGAAGCACCTTCTACGCAGAGTCCGTGAAGGGCCGGCTCA CCATTTCCAGAGACACTGCCAAGAATACAGTGTATCTGCAAATGAACAACCT GAGAGCCGAAGACACGGCCATGTATTACTGTGCGAAAGGGTCGACTGCGGT ATATCTCTTTGACTCCTGGGGCCAGGGAACCCTGGTCACCGTCTCCTCG SEQ ID NO: 73 |
| NI-302.3D8-V_K | GACATCCAGATGACCCAGTCTCCGTCCTCACTGTCTGCATCTGTAGGGGACA GAGTCACCCTCACTTGTCGGGCGAGTCAGGACATCAGAAATTTCTTGGCCTG GATTCAGCAGAAGCCAGGGAAACCCCCTAAGTCCCTGATCTATGCTGCGTCC ACTTTGCAAAGTGGGGTCCCATCACGATTCAGCGGCAGTGGATCCGGGACA GATTTCACTCTCACCATCAGCAGCCTGCACCCTGAAGATTTTGCTACTTATTA CTGCCAGCAGTTTTATAATTACCCTCCGACGTTCGGCCAAGGGACCAAGGTG GAGATCAAA SEQ ID NO: 75 |
| NI-302.18A1-V_H | CAGCTGCAGCTGCAGGAGTCGGGCCCAGGACTAGTGAAGCCTTCGGAGGCC CTGTCCCTCACCTGCACTGTCTCTGGTGGCTCCATCACTACTGATTATTACTA TTGGGGCTGGATCCGCCAGTCCCCAGGCAAGGGACTAGAGTGGGTTGGGAC AATATACTTTGGTGGGGCCACCTACTACAATCCGTCCCTCAGGAACCGGGTC TCGATATCTGTGGACACGTCCAACACTCGCCTCTCCCTGAGACTTATCTCTCT GAGCGCCGCTGACACGGCCGTCTATTATTGTGCGAGAGTGGGCTACTTGGAT AGGAGTGGTCTTCTTGTGGGCCAGGGCACCCTGGTCACCGTCTCCTCG SEQ ID NO: 77 |
| NI-302.18A1-V_K | GAAATTGTGCTGACGCAGTCTCCACTCTCCGTGCCCGTCACCCCCGGAGAGC CGGCCTCCATCTCCTGCAGGTCTAGTCAGAGCCTCCTGCATAATAATGGATA CAACTATTTGGATTGGTACCTGAAGAAGCCTGGGCAGTCTCCACAACTCCTG ATCTATTTGGGCTCTACTCGGGCCTCCGGGTCCCTGACAGGTTCAGTGCCA GTGGATCAGGCACAGACTTTACACTGGAAATCAGCAGAGTGGAGGCTGAAG ATGTTGGCGTTTACTACTGCATGCAAGCTCTGCAGACTCCTCCGACTTTCGG CAGAGGGACCAAGGTGGAGATCAAA SEQ ID NO: 79 |
| NI-302.52C9-V_H | GAGGTGCAGCTGGTGCAGTCTGGGGGAGGCTTGGTCCAACCTGGGGGGTCC CTGAGACTCTCCTGTGCAGGCTCTGGATTCACCGTCAGTGACACCTACATGA GTTGGGTCCGCCAGGCTCCAGGGAAGGGGCTGGAGTGGGTCTCAGGTATTC ATGCCGGTGGTGAAACATATTACGCAGACTCCGTGAAGGGCCGATTCACCA |

TABLE II-continued

Nucleotide sequences of the $V_H$ and $V_L$ region of antibodies recognizing an epitope of a polyP-region of HTT, i.e exon 1 in aggregated form.

| Antibody | Nucleotide sequences of variable heavy ($V_H$) and variable light ($V_L$) chains |
|---|---|
| | TCTCCAGAGACAACTCCAAGAACACGCTGTATCTTCAAATGAATAGGCTGAC<br>ACCTGAGGACACGGCTGTCTTTTATTGTGCGAGACACTACTACGGTAATGAC<br>GACGACACTGATTATTGGGGCCAGGGAACCCTGGTCACCGTCTCCTCG<br>SEQ ID NO: 85 |
| NI-302.52C9-$V_K$ | GATGTTGTGATGACTCAGTCTCCACTCTCCCTGCCCGTCACCCCTGGAGAGC<br>CGGCCTCCATCTCCTGCAGGTCTAGTCAGAGCCTCCTGCATAGTAATGGATA<br>CAACTATTTGGATTGGTACGTGCAGAAGCCAGGGCAGTCTCCACAGCTCCTC<br>ATCTATTTGGGTTCTACTCGGGCCTCCGGGGTCCCTGACAGATTCAGTGGCA<br>GTGGATCAGGCACAGATTTTACACTGAAAATCAGCAGAGTGGAGGCTGAGG<br>ATGTTGGGGTTTATTACTGCTTACAAGCTCAACAAATTCCGTGGACGTTCGG<br>CCAAGGGACCAAGGTGGAGATCAAA SEQ ID NO: 87 |
| NI-302.46C9-$V_H$ | CAGGTGCAGCTGCAGGAGTCGGGCCCAGGACTGGTAAAGCCTTCACAGACC<br>CTGTCCCTCACCTGCACTGTTTCTGGTGCCTCCGTCAGCAGTGGTGCCTACTA<br>CTGGAGTTGGATCCGGCAGCCCGCCGGGAAGCGACTGGAGTGGATTGGGCG<br>TGTCTATCCCACTTGGAGCACCAACTACAACCCCTCCCTCGAGAGTCGAGTC<br>ACCATATCGTTAGACACGTCCAACAACCAGTTCTCCCTGAAGCTGACCTCTT<br>TGACTGCCGCAGACACGGCCGTTTATTACTGTGCGAGAGAGGCTCCTGGTGA<br>CTACGATGCTGCGCCCCTAGCCTACTGGGGCCAGGGCACCCTGGTCACCGTC<br>TCCTCG SEQ ID NO: 89 |
| NI-302.46C9-$V_K$ | GACATCCAGATGACCCAGTCTCCATCCTCCCTGTCTGCATCTGTTGGAGACA<br>GAGTCACCATCACTTGCCGGGCAAGTCAGTACATTAGCCACTATTTAAATTG<br>GTATCGGCAGAAACCAGGGAAAGCCCCTCAGCTCGTAATCTATGCTGCATCC<br>AGTTTGCAAAGTGAGGTCCCATCAAGGTTCAGTGGGAGTGGATCTGGGCCA<br>GAGTTCACTCTCACCATCAGCAGTCTGCAACCTGAAGATTTTGCAACTTATT<br>ACTGTCAACAGAGTTACACTACCCCTCGAACTTTTGGCCAGGGGACCAAGCT<br>GGAGATCAAA SEQ ID NO: 91 |

TABLE III

Nucleotide sequences of the $V_H$ and $V_L$ region of antibodies recognizing an epitope of the P-rich region of HTT, i.e exon 1 in aggregated form.

| Antibody | Nucleotide sequences of variable heavy ($V_H$) and variable light ($V_L$) chains |
|---|---|
| NI-302.63F3-$V_H$ | CAGGTGCAGCTGGTGCAATCTGGGTCTGCGTTCAAGAAGCCTGGGACCTCA<br>GTGAAAGTTTCCTGCAAGGCCTCTGGATACACCTTCGAGACCCGTTCTATGA<br>ACTGGGTGCGACAGGCCCCTGGACAAGGGCTTGAATACATGGGATGGATCA<br>ACACCAACACTGGCAACCGCACGTATGTCCAGGCCTTCAGAGGACGATTTGT<br>CTTCTCCTTGGACACCTCTGTCAGCACGGCATATCTGCAGATCAGCAACTTA<br>AAGACTGAGGACACTGCCGTGTATTACTGTGCGAGAGGGCAGGTGGGGGA<br>TATTGGTTCGACTCCTGGGGCCAGGGAACCCTGGTCACCGTCTCCTCG<br>SEQ ID NO: 5 |
| NI-302.63F3-$V_K$ | GACATCCAGATGACCCAGTCTCCAGACTCCCTGGCTGTGTCTCTGGGCGAGA<br>GGGCCACCATCAACTGCAAGTCCAATCAGAGTCTTTTCTACAGTTCCAACAA<br>TAACAACTACTTAGCTTGGTACCAGCACAAATCCGGACAGCCTCCTAAGCTG<br>CTCGTTTACTGGGGATCTACCCGGGAATCCGGGGTCCCTGACCGCTTCAGTG<br>GCAGCGGGTCTGGGACTGACTTCACTCTCACCATCAGTAGCCTGCAGGCTGA<br>GGATGTTGCAATTTATTACTGTCACCAATATTATCATAATCCGTACACTTTTG<br>GCCAGGGGACCAAGCTGGAGATCAAA SEQ ID NO: 7 |
| NI-302.31F11-$V_H$ | GAGGTGCAGCTGGTGGAGTCCGAGGAGGCTTGATCCAGCCGGGGGGGTCC<br>CTGAGACTCTCCTGTGCAGCCTCTGGGTTCACCGTCAGCAGCACCTACATGA<br>GTTGGGTCCGCCAGGCTCCAGGGAAGGGGCTTGAGTGCGTCTCAGTTATTTT<br>TAGTGGCGCTGACACATATTACGCAGACTCCGTGAAGGGCCGATTCACCGTC<br>TCCAGAGACAATTCCAAGAACACACTGTTTCTTCAGATGAACAGCCTGAGA<br>GTCGAGGACACGGCCACATATTACTGTGTGAGACATTATTATGGTTCAGACC<br>TTCCATCTGACTTCTGGGGCCAGGGCACCCTGGTCACCGTCTCCTCG<br>SEQ ID NO: 13 |

TABLE III-continued

Nucleotide sequences of the $V_H$ and $V_L$ region of antibodies recognizing an epitope of the P-rich region of HTT, i.e exon 1 in aggregated form.

| Antibody | Nucleotide sequences of variable heavy ($V_H$) and variable light ($V_L$) chains |
|---|---|
| NI-302.31F11-$V_K$ | GATGTTGTGATGACTCAGTCTCCACTCTCCCTGCCCGTCGCCCCTGGAGAGC CGGCCTCCATCTCCTGCAGGTCTAGTCAGAGCCTCCTATACAGTAATGGATA CAACTATTTGGATTGGTACCTGCAGAAGCCAGGGAAGCCTCCACAGCTCCTG GTCTATTTGGGTTCTGATCGGGCCTCCGGGGTCCCTGACAGGTTCAGTGGCA GTGGATCAGGCAAAGATTTTACACTGAACATCAGCAGAGTGGAGGCTGAGG ATGTTGGGGTTTATTACTGCATGCAAGGTCTACAAAGTCCGTGGACGTTCGG CCAAGGGACCAAGCTGGAGATCAAA SEQ ID NO: 15 |
| NI-302.2A2-$V_H$ | GAGGTGCAGCTGGTGGAGTCTGGGGGAGGCTTGGTCCAGCCTGGGGGGTCC CTGAGACTCTCCTGTGCAGCCTCTGGATTCACCTTTAGTACCTATTGGATGA ACTGGGTCCGCCAGGCTCCAGGGAAGGGGCTGGAGTGGGTGGCCAACATAA AACCAGATGGAAGTGACAAATACTATGTGGACTCTGTGAAGGGCCGATTCA CCATCTCCAGAGACAACGCCAAGAACTCACTGTATCTGCAAATGAACAGCC TGAGAGACGAGGACACGGCTGTGTATTACTGTGCGAGAGGGACGGCAGTG GCTGGAACGTCTACTGGGGCCAGGGAACCCTGGTCACCGTCTCCTCG SEQ ID NO: 17 |
| NI-302.2A2-$V_K$ | GACATCCAGATGACCCAGTCTCCAGACTCCCTGGCTGTGTCTCTGGGCGAGA GGGCCACCATCAACTGCAAGTCCAGCCAGAGTCTTTTATACACCTCCAAAAA TAAGGACAGTAAGAACTACTTAGGTTGGTACCAGCAGAAACCAGGACAGCC TCCTAAGCTGCTCATTTACTGGGCATCTACCCGGGAATCCGGGGTCCCTGAC CGATTCAGTGGCAGCGGGTCTGGGACAGATTTCACTCTCACCATCAGCAGCC TGCAGGCTGAGGATGTGGCAGTTTATTACTGTCAGCAGTATTATACTACTCC TCAGTTCGGCGGAGGGACCAAGGTGGAGATCAAA SEQ ID NO: 19 |
| NI-302.15D3-$V_H$ | GAGGTGCAGCTGGTGGAGTCTGGGGGAGACTTAGTTCAGCCTGGGGGGTCC CTAAGACTCTCCTGTGCAGCCTCTGGATTCACCTTCAGTAGCTACTGGATGC ACTGGGTCCGCCAAGCTCCAGGGAAGGGTCTGGTGTGGGTCTCACGTATTAG TAATGATGGCAGTAGCAAAACCTACGCGGACTCCGTGAAGGGCCGATTCAC CATCTCCAGAGACAACGCCAAAAACACGCTGTATCTGCAAATGAACAGTCT GAGAGCCGAGGACACGGCTGTGTATTACTGTGCAATACTTGGCGGATATTGT AGTAGTACCAGTTGTCGTCCCTTTGACAACTGGGGCCAGGGAACCCTGGTCA CCGTCTCCTCG SEQ ID NO: 135 |
| NI-302.15D3-$V_L$ | CAGTCTGCCCTGACTCAGCCTGCCTCCGTGTCTGGGTCTCCTGGACAGTCGA TCACCATCTCCTGCACTGGAACCAGCAGTGACGTTGGTGTTTATAACTATGT CTCCTGGTACCAACAACACCCAGGCAAAGCCCCCAAACTCATGATTTTTGAT GTCAGTAATCGGCCCTCAGGGATTTCTAATCGCTTCTCTGGCTCCAAGTCTG GCAACACGGCCTCCCTGACCATCTCTGGGCTCCAGGCTGAGGACGAGGCTG ATTATTACTGCAGCTCATATACAAGCAGCGACACTTGGGTGTTCGGCGGAGG GACCAAGCTGACCATCCTA SEQ ID NO: 137 |
| NI-30164E5-$V_H$ | GAGGTGCAGCTGGTGGAGACTGGGGGAGGCTTGGTAAAGCCTGGGGGGTCC CTTAGACTCTCCTGTGCAGCCTCTGGATTCACTTTCGACCAGGCCTGGATGA GCTGGGTCCGCCAGGTTCCAGGGAAGGGGCTGGAGTGGGTTGGCCGGATTA AAACGAAAACTGAGGGTGAAGCAACAGACTACGCAGCGCCCGTGAGAGGC AGATTCACCATCTCAAGAGATGATTCAGAAGACACGGTGTTTCTGCAAATGA ACAGCCTGAAAACCGAGGACACAGCCCTGTATTACTGTACGTCAACGGGAG TCTTAGCAGCAGCTGTCGATGTCTACTGGGGCCAGGGAACCCTGGTCACCGT CTCCTCG SEQ ID NO: 164 |
| NI-30164E5-$V_K$ | GACATCCAGTTGACCCAGTCTCCAGACTCCCTGGCTGTGTCTCTGGGCGAGA GGGCCACCATGACCTGCAAGTCCAGCCAGAGTCTTTTCTACAGTTACAACAA TGAGAACTACTTAGCCTGGTATCAGCAGAGACCAGGACAGCCTCCTAAGTT GCTCATTTACTGGGCATCTACCCGGGAATCGGGGTCCCTGACCGATTCAGT GGCAGCGGGTCTGGGACAGATTTCACTCTCACCATCAGCAGCCTGCAGGCTG AAGATGTGGCAGTTTATTACTGTCAGCAATATTATAGTACTCCTCAGACGTT CGGCCAAGGGACCAAAGTGGATATCAAA SEQ ID NO: 166 |

TABLE IV

Nucleotide sequences of the $V_H$ and $V_L$ region of antibodies recognizing an epitope of the C-terminal region of HTT, i.e exon 1 in aggregated form.

| Antibody | Nucleotide sequences of variable heavy ($V_H$) and variable light ($V_L$) chains |
|---|---|
| NI-302.35C1-$V_H$ | GAGGTGCAGCTGGTGGAGTCTGGGGGAAACTTGGTACAGCCGGGGGGGTCC<br>CTGAGACTCTCCTGTACTGCCTCTGGATTCACCTTTAGTATAACGGCCCTGA<br>GTTGGGTCCGCCAGGCTCCAGAAAAGGGGCCGCAGTGGGTCTCAGCAATCA<br>CTGGAAATGCTTATGGGACATACTACGCAGACTCCGTGAAGGGCCGGTTCA<br>CCATTTCCAGAGACAACGCCAAGAACACACTGTACTTGCAAATGAACGGCC<br>TGAGAGCCGAGGACACGGCCATCTATTACTGTGTGAAAGGAATTGCCTCCG<br>ATAGTAGTGGTTATTCTGCCTTCTGGGGCCCGGGCACCCTGGTCACCGTCTC<br>CTCG SEQ ID NO: 9 |
| NI-302.35C1-$V_K$ | GAAATTGTGCTGACTCAGTCTCCAGCCACCCTGTCTTTGTCTCCAGGGGAAA<br>GAGCCACCCTCTCCTGCAGGGCCAGTCAAAGTGTTGACAACCAGTTTGCCTG<br>GTACCAACAGAAACCTGGCCAGGCTCCCAGGCTCCTCATTTATGATGCATCC<br>AGGAGGGCCCCTGGCATCCCAGACAGGTTCAGTGGCAGTGGGTCTGGGACA<br>GACTTCACTCTCACCATTAGCAGCCTAGAGCCTGAAGATTTCGCAATTTATT<br>ACTGTCAGCATCGTTACACCTGGCTCTACACTTTTGGCCAGGGGACACGACT<br>GGAGATTAAA SEQ ID NO: 11 |
| NI-302 .72F10-$V_H$ | GAGGTGCAGCTGGTGGAGACTGGGGGAGGCTTCGTACAGCCTGGGGGGTCC<br>CTGAGACTCTCCTGTGCAGCCTCTGGATTCAACTTCGGCAGTTATGCCATGA<br>GCTGGGTCCGCCAGGCTCCAGGGAAGGGACTGGAGTGGGTGTCAGATATCA<br>GTGGTATTGGTAGTAACACATACTACGCAGACTCCGTGAAGGGCCGTTTCAC<br>CATTTCCAGAGACAATTCCGACAATACGTTGTACCTGGACATGAGCAGCCTG<br>AGAGCCGAGGACACGGCCAGATATTACTGTGCGAAGGATCGAAAGCGCAGT<br>GGCTGGTACGAACAGTGGGGCCAGGGCACCCTGGTCACCGTCTCCTCG<br>SEQ ID NO: 176 |
| NI-302.72F10-$V_K$ | GAGGTGCAGCTGGTGGAGTCTGGGGGAGGCTTCGTACAGCCTGGGGGGTCC<br>CTGAGACTCTCCTGTGCAGCCTCTGGATTCAACTTCGGCAGTTATGCCATGA<br>GCTGGGTCCGCCAGGCTCCAGGGAAGGGACTGGAGTGGGTGTCAGATATCA<br>GTGGTATTGGTAGTAACACATACTACGCAGACTCCGTGAAGGGCCGTTTCAC<br>CATTTCCAGAGACAATTCCGACAATACGTTGTACCTGGACATGAGCAGCCTG<br>AGAGCCGAGGACACGGCCAGATATTACTGTGCGAAGGATCGAAAGCGCAGT<br>GGCTGGTACGAACAGTGGGGCCAGGGCACCCTGGTCACCGTCTCCTCG<br>SEQ ID NO: 178 |

TABLE V

Nucleotide sequences of the $V_H$ and $V_L$ region of antibodies recognizing HTT species and/or fragments thereof.

| Antibody | Nucleotide sequences of variable heavy ($V_H$) and variable light ($V_L$) chains |
|---|---|
| NI-302.6N9-$V_H$ | GAGGTGCAGCTGGTGGAGTCTGGGGGAGACTTGGTGCAGCCTGGGGGGTCC<br>CTGAGACTCTCCTGTGTAGTCTCTGGATTCACCTTTAGTAGTTATGCCATGAC<br>CTGGGTCCGCCAGGCTCCAGGGAAGGGGCTGGCCTGGGTCTCAACAATTAG<br>TGCTACTGGTGGTAGTACATTCTACACAGACTCCGTGAGGGGCCGGTTCACC<br>ATCTCCCGAGACAATTCCAAGAACACACTGTATCTGCAAATGAATAGCCTGA<br>GAACCGACGACACGGCCATATATTATTGTGTGAAAGATCTATTTGGAGTGGA<br>CACCTCCTACTACGGTATGGACGTCTGGGGCCAAGGGACCACGGTCACCGTC<br>TCCTCG SEQ ID NO: 21 |
| NI-302.6N9-$V_K$ | GAAATTGTGTTGACGCAGTCTCCAGGCACCCTGTCTTTGTCTCCAGGGGAAA<br>GAGCCACCCTCTCCTGCAGGCCCAGTCAGAGTGTCAGCGGCAGGTATGTGG<br>CCTGGTATCAGCAGAAACCTGGCCAGGCTCCCAGGCTCCTCTTCTATGCTGC<br>ATCCAACAGGGCCATTGGCATCCCAGACAGGTTCAGTGGCAGTGGGTCTGG<br>GACAGACTTCACTCTCACCATCAGCAGACTGGAGCCTGAAGATTTTGCAGTG<br>TATTACTGTCAGCACTATGGTGCCTCATCGTACACTTTTGGCCCGGGGACCA<br>AAGTGGATATCAAA SEQ ID NO: 23 |
| NI-302.8F1-$V_H$ | GAGGTGCAGCTGGTGGAGTCTGGGGGAGGCTTGGTGAAGCCGGGGGGGTCC<br>CTTACAATCTCCTGTGCAGCCTCTGGTTTCACCTTCAGTAATGCCTGGATGAA<br>CTGGGTCCGCCAGGCTCCAGGTAAGGGGCTGGAGTGGGTCGGCCATATTAG<br>AACGCAAGCTGAAGGAGGGACATCAGACTATGTGCACCCGTGAAAGGCAG<br>ATTCACCATCTCAAGAGATGACTCAAAAAACACGCTGTATCTGCAAATGAA<br>CAGCCTGAAAACCGAGGACACAGCCGTATATTATTGTATCCCCCCCCCCTAC<br>TACTACTATTACGGTCTGGACGTCTGGGGCCAAGGGACCACGGTCACCGTCT<br>CCTCG SEQ ID NO: 81 |

TABLE V-continued

Nucleotide sequences of the V$_H$ and V$_L$ region of antibodies recognizing HTT species and/or fragments thereof.

| Antibody | Nucleotide sequences of variable heavy (V$_H$) and variable light (V$_L$) chains |
|---|---|
| NI-302.8F1-V$_L$ | CAGTCTGCCCTGACTCAGCCTGCCTCCGTGTCTGGGTCTCCTGGACAGTCGA TCACCATCTCCTGCACTGGAGCCAGCAGTGATGTTGGGACTTATGACCTTGT CTCCTGGTACCAACAACATCCAGGCAAAGCCCCCAAACTCATTATTTATGAG GTCAATAAGCGGCCCTCAGGGGTTTCTTATCGCTTCTCTGCCTCCAAGTCTGC CAACACGGCCTCCCTGACAATATCTGGGCTCCAGGCTGAGGACGAGGCTGA ATATTACTGCTGCTCATATGCAGGTTATAGCACGGTATTCGGCGGAGGGACC AAGCTGACCGTCCTA SEQ ID NO: 83 |
| NI-302.4A6-V$_H$ | GAGGTGCAGCTGGTGGAGTCTGGGGGAGGCTTGGTACAGCCTGGGGGGTCC CTGAGACTCTCCTGTGCAGCCTCTGGATTCACCTTTAGCGCTTATGCCATGA GCTGGGTCCGCCAGGCTCCAGGGAAGGGGCTGGAGTGGGTCTCAACTATTA GTGGTAGTGGTGGTAGTACATACTACGCAGACTCCGTGAAGGGCCGGTTCTC CATCTCCAGAGACAACTCCAAAAACACCCTGTATCTGCAAATGAACAGCCT GAGAGCCGAGGACACGGCCGTATATTTCTGTGCGAAAGTTACCACGGAACT CTACGGTGCTAACTCCTACTACTACATGGACGTCTGGGGCAAAGGGACC ACGGTCACCGTCTCCTCG SEQ ID NO: 184 |
| NI-302.4A6-V$_K$ | GAAATTGTGTTGACACAGTCTCCAGGCACCCTGTCTTTGTCTCCAGGGGAAA GAGCCACCCTCTCCTGCAGGGCCAGTCAGAGTGTTGTCAGCAGGTATTTAGC CTGGTACCAGCAAAAACCTGGCCAGGCTCCCAGGCTCCTCATCTATGGTGCA TCCAGCAGGGCCACTGGCATCCCAGACAGGTTCAGTGGCAGTGGGTCTGGG ACAGACTTCACTCTCACCATCAGCAGACTGGAGCCTGAAGATTTTGCAATGT ATTACTGTCAGCTGTATGGTAACTCACAGACGTTCGGCCAGGGGACCAAGGT GGAGATCAAA SEQ ID NO: 186 |
| NI-302.12H2-V$_H$ | GAGGTGCAGCTGGTGCAGTCTGGGGGAGGCTTGGTACAGCCTGGGGGGTCC CTGAGACTTTCCTGTGAAGCCTCTGGATTCACCTTTAGCAACTATGCCATGG GCTGGGTCCGCCAGGCTCCAGGGAAGGGGCTGGAGTGGGTCTCAGTAATTA GTGGTACTGGTGGTAGCACATACTACGCAGACTCCGTGAAGGGCCGGTTCA CCATCTCCAGAGACAATTCCATGAACACGCTGTATCTGCAAATGAACAGCCC GAGAGCCGACGACACGGCCGTATATTACTGTGCGAAAGATCTGAGGAAGAT TAGCGGTCCTTTATACTACTACGGTATGGACGTCTGGGGCCAAGGGACCACG GTCACCGTCTCCTCG SEQ ID NO: 188 |
| NI-302.12H2-V$_K$ | GAGGTGCAGCTGGTGGAGTCTGGGGGAGGCTTGGTACAGCCTGGGGGGTCC CTGAGACTTTCCTGTGAAGCCTCTGGATTCACCTTTAGCAACTATGCCATGG GCTGGGTCCGCCAGGCTCCAGGGAAGGGGCTGGAGTGGGTCTCAGTAATTA GTGGTACTGGTGGTAGCACATACTACGCAGACTCCGTGAAGGGCCGGTTCA CCATCTCCAGAGACAATTCCATGAACACGCTGTATCTGCAAATGAACAGCCC GAGAGCCGACGACACGGCCGTATATTACTGTGCGAAAGATCTGAGGAAGAT TAGCGGTCCTTTATACTACTACGGTATGGACGTCTGGGGCCAAGGGACCACG GTCACCGTCTCCTCG SEQ ID NO: 192 |
| NI-302.8M1-V$_H$ | GAGGTCCAGCTGGTGCAGTCTGGGGCTGAGGTGAAGAAGCCTGGGGCCTCA GTGAAAGTTTCCTGCAAGGCATCCGGATACACCTTCACCATCTACTATATGC ACTGGGTGCGACAGGCCCCTGGACAAGGGCTTGAGTGGATGGGAGGAATCA GCCCGAGTGGTGCCCACACAATGTACGCACAGAATTTCCAGGGCAGAGTCA CCGTGACCAGGGACACGTCCACGAGCACAGTCTACATGGAGCTGAGCAGCC TGAGATCTGAGGACACGGCCGTGTATTACTGTGCGAGAGGGAGCACGGTGA CTAACTATCGACCCTTTGACTACTGGGGCCAGGGAACCCTGGTCACCGTCTC CTCG SEQ ID NO: 194 |
| NI-302.8M1-V$_K$ | GACATCCAGATGACCCAGTCTCCATCCTCCCTGTCTGCATCTGTAGGAGACA GAGTCACTATCACTTGCCGGGCGAGTCAGGACATTAGCAATTATTTAGCCTG GTATCAGCAGAAACCAGGGAAAGTTCCTAAACTCCTGATCTTTGCTGCATCC ACTTTGCAATCAGGGGTCCCGTCTCGGTTCGGTGGCAGTGGATCTGGGACAG ATTTCACTCTCACCATCAGCAGCCTGCAGCCTGAAGATGTTGCAACTTATTA CTGTCAAAACTATAACAGTGGCCCTCCGCCTTTCGGCCCTGGGACCAAAGTG GATATCAAA SEQ ID NO: 198 |

TABLE VI

Nucleotide sequences of the $V_H$ and $V_L$ region of antibodies an epitope of the N-terminal-region of HTT, i.e exon 1 in aggregated form

| Antibody | Nucleotide sequences of variable heavy ($V_H$) and variable light ($V_L$) chains |
|---|---|
| NI-302.15E8-$V_H$ | GAGGTGCAGCTGGTGGAGTCTGGGGGAGGCTTGATACAGCCGGGGGGTCC CTGAGACTCTCCTGTGCAGTCTCTGGATTCACCGTCAGTAGTTATAGCATGA ACTGGGTCCGCCAGGCTCCAGGGAAGGGGCTGGAGTGGGTCTCATACACTA GTAGTAGCAGAAGTAATACCAAAAAGTACGCAGACTCTGTGAAGGGCCGAT TCACCATCTCTAGAGACAATGCCAGGAACTCACTCTATCTGCAAATGAACAG CCTGAGAGACGAGGACACGGCTGTGTATTACTGTGCGAGAGCAGGGGACTT CGGGGAGTTACTCACTGGTGAGGGGTATTACGGTATGGACGTCTGGGGCCA AGGGACCACGGTCACCGTCTCCTCG SEQ ID NO: 131 |
| NI-302.15E8-$V_L$ | TCCTATGAGCTGACTCAGCCACCCTCAGTGTCCGTGTCCCCAGGACAGACAG CCACCATCACCTGCTCGGGAGATGAATTGGGGATAAATATGTTGGTTGGTA TCAACAGAAGCCAGGCCAGTCCCCTCTGCTGGTCATCTATCAAGATGCGAAG CGGCCCTCAGGGATCCCTGAGCGATTCTCTGGCTCCAACTCTGGGAACACAG CCACTCTGACCATCAGCGGGACCCAGGCTATGGATGAGGCTGACTACTACTG TCAGGCGTGGGACAGCGGCACGATGGTTTTCGGCGGAGGGACCAGGCTGAC CGTCCTA SEQ ID NO: 133 |

TABLE VII

Nucleotide sequences of the $V_H$ and $V_L$ region of antibodies recognizing an epitope of the Q/P-rich region of HTT, i.e exon 1 in aggregated form.

| Antibody | Nucleotide sequences of variable heavy ($V_H$) and variable light ($V_L$) chains |
|---|---|
| NI-302.7D8-$V_H$ | CAGGTGCAGCTGGTGCAATCTGGATCTGAGTTGAAGAAGCCTGGGGCCTCA GTGAAGGTTTCCTGCAAGGCTTCTGGATACAACTTCAATAACTATGCCATCA ATTGGTTGCGACAGGCCCCTGGACAAGGGCTTGAGTGGATGGGATGGATCA ACACCATCACTGGGCACCCAACGTATGCCCAGGGCTTCAAAGGACGATTTGT CTTCTCCTTGGACACCTCTGTCAGCACGGCATATCTGCAGATCAGCAGCCTA AAGCCTGAGGACACTGCCGTCTATTACTGTGCGAGAACTTACAGTAACTACG GCGAATTTGACTACTGGGGCCAGGGAACCCTGGTCACCGTCTCCTCG SEQ ID NO: 172 |
| NI-302.7D8-$V_L$ | CAGTCTGCCCTGACTCAGCCTGCCTCCGTGTCTGGGTCTCGTGGACAGTCGA TCACCATCTCCTGCACTGGAACCAGCAGTGATGTTGGAAGTTATAACCTTGT CTCCTGGTACCAACAGTACCCAGGCAAGGCCCCCAAGCTCATAATTCATGAG GGCAGTGAGCGGCCCTCAGGGGTTTCTAATCGCTTCTCTGGCTCCAAGTCTG GCAACACGGCCTCCCTGACAATTTCTGGGCTCCAGGCTGAGGACGAGGCTG ATTATTACTGCTGCTCATATGCAGGTACTACTACTTTCGTGCTATTCGGCGGA GGGACCAAGCTGACCGTCCTC SEQ ID NO: 174 |

Due to the cloning strategy the amino acid sequence at the N- and C-terminus of the heavy chain and light chains may potentially contain primer-induced alterations in FR1 and FR4, which however do not substantially affect the biological activity of the antibody. In order to provide a consensus human antibody, the nucleotide and amino acid sequences of the original clone can be aligned with and tuned in accordance with the pertinent human germ line variable region sequences in the database; see, e.g., Vbase2, as described above. The amino acid sequence of human antibodies are indicated in bold when N- and C-terminus amino acids are considered to potentially deviate from the consensus germ line sequence due to the PCR primer and thus have been replaced by primer-induced mutation correction (PIMC), see Table VI. Accordingly, in one embodiment of the present invention, the polynucleotide comprises, consists essentially of, or consists of a nucleic acid having a polynucleotide sequence of the VH and the VL region of an anti-HTT antibody and/or fragments thereof as depicted in Table VI.

TABLE VIII

Nucleotide sequences of the V_H and V_L region of antibodies recognizing HTT species and/or fragments thereof showing replacement by PIMC (bold).

| Alternative Antibody-regions with PIMC | Nucleotide sequences of variable heavy (V_H) and variable light (V_L) chains |
|---|---|
| NI-302.33C11-PIMC V_H | CAGGTGCAGCTGGTGGAGTCTGGGGGAGGCGTTGTCCAGCCTGGGAACTC CCTGAGACTCTCCTGTGCAGCGTCTGGATTCAGGTTCAGTGACTTTGGCATG CACTGGGTCCGCCAGGCTCCAGGCAAGGGACTGGAGTGGCTGGCACTTATA TGGTATGATGGAGGGTATAAGTACTATGCAGACTCCGTGAAGGGCCGATTC ACCATCTCCAGAGACAATTCCAAGAATACGATGTTTCTACAAATGAACAGCC TGAGAGCCGAGGACACGGCTGTTTATTACTGTGCGACCCACCTAGAATATTG CAGTAGAACCACCTGCTATCTCGGCCACTGGGGCCAGGGAACCCTGGTCAC CGTCTCCTCG SEQ ID NO: 97 |
| NI-302.33C11-PIMC V_K | GACATCCAGTTGACCCAGTCTCCGTCCTTCCTATCTGCGTCTGTGGGAGAC ACAGTCACCTTCACTTGCCGGGCCAGTCAGGGCATTAGCGATTATTTAGCCT GGTTTCAGCAGAAACCAGGGATTGCCCCTAAGCTCCTGATCTATGCTGCGTC CACTTTGCAAACCGGGGTCCCATCAAGGTTCAGCGGCAGTGGATCTGGGAC AGAATTCACTCTCACAATCCGCAGCCTGCAGTCTGAAGATTTTGGAACTTAT TACTGTCAGCAGCTTAAAACTTACCCGTACACTTTTGGCCAGGGGACCAAG CTGGAGATCAAA SEQ ID NO: 99 |
| NI-302.63F3-PIMC V_K | GATATTGTGATGACTCAATCACCAGACTCCCTGGCTGTGTCTCTGGGCGAG AGGGCCACCATCAACTGCAAGTCCAATCAGAGTCTTTTCTACAGTTCCAACA ATAACAACTACTTAGCTTGGTACCAGCACAAATCCGGACAGCCTCCTAAGCT GCTCGTTTACTGGGGATCTACCCGGGAATCCGGGTCCCTGACCGCTTCAGT GGCAGCGGGTCTGGGACTGACTTCACTCTCACCATCAGTAGCCTGCAGGCTG AGGATGTTGCAATTTATTACTGTCACCAATATTATCATAATCCGTACACTTTT GGCCAGGGGACCAAGCTGGAGATCAAA SEQ ID NO: 101 |
| NI-302.63F3-PIMC-NS V_K | GATATTGTGATGACTCAATCACCAGACTCCCTGGCTGTGTCTCTGGGCGAG AGGGCCACCATCAACTGCAAGTCCTCACAGAGTCTTTTCTACAGTTCCAACA ATAACAACTACTTAGCTTGGTACCAGCACAAATCCGGACAGCCTCCTAAGCT GCTCGTTTACTGGGGATCTACCCGGGAATCCGGGTCCCTGACCGCTTCAGT GGCAGCGGGTCTGGGACTGACTTCACTCTCACCATCAGTAGCCTGCAGGCTG AGGATGTTGCAATTTATTACTGTCACCAATATTATCATAATCCGTACACTTTT GGCCAGGGGACCAAGCTGGAGATCAAA SEQ ID NO: 103 |
| NI-302.63F3-PIMC-SG V_K | GATATTGTGATGACTCAATCACCAGACTCCCTGGCTGTGTCTCTGGGCGAG AGGGCCACCATCAACTGCAAGTCCAATCAGGGCCTTTTCTACAGTTCCAACA ATAACAACTACTTAGCTTGGTACCAGCACAAATCCGGACAGCCTCCTAAGCT GCTCGTTTACTGGGGATCTACCCGGGAATCCGGGTCCCTGACCGCTTCAGT GGCAGCGGGTCTGGGACTGACTTCACTCTCACCATCAGTAGCCTGCAGGCTG AGGATGTTGCAATTTATTACTGTCACCAATATTATCATAATCCGTACACTTTT GGCCAGGGGACCAAGCTGGAGATCAAA SEQ ID NO: 105 |
| NI-302.63F3-PIMC-NQ V_K | GATATTGTGATGACTCAATCACCAGACTCCCTGGCTGTGTCTCTGGGCGAG AGGGCCACCATCAACTGCAAGTCCCAACAGAGTCTTTTCTACAGTTCCAACA ATAACAACTACTTAGCTTGGTACCAGCACAAATCCGGACAGCCTCCTAAGCT GCTCGTTTACTGGGGATCTACCCGGGAATCCGGGTCCCTGACCGCTTCAGT GGCAGCGGGTCTGGGACTGACTTCACTCTCACCATCAGTAGCCTGCAGGCTG AGGATGTTGCAATTTATTACTGTCACCAATATTATCATAATCCGTACACTTTT GGCCAGGGGACCAAGCTGGAGATCAAA SEQ ID NO: 107 |
| NI-302.35C1-PIMC V_K | GAAATTGTGCTGACTCAGTCTCCAGCCACCCTGTCTTTGTCTCCAGGGGAA AGAGCCACCCTCTCCTGCAGGGCCAGTCAAAGTGTTGACAACCAGTTTGCCT GGTACCAACAGAAACCTGGCCAGGCTCCCAGGCTCCTCATTTATGATGCATC CAGGAGGGCCCCTGGCATCCCAGACAGGTTCAGTGGCAGTGGGTCTGGGAC AGACTTCACTCTCACCATTAGCAGCCTAGAGCCTGAAGATTTCGCAATTTAT TACTGTCAGCATCGTTACACCTGGCTCTACACTTTTGGCCAGGGGACCAAG CTGGAGATCAAA SEQ ID NO: 109 |
| NI-302.31F11-PIMC V_K | GATATTGTGATGACTCAATCACCACTCTCCCTGCCCGTCGCCCCTGGAGAG CCGGCCTCCATCTCCTGCAGGTCTAGTCAGAGCCTCCTATACAGTAATGAT ACAACTATTTGGATTGGTACCTGCAGAAGCCAGGGAAGCCTCCACAGCTCCT GGTCTATTTGGGTTCTGATCGGGCCTCCGGGTCCCTGACAGGTTCAGTGGC AGTGGATCAGGCAAAGATTTTACACTGAACATCAGCAGAGTGGAGGCTGAG GATGTTGGGGTTTATTACTGCATGCAAGGTCTACAAAGTCCGTGGACGTTCG GCCAAGGGACCAAGGTGGAAATCAAA SEQ ID NO: 111 |
| NI-302.2A2-PIMC V_K | GATATTGTGATGACTCAATCACCAGACTCCCTGGCTGTGTCTCTGGGCGAG AGGGCCACCATCAACTGCAAGTCCAGCCAGAGTCTTTTATACACCTCCAAAA ATAAGGACAGTAAGAACTACTTAGGTTGGTACCAGCAGAAACCAGGACAGC CTCCTAAGCTGCTCATTTACTGGGCATCTACCCGGGAATCCGGGTCCCTGA CCGATTCAGTGGCAGCGGGTCTGGGACAGATTTCACTCTCACCATCAGCAGC CTGCAGGCTGAGGATGTGGCAGTTTATTACTGTCAGCAGTATTATACTACTC CTCAGTTCGGCGGAGGGACCAAGGTGGAAATCAAA SEQ ID NO: 113 |

TABLE VIII-continued

Nucleotide sequences of the V$_H$ and V$_L$ region of antibodies recognizing HTT species and/or fragments thereof showing replacement by PIMC (bold).

| Alternative Antibody-regions with PIMC | Nucleotide sequences of variable heavy (V$_H$) and variable light (V$_L$) chains |
|---|---|
| NI-302.74C11-PIMC V$_H$ | CAGGTGCAGCTGGTGCAATCTGGGACTGAGGTGCAGAAGCCTGGGGCCTC AGTAAAAGTCTCCTGCAAGGCTTCTGGATACAGTTTCACCGGCTACTTTTTG CACTGGGTACGACAGGCCCCTGGACAAGGGCTTGAGTGGATGGGGTGGATC AACCCTAACAGTGGTGACACAAACTATGCAGAGAAGTTTCGGGGCAGAATC ATCATGACCAGGGACACGTCTGTCAGCACAGCCCACATGGAGTTGAGCAGC CTGAGATTTGACGACACGGCCCTATATTACTGTACGAGAGAGGCCCCTGACC CGGGCGCTGAGACGGACGTCTGGGGCCAAGGAACCACGGTCACCGTCTCC TCG SEQ ID NO: 115 |
| NI-302.74C11-PIMC V$_L$ | TCCTATGAGCTGACTCAGCCACCCTCGGTGTCAGTGTCCCCAGGACAGAC GGCCAGGATCACCTGCTCTGGAGATGCAGTGCCAAAGCAGTATATTTATTGG TACCAGCAGAAGCCAGGCCAGGCCCCTATTCTGGTGATATATAAAGACACT CAGAGGCCTTCAGGGATCCCTGAGCGATTCTCTGGCTCCAACTCAGGGACAA CAGTCACGTTGACCATAACTGGCGTCCAGGCAGACGACGAGGGTGACTATT ACTGTCAATCAGCAGACAGTAGTGCTACTTGGGTGTTCGGCGGAGGGACCA AATTGACCGTCCTA SEQ ID NO: 117 |
| NI-302.39G12-PIMC V$_H$ | GAGGTGCAGCTGGTGGAGTCTGGGGGAGGCTTGGTCCACCCTTGGGGGTC CCTGAGACTCTCCTGTGCAGCCTCTGGATTCAGCGTCTCTAATTACGCCATA ACTTGGGTCCGCCGGGCTCCAGGGAAGGGGCTGCAATATATTTCAGTAATTT ATCGTGATGGCAGGACATACTACGGAGACTCCGTGAGGGGCCGCTTCACCA TCTCTAGGGACGATTCCAAGAACACTCTCTATCTTCAAATGAACAGCCTGAG ATTTGAGGACACGGCTGTGTATTACTGTGCGAGAGCGCACGGCCAATATTAC TATGGTGTGGACGTCTGGGGCCAAGGAACCACGGTCACCGTCTCCTCG SEQ ID NO: 119 |
| NI-302.39G12-PIMC V$_K$ | GACATCGTGATGACCCAGTCTCCACTCTCCCTGTCCGTCAGCCCTGGAGAG CCGGCCTCCATCTCCTGCAGGTCTAGTCAGAGCCTCCTACATAGTAATGGAT ACAACTATTTGGATTGGTACCGGCAGAAACCAGGGCAGTCTCCACAGCTCCT GATCTATTTGAGTTCTAATCGGCCCTCCGGGGTCCCTGATAGGTTCAGTGCC AGTGGATCAGGCACAGAGTTCACACTGCAAATCAGCAGAGTGGAGGCTGAG GATGTTGGGGTTTATTACTGCATGCAATCTCTGCAAACGTTCACTTTCGGCG GAGGGACCAAGGTGGAAATCAAA SEQ ID NO: 121 |
| NI-302.11A4-PIMC V$_K$ | GAAATTGTGCTGACTCAGTCTCCAGGCACCCTGTCTTTGTCTCCAGGAGAA AGAGCCACCCTCTCCTGCAGGGCCAGTCAGAGTGTTAGCAGCAGCTACTTCG CCTGGTACCAACAAAAACCTGGCCAGGCTCCCAGGCTCCTCATCTATGGTAC GTCCCGCAGGGCCACTGCCATCCCAGACAGGTTCAGTGGCAGTGGGTCTGG GACAGACTTCACTCTCACCATCAGCAGACTGGAGCCTGAAGATTTTGCAGTG TATTACTGTCAACAGTATGGTAGCTCGTGGACGTTCGGCCCAGGGACCAAG GTGGAAATCAAA SEQ ID NO: 123 |
| NI-302.22H9-PIMC V$_K$ | GATATTGTGATGACTCAATCACCACTCTCCCTGTCCGTCAGCCCTGGAGAG CCGGCCTCCATCTCCTGCAGGTCTAGTCAGAGCCTCCTACATAGTAATGGAT ACAACTATTTGGATTGGTACCGGCAGAAACCAGGGCAGTCTCCACAACTCCT GATCTATTTGAATTCTAATCGGGCCTCCGGGGTCCCTGATAGGTTCAGTGGC AGTGGATCAGGCACAGAGTTCACACTGACAATCAGCAGAGTGGAGGCTGAG GATGTTGGGGTTTATTACTGCATGCAATCTCTGCAAACGTTCACTTTCGGCG GAGGGACCAAGGTGGAAATCAAA SEQ ID NO: 125 |
| NI-302.44D7-PIMC V$_H$ | GAGGTGCAGCTGGTGGAGTCTGGGGGAGGCTTGGTACAGCCTGGGGGGT CCCTGAGACTCTCCTGTGCAGCCTCTGGATTCACCTTTAGCAGCTATGCCAT GAGTTGGGTCCGCCAGGCTCCAGGGAAGGGGCTGGAGTGGGTCTCAGGTAT TGGTTATAGTGATACTAGCACATATTACGCAGACTCCGTGAAGGGCCGCTTC ACCGTCTCCAGAGACATTTCCAAGAACACGCTGTATCTGCAAATGAATAGCC TGAGGGCCGAGGACACGGCCGTATATTACTGCGCGAAAGGTACCAGGGACT ATTACGGTATGGACGTCTGGGGCCAAGGAACCACGGTCACCGTCTCCTCG SEQ ID NO: 127 |
| NI-302.78H12-PIMC V$_H$ | CAGCTGCAGCTGCAGGAGTCGGGCCCAGGACTGGTGAAGCCTTCGGAGA CCCTGTCCCTCACCTGTCTTGTCTCTAGTTACTCCATCAGCAATGGTTACTAC TGGGGCTGGATTCGGCAGCCCCCAGGGAAGGGGCTGGAGTGGATTGGGAGT ATCTATCATAATGGGAACACCTATTACAACCCGTCCCTCAAGAGTCGAGTCA TCATTTCAGTAGACACGTCCAAGAACCAGTTCTCCCTGAAGTTGAGGTCTGT GACCGCCGCAGACACGGCCGTGTACTACTGTGCGATGCCAAGTGCCACCTAT TATTATGGTTCGGGGACTCAATTCCATGCGTTTGATGTCTGGGGCCAAGGGA CAATGGTCACCGTCTCTTCG SEQ ID NO: 129 |
| NI-302.64E5-PIMC V$_H$ | GAGGTGCAGCTGGTGGAGTCTGGGGGAGGCTTGGTAAAGCCTGGGGGGT CCCTTAGACTCTCCTGTGCAGCCTCTGGATTCACTTTCGACCAGGCCTGGAT GAGCTGGGTCCGCCAGGTTCCAGGGAAGGGGCTGGAGTGGGTTGGCCGGAT |

TABLE VIII-continued

Nucleotide sequences of the $V_H$ and $V_L$ region of antibodies recognizing HTT species and/or fragments thereof showing replacement by PIMC (bold).

| Alternative Antibody-regions with PIMC | Nucleotide sequences of variable heavy ($V_H$) and variable light ($V_L$) chains |
|---|---|
| | TAAAACGAAAACTGAGGGTGAAGCAACAGACTACGCAGCGCCCGTGAGAG<br>GCAGATTCACCATCTCAAGAGATGATTCAGAAGACACGGTGTTTCTGCAAAT<br>GAACAGCCTGAAAACCGAGGACACAGCCCTGTATTACTGTACGTCAACGGG<br>AGTCTTAGCAGCAGCTGTCGATGTCTACTGGGGCCAGGGCACCCTGGTCAC<br>CGTCTCCTCG SEQ ID NO: 166 |
| NI-302.64E5-PIMC $V_K$ | GATATTGTGATGACTCAATCACCAGACTCCCTGGCTGTGTCTCTGGGCGAG<br>AGGGCCACCATGACCTGCAAGTCCAGCCAGAGTCTTTTCTACAGTTACAACA<br>ATGAGAACTACTTAGCCTGGTATCAGCAGAAGACCAGGACAGCCTCCTAAGT<br>TGCTCATTTACTGGGCATCTACCCGGGAATCCGGGGTCCCTGACCGATTCAG<br>TGGCAGCGGGTCTGGGACAGATTTCACTCTCACCATCAGCAGCCTGCAGGCT<br>GAAGATGTGGCAGTTTATTACTGTCAGCAATATTATAGTACTCCTCAGACGT<br>TCGGCCAAGGGACCAAGGTGGAAATCAAA SEQ ID NO: 170 |
| NI-302.72F10-PIMC $V_H$ | GAGGTGCAGCTGGTGGAGTCTGGGGGAGGCTTCGTACAGCCTGGGGGGT<br>CCCTGAGACTCTCCTGTGCAGCCTCTGGATTCAACTTCGGCAGTTATGCCAT<br>GAGCTGGGTCCGCCAGGCTCCAGGGAAGGGACTGGAGTGGGTGTCAGATAT<br>CAGTGGTATTGGTAGTAACACATACTACGCAGACTCCGTGAAGGGCCGTTTC<br>ACCATTTCCAGAGACAATTCCGACAATACGTTGTACCTGGACATGAGCAGCC<br>TGAGAGCCGAGGACACGGCCAGATATTACTGTGCGAAGGATCGAAAGCGCA<br>GTGGCTGGTACGAACAGTGGGGCCAGGGCACCCTGGTCACCGTCTCCTCG<br>SEQ ID NO: 178 |
| NI-302.72F10-PIMC $V_K$ | GAAATTGTGCTGACTCAGTCTCCAGCCACCCTGACTTTGTCTCCAGGGGAA<br>AGAGCCACCCTCTCCTGCAGGGCCAGTCAGAGTATTAGCGCCTACTTAGGCT<br>GGTATCAACAAAAACCTGGCCAGGCTCCCAGGCTCCTCATCTATGATGCATC<br>CATTAGGGCCACTGGCATTCCAGACAGGTTTAGTGGCAGTGGGTCTGGGAC<br>AGACTTCACTCTCACCATCAGCAGCCTAGAGCCTGAAGATTCTGCAGTTTAT<br>TACTGTCACCAGCGTAGCAAGTGGCCTCTTACTTTCGGCGGAGGGACCAAG<br>GTGGAAATCAAA SEQ ID NO: 182 |
| NI-302.12H2-PIMC $V_H$ | GAGGTGCAGCTGGTGGAGTCTGGGGGAGGCTTGGTACAGCCTGGGGGGT<br>CCCTGAGACTTTCCTGTGAAGCCTCTGGATTCACCTTTAGCAACTATGCCAT<br>GGGCTGGGTCCGCCAGGCTCCAGGGAAGGGGCTGGAGTGGGTCTCAGTAAT<br>TAGTGGTACTGGTGGTAGCACATACTACGCAGACTCCGTGAAGGGCCGGTTC<br>ACCATCTCCAGAGACAATTCCATGAACACGCTGTATCTGCAAATGAACAGCC<br>CGAGAGCCGACGACACGGCCGTATATTACTGTGCGAAAGATCTGAGGAAGA<br>TTAGCGGTCCTTTATACTACTACGGTATGGACGTCTGGGGCCAAGGGACCA<br>CGGTCACCGTCTCCTCG SEQ ID NO: 190 |
| NI-302.8M1-PIMC $V_H$ | CAGGTGCAGCTGGTGCAATCTGGGGCTGAGGTGAAGAAGCCTGGGGCCTC<br>AGTGAAAGTTTCCTGCAAGGCATCCGGATACACCTTCACCATCTACTATATG<br>CACTGGGTGCGACAGGCCCCTGGACAAGGGCTTGAGTGGATGGGAGGAATC<br>AGCCCGAGTGGTGCCCACACAATGTACGCACAGAATTTCCAGGGCAGAGTC<br>ACCGTGACCAGGGACACGTCCACGAGCACAGTCTACATGGAGCTGAGCAGC<br>CTGAGATCTGAGGACACGGCCGTGTATTACTGTGCGAGAGGGAGCACGGTG<br>ACTAACTATCGACCCTTTGACTACTGGGGCCAGGGCACCCTGGTCACCGTC<br>TCCTCG SEQ ID NO: 196 |

The present invention also includes fragments of the polynucleotides of the invention, as described elsewhere. Additionally polynucleotides which encode fusion polynucleotides, Fab fragments, and other derivatives, as described herein, are also contemplated by the invention. The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the HTT-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative, or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses, and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics), or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. In one embodiment, this is accomplished using a proprietary expression vector of Biogen IDEC, Inc., referred to as NEOSPLA, and disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene, and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which preferably are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *Escherichia coli, Bacillus subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *E. coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB 11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska and Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan and Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties.

The expression levels of an antibody molecule can be increased by vector amplification, for a review; see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *E. coli* or *Salmonella*; Bacillaceae, such as *B. subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO 02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye and Inouye, Nucleic Acids Res. 13 (1985), 3101-3109; Van Heeke and Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-HTT antibody or an antibody recognizing mutated and/or aggregated HTT species and/or fragments thereof or immunoglobulin chain(s) thereof, said method comprising:

(a) culturing the host cell as defined hereinabove, which cell comprised a polynucleotide or a vector as defined hereinbefore; and (b) isolating said antibody or immunoglobulin chain(s) thereof from the culture.

Furthermore, in one embodiment the present invention also relates to an antibody or immunoglobulin chain(s) thereof encoded by a polynucleotide as defined hereinabove or obtainable by said method for preparing an anti-HTT antibody or an antibody recognizing mutated and/or aggregated HTT species and/or fragments thereof or immunoglobulin chain(s) thereof.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin HTT-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO 92/08495; WO 91/14438; WO 89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, (1983) 1-12; Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to HTT. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds HTT. In yet another embodiment, a fusion protein for use in the diagnostic and treatment methods disclosed herein comprises a polypeptide having the amino acid sequence of any one, two, three, or more of the $V_H$ CDRs of an antibody and the amino acid sequence of any one, two, three, or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512. Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglu-tinin protein (Wilson et al., Cell 37 (1984), 767), GST, c-mycand the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described hereinbefore.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting a HTT-binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a HTT amyloidosis to indicate the risk of getting a disease or disorder associated with mutated and/or aggregated HTT, to monitor the development or progression of such a disease, i.e. a disease showing the occurrence of, or related to aggregated HTT, or as part of a clinical testing procedure to, e.g., determine the efficacy of a given treatment and/or prevention regimen. In one embodiment thus, the present invention relates to an antibody, which is detectably labeled.

Furthermore, in one embodiment, the present invention relates to an antibody, which is attached to a drug. Detection can be facilitated by coupling the antibody, or antigen-binding fragment, variant or derivative thereof to a detectable substance. The detectable substances or label may be in general an enzyme; a heavy metal, preferably gold; a dye, preferably a fluorescent or luminescent dye; or a radioactive label. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. Therefore, in one embodiment the present invention provides a detectably labeled antibody, wherein the detectable label is selected from the group consisting of an enzyme, a radioisotope, a fluorophore and a heavy metal.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, (ed.), Enzyme Immunoassay, CRC Press, Boca Raton, Fla., (1980); Ishikawa, et al., (eds.), Enzyme Immunoassay, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., (1987) 623-53; Thorpe, "Antibody Carriers Of Cytotoxic Agents In Cancer Therapy: A Review", in Monoclonal Antibodies '84: Biological And Clinical Applications, Pinchera et al. (eds.), (1985) 475-506; "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press (1985) 303-16, and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned HTT-binding molecule, e.g., antibody or antigen-binding fragment thereof of the present invention or derivative or variant thereof, or the polynucleotide, vector or cell of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition.

For use in the treatment of a disease or disorder showing the occurrence of, or related to mutated and/or aggregated HTT, such as HTT amyloidosis, the additional agent may be selected from the group consisting of small organic molecules, anti-HTT antibodies, and combinations thereof. Hence, in a particular preferred embodiment the present invention relates to the use of the HTT-binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of Huntington's disease (HD) and/or a disease or disorder associated with HTT and/or HTT amyloidosis, monitoring the progression of HD and/or a disease or disorder associated with HTT and/or HTT amyloidosis or a response to a HTT amyloidosis treatment in a subject or for determining a subject's risk for developing a disease or disorder associated with HTT.

Hence, in one embodiment the present invention relates to a method of treating a disease or disorder characterized by abnormal accumulation and/or deposition of HTT and/or aggregated and/or mutated HTT in affected systems and organs which method comprises administering to a subject in need thereof a therapeutically effective amount of any one of the afore-described HTT-binding molecules, antibodies, polynucleotides, vectors or cells of the instant invention.

A particular advantage of the therapeutic approach of the present invention lies in the fact that the recombinant antibodies of the present invention are derived from B cells or memory B cells from healthy human subjects with no signs or symptoms of a disease, e.g. carrying an asymptomatic mutation and/or mutations, showing the occurrence of, or related to aggregated HTT and thus are, with a certain probability, capable of preventing a clinically manifest disease related to mutated and/or aggregated HTT, or of diminishing the risk of the occurrence of the clinically manifest disease or disorder, or of delaying the onset or progression of the clinically manifest disease or disorder. Typically, the antibodies of the present invention also have already successfully gone through somatic maturation, i.e. the optimization with respect to selectivity and effectiveness in the high affinity binding to the target HTT molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human-derived anti-HTT antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-HTT antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of Huntington's disease and/or a disease or disorder which is accompanied with the presence of mutated and/or aggregated HTT, and in particular applicable for the treatment of disorders generally characterized by HTT amyloidosis.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-HTT antibody or HTT-binding fragment, derivative or synthetic or biotechnological variant thereof for passive immunization. As mentioned in the background section mutated and/or aggregated HTT species and/or fragments or derivatives thereof are a major trigger for HTT amyloidosis. Accordingly, it is prudent to expect that passive immunization with human anti-HTT antibodies and equivalent HTT-binding molecules of the present invention will help to circumvent several adverse effects of active immunization therapy concepts and lead to a reduced aggregation of HTT. Therefore, the present anti-HTT antibodies and their equivalents of the present invention will be particularly useful as a vaccine for the prevention or amelioration of diseases or disorders showing the presence of, or caused by aggregated HTT such as HD.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008); S1741-0134, published online ahead, describe the use of chimeric recombinant Fab (rFab) and single chain fragments (scFvs) of monoclonal antibody WO-2 which recognizes an epitope in the N-terminal region of Abeta. The engineered fragments were able to (i) prevent amyloid fibrillization, (ii) disaggregate preformed Abeta1-42 fibrils and (iii) inhibit Abeta1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease, disorder, or symptoms related to the occurrence of mutated and/or aggregated HTT may be desirable. In one embodiment, the additional antibody is comprised in the pharmaceutical composition of the present invention. Examples of antibodies which can be used to treat a subject include, but are not limited to, antibodies targeting CD33, SGLT2, IL-6, and IL-1.

In a further embodiment, co-administration or sequential administration of other agents useful for treating a disease, disorder, or symptoms related to mutated and/or aggregated HTT, may be desirable. In one embodiment, the additional agent is comprised in the pharmaceutical composition of the present invention. Examples of agents which can be used to treat a subject include, but are not limited to: VMAT2 inhibitors targeting involuntary muscle movements such as Xenazine™, anti-inflammatory agents such as diflusinal, corticosteroids, 2-(2,6-dichloranilino) phenylacetic acid (diclofenac), iso-butyl-propanoic-phenolic acid (ibuprofen); diuretics, Epigallocatechin gallate, Melphalan hydrochloride, dexamethasone, Bortezomib, Bortezomib-Melphalan, Bortezomib-dexamethasone, Melphalan-dexamethasone, Bortezomib-Melphalan-dexamethasone; antidepressants, antipsychotic drugs, neuroleptics, antidementiva (e.g. the NMDA-rezeptor antagonist memantine), acetylcholinesterase inhibitors (e.g. Donepezil, HCl, Rivastigmine, Galantamine), glutamat-antagonists and other nootropics blood pressure medication (e.g. Dihydralazin, Methyldopa), cytostatics, glucocorticoides, angiotensin-converting-enzyme (ACE) inhibitors; anti-inflammatory agents or any combination thereof.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

From the foregoing, it is evident that the present invention encompasses any use of an HTT-binding molecule and/or fragments thereof comprising at least one CDR of the above described antibody, in particular for diagnosing and/or treatment of a disease or disorder related to mutated and/or aggregated HTT species and/or fragments thereof as mentioned above, such as HD and/or HTT amyloidosis. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-HTT antibodies in a sample obtained from a subject. In one embodiment thus, the present invention provides an antibody as defined hereinabove and below or a HTT-binding molecule having substantially the same binding specificities of any one thereof, the polynucleotide, the vector or the cell as defined herein or a pharmaceutical or diagnostic composition comprising any one thereof for use in prophylactic treatment, therapeutic treatment and/or monitoring the progression or a response to treatment of a disease or disorder related to HTT, preferably wherein the disorder is associated with HTT amyloidosis, such as Huntington's disease (HD).

In another embodiment the present invention relates to a diagnostic composition comprising any one of the above described HTT-binding molecules, antibodies, antigen-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry, and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the HTT-binding molecules, in particular antibodies of the present invention may also be used in a method for the diagnosis of a disease or disorder in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease or disorder in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In a further embodiment of the present invention the HTT-binding molecules, in particular antibodies of the present invention may also be used in a method for the diagnosis of a disease or disorder in an individual by obtaining a biopsy from the tested individual.

In this context, the present invention also relates to means specifically designed for this purpose. For example, an antibody-based array may be used, which is for example loaded with antibodies or equivalent antigen-binding molecules of the present invention which specifically recognize HTT. Design of microarray immunoassays is summarized in Kusnezow et al., Mol. Cell Proteomics 5 (2006), 1681-1696. Accordingly, the present invention also relates to microarrays loaded with HTT-binding molecules identified in accordance with the present invention.

In one embodiment, the present invention relates to a method of diagnosing a disease or disorder related to mutated and/or aggregated HTT species and/or fragments thereof in a subject, the method comprising determining the presence of HTT and/or mutated and/or aggregated HTT in a sample from the subject to be diagnosed with at least one antibody of the present invention, a HTT-binding fragment thereof or an HTT-binding molecule having substantially the same binding specificities of any one thereof, wherein the presence of pathologically mutated and/or aggregated HTT is indicative for HD and/or HTT amyloidosis and an increase of the level of the pathologically mutated and/or aggregated HTT in comparison to the level of the physiological HTT is indicative for progression of HD and/or HTT amyloidosis in said subject.

The subject to be diagnosed may be asymptomatic or preclinical for the disease. Preferably, the control subject has a disease associated with mutated and/or aggregated HTT, e.g. Huntington's disease (HD), wherein a similarity between the level of pathologically mutated and/or aggregated HTT and the reference standard indicates that the subject to be diagnosed has a HTT amyloidosis or is at risk to develop a HTT amyloidosis. Alternatively, or in addition as a second control the control subject does not have a HTT amyloidosis, wherein a difference between the level of physiological HTT and/or of mutated and/or aggregated HTT and the reference standard indicates that the subject to be diagnosed has a HTT amyloidosis or is at risk to develop a HTT amyloidosis. Preferably, the subject to be diagnosed and the control subject(s) are age-matched. The sample to be analyzed may be any body fluid suspected to contain pathologically mutated and/or aggregated HTT, for example a blood, blood plasma, blood serum, urine, peritoneal fluid, saliva or cerebral spinal fluid (CSF). In another aspect of the present invention, the antibodies of the present invention can be used in detection of soluble and aggregated HTT utilizing e.g. a TR-FRET based duplex immunoassay as described in Baldo et al., Chem. Biol. 19(2) (2012), 264-275 which disclosure content, in particular the experimental procedures at pages 273-274, are incorporated herein.

Furthermore, it has been described in e.g. Ren et al., Nature Cell Biol. 11 (2) (2009), 219-225 that mammalian cells can internalize fibrillar polyglutamine peptide aggregates in culture gaining access to the cytosolic compartment and become co-sequestered in aggresomes together with components of the ubiquitin-proteasome system and cytoplasmic chaperones. These internalized fibrillar aggregates were able to selectively recruit soluble cytoplasmic proteins and to confer a heritable phenotype upon cells expressing the homologous amyloidogenic protein from a chromosomal locus. Therefore, in one embodiment of the present invention the anti-HTT antibody can reduce extracellular spreading or transneuronal propagation of "toxic" HTT species, as shown by Pecho-Vriesling et al. Nat. Neurosci. (2014) doi:10.1038/nn.3761 for huntingtin or other proteins involved in neurodegeneration such as α-synuclein; see e.g. Guo et al., Nat Med. 20(2) (2014), 130-138.

The level of physiological HTT and/or of pathologically mutated and/or aggregated HTT may be assessed by any suitable method known in the art comprising, e.g., analyzing HTT by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of HTT comprises scintigraphy, positron emission tomography (PET), single photon emission tomography (SPECT), near infrared (NIR) optical imaging or magnetic resonance imaging (MRI).

In one embodiment thus, an antibody of the present invention or a HTT-binding molecule having substantially the same binding specificities of any one thereof, the polynucleotide, the vector or the cell as defined hereinabove or a pharmaceutical or diagnostic composition comprising any one thereof is provided for use in prophylactic treatment, therapeutic treatment, and/or monitoring the progression or a response to treatment of a disease or disorder related to HTT. In general thus, the present invention also relates to a method of diagnosing or monitoring the progression of a disease or disorder related to HTT (such as HTT amyloidosis) in a subject, the method comprising determining the presence of HTT in a sample from the subject to be diagnosed with at least one antibody of the present invention or a HTT-binding molecule having substantially the same binding specificities of any one thereof, wherein the presence of mutated, misfolded and/or aggregated HTT species or fragments thereof is indicative for the disease or disorder. In one embodiment said method of diagnosing or monitoring the progression of HTT amyloidosis in a subject is provided, the method comprising determining the presence of mutated and/or aggregated HTT and/or fragments thereof in a sample from the subject to be diagnosed with at least one antibody of the present invention or a HTT-binding molecule having substantially the same binding specificities of any one thereof, wherein the presence of mutated and/or aggregated HTT and/or fragment thereof is indicative of presymptomatic, prodromal or clinical HTT amyloidosis an increase of the level of HTT aggregates in comparison to the level of the physiological HTT or in comparison to a reference sample derived from a healthy control subject or a control sample from the same subject is indicative for progression of presymptomatic, prodromal or established HTT amyloidosis. It would be appreciated by any person skilled in the art that in one embodiment said method is used as well for the diagnosing or monitoring the progression of any other disease or disorder from the group of disorders related to HTT as defined hereinabove.

As indicated above, the antibodies of the present invention, fragments thereof and molecules of the same binding specificity as the antibodies and fragments thereof may be used not only in vitro but in vivo as well, wherein besides diagnostic, therapeutic applications as well may be pursued. In one embodiment thus, the present invention also relates to a HTT binding molecule comprising at least one CDR of an antibody of the present invention for the preparation of a composition for in vivo detection of or targeting a therapeutic and/or diagnostic agent to HTT in the human or animal body. Potential therapeutic and/or diagnostic agents may be chosen from the nonexhaustive enumerations of the therapeutic agents useful in treatment HTT amyloidosis and potential labels as indicated hereinbefore. In respect of the in vivo imaging, in one preferred embodiment the present invention provides said HTT binding molecule comprising at least one CDR of an antibody of the present invention, wherein said in vivo imaging comprises scintigraphy, positron emission tomography (PET), single photon emission tomography (SPECT), near infrared (NIR) optical imaging or magnetic resonance imaging (MRI). In a further embodiment the present invention also provides said HTT-binding molecule comprising at least one CDR of an antibody of the present invention, or said molecule for the preparation of a composition for the above specified in vivo imaging methods, for the use in the method of diagnosing or monitoring the progression of a disease or disorder related to HTT in a subject, as defined hereinabove.

VII. Peptides with Aggregation Specific HTT Epitopes

In a further aspect the present invention relates to peptides having an epitope of a polyP-rich region of HTT specifically recognized by any antibody of the present invention. Preferably, such peptide comprises or consists of an amino acid sequence as indicated in SEQ ID Nos.: 146, 147, 148, 149, 150, 152, 153, 155, 156, 139, 151, 154, 158, 161, 157, 159, 160 as the unique linear epitope recognized by the antibody or a modified sequence thereof in which one or more amino acids are substituted, deleted and/or added, wherein the peptide is recognized by any antibody of the present invention, preferably by antibody NI-302.74C11, NI-302.15F9, NI-302.39G12, NI-302.11A4, NI-302.22H9, NI-302.37C12, NI-302.55D8, NI-302.78H12, NI-302.71F6, NI-302.33C11, NI-302.44D7, NI-302.7A8, NI-302.3D8, NI-302.46C9, NI-302.11H6, NI-302.18A1, NI-302.52C9, and/or NI-302.8F1.

In an additional aspect the present invention relates to peptides having an epitope of the P-rich-region of HTT specifically recognized by any antibody of the present invention. Preferably, such peptide comprises or consists of an amino acid sequence as indicated in SEQ ID Nos. 140, 141, 142, 143, 200 as the unique linear epitope recognized by the antibody or a modified sequence thereof in which one or more amino acids are substituted, deleted and/or added, wherein the peptide is recognized by any antibody of the present invention, preferably by antibody NI-302.63F3, NI-302.31F11, NI-302.2A2, NI302.15D3 and/or NI-302.64E5.

Furthermore, in one embodiment the present invention relates to peptides having an epitope of the C-terminal region of HTT specifically recognized by any antibody of the present invention. Preferably, such peptide comprises or consists of an amino acid sequence as indicated in SEQ ID NO: 145 or SEQ ID NO: 202 as the unique linear epitope recognized by the antibody or a modified sequence thereof in which one or more amino acids are substituted, deleted and/or added, wherein the peptide is recognized by any antibody of the present invention, preferably by antibody NI-302.35C1 or NI-302.72F10.

In an additional aspect the present invention relates to peptides having an epitope of the N-terminal-region of HTT specifically recognized by any antibody of the present invention. Preferably, such peptide comprises or consists of an amino acid sequence as indicated in SEQ ID NOs: 144 as the unique linear epitope recognized by the antibody or a modified sequence thereof in which one or more amino acids are substituted, deleted and/or added, wherein the peptide is recognized by any antibody of the present invention, preferably by antibody NI-302.15E8.

Furthermore, in one embodiment the present invention relates to peptides having an epitope of the Q/P-rich-region of HTT specifically recognized by any antibody of the present invention. Preferably, such peptide comprises or consists of an amino acid sequence as indicated in SEQ ID NO: 201 as the unique linear epitope recognized by the antibody or a modified sequence thereof in which one or more amino acids are substituted, deleted and/or added, wherein the peptide is recognized by any antibody of the present invention, preferably by antibody NI-302.7D8.

In addition, in one embodiment the present invention relates to peptides having an epitope of HTT specifically recognized by any antibody of the present invention, preferably by antibody NI-302.6N9, NI-302.12H2, NI-302.8M1 and/or NI-302.4A6 in which one or more amino acids are substituted, deleted and/or added, wherein the peptide is recognized by any antibody of the present invention.

In one embodiment of this invention such a peptide may be used for diagnosing or monitoring a disease or disorder related to mutated, misfolded and/or aggregated HTT species and/or fragments thereof in a subject, such as HD and/or HTT amyloidosis comprising a step of determining the presence of an antibody that binds to a peptide in a biological sample of said subject, and being used for diagnosis of such a disease in said subject by measuring the levels of antibodies which recognize the above described peptide of the present invention and comparing the measurements to the levels which are found in healthy subjects of comparable age and gender. Thus in one embodiment the present invention relates to a method for diagnosing HTT amyloidosis indicative of presymptomatic or clinical HD in a subject, comprising a step of determining the presence of an antibody that binds to a peptide as defined above in a biological sample of said subject. According to this method, an elevated level of measured antibodies specific for said peptide of the present invention is indicative for diagnosing in said subject presymptomatic or clinical HD or for diagnosing in said subject any other disease or disorder from the group of disorders related to HTT as defined hereinabove. The peptide of the present invention may be formulated in an array, a kit and composition, respectively, as described hereinbefore. In this context, the present invention also relates to a kit useful in the diagnosis or monitoring the progression of HD and/or HTT amyloidosis, said kit comprising at least one antibody of the present invention or a HTT-binding molecule having substantially the same binding specificities of any one thereof, the polynucleotide, the vector or the cell and/or the peptide as respectively defined hereinbefore, optionally with reagents and/or instructions for use.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Isolation and Identification of Anti-HTT Antibodies

Human-derived antibodies targeting HTT and/or mutated and/or aggregated HTT species and/or fragments thereof were identified utilizing the method described in the international application WO 2008/081008 the disclosure content of which is incorporated herein by reference, with modifications. In particular, wild-type and mutant HTT proteins obtained by recombinant expression were used in both native and mutated-aggregated conformations for the identification of HTT-targeting antibodies. The mutated-aggregated conformations were produced in vitro, using a procedure similar to the one described in Example 3.

Example 2: Determination of Antibody Sequence

The amino acid sequences of the variable regions of the above identified anti-HTT antibodies were determined on the basis of their mRNA sequences, see FIG. 1. In brief, living B cells of selected non-immortalized memory B cell cultures were harvested. Subsequently, the mRNAs from cells producing selected anti-HTT antibodies were extracted and converted in cDNA, and the sequences encoding the antibody's variable regions were amplified by PCR, cloned into plasmid vectors and sequenced.

In brief, a combination of primers representing all sequence families of the human immunoglobulin germline repertoire was used for the amplifications of leader peptides, V-segments and J-segments. The first round of amplification was performed using leader peptide-specific primers in 5'-end and constant region-specific primers in 3'-end (Smith et al., Nat Protoc. 4 (2009), 372-384). For heavy chains and kappa light chains, the second round of amplification was performed using V-segment-specific primers at the 5'-end and J-segment-specific primers at the 3'-end. For lambda light chains, the second round amplification was performed using V-segment-specific primers at the 5'-end and a C-region-specific primer at the 3'-end (Marks et al., Mol. Biol. 222 (1991), 581-597; de Haard et al., J. Biol. Chem. 26 (1999), 18218-18230).

Identification of the antibody clone with the desired specificity was performed by re-screening on ELISA upon recombinant expression of complete antibodies. Recombinant expression of complete human IgG1 antibodies was achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins were expressed by inserting the immunoglobulin heavy chain RT-PCR product in frame into a heavy chain expression vector bearing a signal peptide and the constant domains of human or mouse immunoglobulin gamma 1. Kappa light chain immunoglobulins were expressed by inserting the kappa light chain RT-PCR-product in frame into a light chain expression vector providing a signal peptide and the constant domain of human kappa light chain immunoglobulin. Lambda light chain immunoglobulins were expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK 293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification. Recombinant human monoclonal antibody can produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)$_2$ and scFv can also be generated from these Ig-variable regions. The framework and complementarity determining regions were determined by comparison with reference antibody sequences available in databases such as Abysis (www.bioinf.org.uk/abysis/) and (www.imgt.org/), and annotated using the Kabat numbering scheme (www.bioinf.org.uk/abs/).

Example 3: Expression of HTT Exon 1 Proteins

Methods

Recombinant huntingtin exon1 proteins GST-HttExon1Q21 (GST-HD21), GST-HttExon1Q35 (GSTHD35), and GST-HttExon1Q49 (GST-HD49) expression and purification pGEX-6P-1 expression vector (GE Healthcare) encoding Exon1 of human huntingtin with polyQ length of 21, 35 or 49 CAG repeats, respectively (compare FIG. 2A) fused with a PreScission cleavage site to an N-terminal Glutathione S-transferases (GST)-tag were expressed in E. coli strain BL21. Overnight bacterial cultures (37° C., 220 rpm) were diluted 1:25 and expression was induced at an Absorption 600 of 0.5-0.6 for 4 hrs by addition of 1 mM IPTG (Sigma 11284) and further incubation at 36° C., 220 rpm. Cultures were grown in LB medium containing 100 µg/ml ampicillin at 37° C., for overnight cultures in addition with 1% glucose. Recombinant GST-HttExon1 proteins were purified by binding to glutathione agarose (Sigma G4510). Briefly, the bacteria pellet was resuspended in 20-40 ml of cold buffer 1 (50 mM NaH2PO4, 5 mM Tris, 150 mM NaCl, 1 mM EDTA pH8, 5 mg/ml final lysozyme, protease inhibitor complete (Roche)) were incubated for 60 min on ice, ultrasonicated, Triton-X100 added (0.1% final) and centrifuged for 90 min at 14,000 g after incubation on ice for 5 min. Glutathione agarose was added to the supernatant, incubated for 2 hrs at 4° C., spun down for 10 min at 1000 g and washed 2× with cold PBS after removal of the supernatant. Elution was performed for 5 min in 1 ml buffer 1 with 10 mM reduced glutathione pH 9. This step was repeated 5 to 15 times until no further protein was eluted. The pooled supernatants were dialyzed against buffer (50 mM tris pH7.4, 150 mM NaCl, 1 mM EDTA, 1% glycerol) over night (10 kD MWCO, Pierce) and aliquots were stored at −80° C.

SDS-PAGE analysis Purified recombinant GST-HttEx1 proteins were resolved by gradient SDS-PAGE (NuPAGE Bis-Tris 4-12%; Invitrogen, Basel, Switzerland) followed by staining with Coomassie brilliant blue or electroblotting on nitrocellulose membranes. Blots were incubated with primary antibodies Mab 5492 (Chemicon N-terminal aa1-82 epitope, P-rich domain) or NI-302.37C12 followed by a goat antimouse IgG secondary antibody conjugated with HRP or donkey anti-human IgG secondary antibody conjugated with HRP. Blots were developed using ECL and ImageQuant LAS 4000 detection (GE Healthcare, Switzerland).

As shown in FIG. 2B the different recombinant GST-HttEx1 proteins were successfully expressed and purified as demonstrated by Coomassie staining after SDS-PAGE.

Example 4: Characterization of Aggregation State by Dot Blot and Filter Retardation To characterize HD21, HD35 and HD49 protein aggregation kinetics filter retardation and dot-blot analyses were performed.

Therefore, at the beginning an aggregation reaction was performed as follows: Recombinant GST-HttExon1 proteins can be expressed and purified as a fusion protein. As soon as the GST tag is cleaved off from the fusion protein by the PreScission Protease (PP) the aggregation reaction of the huntingtin Exon1 protein starts immediately. Before the start of reactions the GST-HttExon1 proteins were centrifuged at 100,000 g for 30 minutes. The cleared protein solution were diluted to 2 µM protein concentration in cold aggregation buffer (0.05 M Tris/HCL pH 7, 0.15 M NaCl, 1 mM EDTA) and 1 mM DTT and PreScission Protease (GE Healthcare) were added. The reaction was incubated at room temperature with rotating at 300 rpm and the aggregation reactions were stopped by snap freezing at −80° C. after the indicated time intervals. Aliquots of HD21, HD35 and HD49 aggregation reactions were subsequently removed after 1, 3, 5, 7 and 24 hrs of incubation time, respectively, snap frozen on dry ice and stored at −80° C.

For the dot blot analysis samples were thawed on ice, diluted and transferred onto a nitrocellulose transfer membrane with a filter device applying vacuum in the chamber below the membrane. To that end, the membrane was equilibrated with PBS, mounted in the chamber and washed with 1000 µl PBS per well. The samples were loaded and completely sucked through the membrane followed by 3 washes with PBS. The device was dissembled and the membrane was briefly air-dried for 15 min at room temperature, blocked for 1 hour at room temperature with blocking buffer (3% BSA, 0.1% Tween 20 in PBS buffer) and incubated with polyclonal HD-1 antibody (1:10'000, kind gift of Prof. E. Wanker, MDC, Berlin). After washing, the membrane was incubated for 1 h at RT with an anti-rabbit IgG antibody coupled to HRP and blots were developed using ECL and ImageQuant LAS 4000 detection (GE Healthcare, Switzerland).

As evident from the dot blot shown in FIG. 2C, left side, polyclonal HD-1 antibody detected HD21, HD35 and HD49 proteins irrespective of their aggregation state.

For filter retardation assays samples were thawed on ice, diluted in denaturation buffer (4% SDS, 100 mM DTT) and transferred through a cellulose acetate membrane with a pore size of 0.2 um using a vacuum chamber: To that end, the membrane was equilibrated in 0.1% SDS in PBS, mounted on the vacuum chamber and the wells were washed with 0.1% SDS. The samples were added, filtered through the membrane by vacuum and washed 3 times with 0.1% SDS. The membrane was then removed from the chamber, briefly air-dried, blocked for 1 h at RT in blocking buffer (5% milk, 0.1% Tween 20 in PBS buffer), incubated with polyclonal HD-1 antibody (1:5'000, Scherzinger et al., Cell 90 (1997), 549-558) and processed further as described above.

In the filter retardation assay, the first aggregates retained by the membrane were detected for HD35 after 24 hours of incubation. HD49 proteins with an extended polyQ tract form insoluble aggregated as early as 3 hrs after cleavage of the GST tag, see FIG. 2C right side (FRA).

Example 5: Characterization of Huntingtin Exon1 Aggregates

To verify and characterize HD35 and HD49 Exon1 aggregate formation electron microscopy (EM) was performed. In brief, HD49 aggregation reactions after 1, 3 and 24 hrs, respectively or samples from HD35 after 24 hrs were analyzed by electron microscopy. Samples were adsorbed onto glow-discharged carboncoated copper grids. Excess sample was removed by blotting on filter paper. Grids were stained with 2% (w/v) uranyl acetate for 1 min and excess uranyl acetate was washed with distilled deionized water. Grids were air-dried and imaged using a Philips CM100 transmission electron microscope with an acceleration voltage of 100 kV.

EM analysis of the HD35 aggregation reaction revealed larger aggregates visible by EM resembling protofibrillar structures after 24 hrs of incubation (FIG. 2D [E]). HD49 displayed a more rapid aggregation kinetics with fibrils being detectable already after 1 hour of incubation (FIG. 2D [F]) and increasing in size and number with aggregation time (FIG. 2D [C, D, G, H]). These observations were consistent with the results obtained in the filter retardation assays where aggregates larger than 0.2 μm are retained on the cellulose acetate membrane and confirm the successful preparation of huntintingtin exon 1 aggregates; see also Example 4.

Example 6: Binding Affinity of Anti-polyP Domain NI-302.33C11 Antibody Utilizing Direct ELISA and $EC_{50}$ To determine the half maximal effective concentration ($EC_{50}$) of recombinant human-derived HTT antibody NI-302.33C11 to soluble and aggregated huntingtin Exon1 proteins with 21 or 49 polyQ repeats direct ELISA was performed. In brief, 96 well microplates (Corning) were coated with either GST-HD21, GST-HD49 or aggregated HD21 or HD49 at a concentration of 5 μg/ml in coating buffer (15 mM Na2CO3, 35 mM NaHCO$_3$, pH 9.42). Nonspecific binding sites were blocked for 1 h at RT with PBS/0.1% Tween®-20 containing 2% BSA (Sigma-Aldrich, Buchs, Switzerland). Primary antibodies were diluted to the indicated concentrations and incubated 1 h at RT. Binding was determined using either a donkey anti-human IgG Fcγ-specific antibody conjugated with HRP or a goat anti-mouse IgG (H+L)-specific antibody conjugated with HRP, followed by measurement of HRP activity in a standard colorimetric assay. Subsequently, $EC_{50}$ values were estimated by a non-linear regression using GraphPad Prism software (San Diego, USA).

The $EC_{50}$ of human-derived HTT antibody NI-302.33C11 for aggregated and soluble HTT exon 1 proteins with 21 or 49 poly Q repeats was determined by direct ELISA with coating of the different preparations at 5 μg/ml concentration. As shown in FIGS. 3A and B antibody NI-302.33C11 bound with similar high affinity to all four species including the pathologically aggregated HTT Exon1 HD49 with an EC50 of approximately 100 pM.

Example 7: Binding Selectivity of Anti-HTT Antibodies Utilizing Dot Blot and Filter Retardation Assay To characterize recombinant human-derived HTT antibody NI-302.33C11 to soluble and aggregated huntingtin Exon 1 proteins with 21, 35 or 49 polyQ repeats filter retardation assay and dot-blot were performed. For this reason, aliquots of HD21, HD35 and HD49 aggregation reactions as described in Example 4 were removed after 1, 3, 5, 7 and 24 hrs of incubation time, snap frozen on dry ice and stored at −80° C. and a dot blot was performed as described in Example 4. Filter retardation assay was also performed as described in Example 4, with the exception that the membrane was incubated with NI-302.33C11 (1 μg/ml).

It could be shown that on the dot blot (FIG. 3C, left side), antibody NI-302.33C11 preferentially detects proteins of huntingtin with expanded polyQ tracts (HD49>>HD35>HD21). Furthermore, the signal intensity increased with increasing incubation times of the aggregation reactions of HD35 and HD49.

This is also true for the results shown in the filter retardation analysis (FIG. 3C, right side), which showed that NI-302.33C11 detects HD35 and HD49 aggregates that were retained on the 0.2 μm pore size membrane. These findings based on spotted protein preparations suggested that antibody NI-302.33C11 has a preference for aggregated HTT conformations with pathogenic polyQ expansions.

Example 8: Binding Specificity and Selectivity of Anti-HTT Antibodies to Unrelated Aggregating Protein Targets Utilizing Direct ELISA To determine the binding specificity antibody NI-302.33C11 recombinant antibody binding to the polyP-region of HTT and not to unrelated aggregating protein targets direct ELISA was performed on 96 well microplates (Corning) coated with different target proteins at a concentration of 1-10 μg/ml in coating buffer (15 mM Na$_2$CO$_3$, 35 mM NaHCO$_3$, pH 9.42). Non-specific binding sites were blocked for 1 h at RT with PBS/0.1% Tween®-20 containing 2% BSA (Sigma-Aldrich, Buchs, Switzerland). NI-302.33C11 antibody was diluted to the indicated concentrations and incubated 1 h at RT. Binding was determined using donkey anti-human IgG Fcγ-specific antibody conjugated with HRP followed by measurement of HRP activity in a standard colorimetric assay. Signals for target protein were calculated in fold increase above median.

It could be shown that human-derived NI-302.33C11 binds specifically to HTT, i.e. aggregated HD49, with absent binding to the other unrelated protein targets including prominent amyloid-forming proteins, see FIG. 16A.

Example 9: Assessment of the Binding Epitope of the HTT Antibody NI-302.33C11

To map the huntingtin (HTT) epitope recognized by the NI-302.33C11 human-derived antibody epitope mapping by peptide scanning analysis with synthetic peptides was performed. In brief, scans of overlapping peptides were used for epitope mapping. The sequence of human HTT Exon 1 sequence was synthesized as a total of 16 linear 15-meric peptides with 10 aa overlap between individual peptides (JPT Peptide Technologies, Berlin, Germany) and spotted onto nitrocellulose membranes. The membrane was activated for 5 min in methanol and then washed at RT in TBS for 10 min. Non-specific binding sites were blocked for 2 hours at room temperature with Roti®-Block (Carl Roth GmbH+Co. KG, Karlsruhe, Germany). Human NI-302.33C11 antibody (1 μg/ml) was incubated for 3 hrs at RT in Roti®-Block. Binding of primary antibody was determined using HRP conjugated donkey-anti human IgGγ secondary antibody. Blots were developed using ECL and ImageQuant LAS 4000 detection (GE Healthcare, Switzerland).

As shown in FIG. 4, prominent binding of NI-302.33C11 was observed to peptides number 7, 8, 9, 13 and 14 indicating that the epitope recognized by this antibody is localized in the polyP repeat domain of huntingtin. The NI-302.33C11 binding epitope is therefore predicted to be localized within HTT amino acids 35-PPPPPPPP-42 (SEQ ID No.: 139) and amino acids 63-PPPPPPPPPP-72 (SEQ ID No.: 162).

Example 10: Epitope Mapping by Direct ELISA Binding to Different Exon1 Peptides of the HTT Antibody NI-302.33C11

To determine the half maximal effective concentration ($EC_{50}$) of recombinant human-derived HTT antibody NI-302.33C11 to BSA-coupled peptide fragments of the huntingtin Exon 1 direct ELISA with BSA-coupled Htt Exon1 domain peptides was performed.

In brief, 96 well microplates (Corning) were coated with BSA-coupled synthetic peptides (Schafer-N, Denmark) of the N-terminal amino acid 1-19 (MATLEKLMKAFESLKSFQQ, SEQ ID No.: 93), the P-rich domain sequence (PPQLPQPPPQAQPLLPQPQPP, SEQ ID No.: 94), the polyP repeat sequence (PPPPPPPPPPP, SEQ ID No.: 95) or the 14 C-terminal amino acids (PPGPAVAEEPLHRP, SEQ ID No.: 96) or with the full lengths GST-HD49 Exon 1 protein at 5 µg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). Primary antibodies were diluted to the indicated concentrations and incubated 1 h at RT. Binding was determined using donkey anti-human IgG Fcγ-specific antibody conjugated with HRP, followed by measurement of HRP activity in a standard colorimetric assay and the $EC_{50}$ values were estimated by a non-linear regression using GraphPad Prism software (San Diego, USA).

As shown in FIG. 5 NI-302.33C11 bound with high affinity to the BSA-coupled polyP peptide as well as to full-length GST-HD49 with an equivalent $EC_{50}$ of 30 pM. This confirms the epitope mapping to the polyP sequence as shown in Example 9.

Example 11: Assessment of the Purity and Integrity of Recombinant Human NI-302.33C11 Anti-polyP Domain Antibody To assess the purity and integrity of recombinant human NI-302.33C11 anti-polyP domain lead antibody human NI-302.33C11 anti-polyP domain antibody was expressed by transient transfection of CHO-S cells and purified by protein A affinity purification on an Akta system. After PD-10 column desalting the antibody was formulated in PBS. Subsequently SDS-PAGE analysis was performed, wherein two and 10 µg of purified recombinant human NI-302.33C11 anti-polyP domain antibody were resolved under reducing conditions by gradient SDS-PAGE (Nu-PAGE 4-12% Bis-Tris gel; Invitrogen) followed by Coomassie staining (SimplyBlue SafeStain, Invitrogen).

The SDS-PAGE analysis under reducing conditions of the recombinant human NI-302 anti-polyP domain lead antibody revealed two major bands corresponding to the antibody heavy and light chains at the expected size as shown in FIG. 6, while no significant contaminations or proteolytic degradation products were detected.

Example 12: Characterization of HTT Antibody NI-302.33C11 in Human HTT Transgenic Mice To assess the binding of NI-302.33C11 antibody to huntingtin pathology in human HTT transgenic mouse brain tissues immunohistochemistry was performed. The B6.Cg-Tg(HDexon1)61Gpb/J transgenic mouse line (Mangiarini et al., Cell 87 (1996), 493-506) is a well characterized mouse model for Huntington's Disease (HD). Starting at around 9 weeks of age, this animal model develops a progressive pathology characterized by intranuclear inclusions of huntingtin reminiscent of human Huntington's disease (Naver et al., Neuroscience 122 (2003), 1049-1057). Hemibrains of these B6.Cg-Tg(HDexon1)61Gpb/J transgenic mice at a progressed stage of disease (270 days) were fixed in phosphate-buffered 4% paraformaldehyde solution, paraffin-embedded, and 5-µm sections were prepared. After formic acid and citrate buffer pretreatment, sections were incubated with 1, 5 or 50 nM human NI-302.33C11 anti-HTT antibody followed by incubation with biotinylated donkey-anti-human secondary antibody (Jackson Immunoresearch; 1:250). Antibody signal was amplified with the Vectastain ABC kit (Vector Laboratories) and detected with diaminobenzidine (Pierce). As shown in FIG. 27 human-derived polyP domain antibody NI-302.33C11 revealed a very prominent staining of neuronal intranuclear inclusion pathology already at the lowest 1 nM concentration (FIG. 27 [E-H]) consistent with the high affinity binding to huntingtin aggregates as determined by ELISA and dot blot analyses. At a concentration of 5 nM or higher, the antibody stained in addition entire medium spiny neurons and produced a more generalized diffuse staining which was also detectable on nontransgenic brain sections. A certain degree of cross-reactivity cannot be excluded as the polyp epitope targeted by NI-302.33C11 was present also in numerous unrelated proteins (FIG. 27 [F-H]).

Example 13: Characterization of Binding Affinity and Selectivity of Anti-P-Rich Domain NI-302.63F3 Antibody Utilizing Direct ELISA and $EC_{50}$ To determine the half maximal effective concentration ($EC_{50}$) of recombinant human-derived HTT antibody NI-302.63F3 to soluble and aggregated HTT Exon1 proteins with 21 or 49 polyQ repeats direct ELISA and $EC_{50}$ determination was performed as described in Example 6, supra.

It could be shown that NI-302.63F3 binds with similar high affinity to all four species including the aggregated HTT Exon 1 HD49 with an $EC_{50}$ of approximately 200 to 400 pM FIGS. 7A and B. Accordingly, the human-derived HTT anti-P-rich domain antibody NI-302.63F3 targets an epitope exposed in aggregated as well as in an uncut, more linear structure of HTT Exon1 protein with high-affinity in the subnanomolar range.

Additionally, to characterize the binding of recombinant human-derived HTT antibody NI-302.63F3 to soluble and aggregated HTT Exon1 proteins with 21, 35 or 49 polyQ repeats using filter retardation assay and dot blot as described in Example 7, supra, with the small modification that the incubation was performed with 1 µg/ml of NI-302.63F3 antibody.

On the dot blot, antibody NI-302.63F3 most prominently detected the HD49 protein with an expanded polyQ tract (FIG. 7C, left side). In the filter retardation analysis NI-302.63F3 detected HD35 and HD49 aggregates that were retained on the 0.2 µm pore size membrane (FIG. 7C, right side). These findings based on spotted protein preparations demonstrate that antibody NI-302.63F3 recognizes aggregated HTT conformations with pathogenic polyQ expansions.

Furthermore, to determine the binding of NI-302.63F3 recombinant antibody to unrelated aggregating protein targets, direct ELISA was performed as described in Example 8, supra. As shown in FIG. 16B human-derived NI-302.63F3 bound specifically to HTT while a binding to unrelated proteins could not be shown.

Example 14: Assessment of the Binding Epitope of the HTT Antibody NI-302.63F3

To map the huntingtin epitope recognized by the NI-302.63F3 human-derived antibody epitope mapping with synthetic peptides was performed as described above in Example 9.

As shown in FIG. 8, prominent binding of NI-302.63F3 was observed to peptides number 10 and 11 with a weak signal on peptide 8 and 9 indicating that the epitope recognized by this antibody is localized in the P-rich domain (between the polyP repeat regions) of HTT. The NI-302.63F3 binding epitope was therefore predicted to be localized within HTT amino acid sequence 43-(PPPQL) PQPPPQAQPL-57 (SEQ ID Nos.: 161 and 140).

Example 15: Epitope Mapping by Direct ELISA Binding to Different Exon1 Peptides of the HTT Antibody NI-302.63F3

To determine the half maximal effective concentration (EC50) of recombinant human-derived HTT antibody NI-302.63F3 to BSA-coupled peptide fragments of the huntingtin Exon 1 direct ELISA with BSA-coupled Htt Exon1 domain peptides and $EC_{50}$ determination were performed as described in Example 10.

As shown in FIG. 9 NI-302.63F3 binds with high affinity to the BSA-coupled P-rich domain peptide as well as to full-length GST-HD49 with a similar $EC_{50}$ of 200 to 300 pM. This confirms the epitope mapping to the P-rich domain sequence as shown in Example 14.

Example 16: Assessment of the Purity and Integrity of Recombinant Human NI-302.63F3 Anti-P-Rich Domain Antibody To assess the purity and integrity of recombinant human NI-302.63F3 anti-proline-rich domain antibody SDS-PAGE analysis was performed as already described in Example 11, supra. SDS-PAGE analysis under reducing conditions of the recombinant human NI-302.63F3 anti-P-rich domain antibody revealed two major bands corresponding to the antibody heavy and light chains at the expected size. No significant contaminations or proteolytic degradation products were detected as shown in FIG. 10.

Example 17: Characterization of HTT Antibody NI-302.63F3 in Human HTT Transgenic Mice The assessment of the binding of NI-302.63F3 anti-P-rich domain antibody to HTT pathology in human HTT transgenic mouse brain tissues was assessed as described in Example 12, supra with the difference that the incubation of the sections was performed with 1 or 50 nM of the anti-P-rich domain antibody.

As shown in FIG. 28 [E-F] the human-derived NI-302.63F3 anti-P-rich domain antibody revealed a prominent and highly specific staining of neuronal intranuclear inclusion pathology at 1 and 50 nM concentration in the striatum and cortex of R6/1 transgenic animals consistent with the high affinity binding to HTT aggregates as determined by ELISA and dot blot analysis. However as shown in FIG. 28 [F] at a concentration of 50 nM the antibody NI-302.63F3 stained additionally weakly the entire nucleus of the medium spiny neurons.

Example 18: Characterization of Binding Affinity and Selectivity of Anti-C-Terminal Domain Antibodies NI-302.35C1 and NI-302.72F10 Utilizing Direct ELISA and $EC_{50}$ To determine the half maximal effective concentration ($EC_{50}$) of recombinant human-derived HTT antibodies NI-302.35C1 and NI-302.72F10 to soluble and aggregated HTT Exon 1 proteins with 21 or 49 polyQ repeats direct ELISA and $EC_{50}$ determination was performed as described in Example 6, supra.

It could be shown that NI-302.35C1 binds with high affinity to all four species including the aggregated HTT Exon1 HD49 with an $EC_{50}$ of approximately 2.7 nM; see FIGS. 11A and B. Similarly, NI-302.72F10 binds to all four species albeit with a different affinity than NI-302.35C1 (aggregated HD21>>GST-HD21>>aggregated HD49>>GST-HD49) (FIG. 31C) which may be explained with the different epitopes recognized by both antibodies (FIG. 20).

Accordingly, the human-derived HTT anti-C-terminal domain antibodies NI-302.35C1 and NI-302.72F10 target an epitope exposed in aggregated as well as in soluble forms of HTT with low nanomolar affinity.

Additionally, to characterize the binding of recombinant human-derived HTT antibodies NI-302.35C1 and NI-302.72F10 to soluble and aggregated HTT Exon1 proteins with 21, 35 or 49 polyQ repeats filter retardation assay and dot blot as described in Example 7, supra, was performed.

On the dot blot, antibody NI-302.35C1 preferentially detected constructs of HTT with expanded polyQ tracts (HD49>HD35>>HD21, FIG. 11C, left side). Furthermore, the signal intensity increases with increasing incubation times of the aggregation reactions of HD35 and HD49. Similarly, antibody NI-302.72F10 detected constructs of HTT with expanded polyQ tracts albeit with a different preference (HD35>>HD49>HD21) whereas the signal intensity increases with increasing incubation times of the aggregation reactions of HD35 only (FIG. 32C).

In the filter retardation analysis NI-302.35C1 detected HD35 and HD49 aggregates that were retained on the 0.2 μm pore size membrane (FIG. 11C, right side) whereas NI-302.72F10 detected HD35 aggregates only (FIG. 32C, right side). These findings based on membrane bound protein preparations suggested that antibodies NI-302.35C1 and NI-302.72F10 preferentially targets aggregated HTT conformations with pathogenic polyQ expansions.

Furthermore, to determine the binding of NI-302.35C1 and NI-302.72F10 recombinant antibodies to unrelated aggregating protein targets, direct ELISA was performed as described in Example 8, supra. As shown in FIG. 16C human-derived NI-302.35C1 as well as shown in FIG. 33C human-derived NI-302.72F10 bound specifically to HTT while a binding to unrelated proteins could not be shown.

Example 19: Assessment of the Binding Epitope of the HTT Antibody NI-302.35C1

To map the huntingtin epitope recognized by the NI-302.35C1 human-derived antibody epitope mapping with synthetic peptides was performed as described above in Example 9.

Determination of NI-302.35C1 antibody binding epitope by scan of overlapping peptides did not result in specific signal. Therefore, processing this antibody in the way it was done for the other HTT NI-302 antibodies did not results in any specific signal on the individual peptides for unknown reasons. The epitope was successfully mapped to a C-terminal peptide by coupling it to BSA, see also Example 20.

Example 20: Epitope Mapping by Direct ELISA Binding to Different Exon1 Peptides of the C-Terminal Domain HTT Antibody NI-302.35C1

To determine the half maximal effective concentration ($EC_{50}$) of recombinant human-derived HTT antibody NI-302.35C1 to BSA-coupled peptide fragments of the HTT Exon 1 direct ELISA with BSA-coupled Htt Exon1 domain peptides and $EC_{50}$ determination were performed as described in Example 10.

As shown in FIG. 12 NI-302.35C1 binds with high affinity to the BSA-coupled C-terminal peptide as well as to full-length GST-HD49 with an $EC_{50}$ value of approximately 0.7 nM and 3.2 nM, respectively. This locates the epitope to the C-terminal region of HTT Exon1 sequence (71-PPGPA-VAEEPLHRP-85, SEQ ID No: 96). If the same C-terminal peptide was coated directly to the plate only weak binding was observed ($EC_{50}$>100 nM, data not shown) suggesting that the presentation of the peptide coupled to BSA increases the binding to the epitope and might be an explanation why the epitope mapping by peptide scanning analysis as shown in Example 20 did not work.

Example 21: Assessment of the Purity and Integrity of Recombinant Human NI-302.35C1 Anti-P-Rich Domain Antibody To assess the purity and integrity of recombinant human NI-302.35C1 anti-C-terminal domain antibody SDS-PAGE analysis was performed as already described in Example 11, supra.

SDS-PAGE analysis under reducing conditions of the recombinant human NI-302.35C1 anti-C-terminal domain antibody revealed two major bands corresponding to the antibody heavy and light chains at the expected size, while no significant contaminations or proteolytic degradation products were detected (FIG. 13).

Example 22: Characterization of HTT Antibody NI-302.35C1 in Human HTT Transgenic Mice The assessment of the binding of NI-302.35C1 anti-C-terminal domain antibody to HTT pathology in human HTT transgenic mouse brain tissues was assessed as described in Example 12, supra with the difference that the incubation of the sections was performed with 5 or 50 nM of the anti-C-terminal domain antibody.

As shown in FIG. 29 [E-F] the human-derived NI-302.35C1 anti-C-terminal domain antibody revealed a prominent staining of neuronal intranuclear inclusion pathology at 5 and 50 nM concentration in striatum of R6/1 transgenic animals consistent with the high affinity binding to HTT aggregates as determined by ELISA and dot-blot analyses.

Example 23: Assessment of the Effects of Human-Derived Antibodies Targeting HTT on Spine Density in Hippocampal Slice Cultures Antibody Expression and Purification Human-derived antibodies targeting distinct domains in HTT exon 1 were expressed by transient transfection of CHO-S cells and purified by protein A affinity purification on the Akta system. After PD-10 column desalting the antibodies were formulated in PBS. Endotoxin levels were confirmed to be <10 EU/ml.

Hippocampal Slice Culture

Organotypic hippocampal slice cultures were prepared and cultured according to Stoppini et al., J Neurosci Methods. (1991) 37(2):173-82. In short, 6- to 8-d-old B6CBA-Tg(HDexon1)62Gpb/1J transgenic and nontransgenic littermates were decapitated, brains were removed, and both hippocampi were isolated and cut into 400-µm thick slices. This method yields thin slices which remain 1-4 cell layers thick and are characterized by a well preserved organotypic organization. Slices were cultured on Millicell culture plate inserts (0.4 µm, Millipore) in six-well plates containing 1 ml of culture medium (46% minimum essential medium Eagle with HEPES modification, 25% basal medium with Earle's modification, 25% heat-inactivated horse serum, 2 mM glutamine, 0.6% glucose, pH 7.2). Culture plates were kept at 37° C. in a humidified atmosphere containing 5% CO2. Slices were kept in culture for 7 d before the experiments. Culture medium was exchanged every second or third day. On day 7 antibodies were added at a concentration of 10 µg/ml. On day 10 in vitro slice cultures were infected with Sindbis virus using a droplet method (Shahani et al., J Neurosci. 31 (2006), 6103-6114). For spine analysis, cultures were fixed at day 4 post infection (14 days in vitro). Slices were left attached to the culture plate membrane to preserve hippocampal structure and rinsed with PBS. Slices were then fixed with 4% paraformaldehyde in PBS containing 4% sucrose for 2 h at 4° C. For each dendrite a picture was taken and spines were analyzed over a length of 30-45 µm. Eight to 13 slices per group from a total of 12 transgenic animals were quantified for each antibody treatment. Data represent the mean±SEM. *p<0.05 (MWU), #p=0.05.

The quantification of dendritic spine density in hippocampal slice cultures of Tg(HDexon1)62Gpb/1J transgenic mice (FIG. 17 B, D) revealed a significant reduction by 53% compared to non-transgenic littermates (FIG. 17 A, C, E) using hippocampal slices of postnatal day 6 animals after 14 days in vitro with the experimental design described above. Upon addition of human-derived NI-302 antibodies at concentration of 10 µg/ml for seven days a significant attenuation of spine density loss was observed for antibodies NI-302.31F11 (FIG. 17 F, p<0.05, t-test) and NI-302.63F3 (p=0.05, t-test), whereas antibody NI-302.33C11 and NI-302.35C1 did not show a clear effect under the conditions tested.

The significant reduction of spine density compared to non-transgenic littermate in displayed in hippocampal slice cultures of Tg(HDexon1)62Gpb/1J transgenic mice led to the suggestion that this is a suitable model for in vitro testing of HTT candidate antibodies for their activity towards interference with HTT toxicity. In this model, antibodies NI-302.63F3 and NI-302.11F11 that both targeted the P-rich domain within HTT exon 1 were able to improved spine density compared to an isotype control antibody. This suggests that these antibodies can attenuate the toxic effects on spine density driven by expression of pathological poly-Q-expanded HTT.

Example 24: Penetration of NI-302 Antibodies in the Brain of R6/1 Animal Model To test the penetration of the anti-HTT antibodies of the present invention a transgenic mice model was utilized. In particular, Tg(HDexon1)61Gpb/J transgenic mice harbor a 1.9 kb transgene which was isolated from a phage genomic clone derived from an Huntington's disease (HD) patient and contained the 5' end of the human huntingtin (HTT) gene. It was composed of approximately 1 kb of 5' UTR sequences, exon 1 (carrying expanded CAG repeats of ~130 units) and the first 262 bp of intron 1. This construct was microinjected into single cell CBAxC57BL/6 embryos. Male founder R6 was bred to CBAxC57BL/6 females, producing several founder lines. Mice from founder line R6/1 have the transgene integrated as a single intact copy which is ubiquitously expressed. Transgenic mice on a mixed CBAxC57BL/6 genetic background were backcrossed to C57BL/6J for more than 12 to generate the congenic strain B 6.Cg-Tg(HDexon1)61Gpb/J.

R6/1 transgenic mice exhibit a progressive neurological phenotype that mimics many of the features of HD, including choreiform-like movements, involuntary stereotypic movements, tremor, and epileptic seizures, as well as non-movement disorder components, including unusual vocalization. They urinate frequently and exhibit loss of body weight and muscle bulk through the course of the disease. Neurologically they develop neuronal intranuclear inclusions (NII) which contain both the HTT and ubiquitin proteins. These NII have also been identified in human HD patients. The age of onset of HD symptoms is reported to occur between 15 and 21 weeks for this 6/1 line.

The study animals displayed the following properties and were identified by classical ear marking:
Strain: Hemizygous B6.Cg-Tg(HDexon1)61Gpb/J (Mangiarini et al., Cell, 87 (1996), 493-506)
Source: Jackson Laboratory, Maine, USA
Sex: Males and females
Age start: 230 to 260 days
Cohorts: NI-302.31F11 Total: 3 males
NI-302.35C1 Total: 3 males
Vehicle Total: 3 males For the spinal cord homogenization B6.Cg-Tg(HDexon1)61Gpb/J transgenic mice were deeply anesthetized and transcardially perfused with cold phosphate-buffered saline through the left ventricle by mean of a peristaltic pump. The brain was dissected out and snap frozen on dry ice. The tissue samples were homogenized in 1:10 w/v DEA-Buffer (50 mM NaCl, 0.2% DEA, protease inhibitor complete, Roche Diagnostics) with a hand-sonicator (Sartorius, Labsonic M). Samples were centrifuged for 30 minutes at 100'000×g at 4° C. and aliquots of the supernatant were stored at −80° C. before analysis.

In the following human IgG drug level sandwich ELISA the human NI-302.35C1, NI-302.11F11 antibody plasma levels were determined using the corresponding recombinant antibody of known concentration as standard. 96 well microplates (Corning) were coated with donkey anti human IgG (709-005-149, Jackson Immunoresearch) at 1 µg/ml in 50 mM carbonate coating buffer pH 9.6. Non-specific binding sites were blocked for 1 hr at RT with PBS/0.1% Tween®-20 containing 2% BSA (Sigma, Buchs, Switzerland). Plasma samples were diluted 1:20'000 and 1:100'000, brain homogenates were diluted 1:5 and 1:50 and both were incubated 1 hr at RT together with the standard dilution curves. Binding was determined using the detection antibody anti human HRP (709-036-098, Jackson Immunoresearch), followed by measurement of HRP activity in a standard colorimetric assay. Concentrations of plasma and spinal cord samples were calculated based on the individual standard curve. Values shown in table 6-1 are average values of 2 independent ELISA experiments.

Plasma and brain samples were obtained 2 days after a single intraperitoneal injection of 50 mg/kg of antibodies NI-302.31F11, NI-302.35C1 in R6/1 transgenic mice. Antibody levels in plasma and brain homogenates were determined by human sandwich IgG ELISA (FIGS. 18A and B). The ratio of brain versus plasma drug levels was determined at 0.13±0.02% and 0.21±0.06% for human-derived antibodies NI-302.31F11 and NI-302.35C1, respectively. These results suggest a 48 h brain penetration of the tested NI-302 antibodies in the expected range in HTT transgenic mice.

Example 25: Characterization of Binding Affinity and Specificity of Further Antibodies Identified in Accordance with the Present Invention To determine the half maximal effective concentration ($EC_{50}$) of further identified recombinant human-derived HTT antibodies to soluble and aggregated HTT Exon1 proteins with 21 or 49 polyQ repeats direct ELISA with coating of the different preparations at 5 µg/ml concentration and $EC_{50}$ determination was performed as described in Example 6, supra.

The determined $EC_{50}$ for the different HTT species are shown in FIG. 19 as well as FIG. 31 (A, D-F) and summarized in FIG. 20. Most human-derived antibodies bound with high affinity at subnanomolar or low nanomolar $EC_{50}$. Some candidates such as NI-302.37C12, NI-302.55D8, NI-302.11A4, NI-302.22H9 or NI-302.64E5 seemed to have preferred binding to uncut GST-HTT protein, other antibodies such as NI-302.74C11, NI-302.71F6, NI-302.4A6, NI-302.12H2 or NI-302-8M1 showed high affinity binding with similar $EC_{50}$-values to all HTT preparation in the ELISA assay. NI-302.15F9 showed about a 5-fold preference of HD49 vs. HD21 with $EC_{50}$ values in the range of 5 to 35 nM. Antibody 33C11 served as control in this experiment (FIG. 32G).

Therefore, a panel of high affinity recombinant HTT specific human antibodies was cloned from memory B-cells derived from healthy elderly human donor cohorts and recombinantly expressed and characterized. Additionally, a screening campaign for additional backup antibodies was initiated in a cohort of selected presymptomatic patients with Huntington's disease (HD) carrying different lengths CAG repeat expansions.

To further characterize the binding of the identified recombinant human-derived HTT NI-302 antibodies to soluble and aggregated HTT Exon1 proteins with 21, 35 or 49 polyQ repeats filter retardation assay utilizing 0.2 µg/ml primary antibody and dot-blot analysis utilizing 1 µg/ml primary antibody were performed as described in Example 7, supra.

Figure 21:
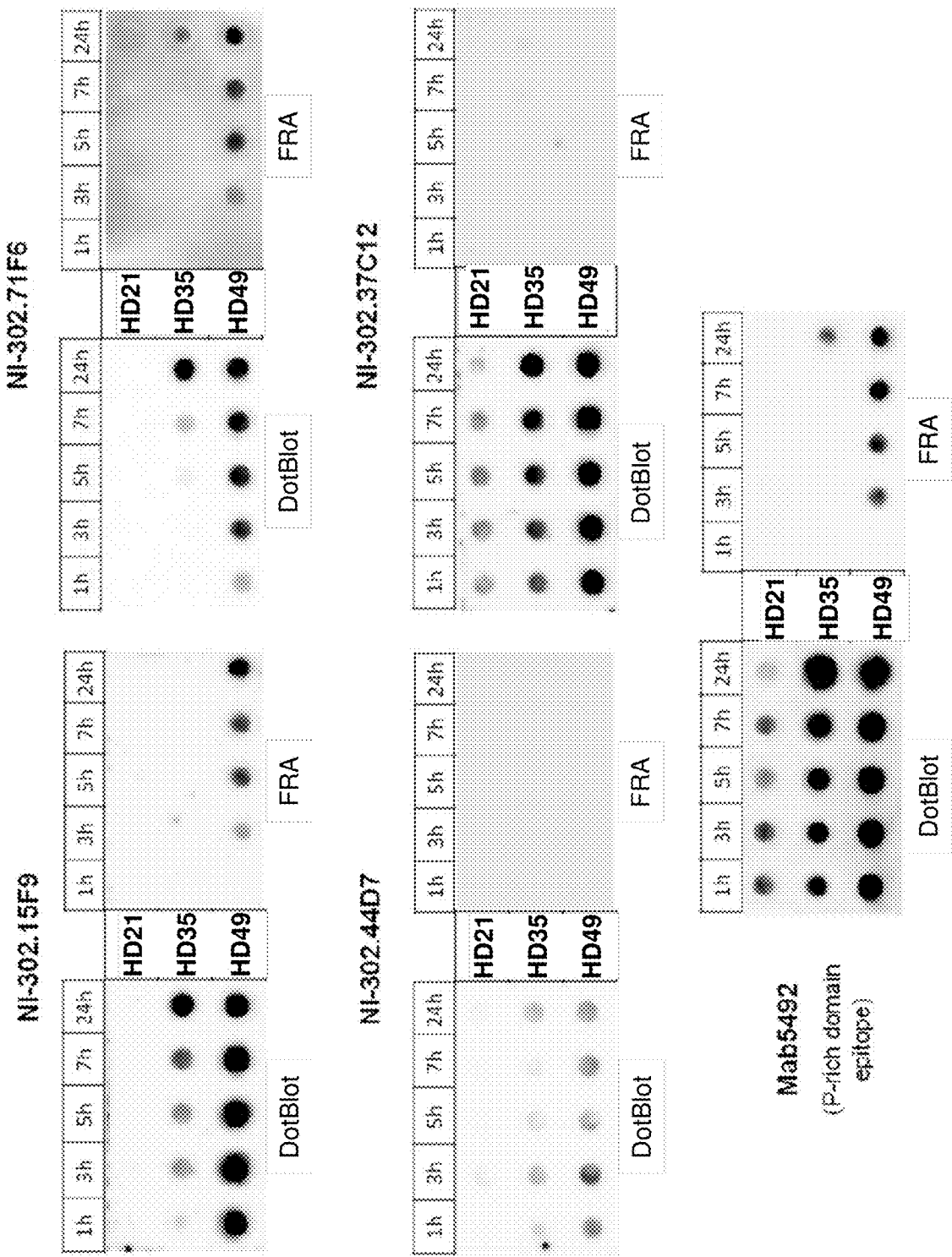

As shown in FIG. 21 and FIG. 32 (A, G), on the dot blot (FIG. left side, DotBlot) most of the antibodies characterized showed a preference for detection of HTT proteins with expanded polyQ tracts (HD49>>HD35>HD21). Furthermore, the signal intensity increased with increasing incubation times of the aggregation reactions of HD35 and HD49 in particular for antibodies NI-302.15F9, NI-302.71F6 (FIG. 21, first row of blots) and NI-302-64E5 (FIG. 32A, left side). In the filter retardation analysis NI-302.15F9, NI-302.71F6 (FIG. 21, right side, FRA) and NI-302-64E5 (FIG. 32 A, right side) detected SDS stable HD35 and HD49 aggregates that were retained on the 0.2 µm pore size membrane whereas other antibodies such as NI-302.44D7 and NI-302.37C12 (FIG. 21, second row of blots) or NI-302.4A6, NI-302.12H2 and NI-302.8M1 (FIG. 32 D, E, F) did not bind to aggregates on the filter. Antibody 33C11 served as control in this experiment (FIG. 32G). These findings based on spotted protein preparations suggest that several of the cloned NI-302 antibodies show a preference for aggregated HTT conformations with pathogenic polyQ expansions.

Additionally, the binding specificity of the identified antibodies to unrelated proteins, in particular to proteins forming aggregates was assessed by direct ELISA (FIG. 22 and FIG. 33A, D-F) as already described in Example 8, supra. The results showed that most of the human-derived NI-302 antibodies tested bind specifically to HTT with absent binding to the other unrelated proteins tested.

Example 26: Assessment of the Binding and Epitope Mapping of Human-Derived HTT Antibodies To map the HTT epitope recognized by the newly identified human-derived antibodies epitope mapping with synthetic peptides was performed as described above in Example 9 (FIG. 23 and FIG. 35 A, D-F). Additionally, the half maximal effective concentration ($EC_{50}$) of the HTT antibodies to BSA-coupled peptide fragments of the HTT Exon 1 by direct ELISA with BSA-coupled Htt Exon1 domain peptides was determined as well as $EC_{50}$ determination were performed as described in Example 10.

Example 27: Assessment of the Binding of HTT Antibodies in Human HTT Transgenic Mice The characterization of the binding of the identified antibodies to HTT pathology in human HTT transgenic mouse brain tissues was assessed as described in Example 12, supra with the difference that the incubation of the sections was performed with 5 nM ffig.3M (74C11, 39C12, 11A4, 22H9, 78H12, 37C12, 7D8, 72F10) or 50 nM concentrations (15F9, 71F6, 55D8, 44D7, 7A8, 64E5) of the anti-HTT antibodies. As shown in FIG. 24 the identified human-derived anti-HTT antibodies revealed a prominent and highly specific staining of neuronal intranuclear inclusion pathology in the striatum and cortex of R6/1 transgenic animals, as also shown for the antibodies NI-302.33C11, NI-302.63F3, and NI-302.35C1, described above. These findings are consistent with the high affinity binding to HTT aggregates as determined by ELISA and dot blot analysis in Example 26.

Example 28: Basic Characterization of Transgenic Mouse Model R6/1 of Huntington's Disease (HD)

Tg(HDexon1)61Gpb/J transgenic mice harbor a 1.9 kb transgene which was isolated from a phage genomic clone derived from an HD patient and contained the 5' end of the human huntingtin (HTT) gene. It was composed of approximately 1 kb of 5' UTR sequences, exon 1 (carrying expanded CAG repeats of ~130 units) and the first 262 bp of intron 1. This construct was microinjected into single cell CBAxC57BL/6 embryos. Male founder R6 was bred to CBAxC57BL/6 females, producing several founder lines (Mangiarini et al., Cell 87 (1996), 493-506). Mice from founder line R6/1 have the transgene integrated as a single intact copy which is ubiquitously expressed. Transgenic mice on a mixed CBAxC57BL/6 genetic background were backcrossed to C57BL/6J for more than 12 to generate the congenic strain B6.Cg-Tg(HDexon1)61Gpb/J. R6/1 transgenic mice exhibit a progressive neurological phenotype that mimics many of the features of HD, including choreiform-like movements, involuntary stereotypic movements, tremor, and epileptic seizures, as well as nonmovement disorder components, including unusual vocalization. They urinate frequently and exhibit loss of body weight and muscle bulk through the course of the disease. Neurologically they develop neuronal intranuclear inclusions (NII) which contain both the HTT and ubiquitin proteins. These NII have also been identified in human HD patients. The age of onset of HD symptoms is reported to occur between 15 and 21 weeks for this 6/1 line (Naver et al, Neuroscience 122 (2003), 1049-1057; Hodges et al, Genes Brain Behav. 7(3) (2008), 288-299).

R6/1 transgenic mice obtained from Jackson Laboratories were expanded and longitudinally characterized with respect to behavior phenotype, longitudinal development of body weight, total brain weight, histopathological analysis and survival, as shown in FIG. 25. The findings obtained by in large were in line with the published data and identified this mouse line as a suitable preclinical model for efficacy studies with human-derived NI-302 antibodies targeting aggregated HTT.

Example 29: Basic Characterization of Transgenic Mouse Model N171-82Q of HD

The B6C3-Tg(HD82Gln)81Dbo/J (N171-82Q) transgenic mouse line (Schilling et al., Hum Mol Genet. 8(3) (1999), 397-407) is a well characterized mouse model for HD. B6C3-Tg(HD82Gln)81Dbo/J (N171-82Q) transgenic mice expresses an N-terminally truncated human HTT cDNA that encodes 82 glutamines and encompasses the first 171 amino acids. The altered HTT cDNA is under control of a mouse prion protein promoter. Expression is observed in neurons of the central nervous system. Mice expressing this transgene appear normal at birth through 1-2 months. However, the mice fail to gain weight, develop tremors, hypokinesis and lack coordination. They exhibit an abnormal gait and frequent hind limb clasping. Their life expectancy is 5-6 months. Studies using HTT antibodies indicated diffuse nuclear labeling and numerous immunoreactive nuclear inclusions in multiple neuron populations. Additionally neuritic damage was evident.

N171-82Q transgenic mice obtained from Jackson Laboratories were expanded and longitudinally characterized with respect to behavior phenotype, longitudinal development of body weight, total brain weight at endstage, histopathological analysis and survival (FIG. 26). These findings by in large were in line with published data and identified this mouse line additionally to the mouse line described in Example 29, as a suitable preclinical model for efficacy studies with human-derived NI-302 antibodies targeting aggregated HTT.

Example 30: Assessment of Neuronal Inclusion Staining in Huntington's Disease (HD) Patients To assess the staining of neuronal inclusions by the identified antibodies of the present invention in patients immunochistochemical analysis was performed. The assessment of the binding of identified antibodies to HTT pathology in human brain tissues was assessed as described in Example 12, supra with the difference that the incubation of the sections was performed with 50 nM of NI-302.33C11, 50 nM of NI-302.63F3 or 100 nM of NI-302.35C1 antibody.

As shown in FIG. 27 the immunohistochemical analysis with the polyP-region binding antibody NI-302.33C11 showed a staining of neuronal intranuclear inclusions in cortical neurons of Huntington Disease patients (FIG. 27A-D) at 50 nM and in striatal neurons of 270 day old, late disease stage B6.Cg-Tg(HDexon1)61Gpb/J) transgenic animals at 1 (E) and 5 nM (F) concentration, while no staining was detected in non-transgenic littermates (G), when the primary antibody was omitted during the staining (H) or if tissue of non-Huntington Disease controls was stained with 50 nM of NI-302.33C11. The P-rich-domain antibody NI-302.63F3 (FIG. 28) and anti-C-terminal domain antibody NI-302.35C1 (FIG. 29) showed within the immunohistochemical analysis with 50 nM of NI-302.63F3 or 100 nM of NI-302.35C1 a staining of neuronal intranuclear inclusions (A-C) and staining of some neurites (D) of cortical neurons of four different Huntington Disease patients (A-D). A staining could also be observed in the striatal neurons of 270 day old, late disease stage B6.Cg-Tg(HDexon1)61Gpb/J) transgenic animals at 1 (E) and 50 nM (F) concentration. No staining was detected in non-transgenic littermates (G), if primary antibody was omitted during the staining (H) or if tissue of non-Huntington Disease controls was stained with 50 nM of NI-302.63F3 or 100 nM of NI-302.35C1, respectively.

In contrast to the specific anti-HTT antibodies of the present invention, immunohistochemical analysis with the commercially available anti-polyQ antibody Mab1574 (1:2000, Chemicon) showed additional staining of tissue, i.e. a more general nuclear and cytoplasmic staining and staining of some neurites (FIG. 30A, D) of cortical neurons of four different Huntington Disease patients and in striatal neurons of presymptomatic, 150 day old (FIG. 30E) and 270 day old (FIG. 30F), late disease stage B6.Cg-Tg(HDexon1) 61Gpb/J) transgenic animals.

Example 31: Characterization of Binding Affinity and Selectivity of Anti-Poly Q/P Domain NI-302.7D8 Antibody Utilizing Direct ELISA and $EC_{50}$ To determine the half maximal effective concentration ($EC_{50}$) of recombinant human-derived HTT antibody NI-302.7D8 to soluble and aggregated HTT Exon1 proteins with 21 or 49 polyQ repeats direct ELISA and EC50 determination was performed as described in Example 6, supra.

It could be shown that NI-302.7D8 binds with similar high affinity to soluble GST-HD21 and aggregated HD21 with an $EC_{50}$ of approximately 50 to 100 nM albeit showing a preference to the elongated more pathogenic form of aggregated HD49 and soluble GST-HD49 with an $EC_{50}$ of 17 and 6 nM respectively (FIG. 31B)

Accordingly, the human-derived HTT anti-poly Q/P domain antibody NI-302.7D8 targets an epitope exposed in aggregated as well as in an uncut, more linear structure of HTT Exon1 protein with high-affinity in the low nanomolar range.

Additionally, to characterize the binding of recombinant human-derived HTT antibody NI-302.7D8 to soluble and aggregated HTT Exon1 proteins with 21, 35 or 49 polyQ repeats using filter retardation assay and dot blot at a concentration of 1 ug/ml. as described in Example 7, supra.

It could be shown that on the dot blot (FIG. 32B, left side), antibody NI-302.7D8 equally good detected proteins of huntingtin with expanded polyQ tracts (HD49=HD35=HD21). In the filter retardation analysis (FIG. 32B, right side, FRA) NI-302.7D8 did not bind to SDS stable HD21, HD35 or HD49 aggregates on the filter membrane.

Furthermore, to determine the binding of NI-302.7D8 recombinant antibody to unrelated aggregating protein targets, direct ELISA was performed as described in Example 8, supra. As shown in FIG. 33B human-derived NI-302.7D8 bound specifically to HTT while a binding to unrelated proteins could not be shown.

Example 32: Assessment of the Binding Epitope of the HTT Antibodies NI-302-64E5, NI-302.7D8 and NI-302.72F10

To map the huntingtin epitope recognized by the NI-302-64E5, NI-302.7D8 and NI-302.72F10 human-derived antibody epitope mapping with synthetic peptides was performed as described above in Example 9.

FIG. 35A shows a prominent binding of NI-302-64E5 to peptides number 10 to 12 indicating that the epitope recognized by this antibody is localized in the P-rich repeat domain of huntingtin. The NI-302.64E5 binding epitope is therefore predicted to be localized within HTT amino acids 48-PQPPPQAQPL-58 (SEQ ID No.: 200). As shown in FIG. 35B, prominent binding of NI-302.7D8 was observed to peptides number 6 to 8 indicating that the epitope recognized by this antibody is localized in the polyQ/polyP repeat domain of huntingtin. The NI-302.7D8 binding epitope is therefore predicted to be localized within HTT amino acids 28-QQQQQQQPPP-37 (SEQ ID No.: 201). In contrast, prominent binding of NI-302.72F10 was observed to peptides number 15 and 16 indicating that the epitope recognized by this antibody is localized at the anti-N-terminal domain of HTT (FIG. 35C). The NI-302.72F10 binding epitope was therefore predicted to be localized within HTT amino acids 70-PPPGPAVAEEPLH-82 (SEQ ID No.: 202).

Example 32: Characterization of Binding Affinity and Selectivity of Anti-N-Terminal Domain Antibody NI-302.15E8 Utilizing Direct ELISA and $EC_{50}$ To determine the half maximal effective concentration ($EC_{50}$) of recombinant human-derived HTT antibody NI-302.15E8 to soluble and aggregated HTT Exon1 proteins with 21 or 49 polyQ repeats direct ELISA and $EC_{50}$ determination was performed as described in Example 6, supra.

It could be shown that NI-302.15E8 binds with higher affinity to non-aggregated GST-HD49 and GST-HD21 and less affinity to aggregated HD49 and HD21, see FIGS. 14A and B. Accordingly, the human-derived HTT anti-N-terminal domain antibody NI-302.15E8 target an epitope exposed in both aggregated as well as in soluble forms of HTT, albeit with a higher affinity to soluble forms of HTT.

Example 33: Epitope Mapping by Direct ELISA Binding to Different Exon1 Peptides of the HTT Antibody NI-302.15E8

To determine the half maximal effective concentration (EC50) of recombinant human-derived HTT antibody NI-302.15E8 to BSA-coupled peptide fragments of the huntingtin Exon 1 direct ELISA with BSA-coupled Htt Exon1 domain peptides and $EC_{50}$ determination were performed as described in Example 10.

As shown in FIG. 15 NI-302.15E8 binds with high affinity to the first 19 BSA-coupled amino acids at the N-terminus as well as to full-length GST-HD49 with an $EC_{50}$ of approx. 0.1 or 15, respectively.

Example 34: Impact of HTT Antibody NI-302.35C1 on Behavioral Deficits in Human HTT Transgenic Mice An Elevated Plus Maze test to measure anxiety-like behavior and a Pole test to measure motor performance and coordination in human HTT mice were performed to study the anti-HTT antibody NI-302.35C1 in vivo.
Groups and Treatment For the behavioral analysis two groups of mice with n=24 (12/12 male/female) B6.Cg-Tg(HDexon1)61Gpb/J transgenic (tg) mice as described in Example 12 and one group of wild type (wt) mice were used. The groups of transgenic mice received intraperitoneal treatment of either 30 mg/kg mouse chimeric NI-302.35C1 or vehicle starting at an age for 6-7 weeks until end stage phenotype of the mice between 7 to 9 months of age and the wild type mice were injected with the same volume of vehicle. The Elevated-Plus-Maze and pole test behavioral tests were performed at an age of 16 and 18 weeks of age respectively.
Elevated Plus Maze Test The Elevated Plus Maze test was performed according to Naver et al., Neursoscience 122 (2003), 1049-1057. The maze was elevated 50 cm above the floor. Four maze arms (30 cm×5 cm) originated from a central platform forming a cross. Two of the arms located opposite each other were enclosed by 15 cm high walls (closed arms) while the other arms did not have any kind of screening (open arms). The test were performed at the beginning of the dark phase of the animals and the illumination on the open arm was in the range of 40 lux. Each mouse was placed in the center of the Plus Maze facing an open arm. The experiment lasted for 5 min and was recorded with a videotracking system (Video-Mot Software, TSE Systems). Between the sessions, the maze was rinsed with water and dried with a paper towel. Subsequently the number of entries made into open and closed arms as well as the time spent in open and closed compartments were evaluated. An entry was defined as all four paws in one arm. The number of entries into the open arms and the time spent in the open arms are used as indices of open space-induced anxiety in mice.
Pole Test The pole test is used widely to assess basal ganglia-related movement disorders in mice; see, e.g. Matsuura et al. J. Neurosci. 73 (1997), 45-48; Sedelis et al. Behav Brain Res. 125 (2001), 109-125, Fernagut et al., Neuroscience 116 (2003), 1123-1130. Briefly, animals were placed head-up on top of a vertical wooden pole 50 cm long (1 cm in diameter). The base of the pole was placed in the home cage. When placed on the pole, animals orient themselves downward and descend the length of the pole back into their home cage. On the test day, animals received three trials, and the total time to descend (t-total) were measured. The results of the third trial of the day is shown in FIG. 24B.

As shown in FIG. 34A NI-302.35C1 treated R6/1 animals spend less time in the open arms, entered the open arms less frequently and did less unprotected head dips on the open arm compared to vehicle treated R6/1 animals. Hence the NI-302.35C1 treated R6/1 mice displayed a more anxious phenotype, comparable to the non-transgenic littermates. Furthermore, as shown in FIG. 24B NI-302.35C1 treated R6/1 animal showed an improved performance in the pole test compared to vehicle treated R6/1 animals reaching levels similar to non-transgenic animals. In summary, the antibody NI-302.35C1 of the present invention has a beneficial impact on behavioral performance and motor-related tasks in human HTT transgenic mice.

Example 35: Sequence Alignment of HTT Antibodies

The determination of percent identity or similarity was performed with the standard parameters of the BLASTn program as described in section "Definitions" of the present invention. As shown in FIG. 36 all antibodies of the present invention are rich of tyrosines in the CDRs.

Example 36: Generation of Bispecific Anti-HTT Antibodies

The generation of bispecific antibodies can be performed as generally described in Brennan; see supra. Starting material for producing bispecific antibodies are intact IgG anti-HTT antibodies of the present invention recognizing either a polyP-region, a polyQ/polyP-region, the P-rich-region, the C terminal-region or the N-terminal region of HTT exon 1 protein as described in the Examples and summarized in FIG. 20. The antibodies are treated with pepsin for three hours at 37° C. treated in acetate buffer pH 4.0, to cleave the Fc portion of the antibody. The reaction is stopped by increasing the pH to 8 with Tris buffer. Subsequently the solution is filled up with an equal volume of a mixture of 5,5'-dithiobis-2-nitrobenzoic acid (DTNB) and incubated with thionitrobenzoate (TNB) for 20 hours at room temperature. The molar ratio of the DTNB-TNB mixture is 20:30 being established by incubating a 40 mM DTNB solution with a 10 mM DTT solution for several minutes. After further reduction of the two modified F(ab') fragments with 0.1 mM DTT for one hour at 25° C., the thus obtained F(ab')-TNB and F(ab')-SH fragments are hybridized to a bispecific F(ab')2-fragment for 1 h at 25° C. Bispecific $F(ab')_2$-fragments were purified via gel filtration (Superdex 200 column).

Example 37: Characterization of Binding Affinity and Selectivity of Bispecific Anti-HTT Antibodies Utilizing Direct ELISA and $EC_{50}$ To determine the half maximal effective concentration ($EC_{50}$) of bispecific HTT antibodies to soluble and aggregated HTT Exon1 proteins with 21 or 49 polyQ repeats direct ELISA and $EC_{50}$ determination is performed as described in Example 6, supra. The bispecific HTT antibodies bind with high affinity to all four species including the aggregated HTT Exon1 HD49, equally targeted their respective epitopes exposed in aggregated as well as in soluble forms of HTT with low nanomolar affinity. Additionally, to characterize the binding of bispecific HTT antibodies to soluble and aggregated HTT Exon1 proteins with 21, 35 or 49 polyQ repeats filter retardation assay and dot blot as described in Example 7, supra, are performed. On the dot blot, bispecific HTT antibodies preferentially detect constructs of HTT with expanded polyQ tracts. Furthermore, the signal intensity increases with increasing incubation times of the aggregation reactions of HD35 and HD49. In the filter retardation analysis bispecific HTT antibodies detect HD35 and HD49 aggregates that are retained on the 0.2 μm pore size membrane. Based on their dual specificity to HTT and the previous findings for the binding of the individual antibodies on membrane bound protein preparations it is expected that bispecific HTT antibodies preferentially target aggregated HTT conformations with pathogenic polyQ expansions. Furthermore, to determine the binding of bispecific anti-HTT antibodies to unrelated aggregating protein targets, direct ELISA is performed as described in Example 8, supra. In this context, bispecific anti-HTT antibodies bind specifically to HTT while a binding to unrelated proteins may not be shown.

The invention claimed is:

1. A human-derived monoclonal anti-huntingtin (HTT) antibody, or an HTT-binding fragment thereof, which recognizes an epitope in the P-rich region of the amino acid sequence of exon 1 of the HTT gene, and comprises: a heavy chain variable region ($V_H$) comprising three complementarity determining regions (VH-CDR1, VH-CDR2, and VH-CDR3) and a light chain variable region ($V_L$) comprising three complementarity determining regions (VL-CDR1, VL-CDR2, and VLH-CDR3), wherein:
   (a) (i)
     the VH-CDR1 has the amino acid sequence of positions 31-35 of SEQ ID NO: 14,
     the VH-CDR2 has the amino acid sequence of positions 50-65 of SEQ ID NO: 14,
     the VH-CDR3 has the amino acid sequence of positions 98-108 of SEQ ID NO:14,
     the VL-CDR1 has the amino acid sequence of positions 24-39 of SEQ ID NO: 16 or SEQ ID NO: 112,
     the VL-CDR2 has the amino acid sequence of positions 55-61 of SEQ ID NO: 16 or SEQ ID NO: 112, and
     the VL-CDR3 has the amino acid sequence of positions 94-102 of SEQ ID NO: 16; or
   (ii) the $V_H$ comprises the amino acid sequence of SEQ ID NO: 14 and the $V_L$ comprises the sequence of SEQ ID NO: 16 or SEQ ID NO: 112, and
   (b) the antibody comprises a constant region that is a human constant region or any domain thereof which is of different origin as the CDRs and the VH and/or VL chain, respectively.

2. The antibody, or the HTT-binding fragment thereof, of claim 1, which has a binding affinity corresponding to an EC50 (half maximal effective concentration) value of ≤20 nM for binding HD49 (aggregated and soluble HTT exon 1 protein with 49 poly-glutamine repeats) and an EC50 value of 40 nM for binding HD21 (aggregated and soluble HTT exon 1 protein with 21 poly-glutamine repeats).

3. The antibody or the HTT-binding fragment thereof, of claim 1, wherein the antibody:
   (a) is of the IgG type; and/or
   (b) comprises a kappa (κ) light chain.

4. The antibody or the HTT-binding fragment thereof, of claim 1, wherein the HTT-binding fragment is selected from the group consisting of a single chain Fv fragment (scFv), an F(ab) fragment, an F(ab') fragment, an F(ab')2 fragment, and a disulfide-linked Fv fragment (sdFv) of the antibody of claim 1.

5. A fusion protein comprising the antibody or the HTT-binding fragment thereof according to claim 1 and a heterologous polypeptide, wherein the heterologous polypeptide comprises a sequence which is heterologous to the VH and/or VL region and is fused to or conjugated at the N- or C-terminus of the antibody or the HTT-binding fragment thereof; and is to increase the in vivo half-life of the antibody or the HTT-binding fragment thereof, or is a tag for purification or detection in immunoassays.

6. A conjugate comprising the antibody, or the HTT-binding fragment thereof, of claim 1 and a functional moiety selected from the group consisting of a PEG, a toxin, a biotin, and a detectable substance that is an enzyme, a heavy metal, gold a fluorescent or luminescent dye, or a radioactive label.

7. A pharmaceutical or diagnostic composition comprising the antibody, or the HTT-binding fragment thereof, of claim 1.

8. A kit for the diagnosis or monitoring of disorders associated with HTT amyloidosis, said kit comprising:
   the antibody, or the HTT-binding fragment thereof, of claim 1.

9. An isolated polynucleotide molecule comprising a polynucleotide encoding the antibody or the HTT-binding fragment thereof, of claim 1.

10. A vector comprising the polynucleotide molecule of claim 9.

11. An isolated host cell comprising the polynucleotide molecule of claim 9.

12. A method for preparing the anti-HTT antibody, or the HTT-binding fragment thereof, of claim 1 said method comprising
   (a) culturing an isolated host cell comprising an isolated polynucleotide molecule comprising a polynucleotide encoding the anti-HTT antibody, or the HTT-binding fragment thereof; and
   (b) isolating the anti-HTT antibody, or the HTT-binding fragment thereof, from the culture.

* * * * *